(12) United States Patent
Gryaznov et al.

(10) Patent No.: US 12,428,441 B2
(45) Date of Patent: *Sep. 30, 2025

(54) MODIFIED NUCLEOSIDE PHOSPHORAMIDITES

(71) Applicant: Janssen BioPharma, Inc., South San Francisco, CA (US)

(72) Inventors: Sergei Gryaznov, San Mateo, CA (US); Jin Hong, Pacifica, CA (US); Vivek Kumar Rajwanshi, Cupertino, CA (US); Leonid Beigelman, San Mateo, CA (US)

(73) Assignee: Janssen BioPharma, Inc., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/672,651

(22) Filed: May 23, 2024

(65) Prior Publication Data

US 2024/0309040 A1 Sep. 19, 2024

Related U.S. Application Data

(63) Continuation of application No. 17/514,168, filed on Oct. 29, 2021, now Pat. No. 12,030,907, which is a continuation of application No. 16/647,236, filed as application No. PCT/IB2018/057077 on Sep. 14, 2018, now Pat. No. 11,180,524.

(60) Provisional application No. 62/558,763, filed on Sep. 14, 2017.

(51) Int. Cl.
*C07H 19/10* (2006.01)
*C07H 1/00* (2006.01)
*C07H 19/20* (2006.01)

(52) U.S. Cl.
CPC ........... *C07H 19/10* (2013.01); *C07H 1/00* (2013.01); *C07H 19/20* (2013.01)

(58) Field of Classification Search
None
See application file for complete search history.

(56) References Cited

U.S. PATENT DOCUMENTS

| | | | |
|---|---|---|---|
| 6,835,826 B2 | 12/2004 | Gryaznov et al. | |
| 8,933,214 B2 | 1/2015 | Srivastava et al. | |
| 11,180,524 B2 * | 11/2021 | Gryaznov | C07H 19/20 |
| 12,030,907 B2 * | 7/2024 | Gryaznov | C07H 1/00 |
| 2008/0064867 A1 | 3/2008 | Leuck et al. | |
| 2011/0137010 A1 | 6/2011 | Srivastava et al. | |
| 2013/0323836 A1 | 12/2013 | Manoharan et al. | |
| 2016/0130580 A1 | 5/2016 | Gryaznov et al. | |

FOREIGN PATENT DOCUMENTS

| | | |
|---|---|---|
| CL | 201801870 | 7/2017 |
| CL | 202000657 | 3/2020 |
| CN | 1373768 A | 10/2002 |
| CN | 102439025 A | 5/2012 |
| CN | 103068834 A | 4/2013 |
| CN | 109952378 A | 6/2019 |
| JP | A-2002-255990 | 9/2002 |
| JP | 2003/513887 | 4/2003 |
| JP | 2019-529406 | 10/2019 |
| JP | 6970187 | 11/2021 |
| WO | WO 2001/18015 A1 | 3/2001 |
| WO | WO 2002/100152 A2 | 12/2002 |
| WO | WO 2017/123669 A1 | 7/2017 |
| WO | WO 2018/053185 A1 | 3/2018 |
| WO | WO 2019/053659 | 3/2019 |

OTHER PUBLICATIONS

Madsen et al., Organic & Biomolecular Chemistry, 2010, 8(21), pp. 5012-5016. (Year: 2010).*
Christensen et al., "Incorporation of alpha- and beta-LNA (Locked Nucleic Acid) Monomers in Oligodeoxynucleotides with Polarity Reversal," *Bioorganic & Medicinal Chemistry Letters*, vol. 11(13): pp. 1765-1768 (Jul. 2001) (Waltham, MA, US).
Gryaznov et al., "RNA Mimetics: Oligoribonucleotide N3'P5' Phosphoramidates," *Nucleic Acids Research*, vol. 26(18), pp. 4160-4167 (Sep. 1998) (Oxford, England, UK).
Hudson et al., "Divergent solid-phase synthesis of nucleic acid dendrimers," *Tetrahedron Letters*, 39(11); pp. 1299-1302 (1998) (Amsterdam, The Netherlands).
International Search Report and Written Opinion mailed on Dec. 12, 2018 for PCT Application No. PCT/IB2018/057077.
Ma et al., Synthesis and antisense properties of 2'β-F-and 2'α-F-2'deoxy-uridines modified oligonucleotides with 4'-C-(2-methoxyethoxy) substituent, *Acta Pharmaceutica Sinica*, 51(8), pp. 1721-1731 (2016) (Beijing, China).
Madsen et al., "LNA 5-phosphoramidites for 5-3 oligonucleotide synthesis," *Organic & Biomolecular Chemistry*, vol. 8(21), pp. 5012-5016 (Jan. 2010) (London, England, UK).
Matray et al., "A Remarkable Stabilization of Complexes Formed by 2,6-Diaminopurine Oligonucleotide N3'-P5' Phosphoramidates," *Nucleosides, Nucleotides and Nucleic Acids*, vol. 19 (1012): pp. 1553-1567, (Oct. 2000).
Matray et al., "Synthesis and properties of RNA analogs—oligoribonucleotide N3'-P5' phosphoramidates," *Nucleic Acids Research*, vol. 27(20), pp. 3976-3985 (Jan. 1999) (Oxford, England, UK).
Obika et al., "Synthesis and properties of 3'-amino-2',4'-BNA, a bridged nucleic acid with a N3'-P5' phosphoramidated linkage," *Bioorganic & Medicinal Chemistry*, vol. 16(20), pp. 9230-9237 (Oct. 2008) (Amsterdam, The Netherlands).
Ravikumar et al., "Stereoselective synthesis of Alkylphosphonates: A Facile Rearrangement of Cyanoethl-protected Nucleoside Phosphoramidites," *Organic Process Research & Development*, vol. 8(4): pp. 603-608 (Jul. 2004) (Washington, DC, US).
Search Report dated Feb. 20, 2023 issued in Chinese Appln. CN201880073842.6.
Zhou et al., "Nucleotide Libraries as a Source of Biologically Relevant Chemical Diversity: Solution-phase Synthesis," *Bioorganic & Medicinal Chemistry Letters*, vol. 10(11), pp. 1249-1252 (Jun. 2000) (Amsterdam, The Netherlands).

* cited by examiner

*Primary Examiner* — Traviss C McIntosh, III

(74) *Attorney, Agent, or Firm* — Arnold & Porter Kaye Scholer LLP

(57) ABSTRACT

The present disclosure relates to compounds and compositions containing 5'-phosphoramidite nucleoside monomers, and methods of making and use.

18 Claims, No Drawings

MODIFIED NUCLEOSIDE PHOSPHORAMIDITES

CROSS-REFERENCE TO RELATED APPLICATIONS

The present application is a continuation of U.S. application Ser. No. 17/514,168, filed Oct. 29, 2021 (allowed), which is a continuation of U.S. application Ser. No. 16/647,236, filed Mar. 13, 2020 (now U.S. Pat. No. 11,180,524), which is a U.S. National Stage filing under 35 U.S.C. § 371 of International Application No. PCT/IB2018/057077, filed Sep. 14, 2018, which claims the benefit of priority to U.S. Provisional Application No. 62/558,763, filed Sep. 14, 2017, the entireties of each of which are hereby incorporated by reference.

BACKGROUND

Oligonucleotide synthesis is extremely important for providing access to custom-made oligonucleotides of the desired sequence. To obtain the desired oligonucleotide, the building blocks (monomers) are sequentially coupled to the growing oligonucleotide chain in the order required by the sequence of the product.

Modified oligonucleotides, having modifications at, e.g., the 2' and/or 3' position have received increased interest over the past years as useful in, e.g., therapeutic applications. While synthetic methods for constructing modified oligonucleotides exist, there is a need for additional synthetic options to synthesize a diverse array of modified oligonucleotides. New monomeric nucleosides of high purity, and which are capable of being synthesized at higher yield and at high volume, are needed to meet the demand for new modified oligonucleotides.

Monomers described herein meet this need by providing novel monomers useful for the synthesis of modified oligonucleotides.

SUMMARY

The present disclosure relates to compounds and compositions containing 5'-phosphoramidite nucleoside monomers, and methods of making and use.

The present disclosure is directed to compounds having a structure represented by Formula (I):

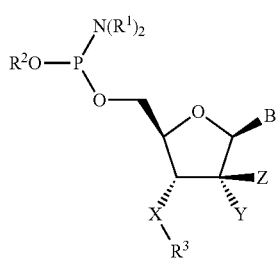

(I)

X is O or NH; Y is selected from the group consisting of O-PG, $-O(CR^4_2)_a CR^4_3$, $-O(CR^4_2)_b OCR^4_3$ and $-O(CR^4_2)_b-CR^4=CR^4_2$; Z is H; PG is a protecting group; B is a natural or an unmodified nucleobase or a modified nucleobase or a protected version thereof; each $R^1$ is independently $C_{1-6}$ alkyl or cycloalkyl; $R^2$ is $CH_2CH_2CN$ or $C_{1-6}$ alkyl; or one $R^1$ and $R^2$ together form an optionally substituted $C_{1-6}$ cycloalkyl; $R^3$ is H or PG; $R^4$ is independently in each instance H or F; a is an integer of 0-2; and b is an integer of 1-3. In some embodiments, when X is O, then Y is $-O(CR^4_2)_a CR^4_3$, $-O(CR^4_2)_b OCR^4_3$ or $-O(CR^4_2)_b-CR^4=CR^4_2$.

The present disclosure is also directed to compounds having a structure represented by Formula (II):

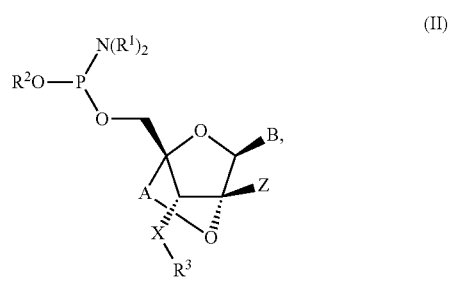

(II)

X is O or NH; Z is H; B is a natural or an unmodified nucleobase or a modified nucleobase or a protected version thereof; $R^1$ is independently a $C_{1-6}$ alkyl or cycloalkyl; $R^2$ is $CH_2CH_2CN$ or a $C_{1-6}$ alkyl; or one $R^1$ and $R^2$ together form an optionally substituted $C_{1-6}$ cycloalkyl; $R^3$ is H or a protecting group; A is $-(CR'R')_{1-2}-$; and R' is independently in each instance H or Me.

In some embodiments, X is NH, Y is O-PG, OEt or O-methoxyethoxy and Z is H.

In some embodiments, $R^1$ is $C_{2-3}$ alkyl. In some embodiments, $R^1$ is isopropyl.

In embodiments, $R^3$ is PG. In some embodiments, PG is trityl. In some embodiments, PG is monomethoxytrityl (MMTr) or trityl when X is NH. In some embodiments, PG is 4,4'-dimethoxytrityl (DMTr) or trityl when X is O.

In some embodiments, B is selected from adenine (A), guanine (G), thymine (T), cytosine (C), uracil (U) and 5-methylcytosine (5-me-C), or a protected version thereof. In some embodiments, B is selected from 6-N-benzoyladenosine ($A^{Bz}$), 4-N-benzoylcytidine ($C^{Bz}$), and 2-N-isobutyrylguanosine ($G^{iBu}$).

The present disclosure is also directed to a composition comprising at least one compound of Formula (I) or Formula (II). In embodiments, the composition further comprises one or more other agents selected from the group consisting of reactants, solvents and impurities. In embodiments, the composition comprises less than 5%, less than 4%, less than 3%, less than 2% or less than 1% impurities. In some embodiments, the composition has a purity of >95%, e.g., 96, 97, 98, 99%, or more.

The present disclosure is further directed to methods of making an oligonucleotide comprising at least one modified nucleoside. The method comprises reacting a compound of Formula (I) with another monomer to form the oligonucleotide.

DETAILED DESCRIPTION

The present disclosure is described herein in greater detail.

Compounds of the Present Disclosure

Compounds of the present disclosure include one or more compounds of the following Formula (I) and/or (II):

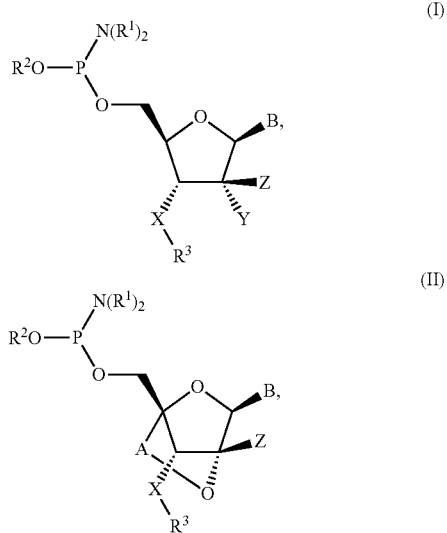

wherein
X is O or NH; Y is selected from the group consisting of O-PG, —O(CR$^4_2$)$_a$CR$^4_3$, —O(CR$^4_2$)$_b$OCR$^4_3$ (e.g., OEt, O-methoxyethoxy, and OCF$_3$); Z is H; PG is a protecting group; B is a natural or an unmodified nucleobase or a modified nucleobase or a protected version thereof; each R$^1$ is independently C$_{1-6}$ alkyl or cycloalkyl; R$^2$ is CH$_2$CH$_2$CN or C$_{1-6}$ alkyl; or one R$^1$ and R$^2$ together form an optionally substituted C$_{1-6}$ cycloalkyl; R$^3$ is H or PG; R$^4$ is independently in each instance H or F; a is an integer of 0-2 (e.g., 0, 1 or 2); and b is an integer of 1-3 (e.g., 1, 2 or 3), A is —(CR'R')$_{1-2}$—; and R' is independently in each instance H or Me.

In some embodiments, when X is O, then Y is —O(CR$^4_2$)$_a$CR$^4_3$, —O(CR$^4_2$)$_b$OCR$^4_3$ or —O(CR$^4_2$)$_b$—CR$^4$=CR$^4_2$. In some embodiments, X is O, Y is OEt or O-methoxyethoxy and Z is H. In other embodiments, X is NH, Y is OP, OEt or O-methoxyethoxy and Z is H.

In nucleotides of Formula (I), Y is —O(CR$^4_2$)$_2$OCR$^4_3$. In some embodiments, R$^4$ is H in each instance. In other embodiments, at least one R$^4$ is F, for example, 1, 2, 3, 4, 5, 6, or 7 R$^4$s are F. In some embodiments, CR$^4_3$ contains 1, 2 or 3 F atoms. For example, in embodiments, Y is selected from the group consisting of —OCH$_2$CH$_2$OCH$_3$ (or MOE), —OCF$_2$CH$_2$OCH$_3$, —OCH$_2$CF$_2$OCH$_3$, —OCH$_2$CH$_2$OCF$_3$, —OCF$_2$CF$_2$OCH$_3$, —OCH$_2$CF$_2$OCF$_3$, —OCF$_2$CH$_2$OCF$_3$, —OCF$_2$CF$_2$OCF$_3$, —OCHFCH$_2$OCH$_3$, —OCHFCHFOCH$_3$, —OCHFCH$_2$OCFH$_2$, —OCHFCH$_2$OCHF$_2$ and —OCH$_2$CHFOCH$_3$.

In the nucleotide of Formula (I), Y is —OCR$^4_3$, —O(CR$^4_2$)$_{1-3}$OCR$^4_3$, or —O(CR$^4_2$)$_{1-2}$CR$^4_3$. In some embodiments, Y is —OCR$^4_3$ or —OCR$^4_2$CR$^4_3$. In some embodiments, R$^4$ is H in each instance. In other embodiments, at least one R$^4$ is F, for example, 1, 2, 3, 4, or 5 R$^4$s are F. In some embodiments, OCR$^4_3$ contains 1, 2 or 3 F atoms. For example, in embodiments, Y is selected from the group consisting of —OCH$_3$ (or Me), —OCFH$_2$, —OCHF$_2$, OCF$_3$, —OCH$_2$OCH$_3$, —OCFH$_2$OCH$_3$, —OCHF$_2$OCH$_3$, —OCF$_3$OCH$_3$, —OCH$_2$OCFH$_2$, —OCH$_2$OCHF$_2$, —OCH$_2$OCF$_3$, —OCFH$_2$OCH$_3$, —OCFH$_2$OCFH$_2$, —OCFH$_2$OCHF$_2$, —OCFH$_2$OCF$_3$, —OCHF$_2$OCH$_3$, —OCHF$_2$OCFH$_2$, —OCHF$_2$OCHF$_2$, —OCHF$_2$OCF$_3$, —O(C R$^4_2$)$_3$OC R$^4_3$, —OCH$_2$CH$_3$ (or Et), —OCFH$_2$CH$_3$, —OCHF$_2$CH$_3$, —OCF$_3$CH$_3$, —OCH$_2$CFH$_2$, —OCH$_2$CHF$_2$, —OCH$_2$CF$_3$, —OCFH$_2$CH$_3$, —OCFH$_2$CFH$_2$, —OCFH$_2$CHF$_2$, —OCFH$_2$CF$_3$, —OCHF$_2$CH$_3$, —OCHF$_2$CFH$_2$, —OCHF$_2$CHF$_2$, —OCHF$_2$CF$_3$, —OCH$_2$CH$_2$CH$_3$, OCF$_2$CH$_2$CH$_3$, OCH$_2$CF$_2$CH$_3$, OCH$_2$CH$_2$CF$_3$, OCF$_2$CF$_2$CH$_3$, OCH$_2$CF$_2$CF$_3$, OCF$_2$CH$_2$CF$_3$, OCF$_2$CF$_2$CF$_3$, OCHFCH$_2$CH$_3$, OCHFCHFOCH$_3$, OCHFCH$_2$CFH$_2$, OCHFCH$_2$CHF$_2$ and OCH$_2$CHFCH$_3$. In embodiments, Y is —OCH$_3$ (or Me) or —OCH$_2$CH$_3$ (or Et).

In some embodiments of Formula (I), Y is —O(CR$^4_2$)$_b$—CR$^4$=CR$^4_2$. In some embodiments, b is 1, 2 or 3. In some embodiments, R$^4$ is H in each instance. In other embodiments, at least one R$^4$ is F, for example, 1, 2, 3, 4, 5, 6, or 7 R$^4$s are F. In some embodiments, a CR$^4_2$ contains 1 or 2 F atoms, e.g. an internal R$^4_2$ contains 1 or 2 F atoms, or the terminal R$^4_2$ contains 1 or 2 F atoms.

In some embodiments, R$^1$ is a C$_{2-3}$ alkyl (e.g., an ethyl or isopropyl).

In some embodiments, R$^3$ is a protecting group, PG. Protecting groups may include an amine or alcohol protecting group, such as a silyl protecting group (e.g., tert-Butyldimethylsilyl ether (TBMDS), tert-Butyldiphenylsilyl (TBDPS), Triisopropylsilyl ether (TIPS)) or monomethoxytrityl (MMTr) or 4,4'-dimethoxytrityl (DMTr) or tritolyl or any other suitable protecting groups such as those in Wuts, Peter GM, and Theodora W. Greene. Greene's protective groups in organic synthesis. John Wiley & Sons, 2006. In some embodiments, when more than one alcohol and/or amine is protected, the alcohols and/or amines may be orthogonally protected.

In compounds of Formula (II), A is —(CR'R')$_{1-2}$—. In some embodiments, A is —(CR'R')— in other embodiments, A is —(CR'R')$_2$—. R' is independently in each instance H or Me. In some embodiments, one R' is Me and the remaining R' are H. In other embodiments all R' are H. In some embodiments, X is NH in Formula (II). In some embodiments, A is not —(CR'R')$_f$— when R'=H and X=NH.

The natural or unmodified nucleobase or a modified nucleobase or a protected version thereof is not particularly limited. In some embodiments, B is selected from purine bases, such as, adenine (A) and guanine (G), diaminopurine (DAP) and pyrimidine bases, such as, thymine (T), cytosine (C) and uracil (U) and/or other synthetic and natural nucleobases such as 5-methylcytosine (5-me-C), 5-hydroxymethyl cytosine. In some embodiments, B is a protected nucleobase, such as a protected U, T, C, 5meC, A or G. Protection moieties are known in the art, and are not particularly limited, but include, for example, amino protecting groups (e.g., acetamide protecting groups, such as benzamide and isobutyramide). In some embodiments, B is 6-N-benzoyladenosine (A$^{Bz}$), 4-N-Benzoylcytidine (C$^{Bz}$), 2-N-isobutyrylguanosine (G$^{iBu}$).

In some embodiments, the compound is selected from the following table.

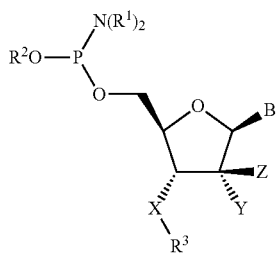

| | X | Y | Z | B | R$^1$ | R$^2$ | R$^3$ |
|---|---|---|---|---|---|---|---|
| | NH | OP | H | U/T/C/5meC/A/G/DAP | iPr | CH$_2$CH$_2$CN | MMTr |
| | NH | OEt | H | U/T/C/5meC/A/G/DAP | iPr | CH$_2$CH$_2$CN | MMTr |
| 5 | NH | O-methoxyethyl | H | U/T/C/5meC/A/G/DAP | iPr | CH$_2$CH$_2$CN | MMTr |
| | NH | OCF$_3$ | H | U/T/C/5meC/A/G/DAP | iPr | CH$_2$CH$_2$CN | MMTr |
| | O | OEt | H | U/T/C/5meC/A/G/DAP | iPr | CH$_2$CH$_2$CN | DMTr |
| 10 | O | O-methoxyethyl | H | U/T/C/5meC/A/G/DAP | iPr | CH$_2$CH$_2$CN | DMTr |

*B may be a protected nucleobase (e.g., A$^{Bz}$, C$^{Bz}$, G$^{iBu}$).

In some embodiments, the compound is selected from the following table.

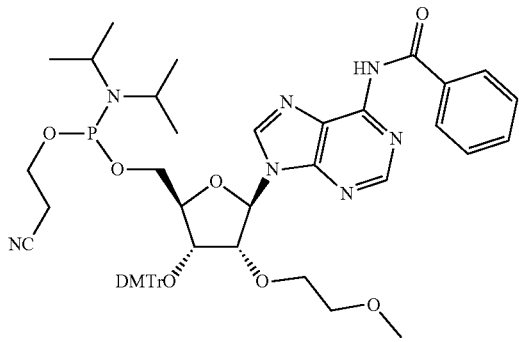

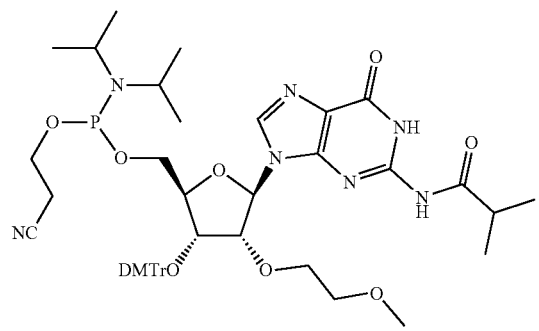

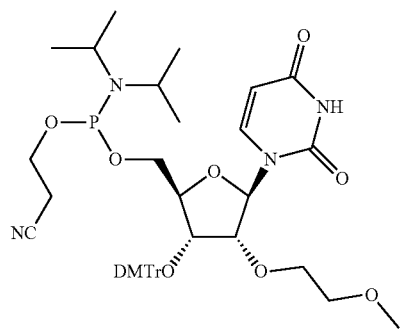

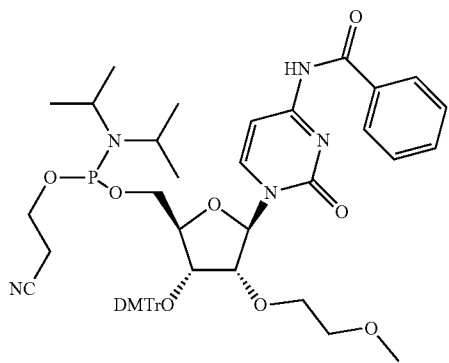
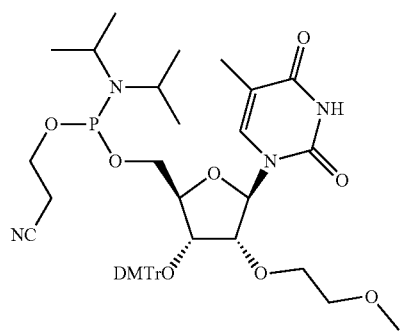
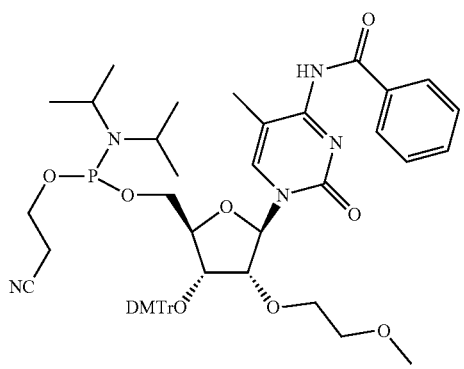
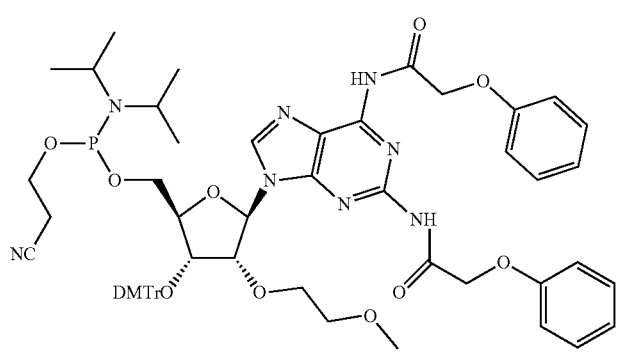

-continued
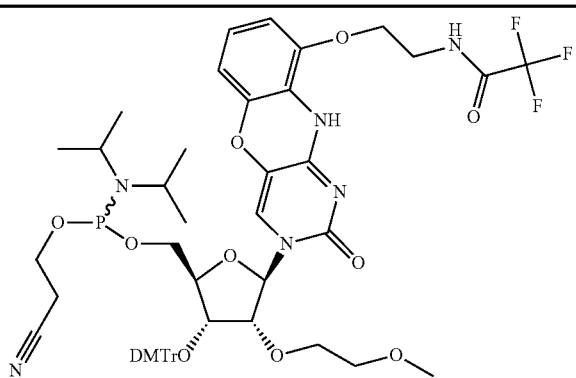
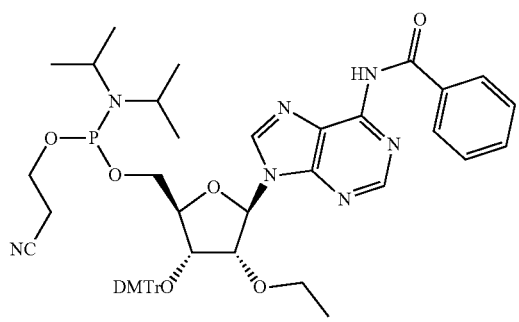
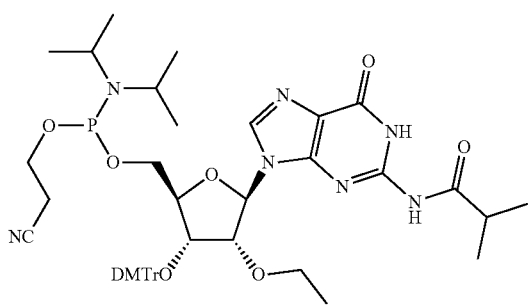
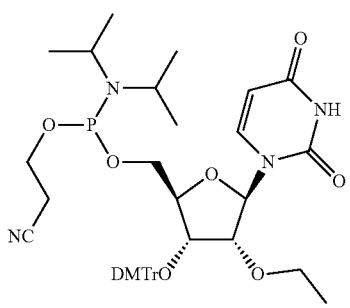
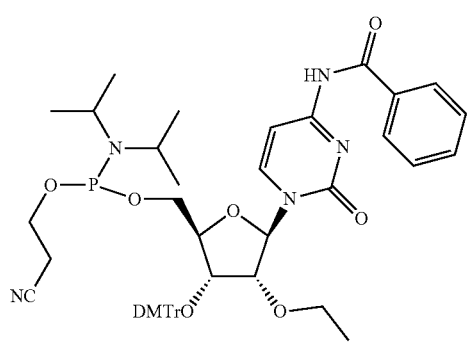

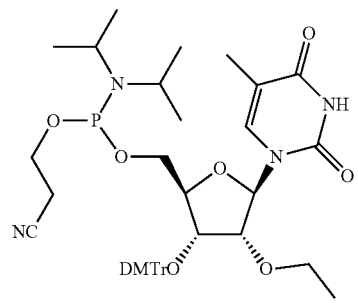
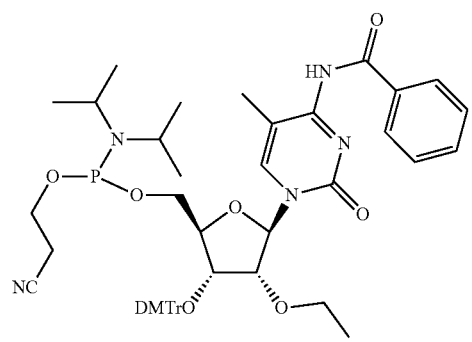
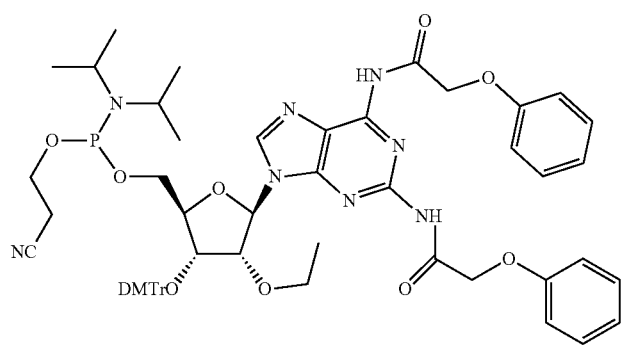
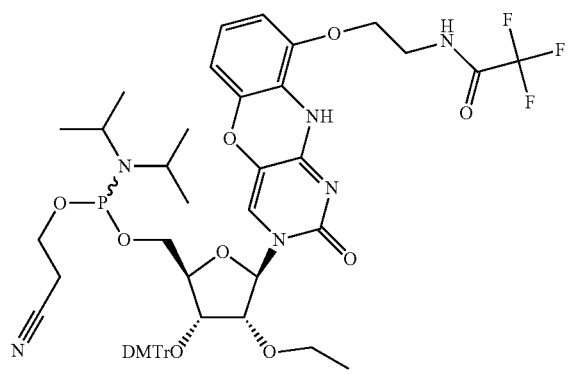

-continued
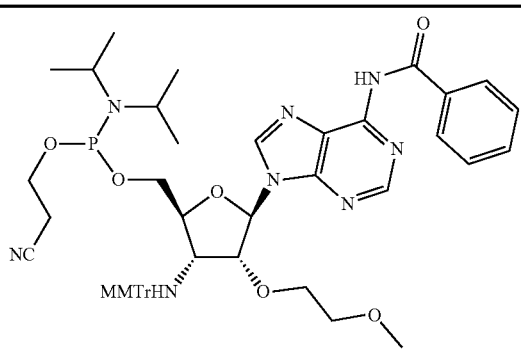
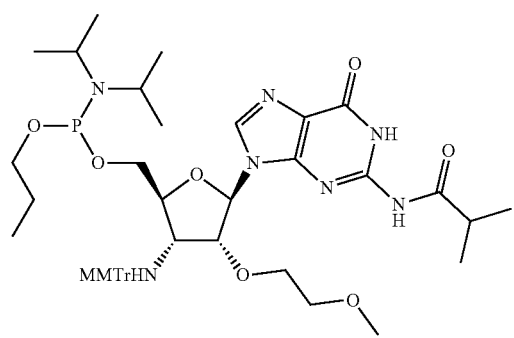
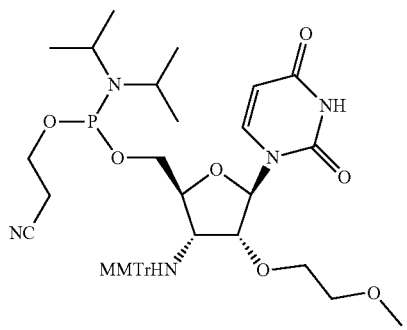
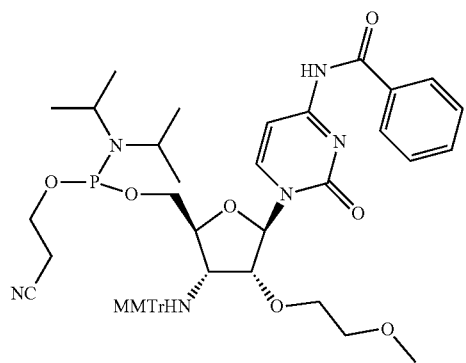

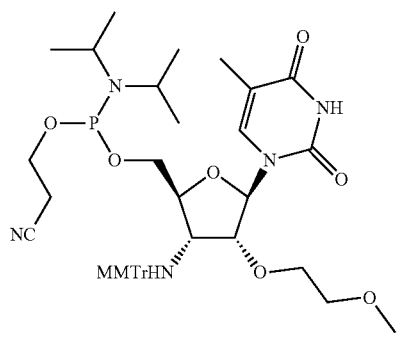
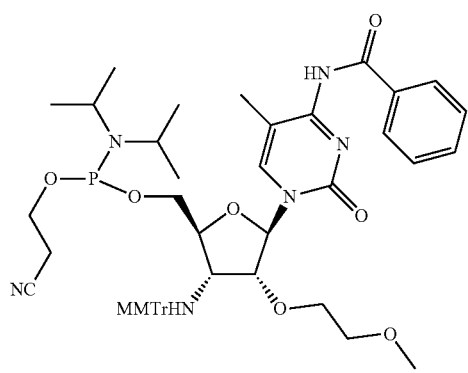
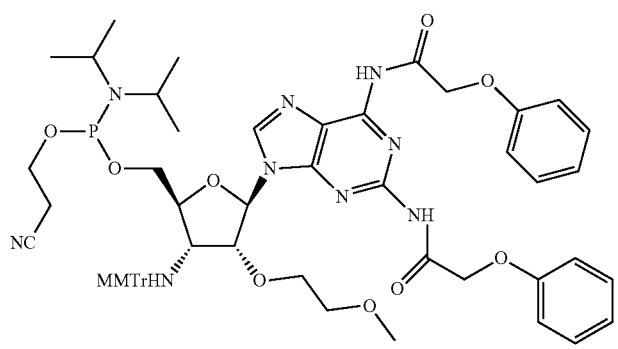
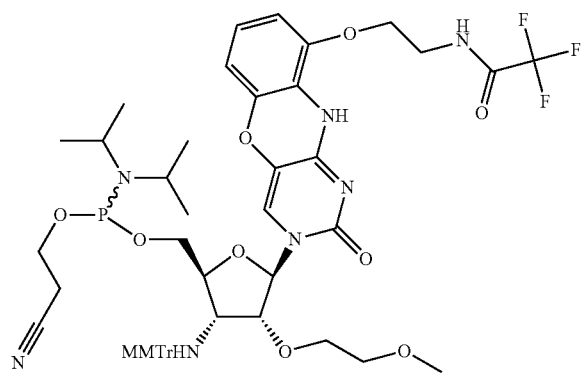

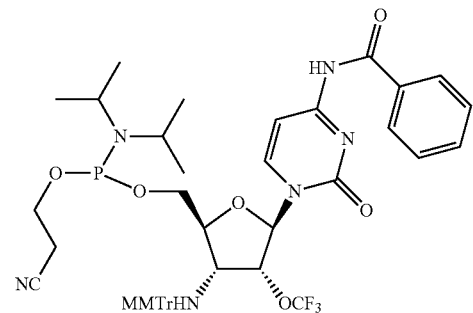
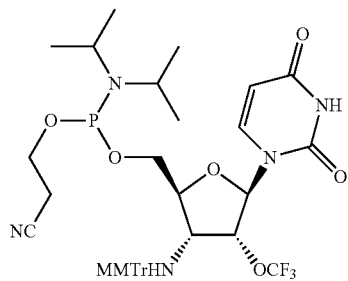
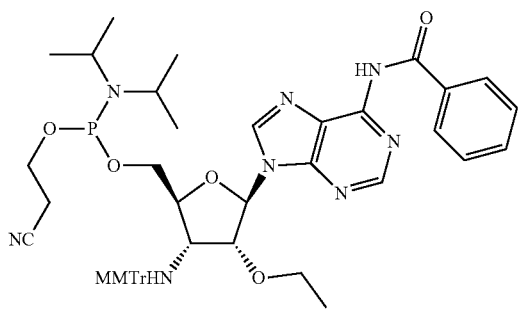
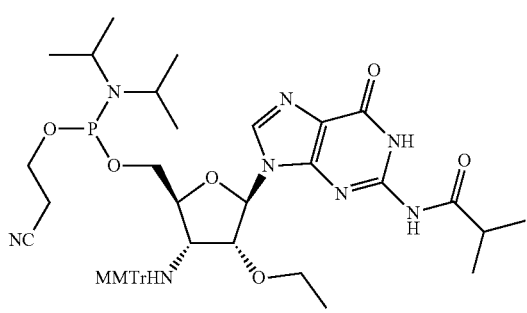
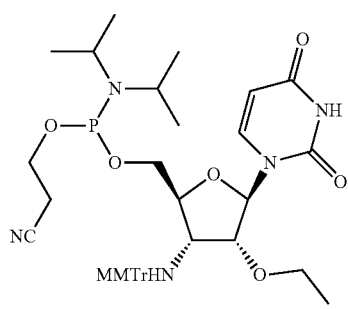

-continued
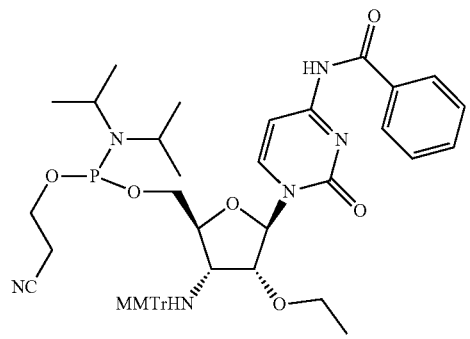
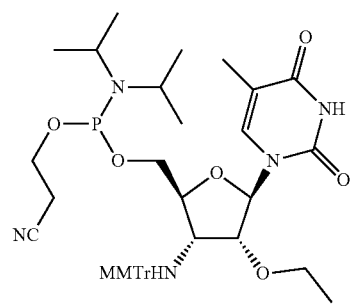
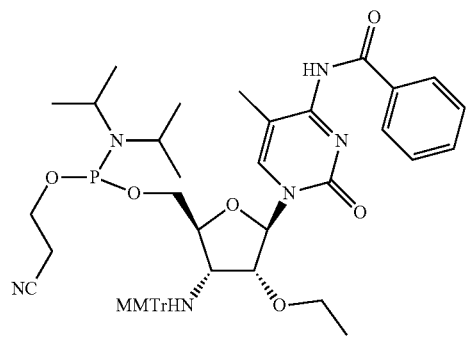
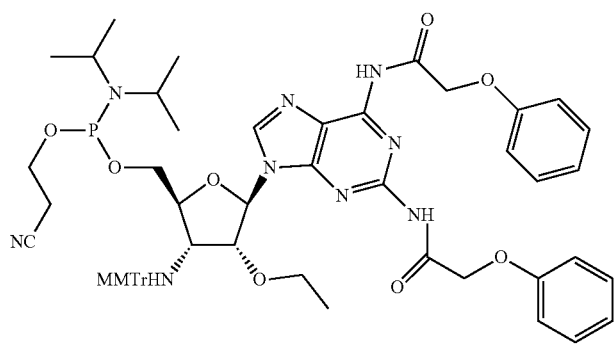

-continued
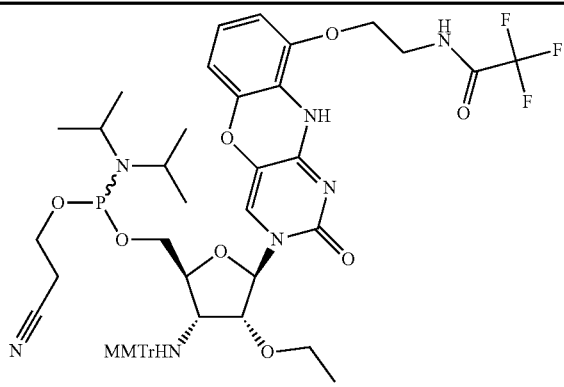
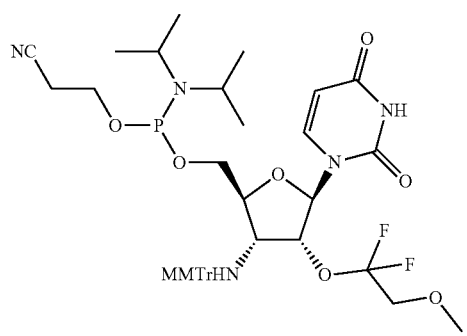
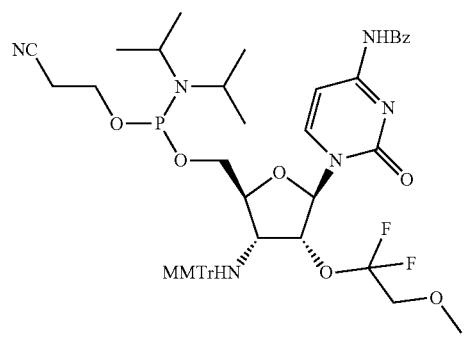
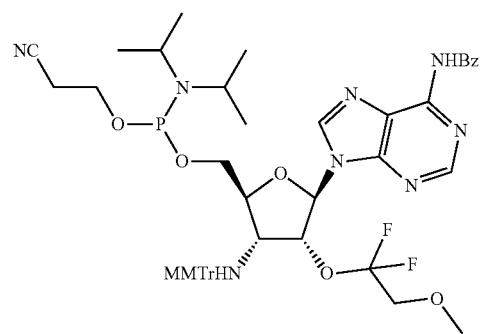

-continued
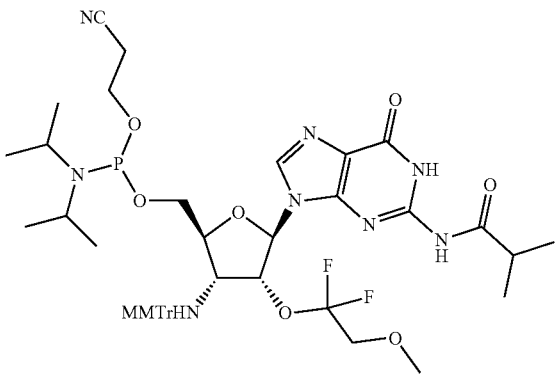
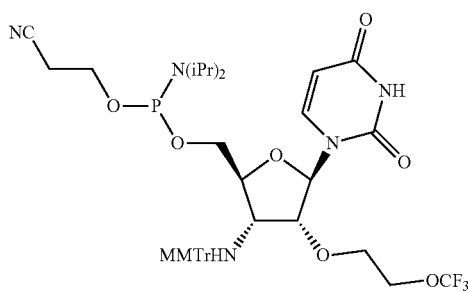
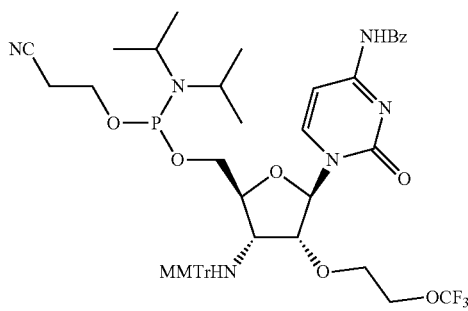
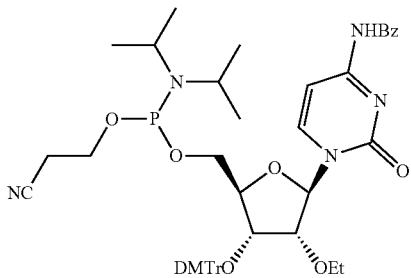
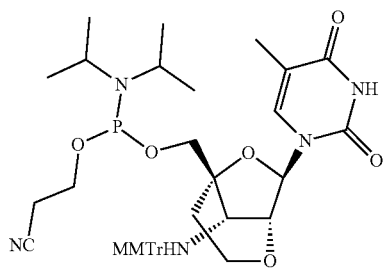

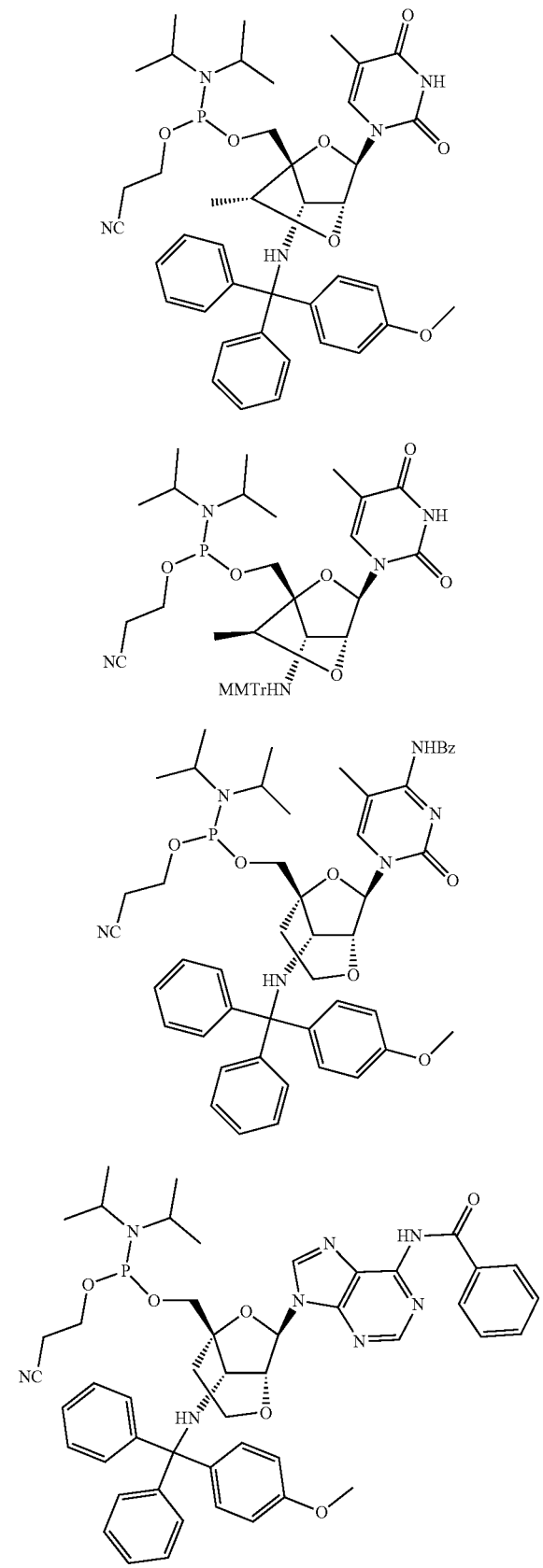

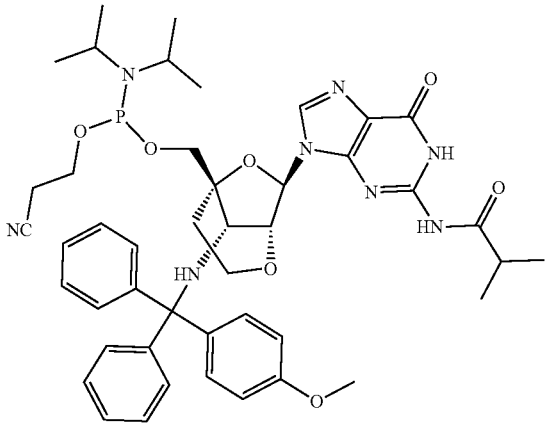 [SMILES: COc1ccc(C(N[C@H]2[C@H]3OCC[C@]2(COP(OCCC#N)N(C(C)C)C(C)C)O[C@H]3n2cnc3c(=O)[nH]c(NC(=O)C(C)C)nc32)(c2ccccc2)c2ccccc2)cc1]

Compositions

The present disclosure also encompasses compositions comprising a compound of the present disclosure and one or more reactants or solvents or impurities.

In some embodiments, the compositions comprising a compound of the present disclosure have a purity of 95%, 96%, 97%, 98%, 99%, 99.5%, 99.6%, 99.7%, 99.8%, 99.9%, 99.95% or more.

Methods of Use

The compositions of the present disclosure may be used as synthetic precursors for oligonucleotides comprising modified nucleosides, e.g., those in U.S. Provisional Applications 62/420,801, 62/394,737, 62/394,738 and 62/394,739, each of which is incorporated by reference. The modified oligonucleotides may be synthesized by methods in the art, e.g., on an ABI-394 synthesizer using the 93-step cycle written with modifications to deblock, coupling and wait steps. The solid support can be 3'-NHTr-5'-LCAA-CPG. Each oligonucleotide is individually synthesized using methods described herein.

Methods of Making

The compositions of the present disclosure may be synthesized by synthetic procedures such as those set forth in the below Examples.

Some embodiments include 2'-O-alkylation of a starting material, such as the following:

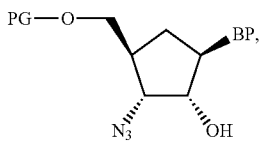

where PG is a protecting group, such as trityl and BP is a protected nucleobase, protected with, e.g., PMB. The compound is alkylated, followed by deprotection of the PGO and reprotection with, e.g., a Bz moiety, followed by deprotection of the nucleobase and subsequent conversion of the $N_3$ to $N-R_3$.

Some embodiments include protection of a compound, such as that in the previous paragraph where the nucleobase is a purine, with C-6-OBn. In some embodiments, this reduces de-purination during deprotection of, e.g., 5'-O-DMTr and C-2-NH-MMTr group under acidic conditions. Other embodiments include protection of the exocyclic amine group in a compound, such as that in the previous paragraph where the nucleobase is a purine, with a bulky protecting group such as 4-monomethoxy trityl group to achieve 2'-O-alkylation in high yield.

Some embodiments include protection of a compound, such as that in the previous paragraph where the nucleobase is a pyrimidine to achieve 2'-O-alkylation by protecting the pyrimidine with a PMB moiety.

Definitions

It is to be understood that the terminology used herein is for the purpose of describing particular embodiments only and is not intended to limit the scope of the present invention. The following definitions shall apply unless otherwise indicated.

"Pharmaceutically acceptable" refers to a material that is not biologically or otherwise undesirable, i.e., the material may be incorporated into a pharmaceutical composition administered to a patient without causing any undesirable biological effects or interacting in a deleterious manner with any of the other components of the composition in which it is contained. When the term "pharmaceutically acceptable" is used to refer to a pharmaceutical carrier or excipient, it is implied that the carrier or excipient has met the required standards of toxicological and manufacturing testing or that it is included on the Inactive Ingredient Guide prepared by the U.S. and Drug administration.

"Modified nucleoside" refers to a nucleoside having, independently, a modified sugar moiety and/or modified nucleobase.

"Unmodified" or "natural" nucleobases include the purine bases adenine (A) and guanine (G), and the pyrimidine bases thymine (T), cytosine (C) and uracil (U). "Modified nucleobases" include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl ($—C≡C—CH_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluorometlhyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified nucleobases include tricyclic pyrimidines such as phenoxazine cytidine(1H-pyrimido[5,4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g. 9-(2-am-oelhoxy)-H-pyrimido[5,4-b][1,4]benzoxazin-2 (3H)-one), carbazole cytidine (2H-pyrimido[4,5-b]indol-2-one), pyridoindole cytidine (H-pyrido[3,2,5]pyrrolo[2,3-d] pyrimidin-2-one). Modified nucleobases may also include those in which the purine or pyrimidine base is replaced with other heterocycles, for example 7-deaza-adenine, 7-deazaguanosine, 2-aminopyridine and 2-pyridone.

In some embodiments, the modified nucleobase is selected from the group consisting of 5-methylcytosine, 2,6-diaminopurine, 5-methyluracil, and a g-clamp. In some embodiments, the g-clamp is

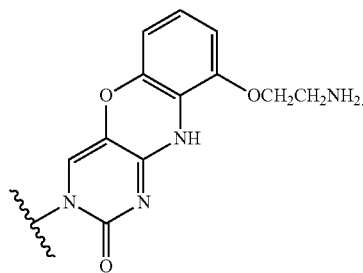

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely", "only" and the like in connection with the recitation of claim elements, or use of a "negative" limitation.

The term "about" will be understood by persons of ordinary skill in the art and will vary to some extent depending upon the context in which it is used. If there are uses of the term which are not clear to persons of ordinary skill in the art given the context in which it is used, "about" will mean up to plus or minus 10% of the particular term. Certain ranges are presented herein with numerical values being preceded by the term "about". The term "about" is used herein to provide literal support for the exact number that it precedes, as well as a number that is near to or approximately the number that the term precedes. In determining whether a number is near to or approximately a specifically recited number, the near or approximating unrecited number may be a number, which, in the context in which it is presented, provides the substantial equivalent of the specifically recited number.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

This disclosure is not limited to particular embodiments described, as such may, of course, vary. It is also to be understood that the terminology used herein is for the purpose of describing particular embodiments only, and is not intended to be limiting, since the scope of the present invention will be limited only by the appended claims.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order that is logically possible.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates that may need to be independently confirmed.

EXAMPLES

The following examples illustrate certain embodiments of the present disclosure to aid the skilled person in practicing the disclosure. Accordingly, the examples are in no way considered to limit the scope of the disclosure.

Examples 1-4

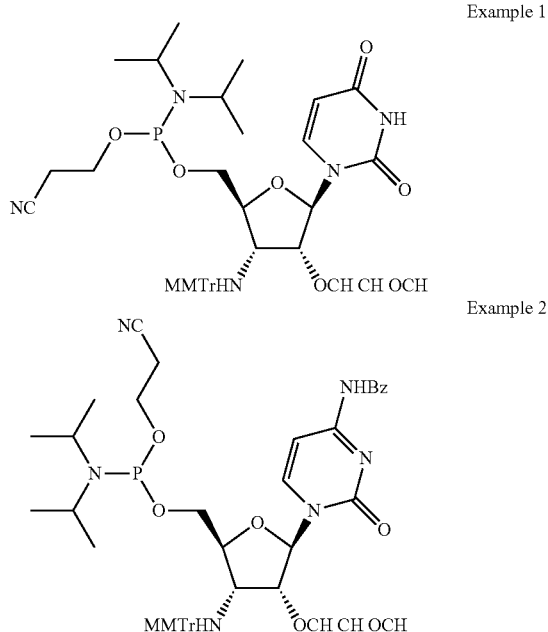

Example 3
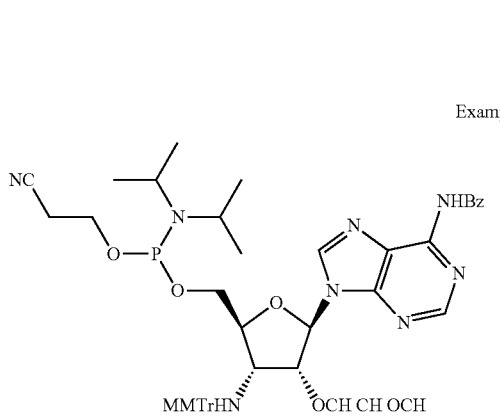
Example 4
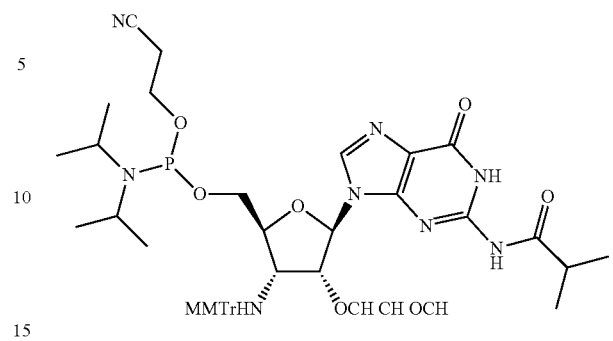
The appropriately protected 2'-O-methoxy ethyl-3'-aminonucleoside-5'-phosphoramidite building blocks (examples 1, 2, 3, and 4 were prepared after chemical transformations shown in Schemes 1, 2, 3, 4, and 5.
Scheme 1
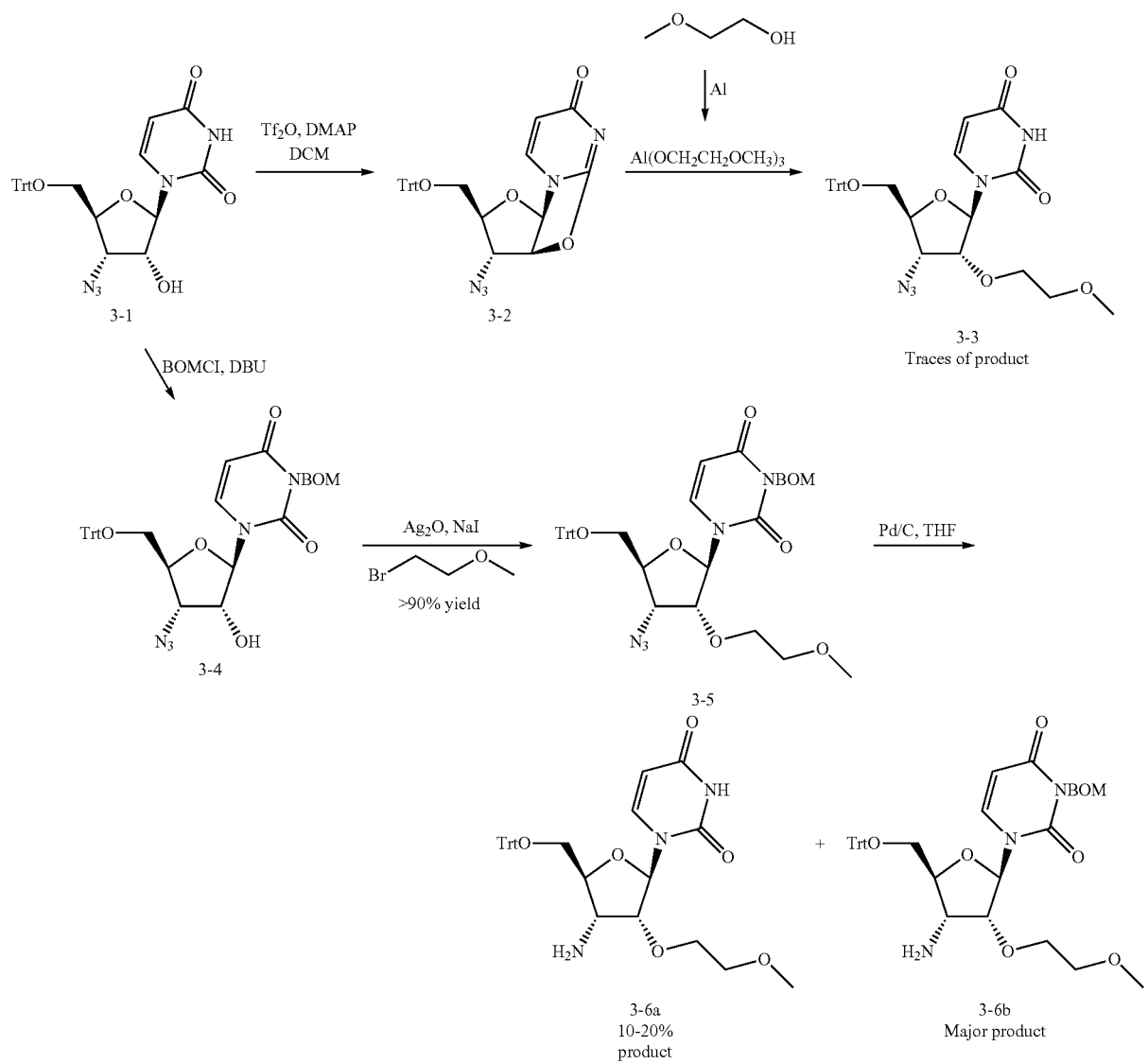

Scheme 1 discloses synthesis of uracil-based 3'-NH-MMTr-2'-O-methoxyethyl phosphoramidites (such as example 1). The key 3'-azido-2'-methoxyethyl Intermediate 3-3 was obtained in low yields via anhydrous Intermediate 3-2.

Due to low yielding alkylation, 3-1 was reacted with BOMCl/DBU to give N-3 protected Intermediate 3-4, which was alkylated by using 2-bromoethyl methyl ether/Ag$_2$O/NaI/DMF to give 2'-O-methoxyethyl derivative 3-5. Deprotection of N-3-BOM group using hydrogenation condition (Pd/C/H$_2$) resulted in 10-20% desired 3'-amino Intermediate 3-6a along with significant over reduced side product 3-6b.

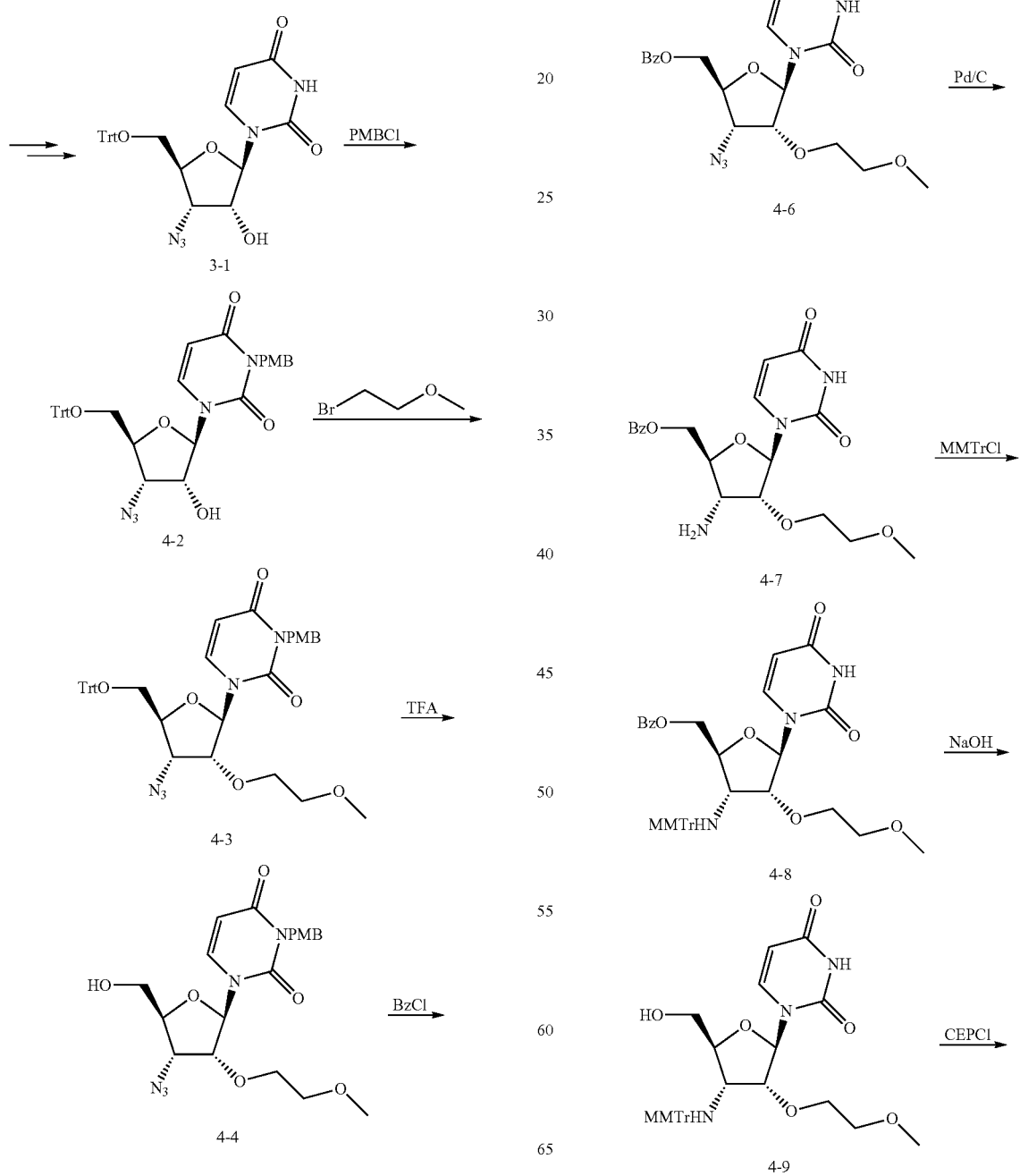

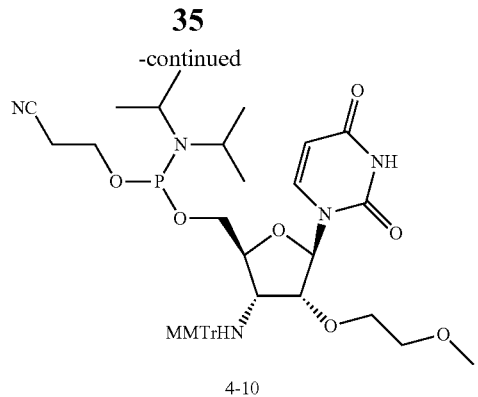

4-10

Scheme 2 discloses an alternative approach to achieve 2'-O-alkylation in high yield. Intermediate 3-1 was treated with PMBCl/DBU/DMF to give N-3 protected Intermediate 4-2, which was subjected to 2'-O alkylation using 2-bromoethyl methyl ether/Ag$_2$O/NaI/DMF to provide a 2'-O-methoxyethyl derivative (Intermediate 4-3). 5'-de-tritylation of Intermediate 4-3 and re-protection of its 5'-hydroxyl group using benzoyl chloride provided Intermediate 4-5

De-protection of PMB group of Intermediate 4-5 in mild conditions to give Intermediate 4-6. 3'-azido group of intermediate 4-6 was reduced to an amine, which was then immediately protected, such as reaction with 4-monomethoxytritylchloride, to give 4-8. The 5'-benzyl ester was then cleaved using an alkaline solution, followed by phosphitylation using known methods to give the desired 2'-O-methoxyethoxy uridine phosphoramidite monomer 4-10.

Preparation of Intermediate (4-2): To a solution of 3-1 (45.30 g, 88.56 mmol) in DMF (120.00 mL) was added PMBCl (20.80 g, 132.84 mmol) and DBU (44.61 g, 177.12 mmol), the mixture was stirred at r.t. for 2 h. Water was added, extracted with EA. The organic layer was concentrated and purified by column to give 4-2 (52.00 g, 82.32 mmol) as a white solid. ESI-LCMS: m/z 632.3 [M+H]$^+$.

Preparation of Intermediate (4-3): To a solution of 4-2 (50.00 g, 79.15 mmol) in DMF (120.00 mL) was added 2-Bromoethyl methyl ether (16.50 g, 118.73 mmol) and Ag$_2$O (18.34 g, 79.15 mmol, 2.57 mL), then NaI (5.93 g, 39.58 mmol) was added. The reaction mixture was stirred at r.t. for 12 h. LC-MS showed work well. Filtered and added water and EA, the organic layer was concentrated and purified by column to give 4-3 (52.00 g, 75.39 mmol) as a colorless oil. ESI-LCMS: m/z 690.4 [M+H]$^+$.

Preparation of Intermediate (4-4): To a solution of 4-3 (52.00 g, 75.39 mmol) in DCM (200.00 mL) was added TFA (150.00 mL). The mixture was stirred at r.t. for 1 h. The reaction mixture was slowly added to cold NH$_4$OH, extracted with DCM. The organic layer was concentrated and purified to give 4-4 (31.00 g, 69.28 mmol) as a colorless oil. ESI-LCMS: m/z 448.2 [M+H]$^+$. $^1$H-NMR (DMSO-d$_6$, 400 MHz): δ ppm 8.02 (d, J=8.12 Hz, 1H), 7.26-7.23 (m, 2H), 6.87-6.84 (m, 2H), 5.87-5.81 (m, 2H), 5.38 (t, J=5.0 Hz, 1H), 4.96-4.85 (m, 2H), 4.36-4.34 (m, 1H), 4.17-4.14 (m, 1H), 4.00-3.97 (m, 1H), 3.83-3.77 (m, 1H), 3.75-3.72 (m, 1H), 3.71 (s, 3H), 3.70-3.68 (m, 1H), 3.61-3.56 (m, 1H), 3.45-3.43 (m, 2H), 3.18 (s, 3H).

Preparation of Intermediate (4-5): To a solution of 4-4 (31.00 g, 69.28 mmol) in Pyridine (200.00 mL) was added BzCl (13.14 g, 93.87 mmol), the reaction mixture was stirred at r.t. for 15 min and concentrated and purified by column to give 4-5 (35.10 g, 63.8 mmol) as a white solid. ESI-LCMS: m/z 552.2 [M+H]$^+$.

Preparation of Intermediate (4-6): To a solution of 4-5 (35.10 g, 63.8 mmol) in acetonitrile (300.00 mL) and water (100.00 mL) was added Ceric ammonium nitrate (105 g, 191.40 mmol), the reaction mixture was stirred at r.t. for 12 h and concentrated and extracted with EA. The organic layer was concentrated and purified by column to give 4-6 (27.5 g, 63.75 mmol) as a yellow solid. ESI-LCMS: m/z 432.2 [M+H]$^+$.

Preparation of Intermediate (4-7): To a solution of 4-6 (27.50 g, 63.75 mmol) in THF (500.00 mL) was added Pd/C (3.00 g), the reaction mixture was stirred at r.t. for 12 h and filtered and concentrated to give 4-7 (25.00 g, 61.67 mmol) as a yellow solid. ESI-LCMS: m/z 406.2 [M+H]$^+$.

Preparation of Intermediate (4-8): To a solution of 4-7 (25.00 g, 61.67 mmol) in DCM (300.00 mL) was added MMTrCl (28.49 g, 92.51 mmol) and Collidine (14.95 g, 123.34 mmol), then AgNO$_3$ (15.7 g, 92.5 mmol) was added. The reaction mixture was stirred at r.t. for 1 h., and filtered and the organic layer was washed water, dried over Na$_2$SO$_4$ and purified by silica gel column to give 4-8 (33.00 g, 48.69 mmol) as a yellow solid.

Preparation of Intermediate (4-9): To a solution of 4-8 (14.50 g, 21.39 mmol) was added 1 N NaOH in methanol (200 mL) in water (20 mL), the reaction mixture was stirred at r.t. for 1 h. and concentrated and extracted with DCM, the organic layer was concentrated and purified by silica gel column to give 4-9 (11.50 g, 20.05 mmol) as a white solid. $^1$H-NMR (DMSO-d$_6$, 400 MHz): δ ppm 11.26 (s, 1H), 7.95 (d, J=8.4 Hz, 1H), 7.47-7.44 (m, 4H), 7.34-7.17 (m, 8H), 6.82 (d, J=8.8 Hz, 2H), 5.50-5.48 (m, 2H), 5.13 (t, J=3.6 Hz, 1H), 4.05-3.98 (m, 3H), 3.78 (s, 3H), 3.52-3.49 (m, 1H), 3.34-3.32 (m, 2H), 3.14 (s, 3H), 3.08-3.04 (m, 1H), 2.89-2.86 (m, 1H), 2.70 (d, J=10.0 Hz, 1H), 1.51 (d, J=4.4 Hz, 1H).

Preparation of (4-10): To a solution of 4-9 (11.50 g, 20.05 mmol) in DCM (100.00 mL) was added DMAP (489.85 mg, 4.01 mmol) and DIPEA (10.36 g, 80.19 mmol, 14.01 mL). Then CEPCl (5.70 g, 24.06 mmol) was added to the solution. The mixture was stirred at r.t. for 30 min. The reaction was quenched with saturated NaHCO$_3$. The organic layer was washed with brine, dried over Na$_2$SO$_4$, concentrated to give the crude product. The crude product was purified by Flash-Prep-HPLC. The product was dissolved in anhydrous toluene and concentrated for three times. Then the product was dissolved anhydrous acetonitrile and concentrated for three times. This resulted in 13 g to give 4-10 as a white solid. MS m/z [M−H]$^-$ (ESI): 772.3; $^1$H-NMR (CDCl$_3$, 400 MHz): 9.01 (s, 1H), 8.07-7.61 (m, 1H), 7.53-7.41 (m, 6H), 7.29-7.15 (m, 5H), 6.79-6.76 (m, 2H), 5.63-5.57 (m, 2H), 4.27-4.15 (m, 2H), 4.06-3.95 (m, 1H), 3.85-3.77 (m, 1H), 3.75 (s, 3H), 3.69-3.35 (m, 7H), 3.23 (d, J=4 Hz, 1H), 2.26-2.91 (m, 3H), 2.59 (t, J=6.4 Hz, 1H), 1.75-1.39 (m, 1H), 1.21-1.11 (m, 12H). $^{31}$PNMR (162 MHz, CDCl$_3$): 149.10, 148.26.

Example 2

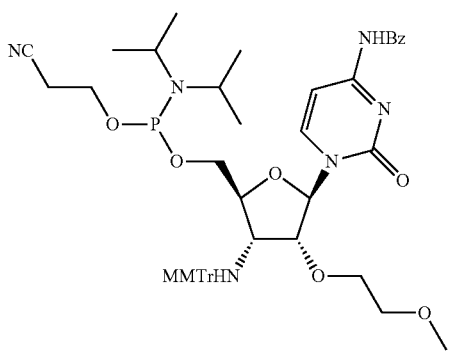

The 2'-O-methoxyethoxy-NH-benzoyl-cytosine phosphoramidite compound 5-4 was obtained by conversion of uridine intermediate 4-8 into 3'-amino cytidine analogue 5-1 followed by phosphitylation using known protocols to give the desired 2'-O-methoxyethoxy cytidine phosphoramidite monomer 5-4 as shown below in scheme 3.

Scheme 3

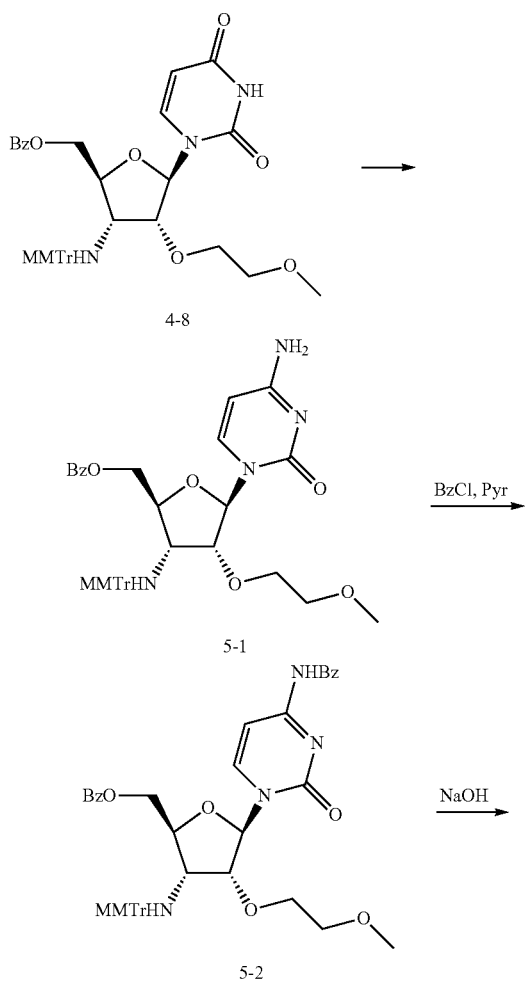

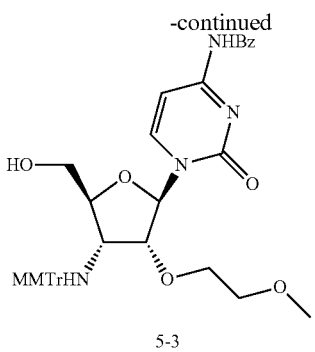

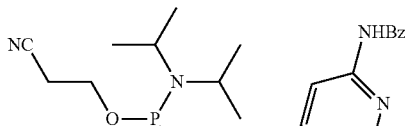

Preparation of Intermediate (5-1): To a solution of 4-8 (18.50 g, 27.30 mmol) in acetonitrile (250.00 mL) was added TPSCl (16.49 g, 54.60 mmol) and DMAP (6.67 g, 54.60 mmol), then TEA (5.52 g, 54.60 mmol, 7.56 mL) was added to the solution. The reaction mixture was stirred at r.t. for 5 h under $N_2$. $NH_4OH$ (50.00 mL) was added to the reaction mixture. The mixture was stirred at r.t. for 12 h. The solution was concentrated and extracted with EA. The organic layer was washed by brine and dried over $Na_2SO_4$. The organic layer was concentrated and purified by silica gel column to give 5-1 (16.00 g, 23.64 mmol) as a yellow solid.

Preparation of Intermediate (5-2): To a solution of 5-1 (16.00 g, 23.64 mmol) in Pyridine (100.00 mL) was added BzCl (4.96 g, 35.46 mmol) at 0° C. The mixture was stirred at r.t. for 1 h. The solution was concentrated and purified by silica gel column to give 5-2 (17.40 g, 22.28 mmol) as a white solid.

Preparation of Intermediate (5-3): Compound 5-2 (17.40 g, 22.28 mmol) was added to 180 mL of 1 N NaOH solution in Pyridine/MeOH/$H_2O$ (65/30/5) at 0° C. The suspension was stirred at 0° C. for 15 min. The reaction mixture was quenched by addition of sat. $NH_4Cl$ solution. The solution was extracted with EA and the combined organic layers were washed with sat. $NaHCO_3$ solution, brine, dried over $Na_2SO_4$, filtered and concentrated. The residue was purified by column to give 5-3 (12.50 g, 18.47 mmol) as white solid. 1H-NMR (DMSO-$d_6$, 400 MHz): δ ppm 12.25 (s, 1H), 8.53 (d, J=7.6 Hz, 1H), 8.01 (d, J=5.2 Hz, 2H), 7.64-7.60 (m, 1H), 7.52-7.42 (m, 6H), 7.31 (d, J=8.8 Hz, 2H), 7.26-7.14 (m, 7H), 6.79 (d, J=8.8 Hz, 2H), 5.55 (s, 1H), 5.23 (t, J=3.6 Hz, 1H), 4.09-3.97 (m, 3H), 3.73 (s, 3H), 3.70-3.66 (m, 1H), 3.38-3.34 (m, 2H), 3.17 (s, 3H), 3.11-3.05 (m, 1H), 2.96-2.91 (m, 1H), 2.68 (d, J=10.8 Hz, 1H), 1.49 (d, J=4 Hz, 1H).

Preparation of (5-4): To a solution of 5-3 (12.50 g, 18.47 mmol) in DCM (100.00 mL) was added DMAP (451.30 mg, 3.69 mmol) and DIPEA (9.55 g, 73.88 mmol, 12.90 mL), then CEPCl (5.25 g, 22.16 mmol) was added. The mixture was stirred at r.t. for 30 min. The reaction was quenched with saturated $NaHCO_3$. The organic layer was washed with brine, dried over Na$_2$SO$_4$, concentrated to give the crude product. The crude was by Flash-Prep-HPLC. The product was dissolved in anhydrous toluene and concentrated for three times. Then the product was dissolved anhydrous acetonitrile and concentrated for three times. This resulted in 13 g to give 5-4 as a white solid. MS m/z [M–H]$^-$ (ESI): 875.4. $^1$H-NMR (400 MHz, CDCl$_3$): δ ppm 8.64-8.20 (m, 2H), 7.90-7.88 (m, 2H), 7.62-7.58 (m, 1H), 7.53-7.39 (m, 8H), 7.25-7.15 (m, 6H), 6.78-6.74 (m, 2H), 5.69 (d, J=1.72 Hz, 1H), 4.37-4.21 (m, 2H), 4.10-4.03 (m, 1H), 3.90-3.79 (m, 2H), 3.75 (d, J=1.64 Hz, 3H), 3.68-3.52 (m, 3H), 3.46-3.42 (m, 2H), 3.26 (d, J=1.2 Hz, 3H), 3.17-2.97 (m, 2H), 2.94-2.87 (m, 1H), 2.67-2.48 (m, 2H), 1.79-1.51 (m, 1H), 1.26-1.18 (m, 12H). $^{31}$PNMR (162 MHz, CDCl$_3$): 148.93, 148.03

Example 3

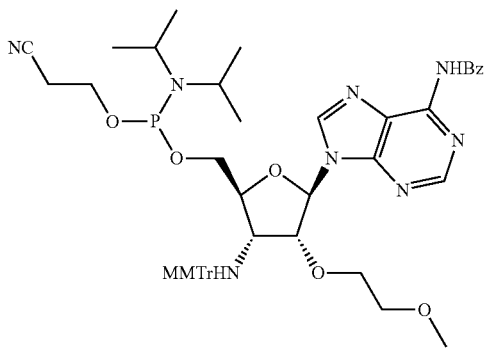

6-10

The synthesis of the 2'-O-methoxyethyl adenosine analogue 6-10 was achieved as shown below in scheme 4. The intermediate 6-2 under basic condition (NH$_3$/MeOH) resulted in diol 6-3, which then upon protection of 5'-hydroxy group using TBDPSCl to give 6-4. Intermediate 6-4. Then, 2'-O alkylation of 6-4 using 2-bromoethyl methyl ether/NaH/DMF to give 2'-O-methoxyethyl derivative 6-5 without the protection of C-6-exocyclic amine of 6-4. In an inventive way selective alkylation of 2'-OH group of intermediate 6-4 was achieved.

Scheme 4

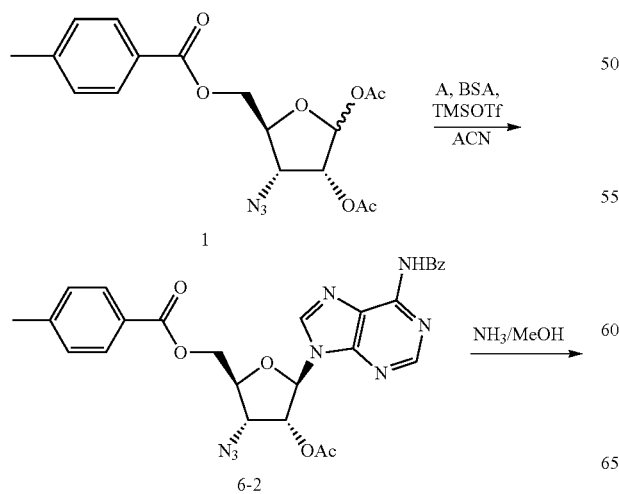

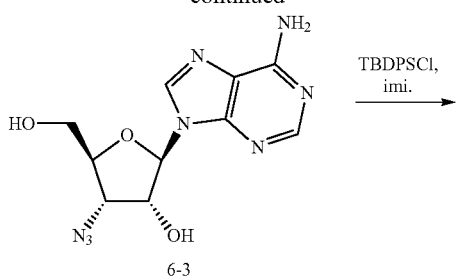

6-3

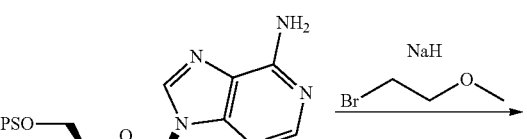

6-4

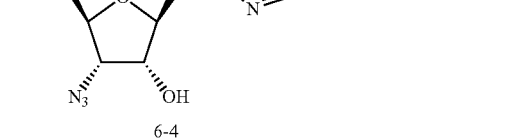

6-5

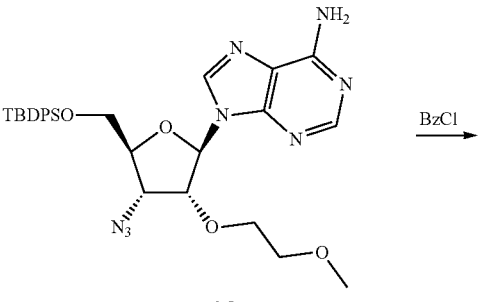

6-6

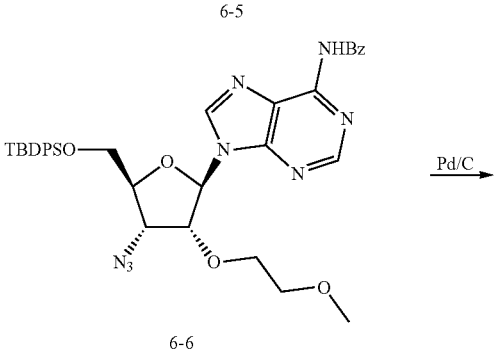

6-7

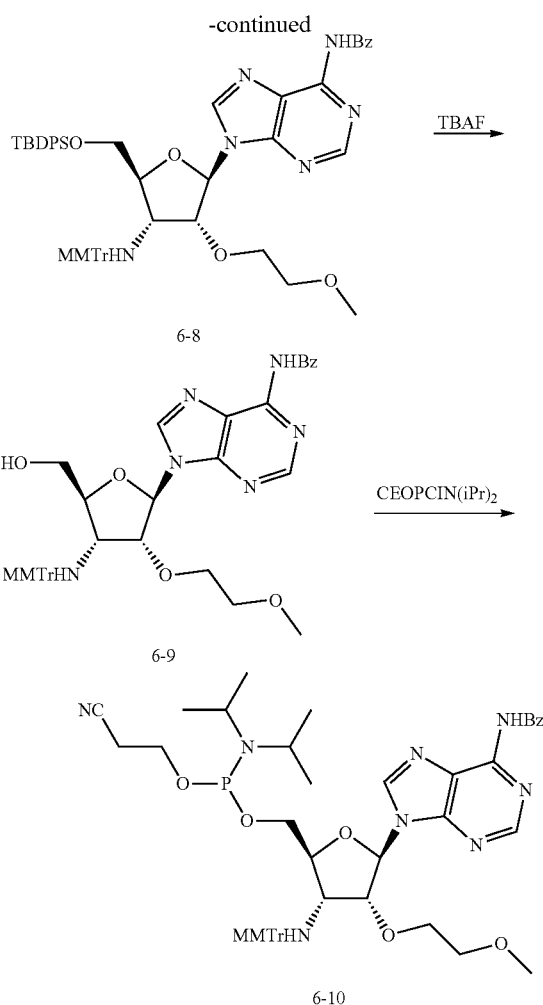

3'-Azido group of intermediate 6-5 was reduced to the amine 6-7, which was then immediately protected, such as reaction with 4-monomethoxytritylchloride, to give the precursor 6-8 after de-protection of 5'-OTBDPS group using TBAF/THF. The phosphitylation of 6-9 using known protocols to give the desired 2'-O-methoxyethoxy adenine-NH-benzoyl phosphoramidite monomer 6-10.

Preparation of Intermediate (6-2): To a solution of compound 1 (79.50 g, 210.68 mmol) in dry ACN (1.20 L) was added N-(5H-Purin-6-yl)benzamide (100.80 g, 421.36 mmol) and BSA (180.07 g, 884.86 mmol). The resulting suspension was stirred at 50° C. until clear. Then the mixture was cooled at −20° C. and TMSOTf (93.54 g, 421.36 mmol) was added by syringe. Then the mixture was stirred at 70° C. for 72 h under $N_2$, and quenched with sat $NaHCO_3$ and extracted with DCM. The organic layer was dried over $Na_2SO_4$, then solvent was evaporated, and the residue was purified on silica gel to afford compound 6-2 (107.50 g, 192.26 mmol, 91.26% yield) as a yellow solid. $^1$H-NMR (400 MHz, DMSO): δ=11.28 (s, 1H), 8.64 (d, J=6.4 Hz, 2H), 8.05 (d, J=8.0 Hz, 2H), 7.84 (d, J=8.0 Hz, 2H), 7.66 (t, J=7.6 Hz, 1H), 7.56 (t, J=8.0 Hz, 2H), 7.33 (d, J=8.0 Hz, 2H), 6.37 (d, J=3.6 Hz, 1H), 6.17 (dd, J=6.0 Hz, 1H), 5.09 (t, J=6.8 Hz, 1H), 4.69-4.56 (m, 2H), 4.40-4.38 (m, 1H), 2.39 (s, 3H), 2.17 (s, 3H). ESI-LCMS: m/z 557.2 [M+H]$^+$.

Preparation of Intermediate (6-3): To a solution of compound 6-2 (107.50 g, 192.26 mmol) dissolved in 33 wt. % methylamine in ethanol (600.00 mL), then the mixture were stirred at 20° C. for 16 h, then solvent was evaporated, washed with 50% EtOAc in petroleum ether (1.5 L), filtered to afford compound 6-3 (52.50 g, 179.64 mmol, 93.44% yield) as a slightly yellow solid. ESI-LCMS: m/z 293.1 [M+H]$^+$.

Preparation of Intermediate (6-4): A solution of compound 6-3 (52.50 g, 179.64 mmol), imidazole (18.32 g, 269.46 mmol) and TBDPS-Cl (54.34 g, 197.60 mmol) in pyridine (500.00 mL) was stirred at 20° C. for 2 h, LC-MS showed 6-3 was consumed. Then quenched with MeOH (30 mL), concentrated to give the crude product which was purified on silica gel with to afford compound 6-4 (72.60 g, 136.81 mmol, 76.16% yield) as a white solid. $^1$H-NMR (400 MHz, DMSO): δ=8.29 (s, 1H), 8.10 (s, 1H), 7.63-7.59 (m, 4H), 7.48-7.33 (m, 8H), 6.36 (d, J=5.6 Hz, 1H), 5.97 (d, J=4.4 Hz, 1H), 5.10-5.06 (m, 1H), 4.47 (t, J=5.6 Hz, 1H), 4.14-4.11 (m, 1H), 3.94 (dd, J=11.2 Hz, 1H), 3.83 (dd, J=11.6 Hz, 1H), 0.99 (s, 9H). ESI-LCMS: m/z 531.3 [M+H]$^+$.

Preparation of Intermediate (6-5): A solution of 6-4 (35.00 g, 65.96 mmol) and 1-Bromo-2-methoxyethane (18.33 g, 131.91 mmol) in dry DMF (400.00 mL), was added NaI (19.77 g, 131.91 mmol) and $Ag_2O$ (15.29 g, 65.96 mmol), the mixture was stirred at room temperature for 5 h. Then the reaction was poured into ice water, extracted with EA, washed with brine and dried over anhydrous $Na_2SO_4$. The solvent was evaporated, and the residue was purified on silica gel to give 6-5 (23.70 g, 40.26 mmol, 61.04% yield) as a white solid and by-product of TBDPS lost 5.20 g, 9.81 mmol, 14.87% yield) as a white solid. $^1$H-NMR (400 MHz, DMSO): δ=8.31 (s, 1H), 8.11 (s, 1H), 7.63-7.60 (m, 4H), 7.47-7.44 (m, 2H), 7.40-7.36 (m, 6H), 6.10 (d, J=4.4 Hz, 1H), 5.02 (t, J=4.8 Hz, 1H), 4.69 (t, J=5.6 Hz, 1H), 4.18-4.14 (m, 1H), 3.95 (dd, J=11.6 Hz, 1H), 3.84 (dd, J=11.6 Hz, 1H), 3.78-3.75 (m, 2H), 3.45 (t, J=4.8 Hz, 1H), 3.16 (s, 3H), 0.99 (s, 9H). ESI-LCMS: m/z 589.5 [M+H]$^+$.

Preparation of Intermediate (6-6): To a solution of 6-5 (31.23 g, 53.04 mmol) in pyridine (300.00 mL) at 0° C., was added BzCl (11.22 g, 79.56 mmol) dropwise. The mixture was stirred at r.t. for 2 h. Then the solution was cooled to 0° C., and ammonium hydroxide (20 mL, 30%) was added and the mixture was allowed to warm to r.t., then the solvent was evaporated, 300 mL $H_2O$ and 600 mL EA were added into separate the solution, the aqueous was extracted by EA, combined the organic and washed with brine, dried over anhydrous $Na_2SO_4$, the solvent was removed and the residue was purified on silica gel to give 6-6 (28.70 g, 41.42 mmol, 78.09% yield) as a white solid. ESI-LCMS: m/z 693.4 [M+H]$^+$.

Preparation of Intermediate (6-7): A solution of 6-6 (28.70 g, 41.42 mmol) in EA (150.00 mL) was added Pd/C (3.00 g) and MeOH (150.00 mL) under $H_2$. The mixture was stirred at r.t. for 5 h. Then the reaction was filtered and the filtrate concentrated to give 6-7 (25.49 g, 38.22 mmol, 92.27% yield) as a gray solid. ESI-LCMS: m/z 667.3 [M+H]$^+$.

Preparation of Intermediate (6-8): To a solution of 6-7 (25.49 g, 38.22 mmol) and $AgNO_3$ (12.98 g, 76.44 mmol) in DCM (300.00 mL) was added collidine (13.89 g, 114.66 mmol) and MMTrCl (19.43 g, 57.33 mmol), the mixture was stirred at r.t. for 2 h. Then the reaction was poured into ice water, the organic layer extracted with DCM, washed with brine and dried over anhydrous $Na_2SO_4$, the solvent was removed and the residue was purified on silica gel to give 6-8 (32.79 g, 34.92 mmol, 91.36% yield) as a gray solid.

Preparation of Intermediate (6-9): A solution of 6-8 (32.79 g, 34.92 mmol) in THF (300.00 mL) was added TBAF (1M, 35.00 mL), the mixture was stirred at room temperature for 15 h. Then the solvent was removed and the residue was purified on silica gel with EA to give 6-9 (22.22 g, 31.71 mmol, 90.82% yield) as a white solid. $^1$H-NMR (400 MHz, CDCl$_3$): δ=8.68 (s, 1H), 8.32 (s, 1H), 8.04 (d, J=7.2 Hz, 2H), 7.61-7.57 (m, 1H), 7.53-7.48 (m, 6H), 7.40 (d, J=8.8 Hz, 2H), 7.21-7.12 (m, 6H), 6.73 (d, J=8.8 Hz, 2H), 6.09 (d, J=2.4 Hz, 2H), 4.08-4.02 (m, 2H), 3.93-3.87 (m, 1H), 3.72 (s, 3H), 3.58-3.53 (m, 1H), 3.43-3.39 (m, 3H), 3.24-3.19 (m, 4H), 2.19 (br, 1H).

Preparation of (6-10): To a solution of 6-9 (14.00 g, 19.98 mmol), DMAP (488.19 mg, 4.00 mmol) and DIPEA (6.46 g, 49.95 mmol, 8.73 mL) in dry DCM (100.00 mL) was added CEPCl (5.68 g, 23.98 mmol) dropwise under Ar. The mixture was stirred at room temperature for 1 h. Then the reaction was washed with 10% NaHCO$_3$ (aq) and brine, dried over Na$_2$SO$_4$, the solvent was removed and the residue was purified by column chromatography, then concentrated to give the crude product. The crude product (10 g, dissolved in 10 mL of ACN) was purified by Flash-Prep-HPLC to obtain 6-10 (12.60 g, 13.98 mmol, 69.99% yield) as a white solid. Then the product was dissolved in dry toluene (15 mL) and concentrated three times, and with dry ACN three times. $^1$H-NMR (400 MHz, CDCl$_3$): δ=9.12 (d, J=46.8 Hz, 1H), 6=8.71 (d, J=11.6 Hz, 1H), 8.50 (s, 0.6H), 8.22 (s, 0.4H), 8.04 (t, J=7.2 Hz, 2H), 7.63-7.59 (m, 1H), 7.55-7.46 (m, 6H), 7.40-7.37 (m, 2H), 7.19-7.06 (m, 6H), 6.69 (dd, J=8.8 Hz, 2H), 6.03 (d, J=3.2 Hz, 1H), 4.36-4.24 (m, 2H), 3.92-3.78 (m, 2H), 3.71 (d, J=11.6 Hz, 3H), 3.67-3.33 (m, 7H), 3.29 (d, J=11.2 Hz, 3H), 3.17-3.10 (m, 1H), 2.88 (dd, J=27.2 Hz, 1H), 2.65-2.50 (m, 2H), 2.38 (d, J=4.4 Hz, 0.4H), 1.80 (d, J=4.0 Hz, 0.6H), 1.23-1.15 (m, 12H). $^{31}$PNMR (400 MHz, CDCl$_3$): 148.86, 148.22. ESI-LCMS: m/z 901.3 [M+H]$^+$.

Example 4

7-13

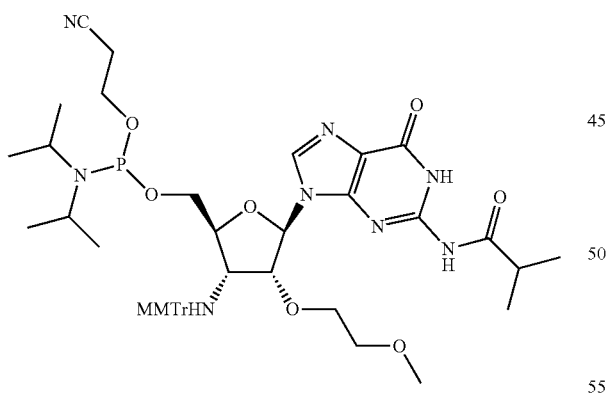

The synthesis of guanosine-based 2'-methoxyethoxy phosphoramidite 7-13 shown in scheme 5. It was envisioned that stereo selective coupling of C-3-azidoribose 1 with nucleobase 2-amino-6-chloropurine was key steps to get various guanosine-based 3'-NH-MMTr-2'-O-alkylated phosphoramidites. This was absolutely required to get efficient 2'-O-alkylations and to eliminate any base alkylations. For this purpose, C-3'-azido-chloro-amine purine nucleoside 7-2 b was synthesized from nucleobase coupling of 1 and 2-amino-6-chloro purine in ~70% isolated yield. Then, the protection of 2-amino group of 7-2 by using MMTrCl to give 7-3, which after deprotection of 2'-O-acetyl and 5'-O-toluoyl group by using NH$_4$OH/0° C. to give 2'-hydroxy intermediate 7-4.

De-protection of 5'-O-toluyl group of intermediate 7-4 by treatment with a base followed by re-protection of 5'-OH group with trityl group afforded key 2'-OH intermediate 9-6 for alkylation. This inventive de-protection and re-protection strategy was necessary for efficient synthesis of 2'-O-alkylated intermediate 7-7 under basic conditions (NaHMDS/DMF).

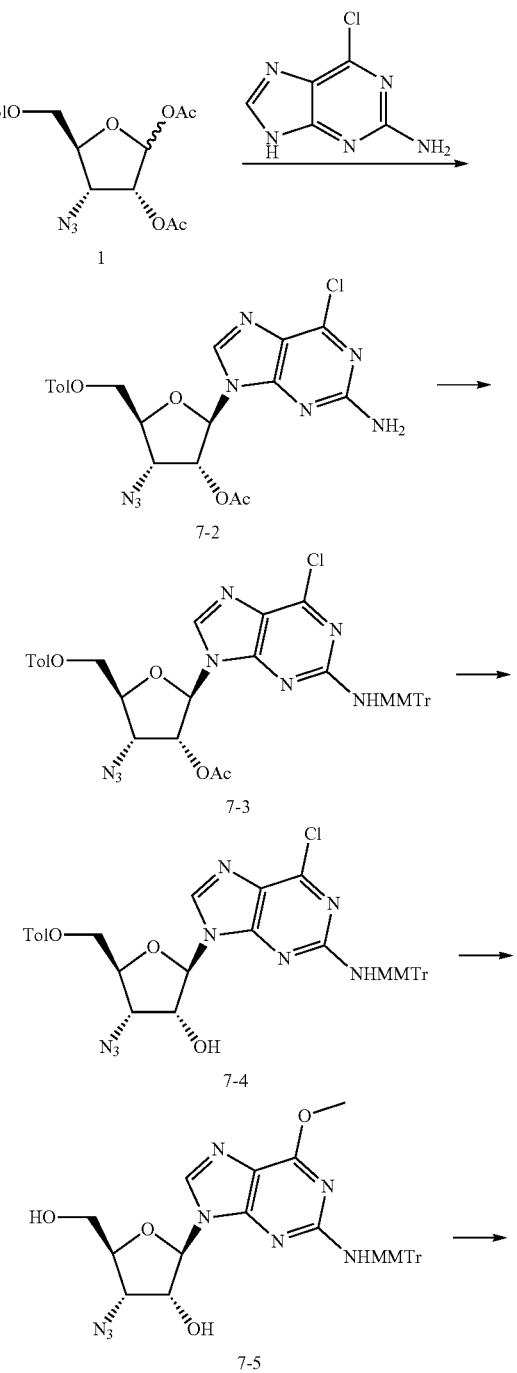

Scheme 5

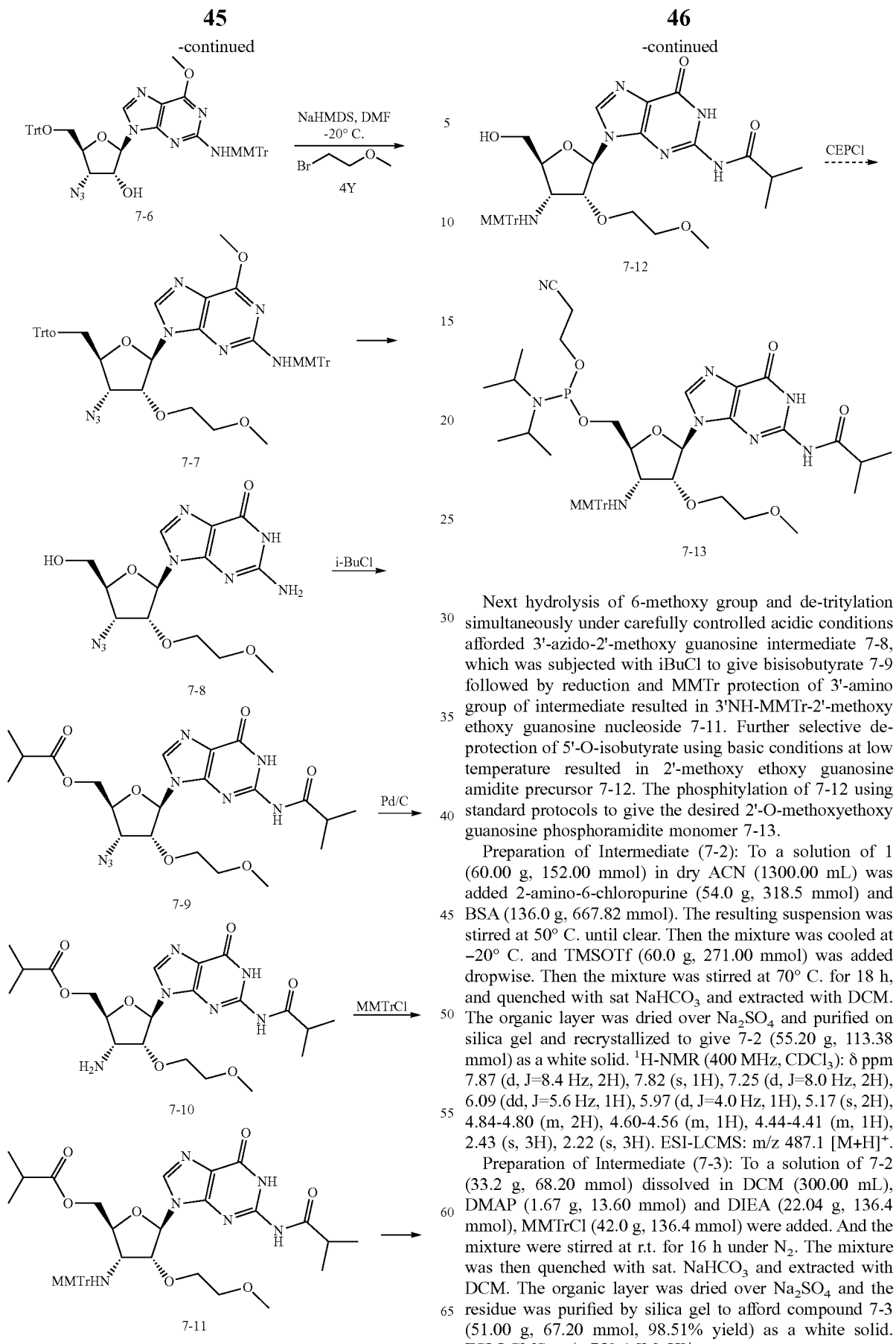

Next hydrolysis of 6-methoxy group and de-tritylation simultaneously under carefully controlled acidic conditions afforded 3'-azido-2'-methoxy guanosine intermediate 7-8, which was subjected with iBuCl to give bisisobutyrate 7-9 followed by reduction and MMTr protection of 3'-amino group of intermediate resulted in 3'NH-MMTr-2'-methoxy ethoxy guanosine nucleoside 7-11. Further selective de-protection of 5'-O-isobutyrate using basic conditions at low temperature resulted in 2'-methoxy ethoxy guanosine amidite precursor 7-12. The phosphitylation of 7-12 using standard protocols to give the desired 2'-O-methoxyethoxy guanosine phosphoramidite monomer 7-13.

Preparation of Intermediate (7-2): To a solution of 1 (60.00 g, 152.00 mmol) in dry ACN (1300.00 mL) was added 2-amino-6-chloropurine (54.0 g, 318.5 mmol) and BSA (136.0 g, 667.82 mmol). The resulting suspension was stirred at 50° C. until clear. Then the mixture was cooled at −20° C. and TMSOTf (60.0 g, 271.00 mmol) was added dropwise. Then the mixture was stirred at 70° C. for 18 h, and quenched with sat NaHCO₃ and extracted with DCM. The organic layer was dried over Na₂SO₄ and purified on silica gel and recrystallized to give 7-2 (55.20 g, 113.38 mmol) as a white solid. $^1$H-NMR (400 MHz, CDCl₃): δ ppm 7.87 (d, J=8.4 Hz, 2H), 7.82 (s, 1H), 7.25 (d, J=8.0 Hz, 2H), 6.09 (dd, J=5.6 Hz, 1H), 5.97 (d, J=4.0 Hz, 1H), 5.17 (s, 2H), 4.84-4.80 (m, 2H), 4.60-4.56 (m, 1H), 4.44-4.41 (m, 1H), 2.43 (s, 3H), 2.22 (s, 3H). ESI-LCMS: m/z 487.1 [M+H]⁺.

Preparation of Intermediate (7-3): To a solution of 7-2 (33.2 g, 68.20 mmol) dissolved in DCM (300.00 mL), DMAP (1.67 g, 13.60 mmol) and DIEA (22.04 g, 136.4 mmol), MMTrCl (42.0 g, 136.4 mmol) were added. And the mixture were stirred at r.t. for 16 h under N₂. The mixture was then quenched with sat. NaHCO₃ and extracted with DCM. The organic layer was dried over Na₂SO₄ and the residue was purified by silica gel to afford compound 7-3 (51.00 g, 67.20 mmol, 98.51% yield) as a white solid. ESI-LCMS: m/z 759.4 [M+H]⁺.

Preparation of Intermediate (7-4): To a solution of 7-3 (54.00 g, 212.06 mmol) in THF (400 L) was added NH$_4$OH (100.00 mL) at 0° C. The reaction mixture was stirred at r.t. for 48 h, and concentrated and purified by silica gel with 1-2% MeOH in DCM to give 7-4 (51.00 g, 178.48 mmol, 99.98% yield) as a yellow solid. $^1$H-NMR (400 MHz, DMSO): δ ppm 8.26 (d, J=4.4 Hz, 1H), 8.17 (s, 1H), 7.78-7.76 (m, 2H), 7.35-7.25 (m, 12H), 7.16 (t, J=7.2 Hz, 2H), 6.82 (dd, J=8.8 Hz, 2H), 6.14 (s, 1H), 5.62 (s, 1H), 4.40-4.35 (m, 4H), 3.69 (s, 3H), 3.36 (s, 1H), 2.39 (s, 3H). ESI-LCMS: m/z 717.4 [M+H]$^+$.

Preparation of Intermediate (7-5): To a solution of sodium methoxide in methanol (300.00 mL, 2N) was added 7-4 (47.00 g, 65.54 mmol), the mixture was stirred at r.t. for 1 h. The mixture was concentrated in vacuo to give the crude product which was purified by CC (DCM: methyl alcohol=50:1) to give 7-5 (36.50 g, 61.38 mmol, 93.66% yield) as white solid. $^1$H-NMR (400 MHz, DMSO): δ ppm 8.15 (s, 1H), 7.47 (s, 1H), 7.41-7.32 (m, 4H), 7.32-7.23 (m, 6H), 7.18 (t, J=7.16 Hz, 2H), 6.85 (d, J=8.68 Hz, 2H), 6.19 (s, 1H), 5.77 (s, 1H), 5.28 (s, 1H), 4.81 (s, 1H), 4.20-4.06 (m, 1H), 3.90 (s, 1H), 3.72 (s, 3H), 3.65-3.50 (m, 2H). ESI-LCMS: m/z 595.4 [M+H]$^+$.

Preparation of Intermediate (7-6): To a solution of 7-5 (36.50 g, 61.38 mmol) in dry DCM (5.00 mL) was added DIPEA (15.87 g, 122.77 mmol, 21.44 mL), DMAP (1.50 g, 12.28 mmol) and TrtCl (20.48 g, 73.66 mmol). The resulting suspension was stirred at r.t. for 20 h under Nitrogen and concentrated in vacuo. The product was purified by cc (PE:EA=10:1-3:1) to give 7-6 (46.00 g, 54.96 mmol, 89.55% yield) as white solid. $^1$H-NMR (400 MHz, DMSO): δ ppm 8.08 (s, 1H), 7.47-7.35 (m, 7H), 7.34-7.10 (m, 20H), 6.80 (d, J=7.76 Hz, 2H), 6.25 (s, 1H), 5.81 (s, 1H), 4.86 (s, 1H) 4.10-3.87 (m, 2H), 3.69 (s, 3H), 3.56-3.30 (m, 2H), 3.29-3.02 (m, 3H). 2.00 (s, 1H). ESI-LCMS: m/z 837.4 [M+H]$^+$.

Preparation of Intermediate (7-7): To a solution of 7-6 (32.00 g, 38.23 mmol) in dry DMF (300.00 mL) was added tetrabutylammonium iodide (3.82 g, 11.47 mmol), 1-bromo-2-methoxyethane (15.94 g, 114.69 mmol) and NaHMDS (21.03 g, 114.69 mmol) added dropwise at −10° C. The resulting suspension was stirred at −10° C. for 30 h and stirred at r.t. for 2 h. The product was quenched with sat. NH$_4$Cl and extracted with DCM. The organic layer was concentrated in vacuo to give the crude product which was purified by silica gel column to give 7-7 (31.46 g, 35.15 mmol, 91.94% yield) as white solid. $^1$H-NMR (400 MHz, DMSO): δ ppm 8.04 (s, 1H), 7.40-7.34 (m, 6H), 7.33-7.08 (m, 20H), 6.78 (d, J=8.9 Hz, 2H), 5.83 (s, 1H), 4.04-3.98 (m, 1H), 3.68 (s, 3H), 3.67-3.46 (m, 3H), 3.44-3.36 (m, 2H), 3.27-3.15 (m, 2H), 3.12 (s, 3H), 2.88 (s, 1H). ESI-LCMS: m/z 895.4 [M+H]$^+$.

Preparation of Intermediate (7-8): To a solution of 7-7 (42.00 g, 46.93 mmol) in 1,4-dioxane (150.00 mL) was added 6 N hydrochloric acid (46.93 mmol, 150.00 mL) at r.t. The resulting suspension was stirred at r.t. for 30 min. The mixture was extracted with petroleum ether. The water layer was stirred at r.t. for 24 h. The mixture was concentrated in vacuo to give 7-8 (20.00 g, 37.12 mmol) as white solid. $^1$H-NMR (400 MHz, DMSO): δ ppm 11.08-10.82 (m, 1H), 8.41-8.13 (m, 1H), 7.35-6.99 (m, 1H), 6.85-6.62 (m, 2H), 5.90-5.78 (m, 1H), 4.71 (t, J=5.16 Hz, 1H), 4.46 (t, J=4.64 Hz, 1H), 4.02-3.97 (m, 1H), 3.78-3.70 (m, 2H), 3.70-3.62 (m, 1H), 3.57 (dd, J=12.12 Hz, 1H), 3.43 (t, J=4.60 Hz, 2H), 3.18 (s, 3H). ESI-LCMS: m/z 367.2 [M+H]$^+$.

Preparation of Intermediate (7-9): To a solution of 7-8 (20.00 g, 54.60 mmol) in pyridine (100.00 mL) was added isobutyl chloride (17.45 g, 163.80 mmol) drop-wise at r.t. The resulting suspension was stirred at r.t. for 1 h. The mixture was extracted with DCM and washed with water. The organic layer was concentrated in vacuo. Dissolved in pyridine and added drop-wise isobutyl chloride (17.45 g, 163.80 mmol) at r.t. The resulting suspension was stirred at r.t. for 1 h., concentrated and purified by silica gel column to give 7-9 (13.00 g, 25.67 mmol) as a white solid. ESI-LCMS: m/z 507.3 [M+H]$^+$.

Preparation of Intermediate (7-10): To a solution of 7-9 (13.00 g, 25.67 mmol) in THF (100.00 mL) was added palladium 10% on carbon (1.30 g), the mixture was stirred at r.t. for 20 h at H2. Filtered and the filtrate was concentrated in vacuo to give 7-10 (11.70 g, 24.35 mmol) as brown solid. ESI-LCMS: m/z 481.3 [M+H]$^+$.

Preparation of Intermediate (7-11): To a solution of 7-10 (11.70 g, 24.35 mmol) in DCM (150.00 mL) was added MMTrCl (11.25 g, 36.53 mmol) and 2,4,6-collidine (5.90 g, 48.70 mmol) at 0° C., the mixture was stirred at r.t. for 30 min and added AgNO$_3$ (6.20 g, 36.53 mmol) at 0° C. The mixture was stirred at r.t. for 2 h under N$_2$, filtered and the organic layer was washed by water and dried over Na$_2$SO$_4$, concentrated to give the crude product which was purified by silica gel column to give 7-11 (8.5 g, 11.22 mmol) as a white solid. ESI-LCMS: m/z 753.5 [M+H]$^+$.

Preparation of Intermediate (7-12): To a solution of 7-11 (8.5 g, 11.29 mmol) in pyridine (50.00 mL) was added 2 N NaOH (50.00 mL) dropwise at 0° C., the mixture was stirred at 0° C. for 20 min. Then the reaction was neutralized with saturated NH$_4$Cl (aq.) to pH=7-8, and 300 mL H$_2$O and 800 mL DCM were added in to separate the solution, the aqueous was extracted by DCM, the combined organic layer was washed with brine, dried over anhydrous Na$_2$SO$_4$, the solvent was removed and the residue was purified on silica gel to give 7-12 (6.3 g, 9.23 mmol, 81.73% yield) as a white solid. $^1$H-NMR (400 MHz, DMSO): δ ppm 11.78 (br s, 1H), 11.41 (s, 1H), 8.11 (s, 1H), 7.46 (t, J=7.28 Hz, 4H), 7.31-7.21 (m, 6H), 7.15 (t, J=7.32 Hz, 2H), 6.76 (d, J=8.92 Hz, 2H), 5.82 (s, 1H), 5.08 (t, J=4.08 Hz, 1H), 3.99-3.85 (m, 3H), 3.65 (s, 3H), 3.62-3.55 (m, 1H), 3.42-3.38 (m, 2H), 3.29-3.19 (m, 1H), 3.10 (s, 3H), 3.06-2.99 (m, 1H), 2.89-2.74 (m, 2H), 1.96 (d, J=4.08 Hz, 1H), 1.20-1.12 (m, 6H). ESI-LCMS: m/z 883.4 [M+H]$^+$.

Preparation of (7-13): To a solution of 7-12 (6.3 g, 9.10 mmol) in DCM (60 mL) was added DMAP (222.00 mg) and DIPEA (5.9 mL). Then CEPCl (2.60 g) was added. The reaction mixture was stirred at r.t. for 1 h., the mixture was washed with saturated NaHCO$_3$ and brine, dried over Na$_2$SO$_4$, purified by Flash-Prep-HPLC. This resulted in 5.04 g 7-13 as a white solid. $^1$H-NMR (400 MHz, CDCl$_3$): δ ppm 11.96 (br s, 1H), 8.57 (s, 1H), 7.98-7.67 (m, 1H), 7.55-7.46 (m, 4H), 7.42-7.34 (m, 2H), 7.25-7.18 (m, 4H), 7.18-7.08 (m, 2H), 6.78-6.68 (m, 2H), 5.79-5.69 (m, 1H), 4.27-4.11 (m, 2H), 4.10-3.73 (m, 2H), 3.73-3.67 (m, 3H), 3.66-3.31 (m, 7H), 3.30-3.21 (m, 3H), 2.07-2.97 (m, 1H), 2.94-2.78 (m, 1H), 2.70-2.50 (m, 3H), 2.30-1.68 (m, 1H), 1.30-1.07 (m, 18H). $^{31}$P NMR (162 MHz, CDCl$_3$): 149.09, 148.09. ESI-LCMS: m/z 883.4 [M+H]$^+$.

Example 5

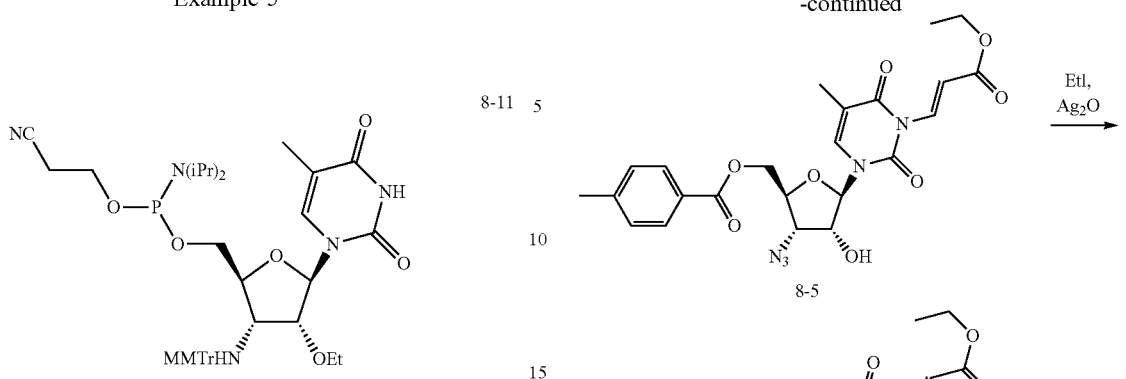

The appropriately protected 2'-O-ethyl-3'-amino-5'-phosphoramidite (example 8, 9, 10, 11), were prepared after chemical transformations shown in Schemes 6-10.

First for the synthesis of thymine based 3'-NH-MMtr-2'-O-ethyl phosphoramidites example 9, intermediate 2 was protected such as methyl propyolate in the presence of dimethylaminopyridine (Scheme 6) to give base N-3 protected intermediate 8-4 to facilitate the 2'-O-alkylation in higher yield. Further deacetylation of 8-4 to give C-2'-hydroxy intermediate 8-5.

Scheme 6

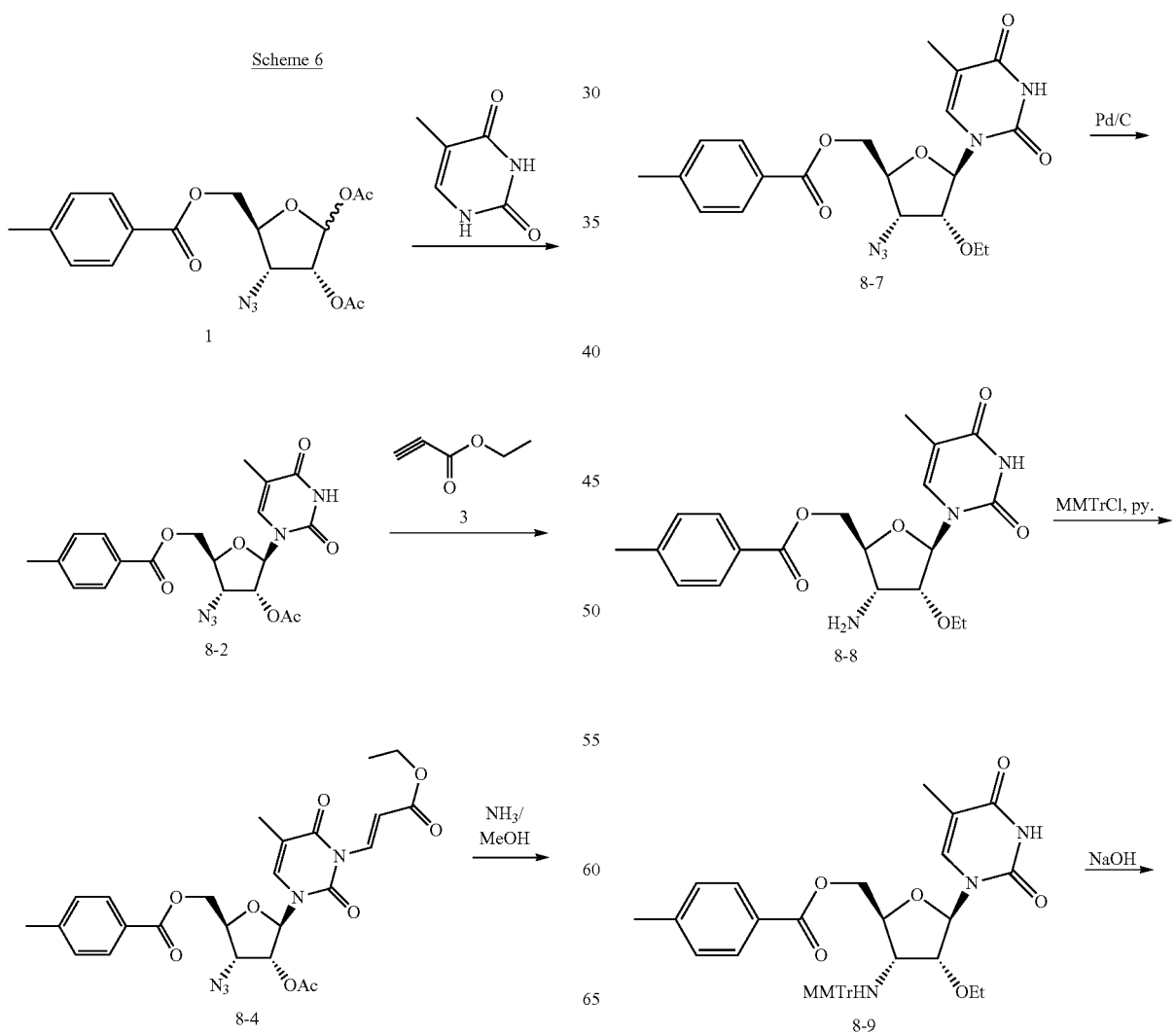

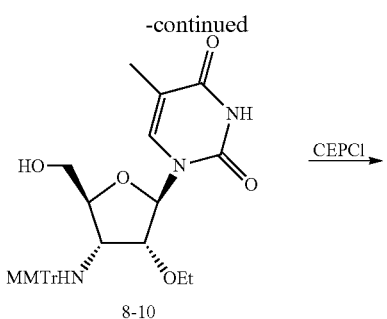

8-10

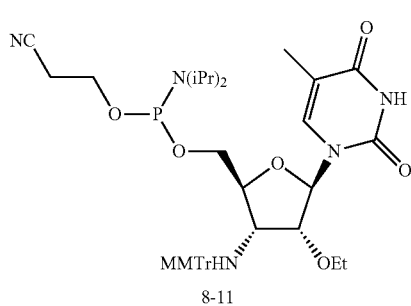

8-11

Further alkylation using iodoethane afforded 2'O-ethyl nucleoside 8-6. Intermediate 8-6 was converted to thymine base 2'-O-ethyl-3'-amino-5'-phosphoramidite 8-11 by following the similar chemistry for compound 4-10 shown in previous Scheme 1.

Preparation of Intermediate (8-4): To a solution of 8-2 (22.0 g, 49.62 mmol) in MeCN (400 mL) was added DMAP (1.2 g, 9.92 mmol). Then 3 (5.8 g, 419.5 mmol) was added, the mixture was stirred at r.t. for 2 h under $N_2$. Concentrated and purified by a silica gel column by (PE:EA=6:1) to afford 8-4 (22.0 g, 40.63 mmol, 81.9% yield) as a yellow oil. ESI-LCMS: m/z 564 [M+Na]$^+$.

Preparation of Intermediate (8-5): To a solution of 8-4 (28.0 g, 51.71 mmol) in MeOH (400 mL) was added con. $NH_4OH$ aqueous solution (28 mL) at 0° C. The reaction mixture was stirred at 0° C. for 1.5 h. Concentrated and purified by a silica gel column by (PE:EA=10:1-2:1) to afford 8-5 (21.0 g, 42.04 mmol, 81.3% yield) as a yellow oil. ESI-LCMS: m/z 522 [M+Na]$^+$.

Preparation of Intermediate (8-6): To a solution of 8-5 (20.0 g, 40.04 mmol) in iodoethane (100 mL) was added $Ag_2O$ (18.6 g, 80.08 mmol). The reaction mixture was stirred at 50° C. for 5 h, filtered with diatomite and concentrated to afford 8-6 (16.0, 30.33 mmol, 75.7% yield) as a yellow oil which was used directly in next step. ESI-LCMS: m/z 528 [M+H]$^+$.

Preparation of Intermediate (8-7): To a solution of 8-6 (16.0 g, 30.33 mmol) in MeCN (400 mL) was added pyrrolidine (8.63 g, 121.32 mol, 12 mL), the reaction mixture was stirred at r.t. overnight. Concentrated and purified by a silica gel column by (DCM:MeOH=100:1-50: 1) to afford 7 (12.0 g, 27.94 mmol, 92.1% yield) as a yellow oil. ESI-LCMS: m/z 430 [M+H]$^+$.

Preparation of Intermediate (8-8): To a solution of 8-7 (12.0 g, 27.94 mmol) in THF (200 mL) was added Pd/C (1.2 g), the mixture was stirred at r.t. under $H_2$ overnight. LC-MS showed 7 was totally consumed. Filtered and washed with DCM (100 mL*3), then concentrated to afford 8-8 (11.0 g, 27.27 mmol, 97.6% yield) as a gray solid which was used directly in next step. ESI-LCMS: m/z 404 [M+H]$^+$.

Preparation of Intermediate (8-9): To a solution of 8-8 (10.0 g, 24.79 mmol) in DCM (80 mL) was added MMTrCl (11.4 g, 37.18 mmol), 2,4,6-collidine (2.0 g, 16.61 mmol, 6.5 mL) and $AgNO_3$ (6.3 g, 37.18 mmol), the mixture was stirred at r.t. for 1.5 h. Filtered and the organic layer was washed with water and dried over $Na_2SO_4$, then concentrated and purified by a silica gel column by (PE:EA=5:1-1:1) to afford 8-9 (16.0 g, 23.68 mmol, 95.5% yield) as a light-yellow solid.

Preparation of Intermediate (8-10): 8-9 (4.0 g, 5.92 mmol) was added to the solution of 1.0 N NaOH solution (20 mL, MeOH/$H_2O$=9:1). The reaction mixture was stirred at 40° C. for 2 h, concentrated and extracted with DCM (20 mL*2), the organic layer was dried over $Na_2SO_4$ and concentrated, the residue was purified by a silica gel column by (DCM: MeOH=200:1-50:1) to afford 8-10 (3.0 g, 53.8 mmol, 90.9 yield) as a white solid.

Preparation of (8-11): To a solution of 8-10 (2.36 g, 4.23 mmol) in DCM (2.0 mL) was added DMAP (103 mg, 0.8 mmol) and DIPEA (2.2 g, 16.92 mmol, 2.96 mL). Then CEPCl (1.0 g, 4.23 mmol) was added. The reaction mixture was stirred at r.t. for 1 h., washed with saturated $NaHCO_3$ (5 mL), separated the organic layer and washed the water layer with DCM (10 mL*2). The combined organic layer was washed with brine, dried over $Na_2SO_4$, concentrated and purified by Flash-Prep-HPLC to afford 8-11 (2.45 g, 3.23 mmol, 76.36% yield) as a white solid. $^1$H NMR (400 MHz, $CDCl_3$) δ 8.62 (s, 1H), 7.74 (dd, J=1.4 Hz, 0.5H), 7.60-7.50 (m, 4H), 7.51-7.41 (m, 2H), 7.34-7.16 (m, 7H), 7.12 (d, J=1.4 Hz, 0.5H), 6.88-6.76 (m, 2H), 5.66 (s, 1H), 4.37-4.23 (m, 1H), 4.16-4.05 (m, 1H), 4.05-3.94 (m, 0.5H), 3.88-3.74 (m, 4.5H), 3.72-3.35 (m, 3H), 3.22 (td, J=10.3, 4.7 Hz, 0.5H), 3.03-2.89 (m, 1.5H), 2.80-2.69 (m, 1H), 2.61 (t, J=6.5 Hz, 1H), 2.37 (td, J=6.6, 1.3 Hz, 1H), 1.97 (d, J=3.5 Hz, 0.5H), 1.91 (dd, J=11.4, 1.2 Hz, 3H), 1.52 (d, J=4.7 Hz, 0.5H), 1.29-1.17 (m, 12H), 1.08 (td, J=7.0, 4.9 Hz, 3H). $^{31}$P NMR (162 MHz, $CDCl_3$) δ 149.31, 147.14. ESI-LCMS: m/z 576 [M+H]$^+$.

Example 6

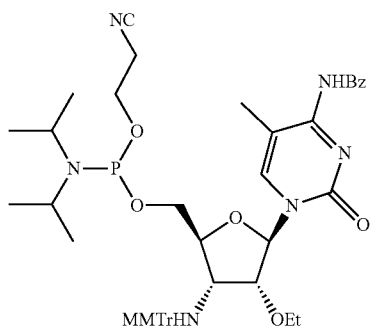

9-3

The 2'-O-ethyl-NH-benzoyl 5-methyl cytosine phosphoramidite 9-3 was obtained by conversion of thymidine intermediate 8-8 into 3'-amino cytidine analogue 9-1 followed by phosphitylation using known protocols to give the desired 2'-O-ethyl cytidine phosphoramidite monomer 9-3 as shown below in scheme 7.

Scheme 7

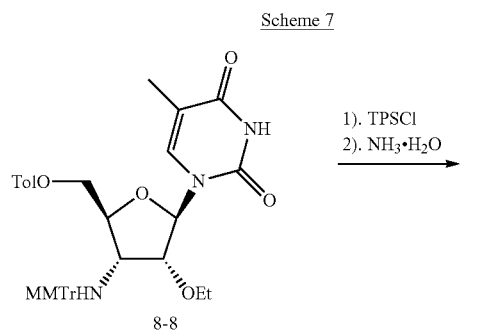

8-8

1). TPSCl
2). NH₃·H₂O

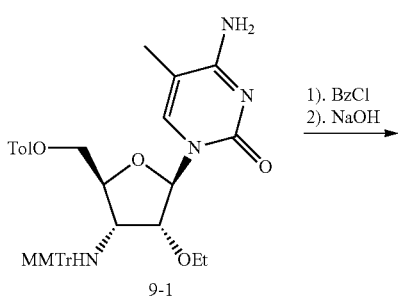

9-1

1). BzCl
2). NaOH

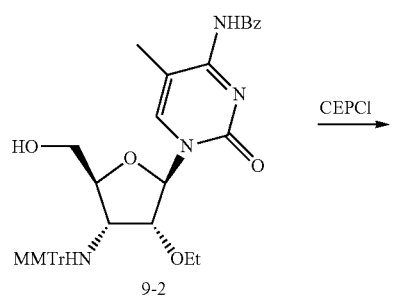

9-2

CEPCl →

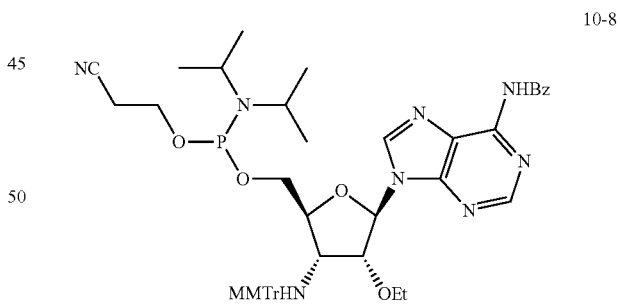

9-3

Preparation of Intermediate (9-1): To a solution of 8-8 (8.2 g, 12.09 mmol) in dry MeCN (40 mL) was added TPSCl (2.5 g, 24.18 mmol) and DMAP (2.95 g, 24.18 mmol), then TEA (2.5 g, 24.18 mmol, 3.4 mL) was added, the reaction mixture was stirred at r.t. for 12 h under N₂. Then con.NH₄OH aqueous solution (20 mL) was added, the result mixture was allowed to stirred at r.t. for another 3 h, then concentrated and purified by silica gel column to afford 9-1 (7.7 g, 11.35 mmol, 93.9% yield) as a light-yellow oil.

Preparation of Intermediate (9-2): To a solution of 9-1 (8.0 g, 11.86 mmol) in pyridine (80 mL) was added benzoyl chloride (2.0 g, 14.23 mmol, 1.6 mL) at 0° C., the reaction mixture was allowed warm to r.t. and stirred for another 1 h, 2.0 N NaOH (80 mL, MeOH/H₂O=9:1) was added at 0° C., and then the mixture was allowed to stirred at 0° C. for another 2 h, quenched with sat. NH₄Cl solution (20 mL) extracted with DCM (30 mL*2) dried over Na₂SO₄, filtered and concentrated. The residue was purified by a silica gel chromatography (DCM:MeOH=200:1-50:1) to afford 9-2 (5.4 g, 8.2 mmol, 66.3% yield) as yellow solid. $^1$H NMR (400 MHz, CDCl₃) δ 13.35 (s, 1H), 8.40-8.28 (m, 2H), 7.93 (d, J=1.3 Hz, 1H), 7.61-7.51 (m, 5H), 7.51-7.43 (m, 4H), 7.33-7.22 (m, 6H), 6.89-6.72 (m, 2H), 5.66 (s, 1H), 4.26-4.19 (m, 2H), 4.08 (dt, J=10.4, 2.0 Hz, 1H), 3.80 (s, 3H), 3.74-3.63 (m, 1H), 3.12 (td, J=10.3, 4.5 Hz, 1H), 2.95-2.84 (m, 2H), 2.05 (d, J=1.1 Hz, 3H), 1.91 (d, J=4.5 Hz, 1H), 1.29 (t, J=7.1 Hz, 1H) 1.13 (t, J=7.0 Hz, 3H).

Preparation of (9-3): To a solution of 9-2 (4.2 g, 6.36 mmol) in DCM (4 mL) was added DMAP (776 mg, 6.36 mmol), DIPEA (821 mg, 6.36 mmol, 1.1 mL) and then CEPCl (1.5 g, 6.36 mmol). The reaction mixture was stirred at r.t. for 1 h., quenched with sat. NaHCO₃ solution, extracted with DCM (30 mL*2), the organic layer was dried over Na₂SO₄ and the solvent was evaporated, the residue was purified by a Flash-Prep-HPLC to afford 9-3 (4.9 g, 5.69 mmol, 89.47% yield) as light yellow solid. $^1$H NMR (400 MHz, CDCl₃) δ 13.31 (s, 1H), 8.40-8.31 (m, 2H), 8.03 (s, 0.5H), 7.60-7.52 (m, 5H), 7.52-7.43 (m, 4H), 7.40 (s, 0.5H), 7.31-7.18 (m, 7H), 6.86-6.78 (m, 2H), 5.67 (d, J=2.3 Hz, 1H), 4.42-4.26 (m, 1H), 4.24-4.11 (m, 1H), 4.06-3.98 (m, 0.5H), 3.90-3.81 (m, 1.5H), 3.79 (d, J=3.0 Hz, 3H), 3.75-3.56 (m, 2H), 3.55-3.37 (m, 1H), 3.22 (td, J=10.4, 4.5 Hz, 0.5H), 3.04-2.87 (m, 1.5H), 2.86-2.73 (m, 1H), 2.63 (t, J=6.4 Hz, 1H), 2.40 (t, J=6.5 Hz, 1H), 2.13 (dd, J=19.9, 1.1 Hz, 3H), 1.99 (d, J=3.8 Hz, 0.5H), 1.54 (d, J=4.5 Hz, 0.5H), 1.31-1.21 (m, 12H), 1.10 (td, J=7.0, 4.8 Hz, 3H). $^{31}$P NMR (162 MHz, CDCl₃) δ 149.48, 147.08. ESI-LCMS: m/z 861 [M+H]⁺.

Example 7

10-8

The synthesis of the 2'-O-ethyl adenosine phosphoramidite 10-8 was achieved as shown below in scheme 8. Protection of exocyclic amine group of 6-4 with bulky protecting group such as 4-monomethoxy trityl group was necessary to achieve 2'-O-alkylation in high yield. Then, intermediate 6-4 by reaction with Ag₂O/EtI afforded 2'-O-ethyl intermediate 10-2 in 94% isolated yield after deprotection of MMTr group. This protection strategy resulted in efficient synthesis of key 3'-azido-2'-OEt intermediate 10-3 in high yields. This intermediate 10-3 was converted to 2'-O-ethyl adenosine phosphoramidite 10-8 by following the similar chemistry described for compound 6-10 (scheme 4).

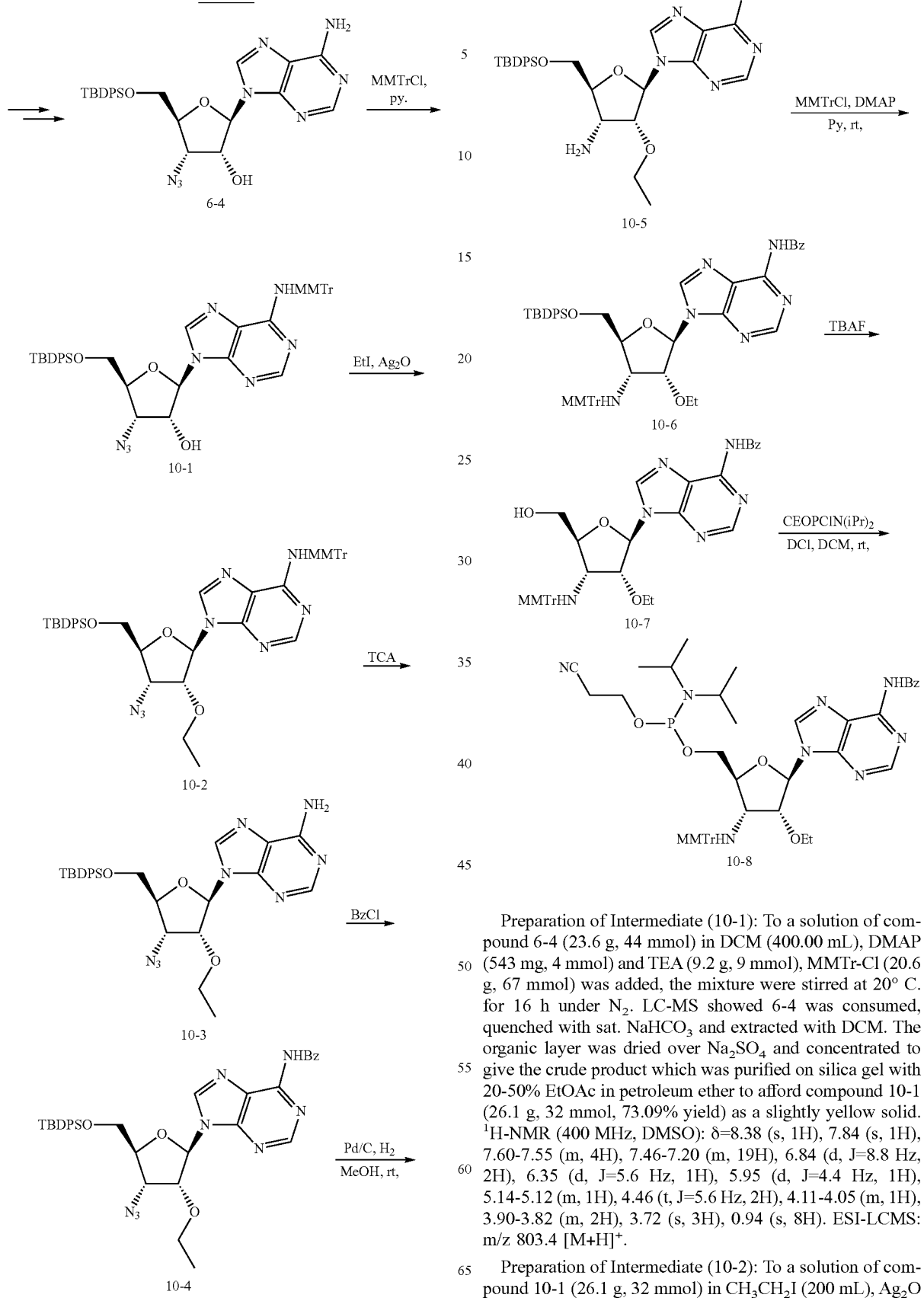

Preparation of Intermediate (10-1): To a solution of compound 6-4 (23.6 g, 44 mmol) in DCM (400.00 mL), DMAP (543 mg, 4 mmol) and TEA (9.2 g, 9 mmol), MMTr-Cl (20.6 g, 67 mmol) was added, the mixture were stirred at 20° C. for 16 h under $N_2$. LC-MS showed 6-4 was consumed, quenched with sat. $NaHCO_3$ and extracted with DCM. The organic layer was dried over $Na_2SO_4$ and concentrated to give the crude product which was purified on silica gel with 20-50% EtOAc in petroleum ether to afford compound 10-1 (26.1 g, 32 mmol, 73.09% yield) as a slightly yellow solid. $^1$H-NMR (400 MHz, DMSO): δ=8.38 (s, 1H), 7.84 (s, 1H), 7.60-7.55 (m, 4H), 7.46-7.20 (m, 19H), 6.84 (d, J=8.8 Hz, 2H), 6.35 (d, J=5.6 Hz, 1H), 5.95 (d, J=4.4 Hz, 1H), 5.14-5.12 (m, 1H), 4.46 (t, J=5.6 Hz, 2H), 4.11-4.05 (m, 1H), 3.90-3.82 (m, 2H), 3.72 (s, 3H), 0.94 (s, 8H). ESI-LCMS: m/z 803.4 [M+H]$^+$.

Preparation of Intermediate (10-2): To a solution of compound 10-1 (26.1 g, 32 mmol) in $CH_3CH_2I$ (200 mL), $Ag_2O$ (9.7 g, 42 mmol) was added. The mixture was refluxed at 80°

C. for 1 h. Then filtered to get the compound 10-2 (25.4 g, 30 mmol, 94.04% yield) as a yellow solid. ESI-LCMS: m/z 831.3 [M+H]$^+$.

Preparation of Intermediate (10-3): A solution of compound 10-2 (25.4 g, 30 mmol) was dissolved in DCM (200 mL) was added TCA (12 mL), the mixture was stirred at 20° C. for 6 h, LC-MS showed 10-2 was consumed, then washed with saturated NaHCO$_3$, concentrated to give the crude product which was purified on silica gel with 1-3% MeOH in DCM to afford compound 10-3 (15.7 g, 28 mmol, 91.95% yield) as a white solid. $^1$H-NMR (400 MHz, DMSO): δ=8.33 (s, 1H), 8.10 (s, 1H), 7.63-7.60 (m, 4H), 7.47-7.37 (m, 8H), 6.09 (d, J=4.0 Hz, 1H), 4.95 (t, J=4.8 Hz, 1H), 4.67 (t, J=5.6 Hz, 1H), 4.17-4.13 (m, 1H), 3.97-3.93 (m, 1H), 3.86-3.82 (m, 1H), 3.68-3.63 (m, 2H), 1.15-1.11 (m, 3H), 0.97 (s, 9H). ESI-LCMS: m/z 589.2 [M+H]$^+$.

Preparation of Intermediate (10-4): To a solution of compound 10-3 (15.7 g, 28 mmol) in pyridine (150 mL) at 0° C., BzCl (4.7 g, 34 mmol) was added by syringe over 5 minutes, then the mixture was allowed to warm up to 20° C. Then stirred at r.t. under N$_2$ for 1 h. The solution was cooled to 0° C., and ammonium hydroxide (20 mL, 30%) was added and the mixture was allowed to warm to r.t. and stirred at r.t. for 2 h. The mixture was diluted with EA and Water, extracted with EA, the combined organic layer was washed with brine, dried over anhydrous Na$_2$SO$_4$, concentrated to give the crude product which was purified on silica gel to afford compound 10-4 (10.9 g, 16 mmol, 58.52% yield) as a white solid. ESI-LCMS: m/z 663.8 [M+H]$^+$.

Preparation of Intermediate (10-5): To a solution of compound 10-4 (10.9 g, 16 mmol) in THF (100 mL), Pd/C (1.9 g) were added, the mixture was stirred at 20° C. for 6 h under H$_2$, then filtered and the filtrate concentrated to afford compound 10-5 (9.8 g, 15 mmol, 93.95% yield) as a white solid. ESI-LCMS: m/z 637.4 [M+H]$^+$.

Preparation of Intermediate (10-6): To a solution of compound 10-5 (9.8 g, 15 mmol) in anhydrous DCM (100 mL), collidine (3.7 g, 31 mmol) and AgNO$_3$ (3.9 g, 31 mmol), MMTr-Cl (5.7 g, 18 mmol) were added, the mixture was stirred at 20° C. for 1 h under N$_2$, then filtered, washed with H$_2$O and dried over Na$_2$SO$_4$, concentrated to give the residue which was purified on silica gel with 20-50% EA in petroleum ether to afford compound 10-6 (10.5 g, 11 mmol, 75.19% yield) as a white solid.

Preparation of Intermediate (10-7): To a solution of compound 10-6 (10.5 g, 11 mmol) in THF (100 mL), TBAF (1M) (11 mmol, 12 mL) was added, the mixture was stirred at 20° C. overnight, then washed with saturated NaHCO$_3$, concentrated to give the residue which was purified on silica gel with 1-2% MeOH in DCM to afford compound 10-7 (5.6 g, 8 mmol, 72.28% yield) as a white solid.

Preparation of (10-8): To a solution of compound 10-7 (5.6 g, 8 mmol) in DCM (50 mL) was added DMAP (204 mg, 2 mmol) and DIPEA (3.2 g, 25 mmol, 4.3 mL), CEPCl (2.3 g, 10 mmol) was added. The reaction mixture was stirred at r.t. for 1 h. TLC showed 10-7 was consumed, washed with saturated NaHCO$_3$ and brine, dried over Na$_2$SO$_4$, concentrated to give the crude product which was purified by column chromatography and Flash-Prep-HPLC to give 10-8 (5.30 g, 6.09 mmol, 72.88% yield) as a white solid. $^1$H-NMR (400 MHz, CDCl$_3$): δ=9.17 (s, 0.5H), 9.07 (s, 0.5H), 8.75 (s, 0.5H), 8.72 (s, 0.5H), 8.51 (s, 0.5H), 8.22 (s, 0.5H), 8.05 (t, J=7.2 Hz, 2H), 7.65-7.61 (m, 1H), 7.57-7.48 (m, 6H), 7.39 (dd, J=8.8 Hz, 2H), 7.21-7.10 (m, 6H), 6.74-6.69 (m, 2H), 6.01 (d, J=3.9 Hz, 1H), 4.40-4.21 (m, 2H), 4.14-4.11 (m, 0.5H), 3.99-3.93 (m, 0.5H), 3.88-3.80 (m, 1H), 3.70-3.50 (m, 7H), 3.41-3.32 (m, 1H), 2.93-2.80 (m, 2H), 2.68-2.50 (m, 2H), 2.27 (d, J=4.0 Hz, 0.5H), 2.27 (d, J=4.0 Hz, 0.5H), 1.25-1.12 (m, 15H). $^{31}$P NMR (162 MHz, CDCl$_3$): 148.79, 148.08. ESI-LCMS: m/z 870.3[M+H]$^+$.

Example 8

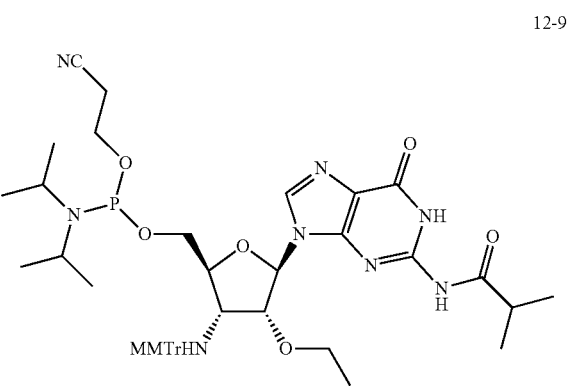

12-9

The synthesis of guanosine-based 2'-O-ethyl phosphoramidite 12-9 shown below in scheme 9 starting from key 2'-hydroxy intermediate 7-4. Intermediate 7-4 was subjected to 2'-O-alkyation using EtI/Ag$_2$O or EtI/K$_2$CO$_3$ desired 2'-OEt intermediate 7-5 could not be obtained in high yield as shown below in scheme 9.

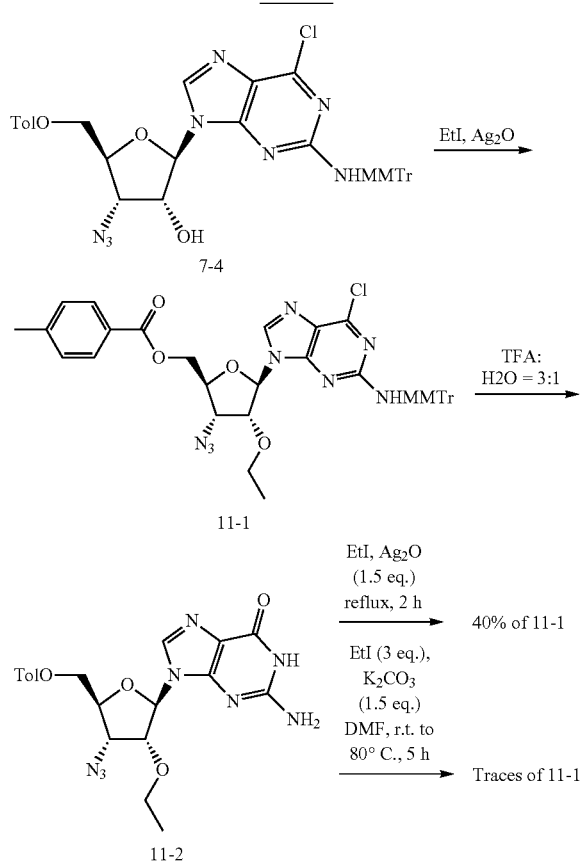

Scheme 9

Therefore, an innovative way to improve on 2'-O alkylation and to make more stable guanosine intermediate under acidic conditions was designed as shown below in scheme 10. The reaction of 6-chloro intermediate 7-4 with NaH/BnOH/THF resulted in simultaneous substitution of C-6-Cl with BnOH and hydrolysis of 5'-O-toluoylester in one step to give C-6-OBn intermediate 12-1.

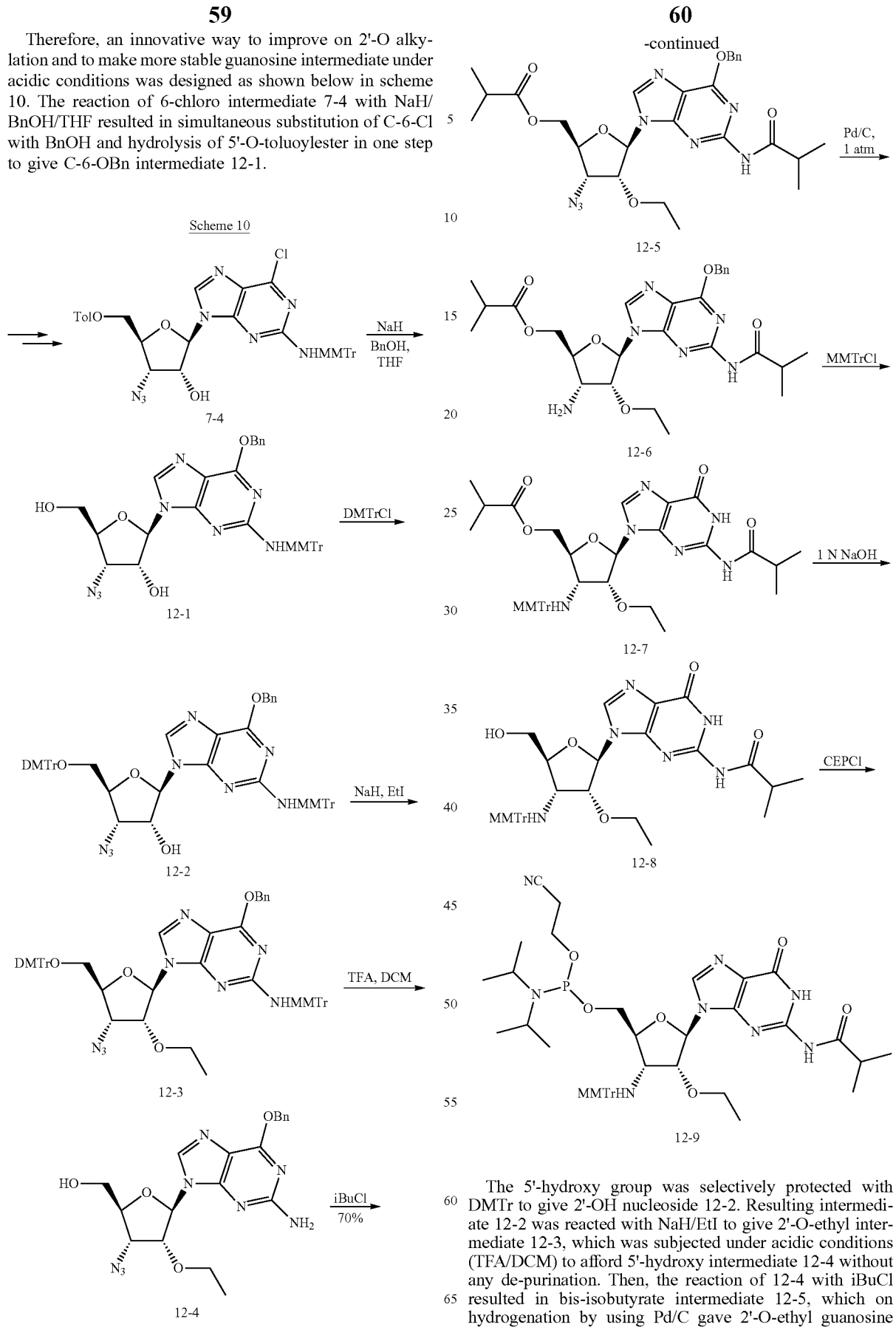

Scheme 10

The 5'-hydroxy group was selectively protected with DMTr to give 2'-OH nucleoside 12-2. Resulting intermediate 12-2 was reacted with NaH/EtI to give 2'-O-ethyl intermediate 12-3, which was subjected under acidic conditions (TFA/DCM) to afford 5'-hydroxy intermediate 12-4 without any de-purination. Then, the reaction of 12-4 with iBuCl resulted in bis-isobutyrate intermediate 12-5, which on hydrogenation by using Pd/C gave 2'-O-ethyl guanosine intermediate 12-6. This de-protection and re-protection strategy were applied successfully for efficient 2'-O-alkylations under basic conditions (NaH/EtI/THF). The resulted 2'-O-ethyl intermediate 12-6 was converted to desired 2'-O-ethylguanosine phosphoramidite monomer 12-9 by following the similar procedure described for compound 7-13 in example 12.

Preparation of Intermediate (12-1): To a solution of compound 7-4 (48.0 g, 66 mmol) in 50 mL of THF was added 90 mL of a sodium benzyloxide solution in benzyl alcohol (freshly prepared by addition of NaH (13 g) in 90 mL of benzyl alcohol). The reaction mixture was stirred at room temperature for 1 h and treated with 50 mL of a saturated solution of NH$_4$Cl. The mixture was extracted with CH$_2$Cl$_2$ and the combined organic layers dried over Na$_2$SO$_4$. The crude product was purified by column chromatography to give 12-1 (17.5 g, 26 mmol, 45.63%). $^1$H-NMR (400 MHz, DMSO): δ ppm 8.13 (s, 1H), 7.59 (s, 1H), 7.34-7.16 (m, 15H), 6.82 (d, J=8.8 Hz, 2H), 6.13 (s, 1H), 5.76 (s, 1H), 5.20-5.12 (m, 1H), 5.10-4.78 (m, 2H), 3.88-3.70 (m, 2H), 3.60 (s, 3H), 3.58-3.51 (m, 1H), 3.34 (s, 1H). ESI-LCMS: m/z 671.2 [M+H]$^+$.

Preparation of Intermediate (12-2): To a solution of compound 12-1 (17.5 g, 26 mmol) in pyridine (200 mL) was added DMTrCl (10.5 g, 31 mmol) at 0° C. Then the mixture was stirred at 35° C. for 4 h. Solvent was evaporated. The crude product was purified by column chromatography to give product 12-2 (21.8 g, 22 mmol, 85.87% yield) as a white solid. ESI-LCMS: m/z 974.6 [M+H]$^+$.

Preparation of Intermediate (12-3): To a solution of 12-2 (21.8 g, 22 mmol) in THF (300 mL) was added NaH (1.1 g, 44 mmol) at 0° C. Then EtI (10.4 g, 67 mmol) was added in reaction mixture and the mixture was stirred at 35° C. for 4 h, then treated with 50 mL of a saturated solution of NH$_4$Cl. The mixture was extracted with CH$_2$Cl$_2$ and the combined organic layers dried over Na$_2$SO$_4$. Solvent was evaporated to give 12-3 (21.2 g, 21 mmol, 94.55% yield) as a yellow solid.

Preparation of Intermediate (12-4): To a solution of 12-3 (21.2 g, 21 mmol) in DCM (200 mL) was added TFA (10 mL) at 0° C. Then the mixture was stirred at 35° C. for 4 h. Quenched with saturated NaHCO$_3$ and washed with brine, dried over Na$_2$SO$_4$, purified by purified by column chromatography to give 12-4 (8.7 g, 20 mmol, 96.32% yield) as a white solid. $^1$H-NMR (400 MHz, DMSO): δ ppm 8.17 (s, 1H), 7.53-7.50 (m, 2H), 7.42-7.36 (m, 3H), 6.61 (d, J=8.8 Hz, 2H), 5.91-5.90 (m, 1H), 5.76 (s, 1H), 5.51-5.50 (m, 2H), 4.76-4.75 (m, 1H), 4.55-4.54 (m, 1H), 4.06-3.97 (m, 3H), 3.64-3.58 (m, 4H), 2.51 (s, 1H). ESI-LCMS: m/z 427.2 [M+H]$^+$.

Preparation of Intermediate (12-5): To a solution of 12-4 (8.7 g, 20 mmol) in pyridine (100 mL) was added iBuCl (5.4 g, 51 mmol), the mixture was stirred at r.t. for 1.5 h. The organic layer was washed by water and dried over Na$_2$SO$_4$ and purified by column chromatography to give 12-5 (8.5 g, 15 mmol, 73.54% yield) as a white solid. ESI-LCMS: m/z 567.4 [M+H]$^+$.

Preparation of Intermediate (12-6): To a solution of 12-5 (8.5 g, 15 mmol) in THF (100 mL) was added Pd/C (801 mg, 6 mmol) at 25° C. Then the mixture was stirred under H$_2$ for 16 h. Filtered and washed by EA, concentrated to give crude product 12-6 (6.7 g, 14 mmol, 99.15% yield) as a yellow solid. ESI-LCMS: m/z 451.3 [M+H]$^+$.

Preparation of Intermediate (12-7): To a solution of compound 12-6 (6.7 g, 14 mmol) in anhydrous DCM (70 mL), collidine (3.7 g, 31 mmol) and AgNO$_3$ (3.0 g, 17 mmol), MMTr-Cl (5.5 g, 17 mmol) were added, the mixture was stirred at 20° C. for 1 h under N$_2$, then filtered, washed with H$_2$O and dried over Na$_2$SO$_4$, concentrated to give the residue which was purified by column chromatography to afford compound 12-7 (8.4 g, 11 mmol, 75.19% yield) as a white solid.

Preparation of Intermediate (12-8): Compound 12-7 (8.4 g, 11 mmol) was added to 80 mL of 1 N NaOH solution in MeOH/THF/H$_2$O (65/30/5) at 0° C. The suspension was stirred at 0° C. for 2 h. The reaction was quenched by addition of sat. NH$_4$Cl solution. The solution was extracted with DCM and the combined organic layers were washed with sat. NaHCO$_3$ solution, brine, dried over Na$_2$SO$_4$, filtered, and concentrated. The residue was purified by column chromatography to give 12-8 (5.60 g, 8.35 mmol, 72.28% yield) as white solid. $^1$H-NMR (400 MHz, DMSO): δ ppm 12.13 (br s, 1H), 11.38 (s, 1H), 8.10 (s, 1H), 7.47-7.44 (m, 4H), 7.30-7.13 (m, 8H), 6.75 (d, J=8.96 Hz, 2H), 5.79 (s, 1H), 5.10 (t, J=4.28 Hz, 1H), 3.95-3.89 (m, 3H), 3.65 (s, 3H), 3.46-3.26 (m, 2H), 2.84-2.80 (m, 2H), 2.79-2.72 (m, 1H), 1.85 (s, 1H), 1.18-1.13 (m, 6H). 1.08-0.98 (m, 3H).

Preparation of (12-9): To a solution of 12-8 (5.60 g, 8.35 mmol) in DCM (50 mL) was added DMAP (220 mg) and DIPEA (3 mL). Then CEPCl (2.6 g) was added. The reaction mixture was stirred at r.t. for 1 h, washed with saturated NaHCO$_3$ and brine, dried over Na$_2$SO$_4$, purified by column chromatography and Flash-Prep-HPLC. This resulted in 5.4 g (70.04%) of 12-9 as a white solid. $^1$H-NMR (400 MHz, CDCl$_3$): δ ppm 12.11 (br s, 1H), 8.88 (s, 1H), 7.97-7.64 (m, 1H), 7.51-7.49 (m, 4H), 7.39-7.34 (m, 2H), 7.23-7.09 (m, 6H), 6.75-6.69 (m, 2H), 5.67-5.65 (m, 1H), 4.22-4.08 (m, 2H), 3.84-3.29 (m, 10H), 2.87-2.51 (m, 5H), 2.08-1.61 (m, 1H), 1.24-1.07 (m, 18H), 1.01-0.98 (m, 3H). $^{31}$PNMR (162 MHz, CDCl$_3$): 149.03, 147.96. ESI-LCMS: m/z 853.4 [M+H]$^+$.

Example 9

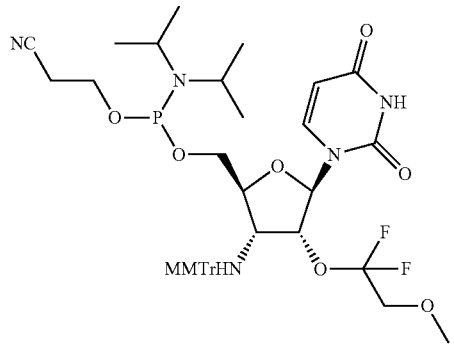

Scheme 11

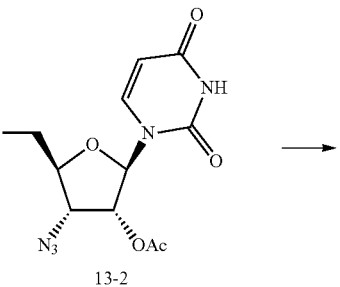

13-2

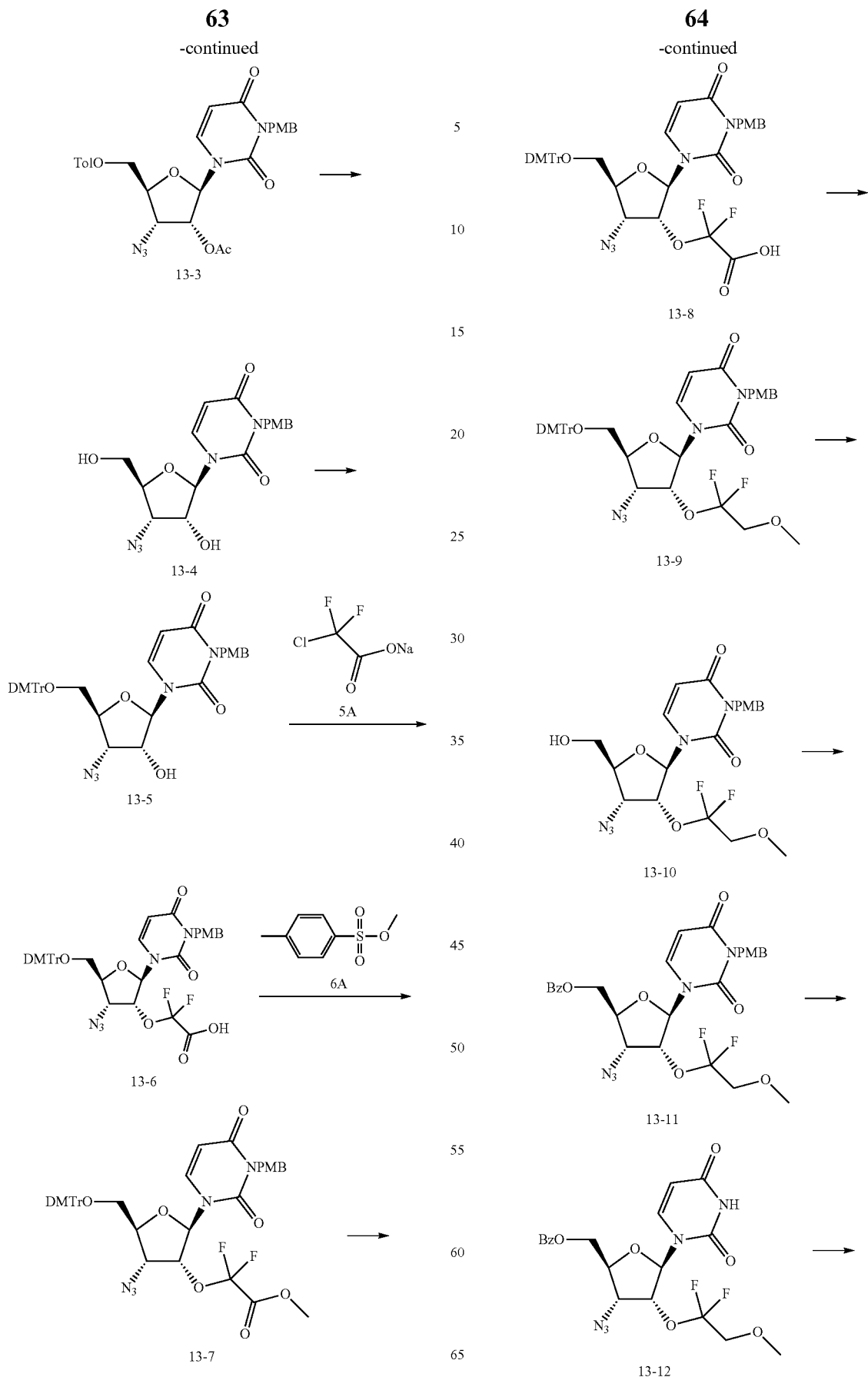

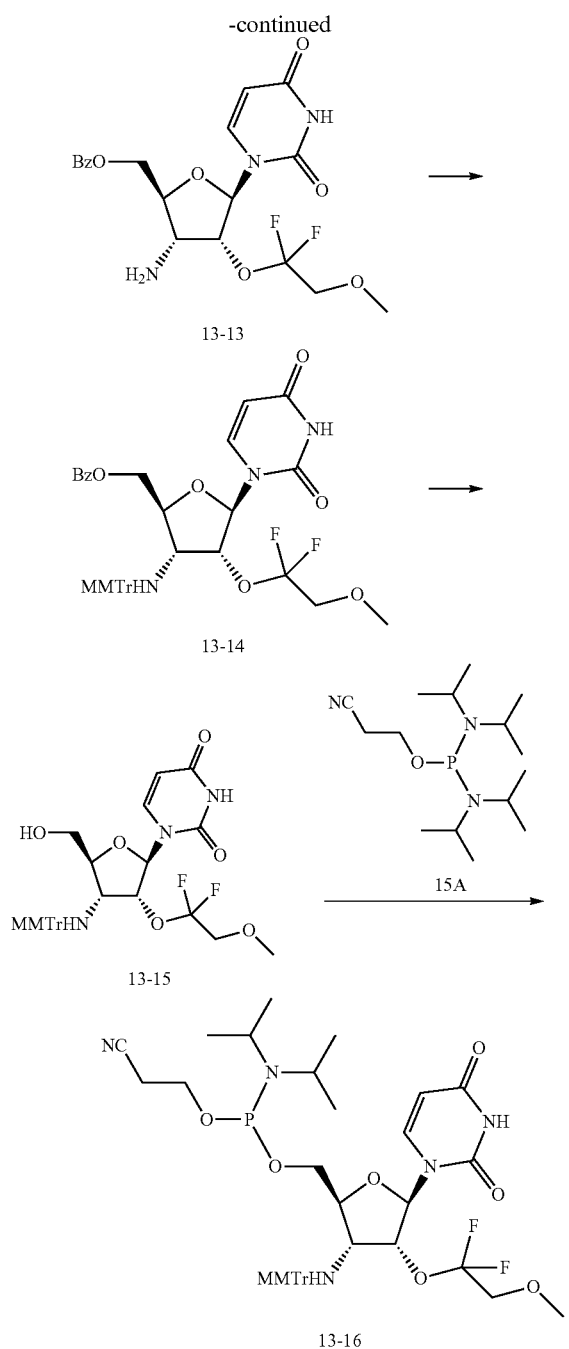

Preparation of Intermediate (13-3): A solution of 13-2 (260.0 g, 605.5 mmol) and DBU (305.0 g, 1.21 mol) in DMF (1.5 L) was added PMBCl (113.7 g, 908.2 mmol). The mixture was stirred at r.t. for 2 h, poured into cold water, extracted with EA, washed with brine and dried over anhydrous $Na_2SO_4$, concentrated to give the crude product 13-3 (460.0 g, crude) as a yellow oil. ESI-LCMS: m/z 550 $[M+H]^+$.

Preparation of Intermediate (13-4): A solution of 13-3 (460.0 g, crude) in the mixture of THF (1.5 L) and $H_2O$ (500 mL) was added NaOH (167.4 g, 4.1 mol). The reaction was stirred at r.t. for 15 h, and then poured into cold water, extracted with EA. The combined organic layer was washed with brine and dried over anhydrous $Na_2SO_4$, concentrated to obtain the crude product which was washed with PE:EA=5:1 to give the product 13-4 (212.0 g, 544.4 mmol, 89.92% yield over two steps) as a white solid. ESI-LCMS: m/z 390 $[M+H]^+$.

Preparation of Intermediate (13-5): A solution of 13-4 (207.0 g, 531.6 mmol) and pyridine (210.2 g, 2.6 mol, 214 mL) in DCM (2 L) was added DMTrCl (197.6 g, 584.8 mmol) under $N_2$. The mixture was stirred at room temperature for 1 h, quenched with MeOH, concentrated to obtain a residue which was purified by column chromatography to give 13-5 (330.0 g, 477.0 mmol, 89.7% yield) as a yellow solid. $^1$H-NMR (400 MHz, DMSO-$d_6$): δ=7.81 (d, J=8.0 Hz, 1H), 7.39 (d, J=7.6 Hz, 2H), 7.33 (t, J=7.6 Hz, 2H), 7.28-7.25 (m, 7H), 6.91 (d, J=7.6 Hz, 4H), 6.86 (d, J=8.4 Hz, 2H), 6.33 (d, J=5.2 Hz, 1H, exchanged with $D_2O$), 5.49 (d, J=8.0 Hz, 1H), 4.91 (s, 2H), 4.51 (dd, J=5.2, 8.8 Hz, 1H), 4.21 (t, J=6.8 Hz, 1H), 4.08-4.05 (m, 1H), 3.75 (s, 6H), 3.72 (s, 3H). ESI-LCMS: m/z 692 $[M+H]^+$.

Preparation of Intermediate (13-6): A solution of 13-5 (150.0 g, 216.8 mmol) in dry THF (750 mL) were added NaH (10.4 g, 433.7 mmol) and Methyl p-toluenesulfonate (66.1 g, 433.7 mmol) at 0° C., the mixture was allowed to stir at r.t., and TBAI (16.0 g, 43.3 mmol) was added. The reaction was stirred at 80° C. for 2 days, and then quenched with sat $NH_4Cl$(aq.), extracted with EA, washed with brine, dried over $Na_2SO_4$, concentrated to obtain a residue which was purified by column chromatography to give 13-6 (55.0 g, 70.0 mmol, 32.28% yield) as a yellow solid. ESI-LCMS: m/z 786 $[M+H]^+$.

Preparation of Intermediate (13-7): A solution of 13-6 (52.0 g, 66.1 mmol) and $K_2CO_3$ (18.2 g, 132.3 mmol) in dry DMF (500 mL) was added Methyl p-toluenesulfonate (18.4 g, 99.2 mmol) under Ar. The mixture was stirred at r.t. for 15 h, poured into cold water, extracted with EA, washed with brine and dried over anhydrous $Na_2SO_4$, concentrated to obtain a residue which was purified by column chromatography to give 7 (38.5 g, 48.1 mmol, 72.74% yield) as a white solid. $^1$H-NMR (400 MHz, DMSO-d6): δ=7.81 (d, J=8.4 Hz, 1H), 7.41-7.38 (m, 2H), 7.34-7.31 (m, 2H), 7.28-7.23 (m, 7H), 6.92-6.90 (m, 4H), 6.84-6.81 (m, 2H), 5.98 (d, J=3.6 Hz, 1H), 5.59 (d, J=8.4 Hz, 1H), 5.40 (dd, J=3.6, 6.4 Hz, 1H), 4.90 (dd, J=14.0, 32.0 Hz, 2H), 4.67 (dd, J=6.4, 7.6 Hz, 1H), 4.09-4.05 (m, 1H), 3.74 (d, J=0.8 Hz, 6H), 3.70 (s, 3H). $^{19}$F-NMR (376 MHz, DMSO-d6): −75.31, −75.69, −76.69, −77.35. ESI-LCMS: m/z 800 $[M+H]^+$.

Preparation of Intermediate (13-8): To a solution of 13-7 (33.0 g, 41.2 mmol) in THF (600 mL) were added $NaBH_4$ (2.3 g, 61.8 mmol) and EtOH (20 mL) at 0° C. The mixture was allowed to stir at r.t. for 4 h, and quenched with sat $NH_4Cl$(aq.), extracted with EA, washed with brine, dried over $Na_2SO_4$, concentrated to obtain a residue which was purified by column chromatography to give 13-8 (25.0 g, 32.3 mmol, 78.51% yield) as a white solid. $^1$H-NMR (400 MHz, DMSO-$d_6$): δ=7.78 (d, J=8.4 Hz, 1H), 7.41-7.38 (m, 2H), 7.34-7.30 (m, 2H), 7.28-7.21 (m, 7H), 6.92-6.89 (m, 4H), 6.84-6.82 (m, 2H), 5.98 (d, J=4.4 Hz, 1H), 5.83 (t, J=6.8 Hz, 1H), 5.60 (d, J=8.0 Hz, 1H), 5.30 (t, J=5.3 Hz, 1H), 4.90 (dd, J=14.0, 33.2 Hz, 2H), 4.61 (t, J=6.0 Hz, 1H), 4.08-4.05 (m, 1H), 3.74 (d, J=0.8 Hz, 6H), 3.70 (s, 3H), 3.39 (dd, J=4.0, 14.8 Hz, 1H), 3.30 (dd, J=2.8, 11.2 Hz, 1H). $^{19}$F-NMR (376 MHz, DMSO-d6): −79.67, −80.04, −80.87, −81.25. ESI-LCMS: m/z 772 $[M+H]^+$.

Preparation of Intermediate (13-9): To a solution of 13-8 (26.0 g, 33.6 mmol) in THF (250 mL) were added NaH (808 mg, 33.6 mmol) and MeI (23.9 g, 168.4 mmol, 10.4 mL) at 0° C. The mixture was allowed to stir at r.t. for 15 h, and poured into cold water, extracted with EA, washed with brine, dried over Na$_2$SO$_4$, concentrated to obtain the crude product 13-9 (29.0 g) as a yellow oil. ESI-LCMS: m/z 786 [M+H]$^+$.

Preparation of Intermediate (13-10): A solution of 13-9 (29.0 g, 36.9 mmol) in DCM (200 mL) was added a solution of p-TsOH (10.0 g) in MeOH (20 mL) The mixture was stirred at r.t. for 0.5 h, and washed with saturated NaHCO$_3$ to pH=7, dried over Na$_2$SO$_4$, concentrated to obtain a residue which was purified by column chromatography to give 13-10 (13.5 g, 27.9 mmol, 82.90% yield over two steps). $^1$H-NMR (400 MHz, DMSO-d6): δ=7.99 (d, J=4.4 Hz, 1H), 7.22 (d, J=8.4 Hz, 2H), 6.85 (d, J=8.8 Hz, 2H), 6.01 (d, J=5.2 Hz, 1H), 5.89 (d, J=8.0 Hz, 1H), 5.46 (t, J=4.8 Hz, 1H), 5.17 (t, J=6.4 Hz, 1H), 4.90 (dd, J=14.0, 32.4 Hz, 2H), 4.43 (t, J=5.2 Hz, 1H), 4.00-3.97 (m, 1H), 3.74-3.67 (m, 6H), 3.64-3.60 (m, 1H), 3.33 (s, 3H). ESI-LCMS: m/z 484 [M+H]$^+$.

Preparation of Intermediate (13-11): To a solution of 13-10 (28.0 g, 57.9 mmol) and TEA (11.7 g, 115.8 mmol, 16 mL) in DCM (300 mL) was added BzCl (12.2 g, 86.8 mmol) under Ar. The mixture was stirred at r.t. for 2 h, and poured into cold water, extracted with EA, washed with brine, dried over Na$_2$SO$_4$, concentrated to obtain a residue which was purified by column chromatography to give 13-11 (31.0 g, 52.7 mmol, 91.10% yield) as a clear oil. $^1$H-NMR (400 MHz, DMSO-d6): δ=8.00 (d, J=3.2 Hz, 1H), 7.77 (d, J=8.0 Hz, 1H), 7.68 (t, J=7.6 Hz, 1H), 7.54 (t, J=7.6 Hz, 1H), 7.20 (d, J=8.8 Hz, 2H), 6.82 (d, J=8.4 Hz, 2H), 5.97 (d, J=4.4 Hz, 1H), 5.78 (d, J=8.4 Hz, 1H), 5.38 (t, J=6.4 Hz, 1H), 4.87 (dd, J=14.0, 27.2 Hz, 2H), 4.65-4.60 (m, 2H), 4.56-4.51 (m, 1H), 4.28-4.24 (m, 1H), 3.76 (t, J=10.4 Hz, 2H), 3.69 (s, 3H), 3.35 (s, 3H). ESI-LCMS: m/z 588 [M+H]$^+$.

Preparation of Intermediate (13-12): A solution of 13-11 (30.0 g, 51.0 mmol) in the mixture of ACN (300 mL) and H$_2$O (100 mL) was added CAN (83.9 g, 153.1 mmol). After the mixture was stirred at 45° C. for 24 h, poured into water, extracted with EA, washed with brine and dried over anhydrous Na$_2$SO$_4$, concentrated to obtain a residue which was purified by column chromatography to give 13-12 (20.0 g, 42.7 mmol, 83.80% yield) as a white solid. ESI-LCMS: m/z 468 [M+H]$^+$.

Preparation of Intermediate (13-13): A solution of 13-12 (13.0 g, 27.8 mmol) in THF (150 mL) were added TPP (10.9 g, 41.7 mmol) and H$_2$O (5.0 g, 278.1 mmol). The mixture was stirred at 60° C. for 5 h, concentrated to obtain a residue which was purified by column chromatography to give 13-13 (11.5 g, 26.0 mmol, 93.67% yield) as a white solid. ESI-LCMS: m/z 442 [M+H]$^+$.

Preparation of Intermediate (13-14): A solution of 13-13 (10.5 g, 23.7 mmol) and DMAP (581 mg, 4.7 mmol) in DCM (100 mL) were added MMTrCl (11.0 g, 35.6 mmol) and TEA (4.8 g, 47.5 mmol, 6.6 mL) under N$_2$. The mixture was stirred at r.t. for 1 h, quenched with MeOH and concentrated to obtain a residue which was purified by column chromatography to give 13-14 (15.7 g, 22.0 mmol, 92.47% yield) as a white solid. ESI-LCMS: m/z 714 [M+H]$^+$.

Preparation of Intermediate (13-15): A solution of 13-14 (4.0 g, 5.6 mmol) in 1 N NaOH(MeOH:H2O=4:1) (80 mL), the mixture was stirred at room temperature for 1 h, and the reaction was neutralized with saturated NH$_4$Cl (aq) to pH=7-8, extracted by EA, washed with brine, dried over anhydrous Na$_2$SO$_4$, concentrated to obtain a residue which was purified by column chromatography to give 13-15 (3.2 g, 5.2 mmol, 93.66% yield) as a white solid. $^1$H-NMR (400 MHz, DMSO-d$_6$): δ=11.37 (d, J=2.4 Hz, 1H, exchanged with D$_2$O), 7.91 (d, J=8.0 Hz, 1H), 7.50-7.48 (m, 4H), 7.39-7.36 (m, 2H), 7.29 (t, J=7.6 Hz, 4H), 7.22-7.18 (m, 2H), 6.86 (d, J=8.8 Hz, 2H), 6.19 (d, J=6.0 Hz, 1H), 5.67 (dd, J=2.0, 8.0 Hz, 1H), 5.16 (t, J=4.8 Hz, 1H), 4.28 (t, J=5.6 Hz, 1H), 3.78 (dd, J=7.6, 12.8 Hz, 2H), 3.73 (s, 3H), 3.38 (s, 3H), 3.31-3.26 (m, 4H), 3.06-3.01 (m, 1H). $^{19}$F-NMR (376 MHz, DMSO-d6): −73.96, −74.34, −78.81, −79.20. ESI-LCMS: m/z 610 [M+H]$^+$.

Preparation of (13-16): A solution of 13-15 (1.5 g, 2.4 mmol) and DCI (145 mg, 1.2 mmol) in dry DCM (30 mL) was added CEP[N(iPr)$_2$]$_2$ (816 mg, 2.7 mmol) under Ar. The mixture was stirred at r.t. for 1 h. The reaction was washed with 10% NaHCO$_3$ (aq.) and brine, dried over Na$_2$SO$_4$ and concentrated to obtain the crude product which was purified by column chromatography. This resulted in to give 13-16 (1.5 g, 1.8 mmol, 75.28% yield) as a white solid. $^1$H-NMR (400 MHz, DMSO-d$_6$): δ=11.41 (s, 1H), 7.64 (dd, J=8.0, 41.6 Hz, 1H), 7.51-7.47 (m, 4H), 7.38-7.36 (m, 2H), 7.29 (t, J=7.6 Hz, 4H), 7.20 (t, J=7.2 Hz, 2H), 6.86 (dd, J=3.6, 8.8 Hz, 2H), 6.14 (dd, J=6.8, 106.8 Hz, 1H), 5.69 (dd, J=8.0, 66.4 Hz, 1H), 3.82-3.63 (m, 7H), 3.61-3.42 (m, 5H), 3.39-3.28 (m, 7H), 3.20-2.93 (m, 1H), 2.75-2.72 (m, 1H), 2.68-2.64 (m, 1H), 1.10 (dd, J=4.8, 6.8 Hz, 6H), 1.00 (dd, J=6.4, 36.4 Hz, 6H). $^{31}$P-NMR (162 MHz, DMSO-d$_6$): 148.37, 147.75. $^{19}$F-NMR (376 MHz, DMSO-d6): −73.87, −74.25, −74.62, −78.45, −78.83, −78.99, −79.37. ESI-LCMS: m/z 808 [M−H]$^-$.

Example 10

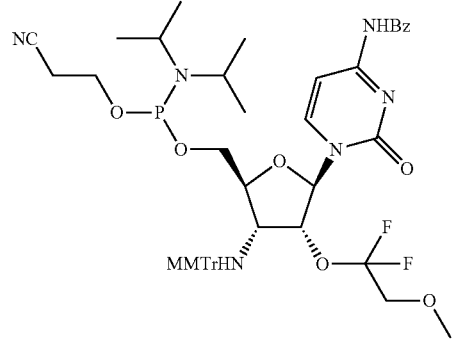

Scheme 12

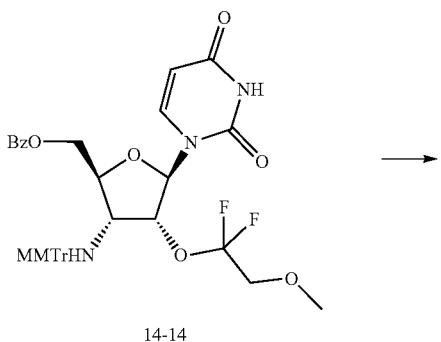

14-14

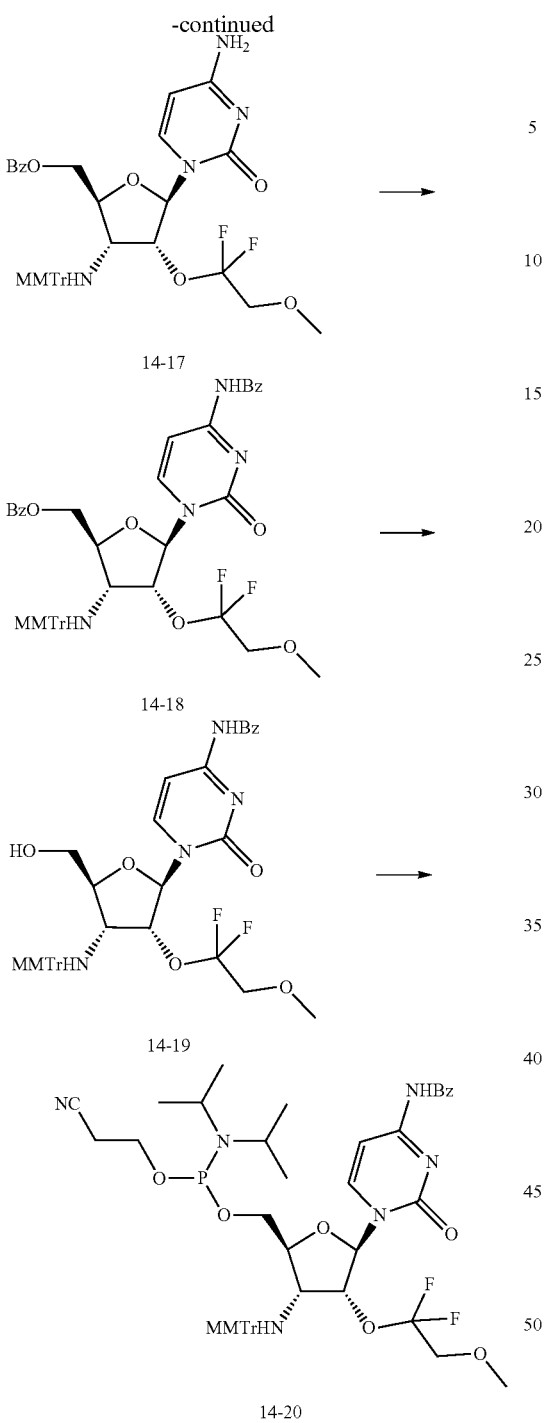

14-17

14-18

14-19

14-20

Preparation of Intermediate (14-17): A solution of 14-14 (7.1 g, 9.9 mmol), DMAP (2.4 g, 19.9 mmol) and TEA (2.0 g, 19.9 mmol, 2.77 mL) in dry ACN (100 mL) was added TIPSCl (4.5 g, 14.9 mmol). After the mixture was stirred at r.t. for 3 h, con.NH$_4$OH (30 mL) was added, and the reaction was stirred at r.t. for 6 h. Upon of completion, the solvent was removed, and the residue was dissolved in EA, washed with sat NH$_4$Cl (aq.) and brine, dried over anhydrous Na$_2$SO$_4$, concentrated to obtain a residue which was purified by column chromatography to give 14-17 (6.1 g, 8.5 mmol, 86.03% yield) as a white solid. ESI-LCMS: m/z 713 [M+H]$^+$.

Preparation of Intermediate (14-18): To a solution of 14-17 (5.1 g, 7.1 mmol) in pyridine (50 mL) at 0° C., was added BzCl (1.5 g, 10.7 mmol) dropwise. After the mixture was stirred for 1 h at r.t., 200 mL H$_2$O and 300 mL EA were added to separate the solution, the aqueous was extracted by EA, the combined organic layer was washed with brine, dried over Na$_2$SO$_4$, concentrated to obtain the crude product 14-18 (6.2 g) as a yellow oil. ESI-LCMS: m/z 817 [M+H]$^+$.

Preparation of Intermediate (14-19): A solution of the crude product 14-18 (6.2 g) in pyridine (60 mL) was added 2N NaOH (in MeOH:H$_2$O=4:1) (30 mL) dropwise at 0° C., the mixture was stirred at 0° C. for 15 min. Neutralized with saturated NH$_4$Cl (aq.) to give the pH=7-8, and 300 mL H$_2$O and 400 mL EA were added in to separate the solution, the aqueous was extracted by EA, the combined organic layer was washed with brine, dried over Na$_2$SO$_4$, concentrated to obtain the crude product which was purified by MPLC to give 14-19 (4.1 g, 5.7 mmol, 80.3% yield over two steps) as a white solid. $^1$H-NMR (400 MHz, DMSO-d$_6$): δ=11.30 (s, 1H, exchanged with D$_2$O), 8.47 (d, J=7.6 Hz, 1H), 8.02 (d, J=7.6 Hz, 2H), 7.63 (t, J=7.2 Hz, 1H), 7.54-7.45 (m, 6H), 7.35-7.25 (m, 7H), 7.19 (t, J=7.2 Hz, 2H), 6.83 (d, J=8.8 Hz, 2H), 6.10 (d, J=3.6 Hz, 1H), 5.19 (t, J=4.0 Hz, 1H), 3.77-3.70 (m, 6H), 3.64-3.61 (m, 2H), 3.46-3.43 (m, 1H), 3.35 (s, 3H), 3.31-3.26 (m, 1H), 3.03 (d, J=8.8 Hz, 1H, exchanged with D$_2$O). $^{19}$F-NMR (376 MHz, DMSO-d6): −73.47, −73.85, −78.26, −79.64. ESI-LCMS: m/z 713 [M+H]$^+$.

Preparation of (14-20): A solution of 14-19 (1.7 g, 2.3 mmol) and DCI (170 mg, 1.1 mmol) in dry DCM (20 mL) was added CEP[N(iPr)$_2$]$_2$ (790 mg, 2.6 mmol) under Ar. The mixture was stirred at r.t. for 1 h. The reaction was washed with 10% NaHCO$_3$ (aq.) and brine, dried over Na$_2$SO$_4$ and concentrated to obtain the crude product which was purified by column chromatography. This resulted in to give 14-20 (1.8 g, 1.9 mmol, 82.7% yield) as a white solid. $^1$H-NMR (400 MHz, DMSO-d$_6$): δ=11.35 (s, 1H), 8.20 (dd, J=8.0, 81.6 Hz, 1H), 8.03-8.00 (m, 2H), 7.64 (t, J=7.6 Hz, 1H), 7.54-7.44 (m, 6H), 7.37-7.16 (m, 9H), 6.82 (dd, J=9.2, 16.4 Hz, 2H), 6.14 (dd, J=4.8, 90.4 Hz, 1H), 4.15-4.02 (m, 1H), 3.90-3.40 (m, 11H), 3.36-3.24 (m, 6H), 3.12-2.98 (m, 1H), 2.77-2.73 (m, 2H), 1.13 (d, J=6.8 Hz, 6H), 1.05 (dd, J=6.8, 28.0 Hz, 6H). $^{31}$P-NMR (162 MHz, DMSO-d$_6$): 148.20, 147.96. $^{19}$F-NMR (376 MHz, DMSO-d6): −73.36, −73.74, −73.98, −74.36, −77.89, −78.28, −78.55, −78.94. ESI-LCMS: m/z 913 [M+H]$^+$.

Example 11

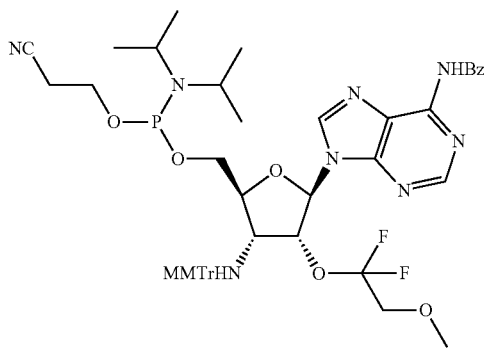

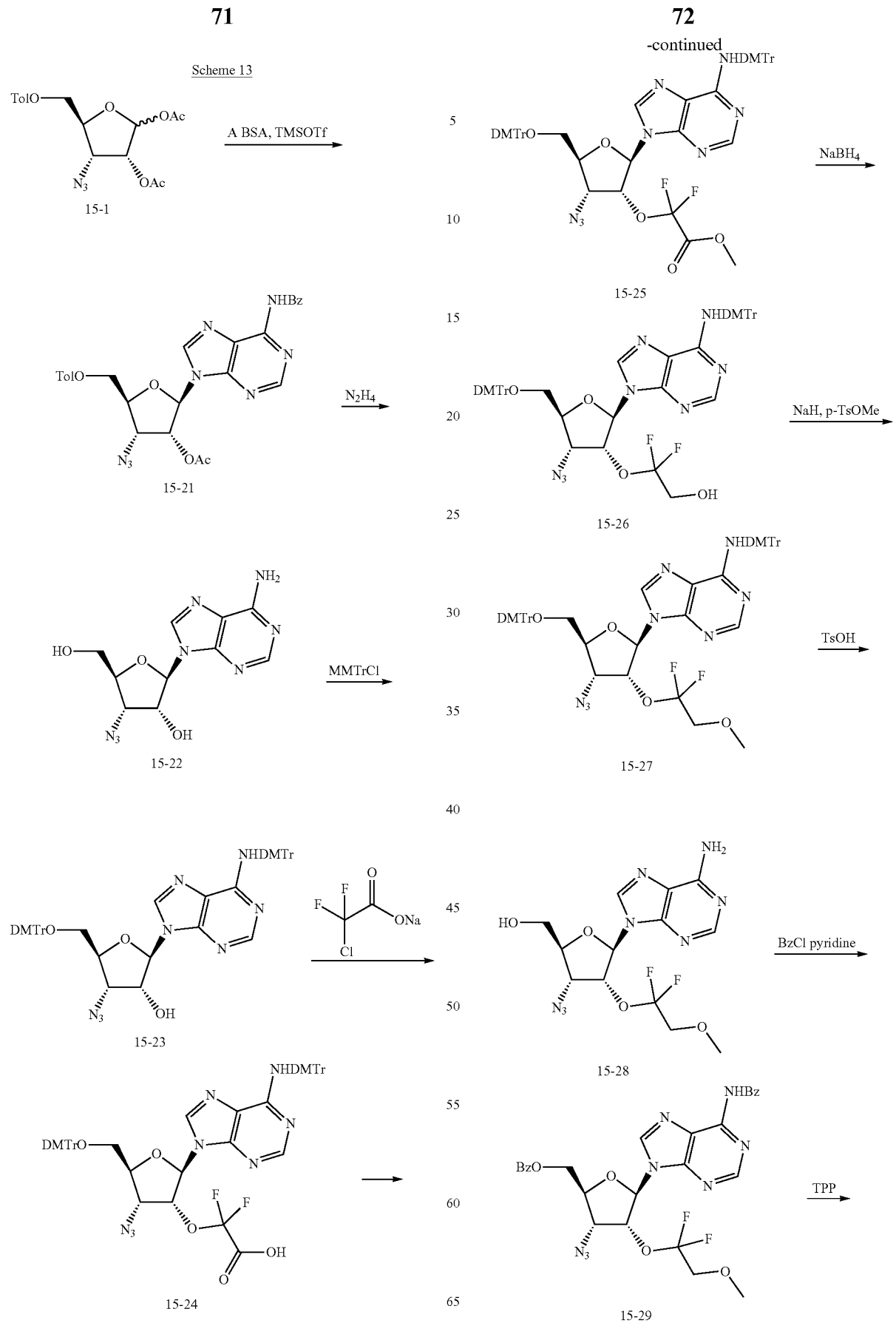

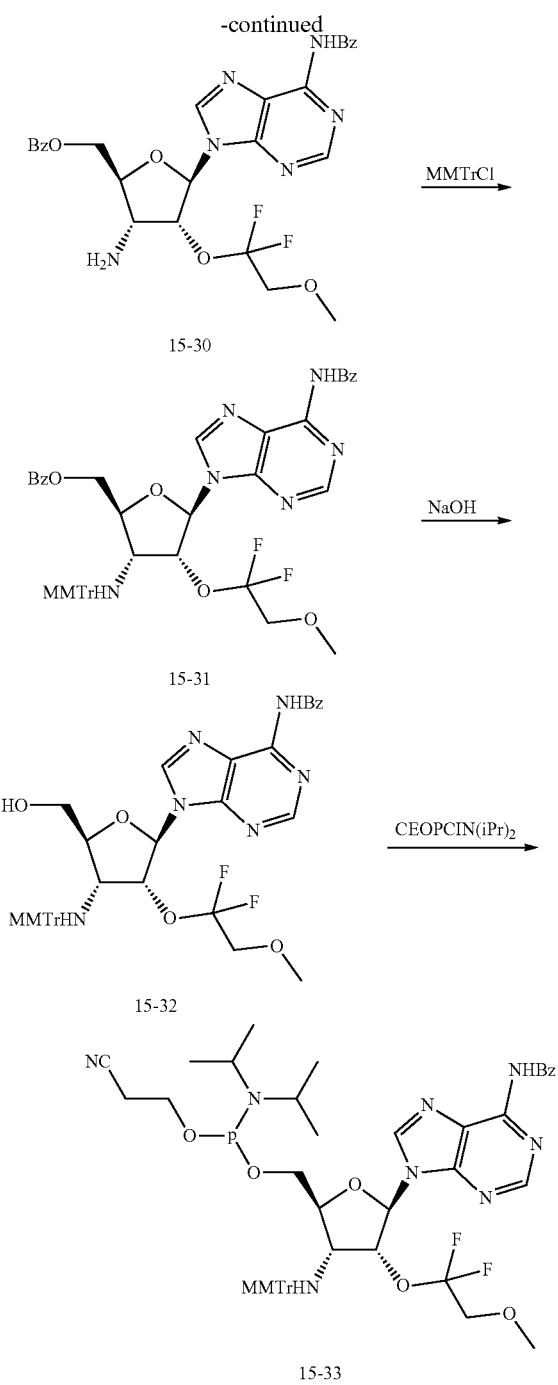

15-30

15-31

15-32

15-33

Preparation of Intermediate (15-21): To a solution of compound 15-1 (90 g, 238.5 mmol) in dry Acetonitrile (900 mL) was added N-(5H-Purin-6-yl)benzamide (85.6 g, 357.7 mmol) and BSA (155.3 g, 763.2 mmol). The resulting suspension was stirred at 50° C. for 30 min. Then the mixture was at −5° C. and TMSOTf (79.5 g, 357.8 mmol) was added by syringe. Then the mixture stirred at 80° C. for 72 h under $N_2$. The mixture was cooled and concentrated. And then added water and extracted with EA. The extract was washed with brine, dried over $Na_2SO_4$, and concentrated to give the residue which was purified by column chromatography to afford 15-21 (120 g, 215.62 mmol, 90.4% yield) as a yellow solid. $^1$H-NMR (400 MHz, DMSO-$d_6$): δ=8.56 (s, 1H), 8.53 (s, 1H), 8.00 (t, J=8.0 Hz, 2H), 7.76-7.74 (d, J=8.0 Hz, 2H), 7.64-7.60 (t, J=7.5 Hz, 1H), 7.54-7.50 (t, J=7.68 Hz, 2H), 7.27-7.25 (d, J=7.8 Hz, 2H), 6.31 (d, J=3.3 Hz, 1H), 6.14-6.11 (m, 1H), 5.05-5.01 (t, J=8.0 Hz, 1H), 4.67-4.63 (m, 1H), 4.53-4.49 (m, 1H), 4.37-4.34 (m, 1H), 2.31 (s, 3H), 2.12 (s, 3H). ESI-LCMS: m/z 556 [M+H]$^+$.

Preparation of Intermediate (15-22): To a solution of 15-21 (120 g, 215.6 mmol) and Methylamine (267.9 g, 8.6 mol) in Methanol (1300 mL) was stirred at r.t for 18 h under $N_2$. The mixture was concentrated and stirred at 25% EA in PET for 1 h to afford 15-22 (52 g, 1778.0 mmol, 82.5% yield) as a white solid. $^1$H-NMR (400 MHz, DMSO-$d_6$): δ=8.36 (s, 1H), 8.15 (s, 1H), 7.40 (s, 2H), 6.24-6.22 (d, J=8.0 Hz, 1H), 5.91-5.90 (d, J=4 Hz, 1H), 5.63-5.60 (m, 1H), 5.04-5.00 (m, 1H), 4.34-4.32 (m, 1H), 3.99-3.98 (d, J=4 Hz, 1H), 3.72-3.55 (m, 2H). ESI-LCMS: m/z 292 [M+H]$^+$.

Preparation of Intermediate (15-23): To a solution of 15-22 (50 g, 171.1 mmol) and DMTrCl (121.7 g, 359.3 mmol) in pyridine (250 mL) was stirred for 2 h at r.t. The mixture was quenched with water, extracted with EA, dried over $Na_2SO_4$, concentrated to give the residue which was purified by column chromatography to afford 15-23 (117 g, 130.4 mmol, 76.2% yield) as a yellow solid. $^1$H-NMR (400 MHz, DMSO-$d_6$): δ=8.29 (s, 1H), 7.76 (s, 1H), 7.20-7.12 (m, 19H), 6.74 (m, 8H), 5.87 (s, 1H), 5.08 (s, 1H), 4.39 (s, 1H), 3.62 (s, 12H), 3.32-3.10 (m, 2H). ESI-LCMS: m/z 896 [M+H]$^+$.

Preparation of Intermediate (15-24): To a solution of 15-23 (115 g, 128.2 mmol) and THF (800 mL) was stirred at 5° C. under $N_2$. NaH (4.0 g, 167.4 mmol) was slowly added below 10° C., and Sodium chlorodifluoroacetate (25.5 g, 167.4 mmol) and TBAI (5.6 g, 16.7 mmol) were added at 5° C. The reaction was refluxed for 18 h. Cooled to r.t., the reaction was quenched with saturated NH$_4$Cl (aq.) and extracted with EA, washed with brine, dried over $Na_2SO_4$, concentrated to give the residue which was purified by column chromatography to give 15-24 (56 g, 56.6 mmol, 48.3% yield) as a yellow crude solid. ESI-LCMS: m/z 990 [M+H]$^+$.

Preparation of Intermediate (15-25): To a solution of 15-24 (56 g, 57.3 mmol), methyl p-toluenesulfonate (15.8 g, 84.8 mmol) and $K_2CO_3$ (15.6 g, 113.0 mmol) in dry DMF (560 mL) was stirred at r.t. for 18 h under $N_2$. The mixture was quenched with water, extracted with EA, wash with brine and concentrated to obtain a residue which was purified by column chromatography to afford 15-25 (33 g, 32.8 mmol, 58.1% yield) as a white solid. $^1$H-NMR (400 MHz, DMSO-d6): δ=8.40 (s, 1H), δ=7.82 (s, 1H), 7.40 (s, 1H), 7.31-7.16 (m, 18H), 6.82-6.79 (m, 8H), 6.24-6.23 (d, J=4.0 Hz, 1H), 6.00-5.99 (t, 1H), 4.88-4.85 (t, 1H), 4.17-4.14 (m, 1H), 3.79 (s, 3H), 3.68 (s, 12H), 3.31-3.30 (m, 2H). $^{19}$F-NMR (376 MHz, DMSO-d6): −75.75, −76.14, −76.89, −77.28. ESI-LCMS: m/z 1004 [M+H]$^+$.

Preparation of Intermediate (15-26): To a solution of 15-25 (30 g, 29.9 mmol) in THF (300 mL) was added NaBH$_4$ (1.7 g, 44.8 mmol) and EtOH (100 mL) at 5° C. The mixture was allowed to stir at r.t. for 1.5 h, and quenched with sat NH$_4$Cl (aq.), extracted with EA, washed with brine, dried over $Na_2SO_4$, concentrated to obtain a residue which was purified by column chromatography to afford 15-26 (22 g, 22.5 mmol, 75.4% yield) as a yellow solid. $^1$H-NMR (400 MHz, DMSO-$d_6$): δ=8.35 (s, 1H), 7.79 (s, 1H), 7.26-7.13 (m, 21H), 6.77-6.75 (m, 9H), 6.14-6.13 (d, J=4.0 Hz, 1H), 5.90 (t, 1H), 4.74-4.72 (t, 1H), 4.11 (s, 1H), 3.63 (s, 12H), 3.28-3.25 (m, 2H). $^{19}$F-NMR (376 MHz, DMSO-d6): −79.94, −80.31, −80.77, −81.15. ESI-LCMS: m/z 976 [M+H]$^+$.

Preparation of Intermediate (15-27): To a solution of 15-26 (20 g, 20.5 mmol) in THF (100 mL) were added NaH (491.7 mg, 20.5 mmol) and Methyl p-toluenesulfonate (11.4 g, 61.5 mmol) at 5° C. The mixture was allowed to stir at r.t. for 3 h, and was poured into cold water, extracted with EA, washed with brine, dried over Na$_2$SO$_4$, concentrated to obtain a residue which was purified by column chromatography to afford 15-27 (16.5 g, 16.7 mmol, 81.3% yield) as a yellow solid. $^1$H-NMR (400 MHz, DMSO-d$_6$): δ=8.40 (s, 1H), 7.86 (s, 1H), 7.37-7.30 (m, 4H), 7.28-7.26 (m, 5H), 7.24-7.18 (m, 12H), 6.84-6.81 (m, 8H), 6.17-6.16 (d, J=4.0 Hz, 1H), 5.92-5.89 (t, 1H), 4.79-4.76 (t, 1H), 4.15-4.11 (m, 1H), 3.70 (s, 12H), 3.31 (s, 5H). $^{19}$F-NMR (376 MHz, DMSO-d6): −76.83, −77.22, −78.05, −78.43. ESI-LCMS: m/z 990 [M+H]$^+$.

Preparation of Intermediate (15-28): To a solution of 15-27 (15.5 g, 15.6 mmol) in DCM (155 mL) was added a solution of TsOH (6.2 g, 36.0 mmol) in MeOH (30 mL). The mixture was stirred at r.t. for 0.5 h, and washed with saturated NaHCO$_3$ to pH=7-8, extracted with EA, dried over Na$_2$SO$_4$, concentrated to obtain a residue which was purified by column chromatography to give 15-28 (4.6 g, 11.4 mmol, 72.8% yield) as a white solid. ESI-LCMS: m/z 386 [M+H]$^+$.

Preparation of Intermediate (15-29): To a solution of 15-28 (4.4 g, 11.3 mmol) in pyridine (40 mL) was slowly added BzCl (8.0 g, 56.7 mmol) at 5° C. The mixture was allowed to stir at r.t. for 2 h, and quenched with little water, ammonium hydroxide was slowly added at 4° C. until intermediate product was disappeared. The mixture was extracted with EA, washed with brine, dried over Na$_2$SO$_4$, concentrated to obtain a crude product which was purified by column chromatography. This resulted in to give 15-29 (6.0 g, 10.1 mmol, 89.1% yield) as a white solid. $^1$H-NMR (400 MHz, DMSO-d$_6$): δ=8.67-8.66 (t, 1H), 8.47-8.44 (t, 1H), 8.02-7.97 (m, 4H), 7.69-7.62 (m, 2H), 7.56-7.52 (m, 4H), 6.32-6.31 (d, J=4.0 Hz, 1H), 6.09-6.06 (m, 1H), 5.00-4.98 (m, 1H), 4.71-4.67 (m, 1H), 4.58-4.54 (m, 1H), 4.43-4.41 (m, 1H), 3.77-3.72 (m, 2H), 3.31 (m, 3H). $^{19}$F-NMR (376 MHz, DMSO-d6): −76.97, −77.35, −78.19, −78.57. ESI-LCMS: m/z 594 [M+H]$^+$.

Preparation of Intermediate (15-30): To a solution of 15-29 (6.0 g, 10.1 mmol) in THF (70 mL) was added PPh$_3$ (4.0 g, 15.1 mmol) and water (1.8 g, 100.9 mmol) under N$_2$. The mixture was stirred at 45° C. for 15 h, poured into cold water, adjusted to pH=1-2 by 2N HCl (aq.), extracted with EA. Then the aqueous phase was adjusted to pH=7-8 with saturated NaHCO$_3$ (aq.), extracted with EA, washed with brine, dried over Na$_2$SO$_4$, concentrated to afford 15-30 (5.5 g, 9.7 mmol, 95.9% yield) as a white solid. $^1$H-NMR (400 MHz, DMSO-d$_6$): δ=8.67 (s, 2H), 8.03-8.01 (m, 2H), 7.88-7.86 (m, 2H), 7.65-7.61 (m, 2H), 7.56-6.46 (m, 5H), 6.30-6.29 (d, J=4.0 Hz, 1H), 5.42-5.40 (m, 1H), 4.69-4.66 (m, 1H), 4.51-4.47 (m, 1H), 4.08-4.09 (m, 2H), 3.87-3.80 (m, 2H), 3.46 (s, 5H). $^{19}$F-NMR (376 MHz, DMSO-d6): −75.65, −76.03, −77.47, −77.86. ESI-LCMS: m/z 568 [M+H]$^+$.

Preparation of Intermediate (15-31): To a solution of 15-30 (5.5 g, 9.6 mmol) in dry DCM (55 mL) was added MMTrCl (4.5 g, 14.5 mmol) and TEA (2.0 g, 19.3 mmol) under N$_2$. The mixture was allowed to stir at r.t. for 1.0 h, and quenched with water, extracted with DCM, washed with brine, dried over Na$_2$SO$_4$, concentrated to obtain a residue which was purified by column chromatography to afford 15-31 (7.3 g, 8.7 mmol, 89.8% yield) as a yellow solid. $^1$H-NMR (400 MHz, DMSO-d$_6$): δ=8.46 (s, 1H), 8.41 (s, 1H), 8.00-7.98 (d, J=8.0 Hz, 2H), 7.62-7.44 (m, 12H), 7.38-7.34 (m, 4H), 7.17-7.12 (m, 4H), 7.06-7.01 (m, 2H), 6.67-6.65 (d, J=8.0 Hz, 2H), 6.17 (s, 1H), 4.57-4.54 (d, J=12 Hz, 1H), 4.35-4.18 (m, 4H), 3.70-3.65 (m, 2H), 3.50 (s, 3H), 3.31 (s, 3H). $^{19}$F-NMR (376 MHz, DMSO-d6): −73.61, −74.00, −77.94, −78.32. ESI-LCMS: m/z 840 [M+H]$^+$.

Preparation of Intermediate (15-32): To a solution of 15-31 (7.2 g, 8.5 mmol) in pyridine (70 mL) was slowly added 2N NaOH (aq.) (510.0 mg, 10.3 mmol) at 5-10° C., The mixture was allow to stir at r.t. for 10 min, neutralized with sat NH$_4$Cl (aq.) to pH 7-8, extracted with EA, washed with brine, dried over Na$_2$SO$_4$, concentrated to obtain a crude product which was purified by column chromatography. This resulted in to give 15-32 (5.8 g, 7.9 mmol, 92.2% yield) as a white solid. $^1$H-NMR (400 MHz, DMSO-d$_6$): δ=8.63 (s, 2H), 7.99-7.97 (d, J=8.0 Hz, 2H), 7.64-7.60 (m, 1H), 7.54-7.50 (m, 2H), 7.42-7.38 (m, 4H), 7.27-7.25 (d, J=8.0 Hz, 2H), 7.21-7.16 (m, 4H), 7.12-7.09 (m, 2H), 6.72-6.70 (d, J=8.0 Hz, 2H), 6.28-6.27 (d, J=8.0 Hz, 1H), 5.59 (m, 1H), 3.96 (s, 4H), 3.76-3.74 (m, 1H), 3.68-3.63 (m, 2H), 3.60 (s, 3H), 3.47-3.41 (m, 2H), 3.27 (s, 3H). $^{19}$F-NMR (376 MHz, DMSO-d6): −74.13, −74.51, −78.09, −78.47. ESI-LCMS: m/z 736 [M+H]$^+$.

Preparation of (15-33): To a solution of 15-32 (3 g, 4.1 mmol) and DCI (240.4 mg, 2.0 mmol) in dry DCM (30 mL) was added CEP[N(iPr)$_2$]$_2$ (1.5 g, 4.9 mmol) under N$_2$. The mixture was allowed to stir at r.t. for 1 h, quenched with sat NaHCO$_3$, washed with brine, dried over Na$_2$SO$_4$, concentrated to obtain a crude product which was purified by column chromatography. This resulted in to give 15-33 (3.1 g, 3.3 mmol, 81.2% yield) as a white solid. $^1$H-NMR (400 MHz, DMSO-d$_6$): δ=11.20 (s, 1H), 8.69-8.68 (d, J=4.0 Hz, 1H), 8.50-8.48 (d, J=8.0 Hz, 1H), 8.05-8.03 (m, 2H), 7.66-7.62 (m, 1H), 7.57-7.45 (m, 6H), 7.40-7.33 (m, 2H), 7.30-7.11 (m, 6H), 6.85-6.76 (m, 2H), 6.45-6.30 (m, 1H), 4.77-4.74 (m, 0.5H), 4.00-3.99 (m, 0.5H), 3.86-3.84 (m, 0.5H), 3.77-3.70 (m, 5H), 3.67-3.59 (m, 4H), 3.56-3.51 (m, 1H), 3.50-3.34 (m, 3H), 3.32 (s, 3H), 3.08-3.06 (m, 0.5H), 2.77-2.65 (m, 2H), 1.08-0.99 (m, 12H). $^{19}$F-NMR (376 MHz, DMSO-d6): −73.92, −74.27, −74.30, −74.65, −77.64, −78.03, −78.55, 78.93. ESI-LCMS: m/z 936 [M+H]$^+$.

Example 12

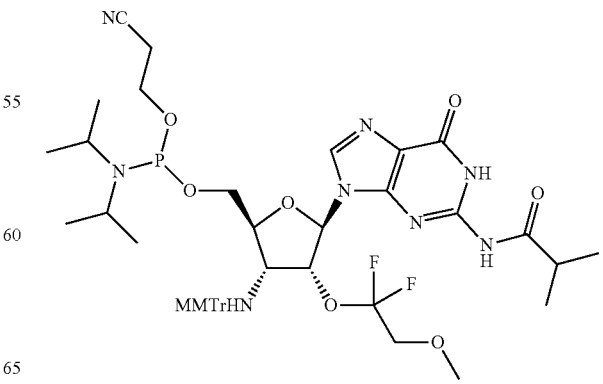

Scheme 14
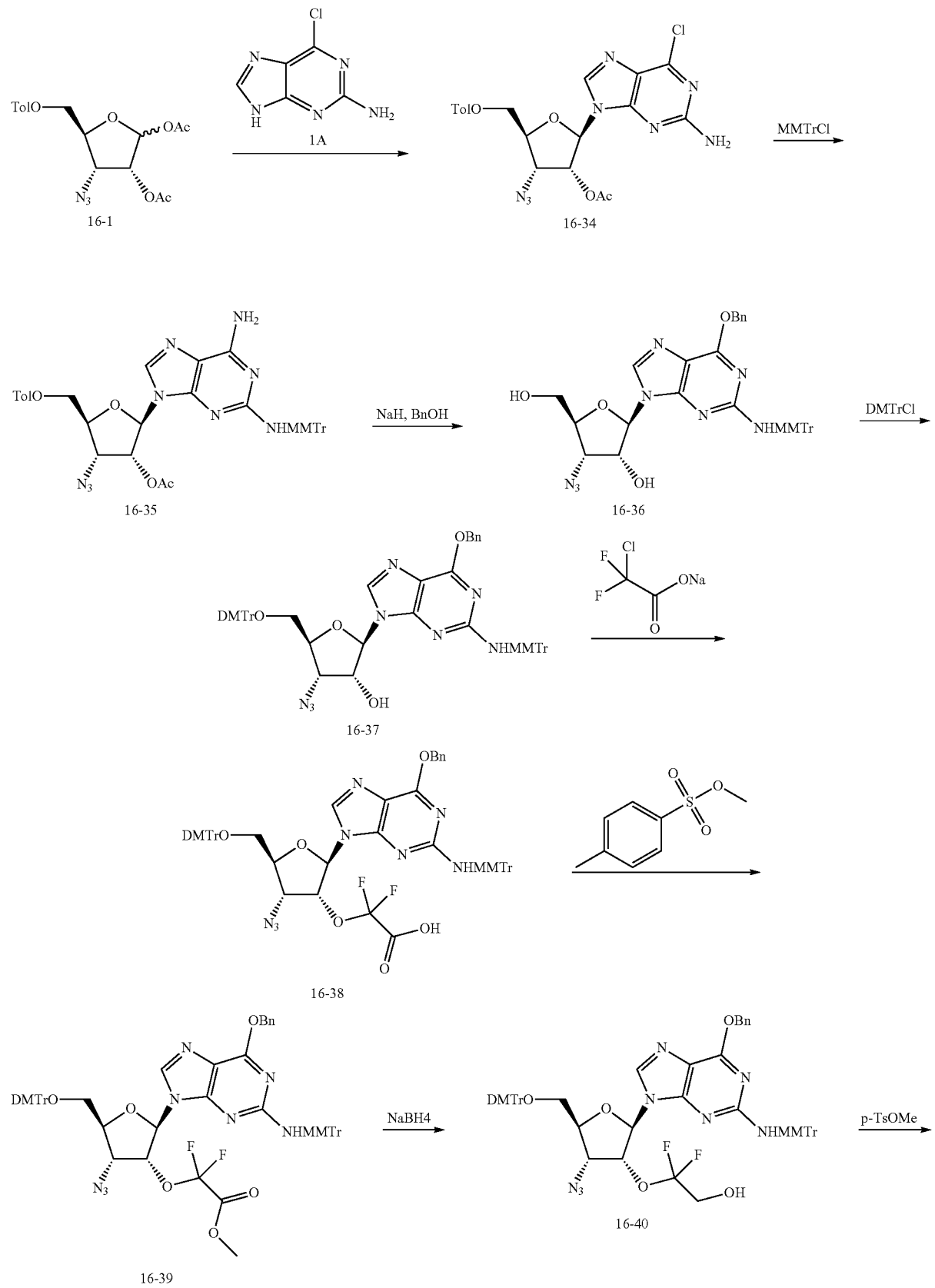

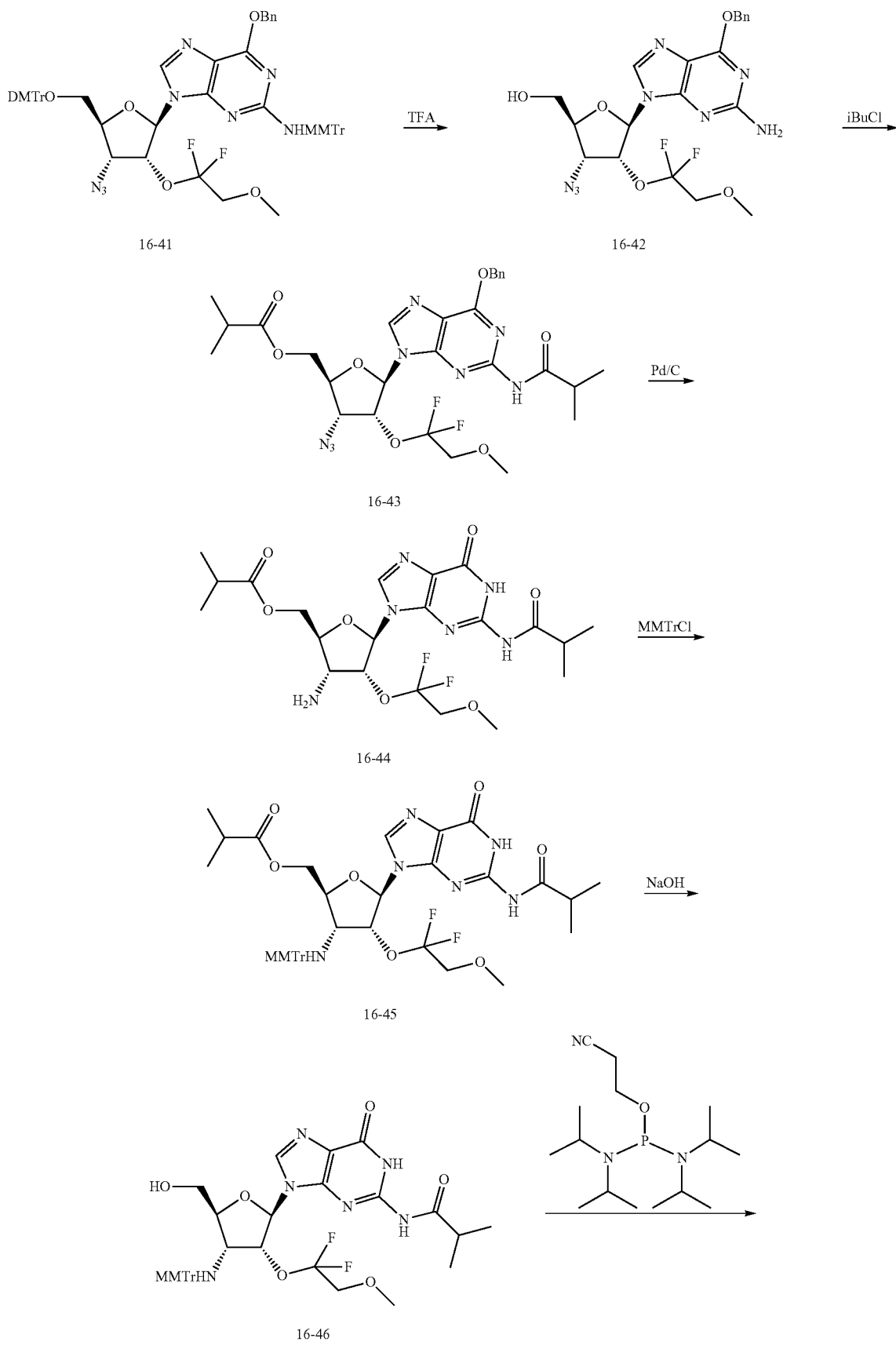

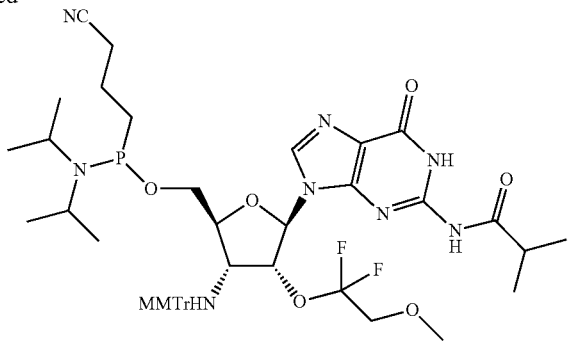

16-47

Preparation of Intermediate (16-34): A solution of 16-1 (150.0 g, 397.5 mmol) and 6-Chloroguanine (101.1 g, 596.3 mmol) in dry ACN (1.5 L) was added BSA (259.5 g, 1.27 mol) under Ar. The resulting suspension was stirred at 50° C. for 1 h. Then the mixture was cooled at −5° C. and TMSOTf (590.5 g, 2.66 mol) was added by syringe. After that the mixture was stirred at 60° C. for 5 h, concentrated to remove ACN and the residue was dissolved in LA (2.0 L), washed with sat NaHCO$_3$(aq.) and brine, dried over Na$_2$SO$_4$, concentrated to give the crude product 16-34 (265.0 g) as a yellow solid. ESI-LCMS: m/z 487 [M+H]$^+$.

Preparation of Intermediate (16-35): A solution of 16-34 (crude, 265 g, 353.8 mmol) and TEA (107.4 g, 1.06 mol, 148 mL) in DCM (2.5 L) was added MMTrCl (164.0 g, 530.7 mmol) and DMAP (8.6 g, 70.8 mmol), the mixture was stirred at r.t. for 5 h, washed with water and brine, dried over Na$_2$SO$_4$, concentrated to obtain the residue which was purified by column chromatography to give 16-35 (160.0 g, 210.8 mmol, 53.0% yield over 2 steps) as a yellow solid. ESI-LCMS: m/z 759 [M+H]$^+$.

Preparation of Intermediate (16-36): To a solution of 35 (20.0 g, 26.39 mmol) in Benzyl alcohol (200 mL) was added NaH (5.3 g, 131.93 mmol) at 0° C. The resulting mixture was allowed to stir at r.t. for 2 h, quenched with cold water, extracted with EA, washed with water and brine, dried over Na$_2$SO$_4$, concentrated to obtain a residue which was purified by column chromatography to give 16-36 (11.2 g, 16.72 mmol, 63.1% yield) as white solid. ESI-LCMS: m/z 671 [M+H]$^+$.

Preparation of Intermediate (16-37): A solution of 16-36 (49.0 g, 73.1 mmol) and pyridine (28.9 g, 365.3 mmol, 29 mL) in DCM (500 mL) was added DMTrCl (27.2 g, 80.4 mmol) at r.t. The mixture was stirred at r.t. for 3 h, washed with water and brine, dried over Na$_2$SO$_4$, concentrated to obtained a residue which was purified by column chromatography to give 16-37 (58.9 g, 60.6 mmol, 82.9% yield) as a white solid. ESI-LCMS: m/z 973 [M+H]$^+$.

Preparation of Intermediate (16-38): A solution of 16-37 (58.9 g, 60.6 mmol) in dry THF (300 mL) were added NaH (5.1 g, 127.8 mmol, 60% purity) and Methyl p-toluenesulfonate (19.5 g, 127.8 mmol) at 0° C., the mixture was allowed to stirred at r.t., and TBAI (4.7 g, 12.8 mmol) was added. After that the mixture was stirred at 80° C. for 24 h, and quenched with sat NH$_4$Cl(aq.), extracted with EA, washed with brine, dried over Na$_2$SO$_4$, concentrated to obtain a residue which was purified by column chromatography to give the crude product 16-38 (30.9 g) as a blank solid. ESI-LCMS: m/z 1067 [M+H]$^+$.

Preparation of Intermediate (16-39): A solution of the crude 16-38 (30.9 g) and K$_2$CO$_3$ (8.0 g, 58.1 mmol) in DMF (200 mL) was added Sodium chlorodifluoroacetate (5.4 g, 29.1 mmol) at r.t. The mixture was stirred at r.t. for 15 h, quenched with sat NH$_4$Cl(aq.), extracted with EA, washed with brine, dried over Na$_2$SO$_4$, concentrated to obtain a residue which was purified by column chromatography to give 16-39 (9.8 g, 9.1 mmol, 15.0% yield over 2 steps) as a yellow solid. ESI-LCMS: m/z 1081 [M+H]$^+$.

Preparation of Intermediate (16-40): A solution of 16-39 (9.3 g, 8.6 mmol) in THF (180 mL) was added NaBH$_4$ (488 mg, 12.9 mmol) and EtOH (15 mL) at 0° C. The mixture was stirred at 0° C. for 1 h, quenched with sat NH$_4$Cl (aq.), extracted with EA, washed with brine, dried over Na$_2$SO$_4$, concentrated to obtain a residue which was purified by column chromatography. This resulted in to give 16-40 (8.5 g, 7.0 mmol, 81.63% yield, 87% purity) as a white solid. ESI-LCMS: m/z 1053 [M+H]$^+$.

Preparation of Intermediate (16-41): A solution of 16-40 (8.3 g, 7.9 mmol) in THF (80 mL) was added NaH (472 mg, 11.8 mmol, 60% purity) and Methyl p-toluenesulfonate (2.9 g, 15.8 mmol) at 0° C. The mixture was allowed to stir at r.t. for 15 h, and poured into cold water, extracted with EA, washed with brine, dried over Na$_2$SO$_4$, concentrated to obtained the crude product 16-41 (9.1 g) as a yellow oil. ESI-LCMS: m/z 1067 [M+H]$^+$.

Preparation of Intermediate (16-42): A solution of crude 16-41 (9.1 g) in DCM (100 mL) was added a solution of p-TsOH (10 g) in MeOH (10 mL). The mixture was stirred at r.t. for 0.5 h, and neutralized with TEA to give pH=7, concentrated to obtain a residue which was purified by column chromatography. This resulted in to give 16-42 (3.2 g, 6.5 mmol, 82.3% yield over 2 steps) as a yellow solid. $^1$H-NMR (400 MHz, DMSO-d$_6$): δ=8.14 (s, 1H), 7.52-7.50 (m, 2H), 7.42-7.33 (m, 3H), 6.62 (s, 2H, exchanged with D$_2$O), 6.01 (d, J=6.4 Hz, 1H), 5.62 (t, J=6.0 Hz, 1H), 5.49 (t, J=12.8 Hz, 2H), 5.39 (t, J=5.6 Hz, 1H, exchanged with D$_2$O), 4.64 (dd, J=3.6, 5.6 Hz, 1H), 4.02 (dd, J=3.6, 7.2 Hz, 1H), 3.74-3.66 (m, 3H), 3.64-3.59 (m, 1H), 3.32 (s, 3H). $^{19}$F-NMR (376 MHz, DMSO-d6): −77.52, −77.91, −78.17, −78.55). ESI-LCMS: m/z 493 [M+H]$^+$.

Preparation of Intermediate (16-43): A solution of 16-42 (3.2 g, 6.5 mmol) in pyridine (30 mL) was added i-BuCl (2.1 g, 19.5 mmol) drop wise at 0° C. The mixture was stirred at 0° C. for 1 h, quenched with MeOH and concentrated to obtain a residue which was purified by column chromatography. This resulted in to give 16-43 (3.2 g, 5.5 mmol, 84.59% yield) as a yellow oil. $^1$H-NMR (400 MHz, DMSO-d$_6$): δ=10.60 (s, 1H, exchanged with D$_2$O), 8.42 (s, 1H), 7.57-7.54 (m, 2H), 7.44-7.35 (m, 3H), 6.20 (d, J=2.8 Hz, 1H), 5.71 (dd, J=2.4, 5.6 Hz, 1H), 5.68-5.64 (m, 3H), 4.41 (dd, J=3.6, 12.0 Hz, 1H), 4.24 (dd, J=5.6, 12.0 Hz, 1H), 4.19-4.15 (m, 1H), 3.80 (t, J=10.4 Hz, 2H), 3.38 (s, 3H), 3.35 (s, 3H), 2.45-2.38 (m, 1H), 1.12 (dd, J=2.4, 6.8 Hz, 6H), 0.97 (dd, J=6.8, 16.4 Hz, 6H). $^{19}$F-NMR (376 MHz, DMSO-d6): −76.48, −76.87, −77.62, −78.01). ESI-LCMS: m/z 633 [M+H]$^+$.

Preparation of Intermediate (16-44): A solution of 16-43 (1.6 g, 2.5 mmol) in THF (20 mL) was added Pd/C (200 mg), the mixture was stirred at r.t. for 5 h under H$_2$. The reaction was filtered and the filtrate was concentrated to give 16-44 (1.2 g, 2.3 mmol, 91.86% yield) as a white solid. $^1$H-NMR (400 MHz, DMSO-d$_6$): δ=11.60 (s, 1H, exchanged with D$_2$O), 8.22 (s, 1H), 6.05 (d, J=2.8 Hz, 1H), 5.14 (dd, J=3.2, 5.6 Hz, 1H), 4.40 (dd, J=2.4, 12.0 Hz, 1H), 4.17 (dd, J=5.6, 12.0 Hz, 1H), 3.93-3.73 (m, 4H), 3.38 (s, 3H), 1.14 (d, J=7.2 Hz, 6H), 1.04 (dd, J=7.2, 12.4 Hz, 6H). $^{19}$F-NMR (376 MHz, DMSO-d6): −75.73, −76.12, −77.46, −77.84). ESI-LCMS: m/z 517 [M+H]$^+$.

Preparation of Intermediate (16-45): A solution of 16-44 (3.0 g, 5.8 mmol) and collidine (1.8 g, 14.5 mmol) in DCM (40 mL) was added MMTrCl (2.7 g, 8.7 mmol) and AgNO$_3$ (986 mg, 5.8 mmol), the mixture was stirred at r.t. for 1 h, filtered and the filtrate was washed with water and dried over anhydrous Na$_2$SO$_4$, concentrated to obtain a residue which was purified by column chromatography to give 16-45 (3.8 g, 4.8 mmol, 82.94% yield) as a white solid. $^1$H-NMR (400 MHz, DMSO-d$_6$): δ=12.16 (s, 1H, exchanged with D$_2$O), 11.48 (s, 1H, exchanged with D$_2$O), 7.86 (s, 1H), 7.50 (dd, J=5.2, 7.2 Hz, 4H), 7.37 (d, J=8.8 Hz, 2H), 7.28 (t, J=7.2 Hz, 4H), 7.20 (t, J=7.2 Hz, 2H), 6.83 (d, J=9.2 Hz, 2H), 6.11 (d, J=3.2 Hz, 1H), 4.18 (dd, J=5.2, 8.8 Hz, 1H), 4.08 (t, J=4.4 Hz, 1H), 4.44-3.97 (m, 1H), 3.74 (dd, J=7.6, 10.4 Hz, 2H), 3.70 (s, 3H), 3.46-3.41 (m, 1H), 3.16 (d, J=8.0 Hz, 1H, exchanged with D$_2$O), 2.86-2.79 (m, 1H), 2.33-2.26 (m, 1H), 1.13 (t, J=7.2 Hz, 6H), 0.89 (dd, J=7.2, 14.8 Hz, 6H). $^{19}$F-NMR (376 MHz, DMSO-d6): −74.01, −74.39, −78.00, −78.38). ESI-LCMS: m/z 789 [M+H]$^+$.

Preparation of Intermediate (16-46): A solution of 16-45 (3.8 g, 4.8 mmol) in pyridine (40 mL) was added 2N NaOH (MeOH:H$_2$O=4:1) (15 mL) at 0° C., the mixture was stirred at 0° C. for 1 h. Then the reaction was neutralized with saturated NH$_4$Cl (aq) to pH=7-8, extracted with EA, washed with brine, dried over anhydrous Na$_2$SO$_4$, concentrated to obtain a residue which was purified by column chromatography. This resulted in to give 16-46 (3.0 g, 4.2 mmol, 87.50% yield) as a white solid. $^1$H-NMR (400 MHz, DMSO-d$_6$): δ=12.16 (s, 1H, exchanged with D$_2$O), 11.68 (s, 1H, exchanged with D$_2$O), 8.19 (s, 1H), 7.51 (dd, J=5.2, 7.2 Hz, 4H), 7.38 (d, J=8.8 Hz, 2H), 7.31 (t, J=7.2 Hz, 4H), 7.21 (t, J=7.2 Hz, 2H), 6.87 (d, J=8.8 Hz, 2H), 6.26 (d, J=6.0 Hz, 1H), 5.15 (t, J=4.4 Hz, 1H), 4.76 (t, J=6.0 Hz, 1H, exchanged with D$_2$O), 3.75-3.70 (m, 5H), 3.42 (d, J=2.4 Hz, 1H), 3.38-3.28 (m, 5H), 3.23 (d, J=6.4 Hz, 1H, exchanged with D$_2$O), 3.16-3.10 (m, 1H), 2.88-2.81 (m, 1H), 1.15 (dd, J=6.4, 7.2 Hz, 6H). $^{19}$F-NMR (376 MHz, DMSO-d6): −74.73, −75.12, −78.79, −79.17. ESI-LCMS: m/z 719 [M+H]$^+$.

Preparation of (16-47): A solution of 16-46 (3.0 g, 4.2 mmol) and DCI (394 mg, 3.3 mmol) in dry DCM (50 mL) was added CEP[N(iPr)$_2$]$_2$ (1.5 g, 5.0 mmol) under Ar. The mixture was stirred at r.t. for 1 h. The reaction was washed with 10% NaHCO$_3$ (aq) and water, dried over Na$_2$SO$_4$ and concentrated to obtain the crude product which was purified by column chromatography. This resulted in to give 16-47 (3.0 g, 3.2 mmol, 77.81% yield) as a white solid. $^1$H-NMR (400 MHz, DMSO-d$_6$): δ=12.13 (s, 1H), 11.65 (d, J=5.6 Hz, 1H), 8.11 (s, 0.35H), 7.95 (s, 0.65H), 7.50 (t, J=7.2 Hz, 4H), 7.38-7.26 (m, 6H), 7.20 (dd, J=8.4, 16.0 Hz, 2H), 6.88 (d, J=9.2 Hz, 0.7H), 6.82 (d, J=8.8 Hz, 1.3H), 6.31 (d, J=6.8 Hz, 0.35H), 6.14 (d, J=4.4 Hz, 0.65H), 4.97 (t, J=6.4 Hz, 0.35H), 3.97 (t, J=4.4 Hz, 0.65H), 3.82-3.54 (m, 9H), 3.48-3.14 (m, 9H), 2.86-2.69 (m, 2H), 1.24-0.92 (m, 18H). $^{31}$P-NMR (162 MHz, DMSO-d$_6$): 148.35, 148.24. ESI-LCMS: m/z 919 [M+H]$^+$.

Example 13

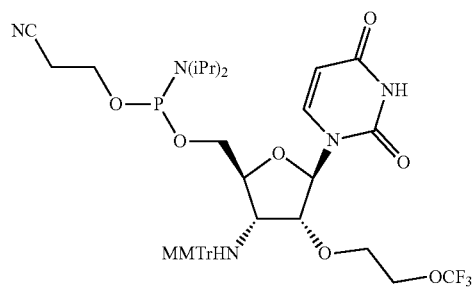

Scheme 15

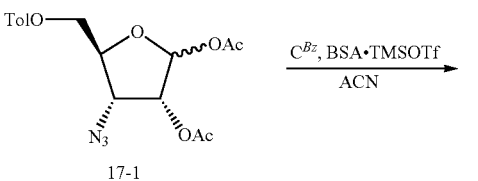

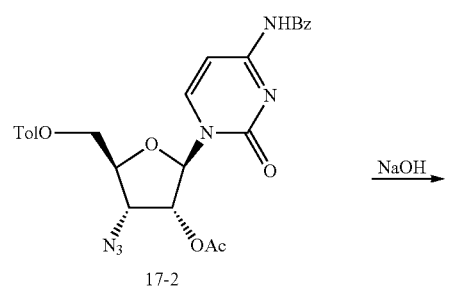

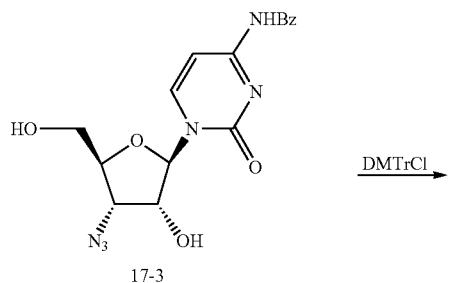

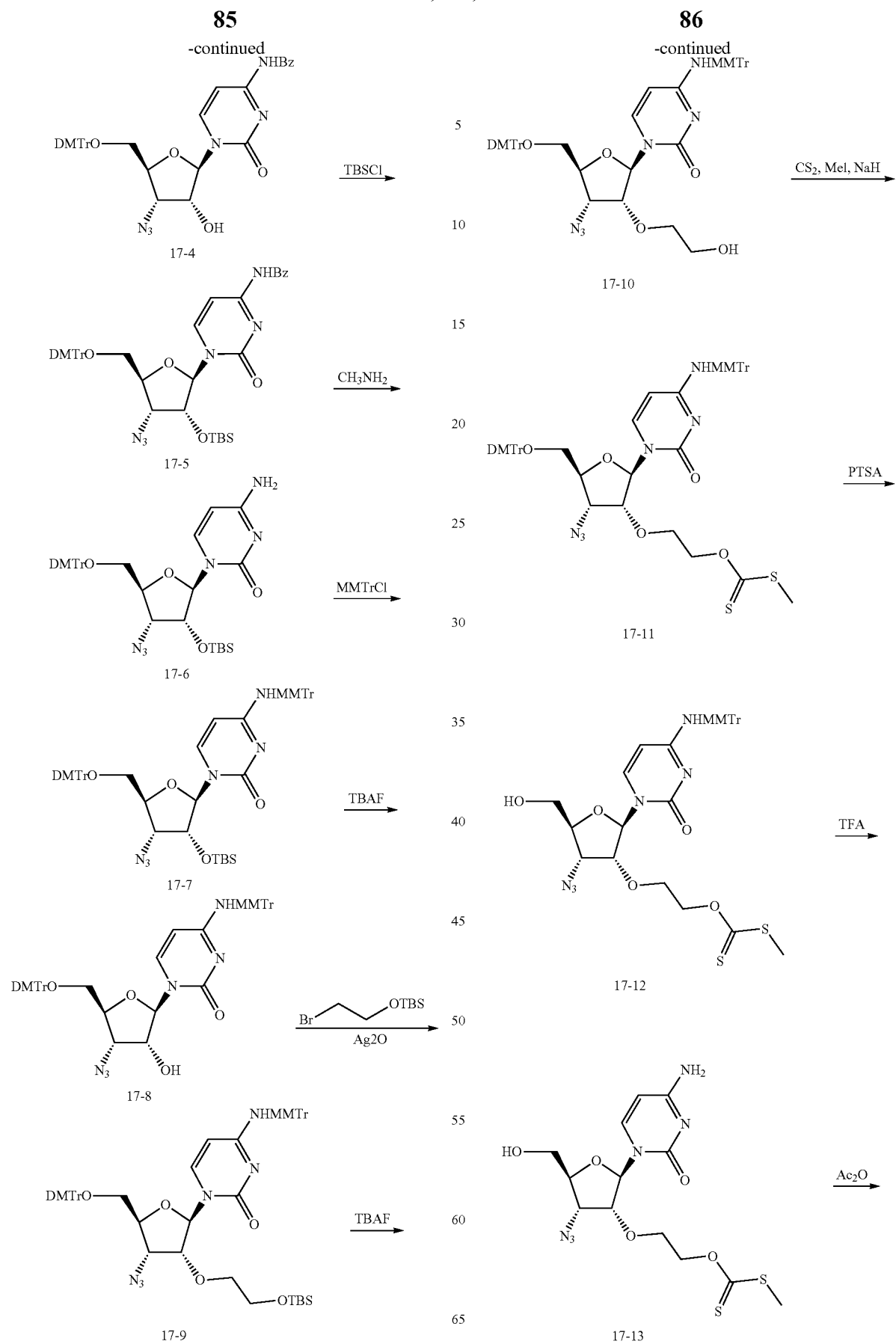

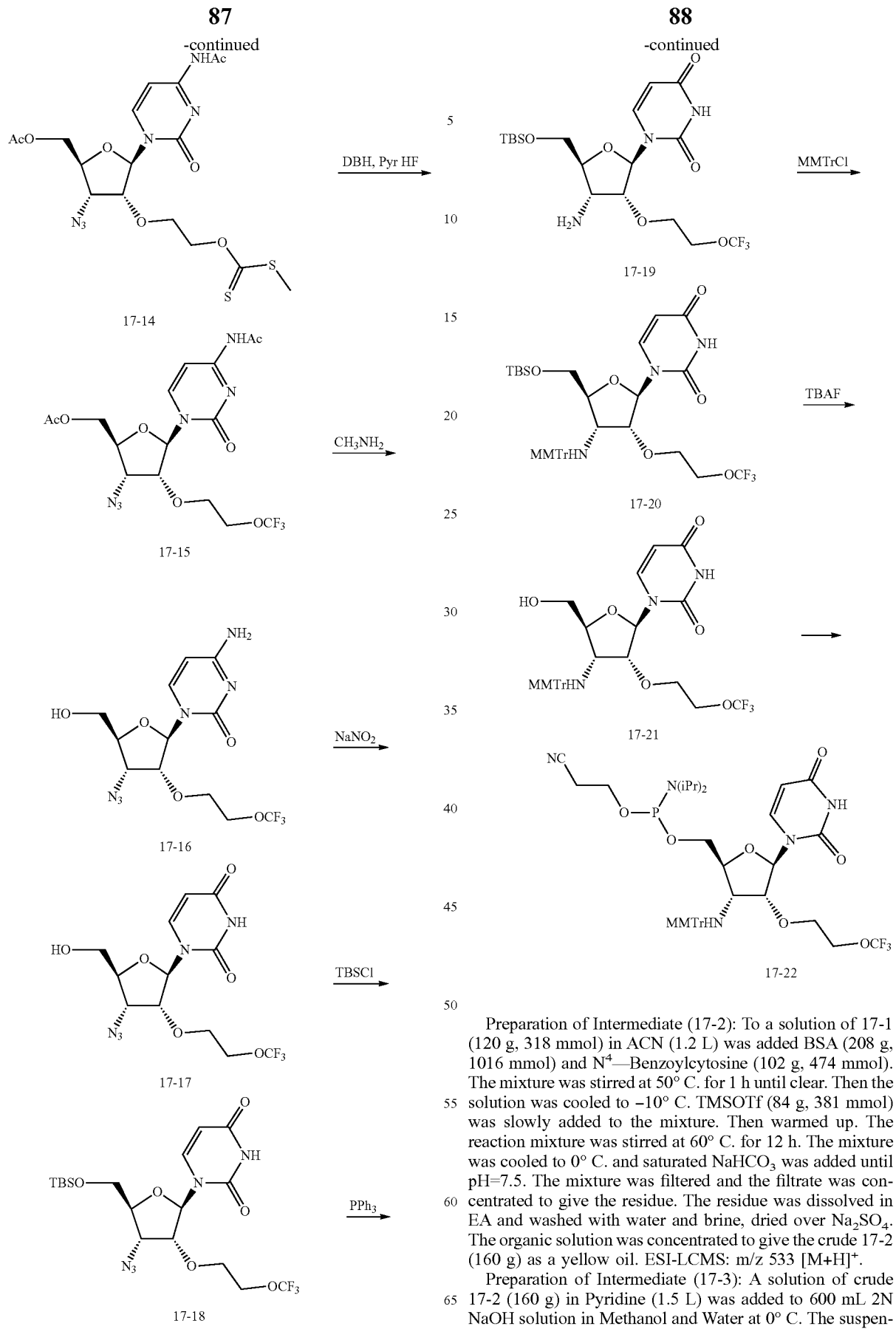

Preparation of Intermediate (17-2): To a solution of 17-1 (120 g, 318 mmol) in ACN (1.2 L) was added BSA (208 g, 1016 mmol) and $N^4$—Benzoylcytosine (102 g, 474 mmol). The mixture was stirred at 50° C. for 1 h until clear. Then the solution was cooled to −10° C. TMSOTf (84 g, 381 mmol) was slowly added to the mixture. Then warmed up. The reaction mixture was stirred at 60° C. for 12 h. The mixture was cooled to 0° C. and saturated $NaHCO_3$ was added until pH=7.5. The mixture was filtered and the filtrate was concentrated to give the residue. The residue was dissolved in EA and washed with water and brine, dried over $Na_2SO_4$. The organic solution was concentrated to give the crude 17-2 (160 g) as a yellow oil. ESI-LCMS: m/z 533 [M+H]$^+$.

Preparation of Intermediate (17-3): A solution of crude 17-2 (160 g) in Pyridine (1.5 L) was added to 600 mL 2N NaOH solution in Methanol and Water at 0° C. The suspension was stirred at 0° C. for 30 min. The reaction mixture was quenched by addition of sat. NH₄Cl solution (1 L). The solution was added to water (15 L) to give the solid. The solid was filtered and washed with (PE:EA=3:1) to give 17-3 (80 g, 214 mmol, 67% over two steps) as white solid. ESI-LCMS: m/z 373 [M+H]⁺.

Preparation of Intermediate (17-4): To a solution of 17-3 (80 g, 214 mmol) in Pyridine (1 L) was added DMTrCl (87 g, 257 mmol). The reaction mixture was stirred at r.t. for 1 h. MeOH (50 ml) was added to the mixture. The solution was concentrated to give the crude. The crude was dissolved in EA and washed with water and brine. The organic layer was dried over Na₂SO₄. The organic solution was concentrated to give the crude 17-4 (160 g) as a yellow oil which was used directly for the next step. ESI-LCMS: m/z 675 [M+H]⁺.

Preparation of Intermediate (17-5): To a solution of crude 17-4 (160 g) in DCM (1 L) was added Imidazole (22 g, 332 mmol) and TBSCl (46 g, 310.62 mmol). The reaction mixture was stirred at r.t. for 12 h. The mixture was diluted with DCM (1 L). Water was added. The organic layer was washed with brine and concentrated to give the crude 17-5 (200 g) which was used directly for the next step. ESI-LCMS: m/z 789 [M+H]⁺.

Preparation of Intermediate 17-6): A solution of crude 17-5 (200 g) in Methylamine (1 L) was stirred at r.t. for 2 h. The solution was concentrated and purified by column chromatography to give 17-6 (130 g, 204.42 mmol, 94.8% yield) as a white solid. ESI-LCMS: n/z 685 [M+H]⁺.

Preparation of Intermediate (17-7): To a solution of 17-6 (142 g, 207.34 mmol) in DCM (1 L) was added collidine (50.25 g, 414.69 mmol) and MMTrCl (95.79 g, 311.01 mmol). Then AgNO₃ (52.83 g, 311.01 mmol) was added to the solution. The reaction mixture was stirred at r.t. for 1 h. The mixture was filtered. The organic solution was washed with water. The organic layer was concentrated to give the crude 17-7 (190 g, 198.50 mmol, 95.73% yield) as a yellow solid which was used directly for the next step. ESI-LCMS: m/z 957.4 [M+H]⁺.

Preparation of Intermediate (17-8): To a solution of 17-7 (190 g, 198.50 mmol) in THF (1 L) was added TBAF (77.85 g, 297.74 mmol). The mixture was stirred at r.t. for 12 h. Water was added. The product was extracted with EA. The organic layer was washed with brine and dried over Na₂SO₄. The organic solution was concentrated and purified by column chromatography to give 17-8 (160 g, 189.81 mmol, 95.6% yield) as a white solid. ESI-LCMS: n/z 843.4 [M+H]⁺.

Preparation of Intermediate (17-9): To a solution of 17-8 (154 g, 182.70 mmol) in DMF (1 L) was added Ag₂O (84.68 g, 365.39 mmol, 11.86 mL), (2-Bromoethoxy)-tert-butyldimethylsilane (78.67 g, 328.85 mmol) and NaI (41.08 g, 274.04 mmol). The reaction mixture was stirred at 45° C. for 12 h. Water was added. The mixture was filtered and product was extracted with EA. The organic solution was concentrated and purified by column chromatography to give 17-9 (90 g, 89.89 mmol, 49.2% yield) as a black solid. ESI-LCMS: m/z 1001.4 [M+H]⁺.

Preparation of Intermediate (17-10): To a solution of 17-9 (90 g, 89.89 mmol) in THF (500 mL) was added TBAF (35.25 g, 134.83 mmol). The reaction mixture was stirred at r.t. for 12 h. Water was added to the mixture. The product was extracted with EA. The organic layer was concentrated and purified by column chromatography to give 17-10 (75 g, 84.56 mmol, 94.1% yield) as a yellows solid. ESI-LCMS: m/z 887.2 [M+H]⁺.

Preparation of Intermediate (17-11): To a solution of 17-10 (54 g, 60.88 mmol) in THF (400 mL) was added NaH (1.75 g, 73.06 mmol) at 0° C. After stirred at r.t. for 30 min, the reaction was cooled to 0° C., CS₂ (9.50 g, 121.76 mmol) was added to the mixture. After 10 min at this temperature, MeI (15.45 g, 109.58 mmol) was added to the mixture. And then the mixture was stirred at r.t. for 12 h. Water was added. The product was extracted with EA. The organic layer was washed with brine and dried over Na₂SO₄. The organic solution was concentrated and purified by column chromatography to obtain 17-11 (50 g, 51.17 mmol, 84.1% yield) as a white solid. ESI-LCMS: m/z 977.2 [M+H]⁺

Preparation of Intermediate (17-12): To a solution of 17-11 (17 g, 17.40 mmol) in DCM (100 mL) was added PTSA (5.99 g, 34.79 mmol) in Methanol (10 mL). The mixture was stirred at r.t. for 1 h. Cooled to 0° C. Con. NH₄OH was added to give pH=7.5. Water was added and the product was extracted with DCM. The organic layer was concentrated and purified by column chromatography to give 17-12 (10 g, 14.82 mmol, 85.2% yield) as a white solid. ESI-LCMS: m/z 675.1 [M+H]⁺.

Preparation of Intermediate (17-13): To a solution of 17-12 (40 g, 59.28 mmol) in DCM (800 mL) was added TFA (150 mL). The mixture was stirred at r.t. for 1 h. Cooled to 0° C. Con. NH4OH was added to the solution to give pH=7.5. Water was added and the product was extracted with DCM. The organic layer solution was dried over Na₂SO₄ and concentrated to give the crude product which was purified by column chromatography to give 17-13 (21 g, 52.18 mmol, 88.0% yield) as a white solid. ESI-LCMS: m/z 403.0 [M+H]⁺.

Preparation of Intermediate (17-14): To a solution of 17-13 (26 g, 64.60 mmol) in Pyridine (500 mL) was added Ac₂O (19.79 g, 193.81 mmol). The reaction mixture was stirred at 40° C. for 1 h. Water was added. The solution was concentrated to give the crude. The crude was purified by column chromatography and MPLC to give 17-14 (21 g, 43.16 mmol, 66.8% yield) as a white solid. ESI-LCMS: m/z 487.0 [M+H]⁺.

Preparation of Intermediate (17-15): To a solution of DBH (4.19 g, 14.64 mmol) in DCM (75 mL) was added HF/Pyridine (10 mL) slowly at −60° C. Then SM-1 (2.5 g, 5.14 mmol) dissolved in DCM was slowly added to the mixture. The reaction mixture was stirred at −40° C. for 1 h. DCM was added to the mixture. Sat. NaHCO₃ was slowly added to the mixture to give the pH=7.0. The solution was concentrated to give the crude product. The crude was purified by column chromatography and MPLC to give 17-15 (1.1 g, 2.37 mmol, 46.1% yield) as a white solid. ESI-LCMS: m/z 465.1 [M+H]⁺. ¹⁹F NMR (376 MHz, Chloroform-d) 6-55.49.

Preparation of Intermediate (17-16): A solution of 17-15 (4.6 g, 9.91 mmol) in Methylamine (30 mL) was stirred at r.t. for 1 h. The solution was concentrated and purified by column chromatography to 17-16 (3.7 g, 9.73 mmol, 98.2% yield) as a white solid. ESI-LCMS: m/z 381.1 [M+H]⁺.

Preparation of Intermediate (17-17): To a solution of 17-16 (1.7 g, 4.47 mmol) in AcOH (5 mL) and Water (5 mL) was added NaNO₂ (30.40 g, 447.04 mmol). The mixture was stirred at r.t. for 3 h. LC-MS showed 70% conversion. EA and water was added. The organic layer was concentrated and purified by MPLC to give 17-17 (1.5 g, 3.93 mmol, 88.0% yield) as a white solid. ESI-LCMS: m/z 382.2 [M+H]⁺.

Preparation of Intermediate (17-18): To a solution of 17-17 (2.23 g, 5.85 mmol) in DCM (30 mL) was added Imidazole (796.36 mg, 11.70 mmol) and TBSCl (1.32 g, 8.77 mmol). The reaction mixture was stirred at r.t. for 12 h. Water was added. The organic layer was washed with brine and dried over Na₂SO₄. The organic layer was concentrated to give the crude 17-18 (2.8 g, 5.65 mmol, 96.6% yield) as a white solid. ESI-LCMS: m/z 496.4 [M+H]⁺.

Preparation of Intermediate (17-19): To a solution of 17-18 (2.8 g, 5.65 mmol) in THF (30 mL) was added PPh₃ (1.78 g, 6.78 mmol) and water (203.59 mg, 11.30 mmol). The mixture was stirred at 50° C. for 2 h under N₂ atmosphere. The mixture was concentrated and purified by column chromatography to give 17-19 (2.5 g, 5.32 mmol, 94.2% yield) as a white solid. ESI-LCMS: m/z 470.3 [M+1H].

Preparation of Intermediate (17-20): To a solution of 17-19 (2.8 g, 5.96 mmol) in DCM (40 mL) was added TEA (1.21 g, 11.93 mmol, 1.66 mL) and MMTrCl (2.76 g, 8.95 mmol). The mixture was stirred at r.t. for 1 h. Water was added. The organic layer was dried over Na₂SO₄ and concentrated, the residue was purified by column chromatography to give 17-20 (3.1 g, 4.18 mmol, 70.1% yield) as a white solid. ¹H NMR (400 MHz, DMSO-d₆) δ 11.36 (d, J=2.2 Hz, 1H), 7.67 (d, J=8.0 Hz, 1H), 7.46 (td, J=8.6, 1.3 Hz, 4H), 7.37-7.30 (m, 2H), 7.25 (t, J=7.5 Hz, 4H), 7.22-7.14 (m, 2H), 6.84-6.77 (m, 2H), 5.54 (s, 1H), 5.44 (dd, J=8.0, 2.2 Hz, 1H), 4.17-4.01 (m, 4H), 3.90 (dd, J=9.8, 2.4 Hz, 1H), 3.70 (s, 4H), 3.07 (td, J=10.1, 4.5 Hz, 1H), 3.03-2.93 (m, 1H), 2.82 (d, J=10.3 Hz, 1H), 1.51 (d, J=4.5 Hz, 1H), 0.84 (s, 9H), 0.12 (s, 3H), −0.03 (s, 3H). ¹⁹F NMR (376 MHz, DMSO-d₆) δ −58.72.

Preparation of Intermediate (17-21): To a solution of 17-20 (3.1 g, 4.18 mmol) in THF (30 mL) was added TBAF (1.64 g, 6.27 mmol). The mixture was stirred at r.t. for 15 h. The mixture was concentrated and purified by column chromatography to give 17-21 (2.2 g, 3.51 mmol, 83.9% yield) as a white solid. ¹H NMR (400 MHz, DMSO-d₆) δ 11.30 (d, J=2.0 Hz, 1H), 7.98 (d, J=8.1 Hz, 1H), 7.52-7.42 (m, 4H), 7.37-7.30 (m, 2H), 7.30-7.23 (m, 4H), 7.23-7.14 (m, 2H), 6.87-6.79 (m, 2H), 5.52 (d, J=2.0 Hz, 1H), 5.50 (d, J=1.5 Hz, 1H), 5.17 (t, J=3.8 Hz, 1H), 4.13 (t, J=4.2 Hz, 2H), 4.05 (dd, J=4.2, 2.1 Hz, 2H), 3.90 (dt, J=10.0, 2.2 Hz, 1H), 3.72 (s, 3H), 3.67 (dt, J=11.4, 3.7 Hz, 1H), 3.39 (td, J=6.4, 5.1 Hz, 1H), 3.10 (td, J=10.3, 4.3 Hz, 1H), 2.97 (dt, J=11.8, 4.7 Hz, 1H), 2.68 (d, J=10.6 Hz, 1H), 1.44 (d, J=4.3 Hz, 1H). ¹⁹F NMR (376 MHz, DMSO-d₆) δ −58.82.

Preparation of (17-22): To a solution of 17-21 (1.4 g, 2.23 mmol) in DCM (10 mL) was added DCI (318.88 mg, 2.23 mmol) and CEP[N(iPr)₂]₂ (872.87 mg, 2.90 mmol). The mixture was stirred at r.t. for 1 h. The solution was diluted with DCM. The organic layer was washed with sat. NaHCO₃, water and brine. The organic layer was dried over Na₂SO₄ and purified by column chromatography to give 1.3 g crude product. The product was drying in vacuum at 40° C. overnight. This resulted in (1.15 g, 1.39 mmol, 62.28% yield) to give 17-22 as a white solid. MS m/z [M−H]⁻ (ESI): 826.4; ¹H NMR (400 MHz, DMSO-d₆) δ 11.37 (s, 1H), 7.78 (d, J=8.1 Hz, 0.6 H), 7.59-7.44 (m, 4.4H), 7.41-7.33 (m, 2H), 7.27 (m, 4H), 7.24-7.14 (m, 2H), 6.88-6.79 (m, 2H), 5.57-5.48 (m, 1.4H), 5.44 (d, J=8.0 Hz, 0.6H), 4.25-4.13 (m, 2H), 4.13-3.90 (m, 3H), 3.79-3.38 (m, 8H), 3.03 (m, 2H), 2.86 (dd, J=26.4, 10.4 Hz, 1H), 2.79-2.67 (m, 2H), 1.67 (d, J=4.5 Hz, 0.4H), 1.26 (d, J=4.5 Hz, 0.6H), 1.18 (d, J=6.7 Hz, 3H), 1.15-1.02 (m, 9H). ³¹P NMR (162 MHz, DMSO-d6) δ 148.03, 146.68.

Example 14

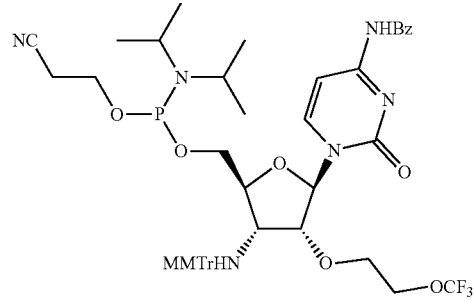

Scheme 16

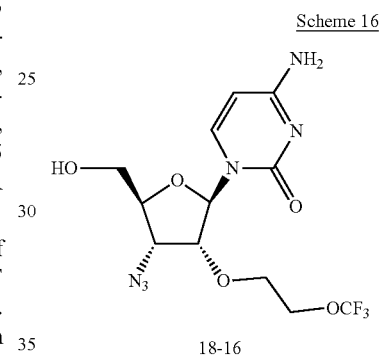

18-16

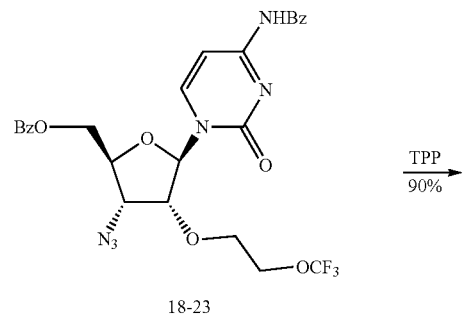

18-23

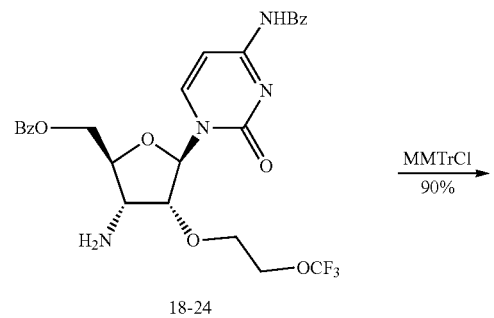

18-24

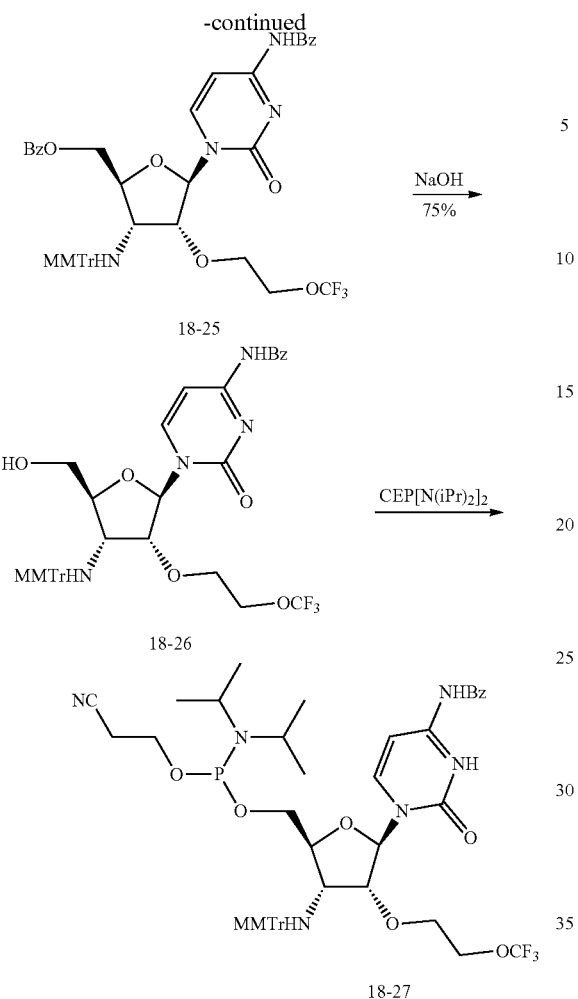

Water (3 mL) at 0° C. The mixture was stirred at r.t. for 0.5 h. Sat. NH₄Cl was added to give pH=8. The product was extracted with EA. The organic layer was concentrated and purified by MPLC to give 18-26 (1.5 g, 2.05 mmol, 85.69% yield) as a white solid. $^1$H NMR (400 MHz, DMSO-d$_6$) δ 11.27 (s, 1H), 8.55 (d, J=7.5 Hz, 1H), 8.11-7.94 (m, 2H), 7.77-7.57 (m, 1H), 7.57-7.40 (m, 6H), 7.40-7.10 (m, 9H), 6.97-6.76 (m, 2H), 5.56 (s, 1H), 5.36-5.18 (m, 1H), 4.15 (dd, J=9.7, 5.4 Hz, 4H), 4.01 (d, J=10.2 Hz, 1H), 3.84 (d, J=11.7 Hz, 1H), 3.72 (s, 3H), 3.18-2.97 (m, 2H), 2.66 (d, J=10.9 Hz, 1H), 1.48 (d, J=4.1 Hz, 1H). $^{19}$F NMR (376 MHz, DMSO-d$_6$) δ −58.75.

Preparation of (18-27): To a solution of 18-26 (1.4 g, 1.92 mmol) in DCM (30 mL) was added DCI (226.08 mg, 1.92 mmol) and CEP[N(iPr)$_2$]$_2$ (749.69 mg, 2.49 mmol). The mixture was stirred at r.t. for 1 h. The solution was diluted with DCM. The organic layer was washed with water and brine. The organic layer was dried over Na$_2$SO$_4$ and concentrated to the crude product. The crude was purified by HPLC. The product was drying in vacuum at 40° C. overnight. This resulted in (1.65 g, 1.77 mmol, 92.51% yield) to give 18-27 as a white solid. ESI-LCMS: m/z 877 [M+H]$^+$. $^1$H NMR (400 MHz, DMSO-d$_6$) δ 11.33 (s, 1H), 8.34 (d, J=7.4 Hz, 0.6H), 8.20 (d, J=7.4 Hz, 0.6H), 8.02 (dt, J=8.3, 1.2 Hz, 2H), 7.73-7.57 (m, 1H), 7.57-7.40 (m, 6H), 7.40-7.30 (m, 3H), 7.30-7.10 (m, 6H), 6.86-6.71 (m, 2H), 5.60 (d, J=1.1 Hz, 1H), 4.41-4.03 (m, 5H), 4.00-3.39 (m, 8H), 3.05 (m, 2H), 2.92-2.70 (m, 3H), 1.53 (d, J=4.2 Hz, 0.4H), 1.29 (d, J=4.2 Hz, 0.6H), 1.26-1.00 (m, 12H). $^{31}$P NMR (162 MHz, DMSO-d6) δ 148.41, 146.88.

Example 15

Preparation of Intermediate (18-23): To a solution of 18-16 (1.2 g, 3.16 mmol) in Pyridine (10 mL) was added BzCl (971.92 mg, 6.94 mmol) at 0° C. The mixture was stirred at r.t. for 1 h. Water was added. The product was extracted with EA. The organic layer was washed with brine and dried over Na$_2$SO$_4$. The organic layer was concentrated and purified by column chromatography to give 18-23 (1.58 g, 2.68 mmol, 85.1% yield) as a white solid. ESI-LCMS: m/z 589.1 [M+H]$^+$ Preparation of Intermediate (18-24): To a solution of 18-23 (1.47 g, 2.50 mmol) in THF (20 mL) was added water (90.00 mg, 5.00 mmol) and PPh$_3$ (786.20 mg, 3.00 mmol). The mixture was stirred at 50° C. under N$_2$ atmosphere. The mixture was concentrated and purified by column chromatography to give 18-24 (1.35 g, 2.40 mmol, 96.1% yield) as a white solid. ESI-LCMS: m/z 563.2 [M+H]$^+$.

Preparation of Intermediate (18-25): To a solution of 18-24 (1.4 g, 2.49 mmol) in DCM (40 mL) was added TEA (503.71 mg, 4.98 mmol, 694.29 uL) and MMTrCl (1.15 g, 3.73 mmol). The mixture was stirred at r.t. for 1 h. Water was added. The organic layer was dried over Na$_2$SO$_4$ and concentrated, the residue was purified by column chromatography to give 18-25 (2 g, 2.40 mmol, 96.3% yield) as a white solid. $^{19}$F NMR (376 MHz, DMSO-d6) δ −58.72.

Preparation of Intermediate (18-26): To a solution of 18-25 (2 g, 2.40 mmol) in Pyridine (30 mL) was added NaOH (287.46 mg, 7.19 mmol) in Methanol (12 mL) and

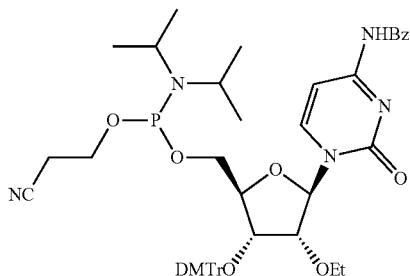

Scheme 17

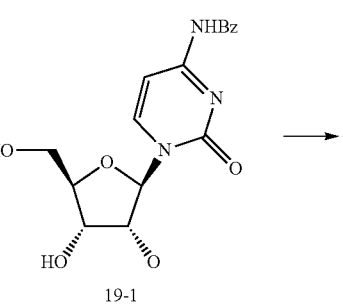

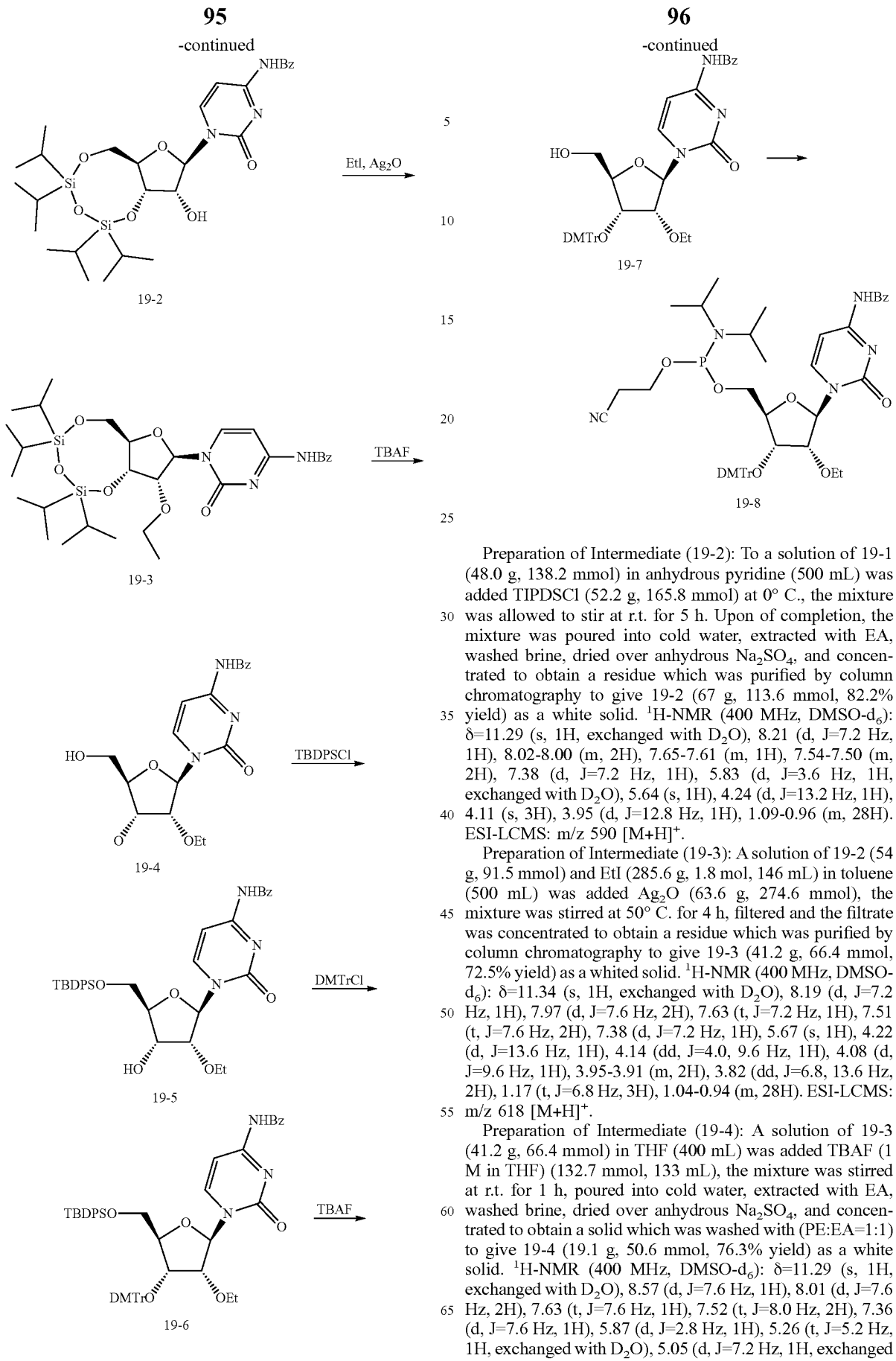

Preparation of Intermediate (19-2): To a solution of 19-1 (48.0 g, 138.2 mmol) in anhydrous pyridine (500 mL) was added TIPDSCl (52.2 g, 165.8 mmol) at 0° C., the mixture was allowed to stir at r.t. for 5 h. Upon of completion, the mixture was poured into cold water, extracted with EA, washed brine, dried over anhydrous $Na_2SO_4$, and concentrated to obtain a residue which was purified by column chromatography to give 19-2 (67 g, 113.6 mmol, 82.2% yield) as a white solid. $^1$H-NMR (400 MHz, DMSO-$d_6$): δ=11.29 (s, 1H, exchanged with $D_2O$), 8.21 (d, J=7.2 Hz, 1H), 8.02-8.00 (m, 2H), 7.65-7.61 (m, 1H), 7.54-7.50 (m, 2H), 7.38 (d, J=7.2 Hz, 1H), 5.83 (d, J=3.6 Hz, 1H, exchanged with $D_2O$), 5.64 (s, 1H), 4.24 (d, J=13.2 Hz, 1H), 4.11 (s, 3H), 3.95 (d, J=12.8 Hz, 1H), 1.09-0.96 (m, 28H). ESI-LCMS: m/z 590 [M+H]$^+$.

Preparation of Intermediate (19-3): A solution of 19-2 (54 g, 91.5 mmol) and EtI (285.6 g, 1.8 mol, 146 mL) in toluene (500 mL) was added $Ag_2O$ (63.6 g, 274.6 mmol), the mixture was stirred at 50° C. for 4 h, filtered and the filtrate was concentrated to obtain a residue which was purified by column chromatography to give 19-3 (41.2 g, 66.4 mmol, 72.5% yield) as a whited solid. $^1$H-NMR (400 MHz, DMSO-$d_6$): δ=11.34 (s, 1H, exchanged with $D_2O$), 8.19 (d, J=7.2 Hz, 1H), 7.97 (d, J=7.6 Hz, 2H), 7.63 (t, J=7.2 Hz, 1H), 7.51 (t, J=7.6 Hz, 2H), 7.38 (d, J=7.2 Hz, 1H), 5.67 (s, 1H), 4.22 (d, J=13.6 Hz, 1H), 4.14 (dd, J=4.0, 9.6 Hz, 1H), 4.08 (d, J=9.6 Hz, 1H), 3.95-3.91 (m, 2H), 3.82 (dd, J=6.8, 13.6 Hz, 2H), 1.17 (t, J=6.8 Hz, 3H), 1.04-0.94 (m, 28H). ESI-LCMS: m/z 618 [M+H]$^+$.

Preparation of Intermediate (19-4): A solution of 19-3 (41.2 g, 66.4 mmol) in THF (400 mL) was added TBAF (1 M in THF) (132.7 mmol, 133 mL), the mixture was stirred at r.t. for 1 h, poured into cold water, extracted with EA, washed brine, dried over anhydrous $Na_2SO_4$, and concentrated to obtain a solid which was washed with (PE:EA=1:1) to give 19-4 (19.1 g, 50.6 mmol, 76.3% yield) as a white solid. $^1$H-NMR (400 MHz, DMSO-$d_6$): δ=11.29 (s, 1H, exchanged with $D_2O$), 8.57 (d, J=7.6 Hz, 1H), 8.01 (d, J=7.6 Hz, 2H), 7.63 (t, J=7.6 Hz, 1H), 7.52 (t, J=8.0 Hz, 2H), 7.36 (d, J=7.6 Hz, 1H), 5.87 (d, J=2.8 Hz, 1H), 5.26 (t, J=5.2 Hz, 1H, exchanged with $D_2O$), 5.05 (d, J=7.2 Hz, 1H, exchanged with D₂O), 4.11-4.06 (m, 1H), 3.94-3.91 (m 1H), 3.86-3.74 (m, 3H), 3.71-3.61 (m, 2H), 1.17 (t, J=7.6 Hz, 3H). ESI-LCMS: m/z 376 [M+H]⁺.

Preparation of Intermediate (19-5): A solution of 19-4 (19.1 g, 50.6 mmol) and imidazole (5.2 g, 75.9 mmol) in pyridine (200 mL) was added TBDPSCl (7.1 g, 60.7 mmol), the mixture was stirred at r.t. for 1 h, poured into cold water, extracted with EA, washed brine, dried over anhydrous Na₂SO₄, and concentrated to obtain a solid which was purified by column chromatography to give 19-5 (20.2 g, 32.6 mmol, 64.4% yield) as a white solid. ESI-LCMS: m/z 614 [M+H]⁺.

Preparation of Intermediate (19-6): A solution of 19-5 (14.0 g, 22.8 mmol) and collidine (6.9 g, 57.0 mmol) in DCM (150 mL) were added DMTrCl (11.6 g, 34.2 mmol) and AgNO₃ (3.9 g, 22.8 mmol) under Ar. The mixture was stirred at r.t. for 15 h, filtered and the filtrate was washed with water, dried over anhydrous Na₂SO₄, and concentrated to give the crude product 19-6 (26.2 g) as a yellow oil. ESI-LCMS: m/z 916 [M+H]⁺.

Preparation of Intermediate (19-7): A solution of 19-6 (26.2 g (crude)) in THF (200 mL) was added TBAF (1 M in THF) (23 mL), the mixture was stirred at 50° C. for 3 h, poured into cold water, extracted with EA, washed brine, dried over anhydrous Na₂SO₄, and concentrated to obtain a residue which was purified by column chromatography to give 19-7 (11.2 g, 16.5 mmol, 72.37% yield over two steps) as a white solid. ¹H-NMR (400 MHz, DMSO-d₆): δ=11.30 (s, 1H, exchanged with D₂O), 8.40 (d, J=7.6 Hz, 1H), 8.02 (d, J=7.6 Hz, 2H), 7.65-7.61 (m, 1H), 7.54-7.49 (m, 4H), 7.35-7.30 (m, 6H), 7.26-7.23 (m, 1H), 6.89-6.86 (m, 4H), 5.96 (d, J=3.2 Hz, 1H), 5.08 (t, J=4.4 Hz, 1H, exchanged with D₂O), 4.01 (t, J=5.2 Hz, 1H), 3.79-3.78 (m, 1H), 3.73 (d, J=1.2 Hz, 6H), 3.66-3.55 (m 2H), 3.40-3.38 (m, 1H), 3.25-3.17 (m, 1H), 2.97-2.95 (m, 1H), 1.17 (t, J=6.8 Hz, 3H). ESI-LCMS: m/z 678 [M+H]⁺.

Preparation of (19-8): A solution of 19-7 (5.0 g, 7.4 mmol) and DCI (2.2 g, 7.4 mmol) in dry DCM (50 mL) was added CEP[N(iPr)₂]₂ (2.7 g, 8.8 mmol) under Ar. The mixture was stirred at r.t. for 1 h. The reaction was washed with 10% NaHCO₃ (aq) and water, dried over Na₂SO₄ and concentrated to obtain the crude product which was purified Flash-Prep-HPLC. This resulted in to give 19-8 (5.5 g, 6.26 mmol, 84.91% yield) as a white solid. ¹H-NMR (400 MHz, DMSO-d6): δ=11.34 (s, 1H), 8.16 (dd, J=7.6, 39.2 Hz, 1H), 8.03-8.00 (m, 2H), 7.65-7.61 (m, 1H), 7.54-7.45 (m, 4H), 7.35-7.24 (m, 8H), 6.88-6.82 (m, 4H), 5.89 (dd, J=3.2, 88.8 Hz, 1H), 4.25-3.86 (m, 3H), 3.75-3.66 (m, 9H), 3.62-3.38 (m, 4H), 3.26-3.05 (m, 1H), 2.78 (dd, J=5.6, 10.4 Hz, 2H), 1.20-1.11 (m, 9H), 1.04 (dd, J=6.4, 27.6 Hz, 6H). ³¹P-NMR (162 MHz, DMSO-d₆): 148.09, 147.84. ESI-LCMS: m/z 878 [M+H]⁺.

Example 16

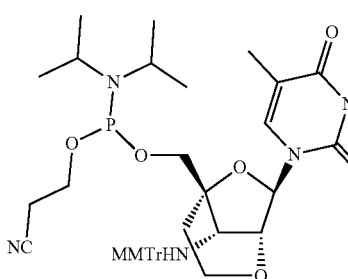

Scheme 18

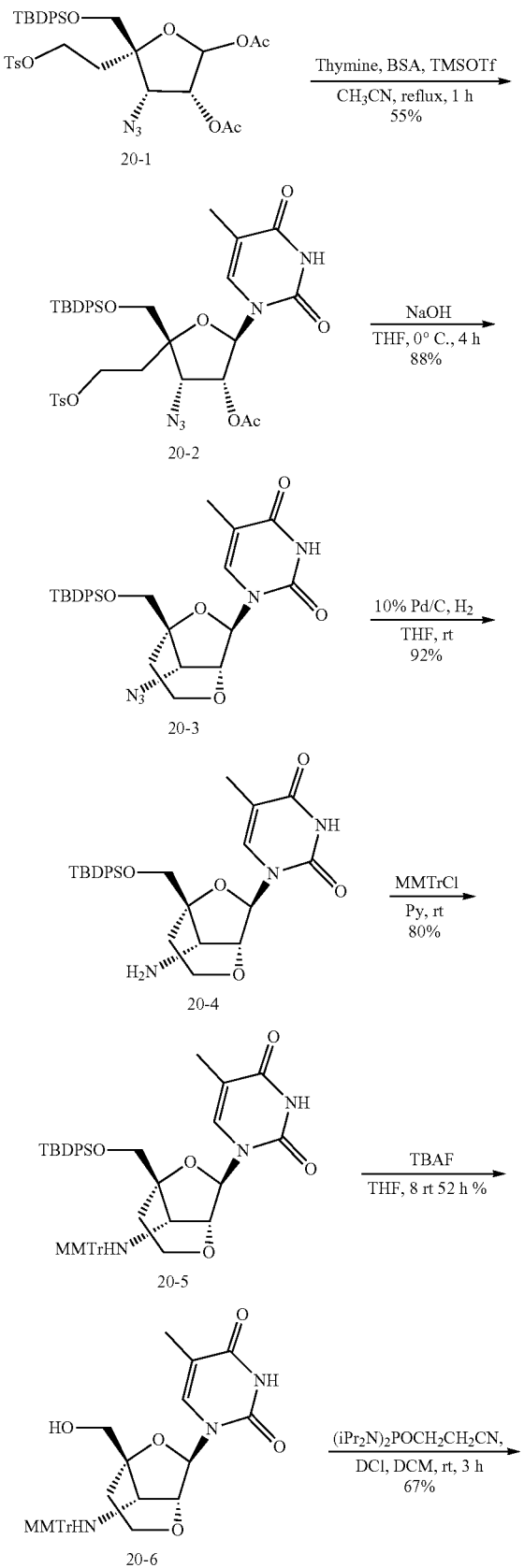

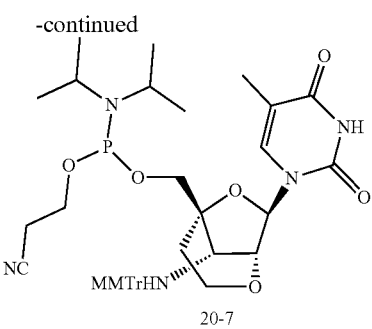

20-7

Preparation of Intermediate (20-2): To a solution of Thymine (8.15 g, 64.68 mmol, 1.5 eq.) in Acetonitrile (300 mL) with an inert atmosphere of nitrogen, was added N,O-Bis(trimethylsilyl)acetamide (39 g, 194.2 mmol, 4.5 eq.) at room temperature. The resulting solution was stirred for 2 h at 80° C. The reaction mixture was cooled to 0° C. and 20-1 (30 g, 43.16 mmol, 1.00 eq.) was added. Then trimethylsilyl trifluoromethanesulfonate (57.48 g, 258.95 mmol, 6.0 eq.) was added dropwise with stirring at 0° C. The resulting solution was allowed to react, with stirring, for an additional 1 h at 80° C. The reaction mixture was cooled to 0° C., quenched by the addition of saturated sodium bicarbonate. The resulting solution was extracted ethyl acetate and the organic layers combined. The organic layer was washed with water and saturated sodium chloride respectively. The residue was purified by column chromatography. This resulted in 18 g (55%) of 20-2 as a brown solid. MS m/z [M+H]+(ESI): 762.

Preparation of Intermediate (20-3): To a solution of 20-2 (18 g, 23.9 mmol, 1.00 eq.) in Tetrahydrofuran (180 mL) with an inert atmosphere of nitrogen, was added sodium hydroxide (47 mL, 2N in water, 4.0 eq.) at 0° C. The resulting solution was stirred for 4 h at 0° C. The resulting mixture was extracted with ethyl acetate, and the organic layers combined. The organic layer was dried over anhydrous sodium sulfate and concentrated. The crude product was purified by Flash-Prep-HPLC. This resulted in 11.4 g (88%) of 20-3 as a white solid. MS m/z [M+H]+(ESI): 548.

Preparation of Intermediate (20-4): To a solution of 20-3 (11.4 g, 20.84 mmol, 1.00 eq.) in Tetrahydrofuran (100 mL) was added 10% Palladium on activated carbon (1.4 g). The flask was evacuated and flushed five times with hydrogen. The resulting solution was stirred for 8 h at room temperature. The solids were filtered out. The resulting mixture was concentrated under reduced pressure. This resulted in 10 g (92%) of 20-4 as a white solid. MS m/z [M+H]+(ESI): 522.

Preparation of Intermediate (20-5): To a solution of 20-4 (10 g, 19.19 mmol, 1.00 eq.) in pyridine (50 mL) with an inert atmosphere of nitrogen, was added 1-(chlorodiphenylmethyl)-4-methoxybenzene (8.8 g, 28.79 mmol, 1.5 eq.) at room temperature. The resulting solution was stirred for 12 h at room temperature. The reaction was then quenched by the addition of methanol (20 mL). The crude product was purified by Flash-Prep-HPLC. The fractions (500 mL) was diluted with dichloromethane and dried over anhydrous sodium sulfate. The solid was filtered out. The filtrate was concentrated under reduced pressure. This resulted in 12.2 g (80%) of 20-5 as a white solid. MS m/z [M-H]- (ESI): 792.

Preparation of Intermediate (20-6): To a solution of 20-5 (4.2 g, 5.29 mmol, 1.00 eq.) in dichloromethane (40 mL) with an inert atmosphere of nitrogen, was added Tetrabutylammonium fluoride (1M in THF, 13.0 mL, 2.5 eq.) at room temperature. The resulting solution was stirred for 10 h at room temperature. The crude product was purified by Flash-Prep-HPLC. The fractions were diluted with dichloromethane and dried over anhydrous sodium sulfate. The solid was filtered out. The filtrate was concentrated under reduced pressure. This resulted in 2.5 g (85%) of 20-6 as a white solid. MS m/z [M-H]- (ESI): 554. 1H NMR: (DMSO-d6, 300 Hz, ppm): δ 11.25 (s, 1H), 7.95 (s, 1H), 7.46 (m, 4H), 7.31-7.11 (m, 8H), 6.76 (m, 2H), 5.61 (s, 1H), 5.22 (t, J=3.0 Hz, 1H), 3.95 (m, 1H), 3.85-3.61 (m, 6H), 2.85 (m, 1H), 2.45 (d, J=9.0 Hz, 1H), 2.23-2.06 (m, 1H), 1.61 (m, 4H), 1.34 (d, J=12.0 Hz, 1H).

Preparation of (20-7): To a solution of 20-6 (2.5 g, 3.78 mmol, 1.00 eq.) in dichloromethane (20 mL) with an inert atmosphere of nitrogen, was added Bis(diisopropylamino)(2-cyanoethoxy)phosphine (1.7 g, 5.67 mmol, 1.5 eq.) at room temperature. To this was added 4, 5-Dicyanoimidazole (440 mg, 4.15 mmol, 1.10 eq.) at room temperature. The resulting solution was stirred for 3 h at room temperature and diluted with dichloromethane, washed with water. The crude product was purified by Flash-Prep-HPLC. The fractions were diluted with dichloromethane and dried over anhydrous sodium sulfate. The solid was filtered out. The filtrate was concentrated under reduced pressure. This resulted in 2.3 g (67%) of 20-7 as a white solid. MS m/z [M-H]- (ESI):754. H-NMR: (DMSO-d6, 300 Hz, ppm): δ 11.31 (s, 1H), 7.76-7.41 (m, 5H), 7.37-7.10 (m, 8H), 6.87-6.68 (m, 2H), 5.66 (m, 1H), 4.04 (m, 1H), 3.83 (m, 2H), 3.70 (m, 3H), 3.69-3.45 (m, 4H), 3.30-3.00 (m, 1H), 2.88-2.54 (m, 3H), 2.45-2.12 (m, 2H), 1.87-1.64 (m, 4H), 1.51 (m, 1H), 1.17 (m, 12H). P NMR (DMSO-d6, 300 Hz, ppm): 152.69, 150.53.

Example 17

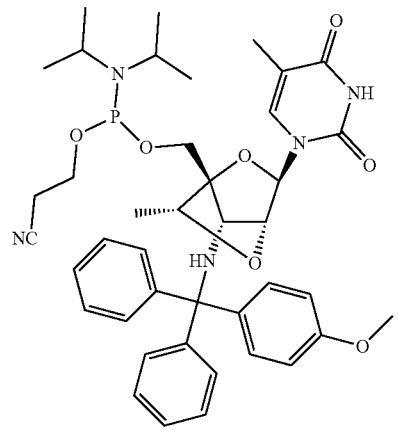 [SMILES: COc1ccc(C(N[C@H]2[C@H]3O[C@H](C)[C@]2(COP(OCCC#N)N(C(C)C)C(C)C)O[C@H]3n2cc(C)c(=O)[nH]c2=O)(c2ccccc2)c2ccccc2)cc1]

Scheme 19

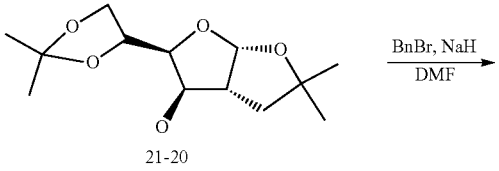

21-20

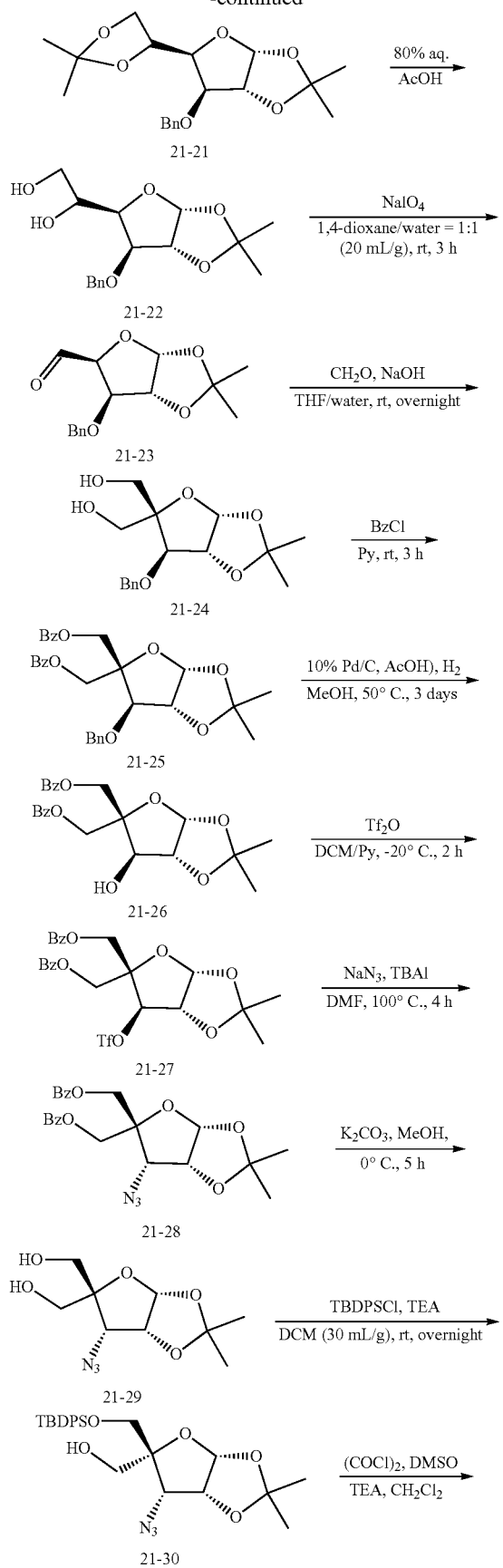
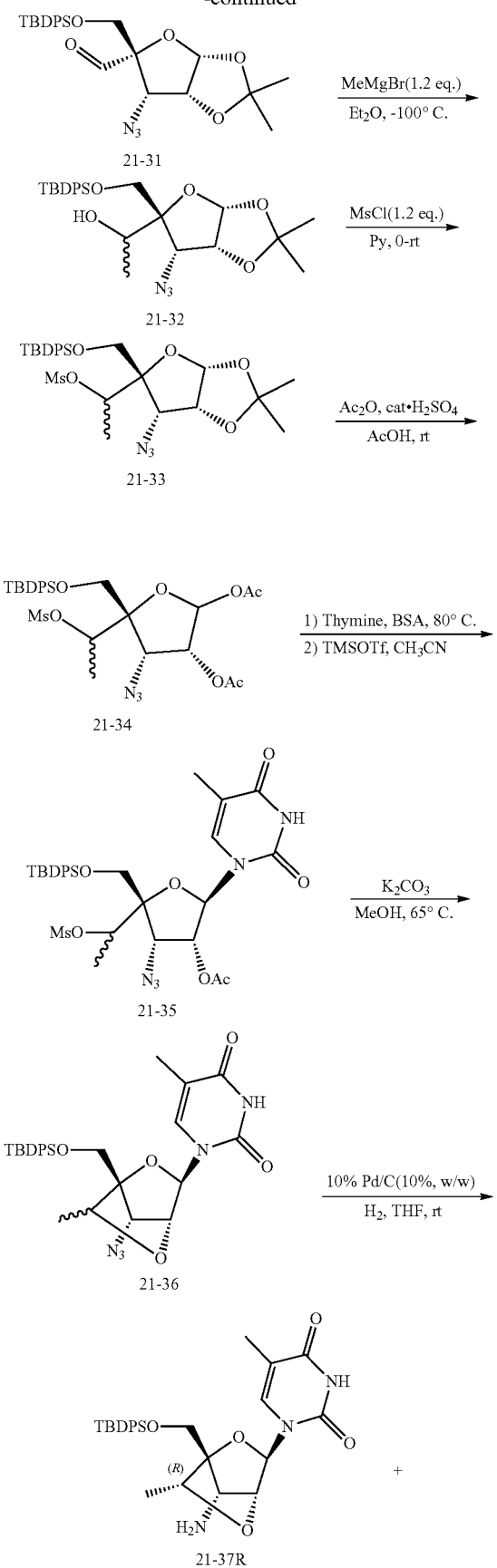

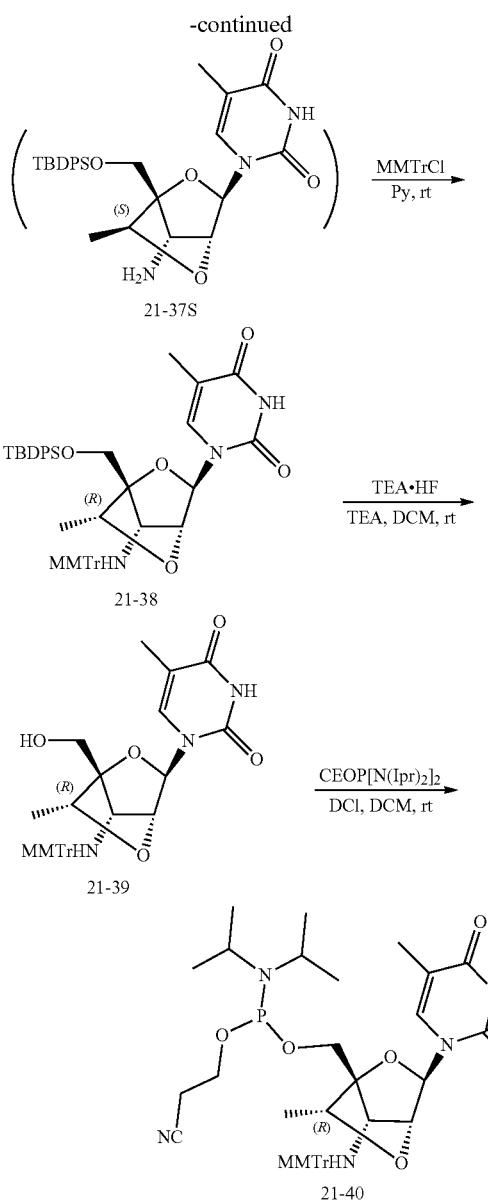

Preparation of Intermediate (21-21): To a solution of (3aR,5S,6S,6aR)-5-(2,2-dimethyl-1,3-dioxolan-4-yl)-2,2-dimethyl-tetrahydro-2H-furo[2,3-d][1,3]dioxol-6-ol (500 g, 1.92 mol, 1.00 eq.) in N,N-dimethylformamide (5000 mL) with an inert atmosphere of nitrogen was added (bromomethyl) benzene (345 g, 2.02 mol, 1.05 eq.) at room temperature. Sodium hydride (123 g, 3.08 mol, 1.60 eq. 60%) was added for several batches at 0° C. The resulting solution was stirred for 2 h at 25° C. The reaction was then quenched by the addition of ammonium chloride (aq). The resulting solution was extracted with ethyl acetate and the organic layers combined and dried over anhydrous sodium sulfate and concentrated under reduced pressure. This resulted in 670 g (crude) of 21-21 as yellow oil. MS m/z [M+H]+(ESI): 351.

Preparation of Intermediate (21-22): 21-21 (500 g, 1.43 mol, 1.00 eq.) was dissolved 80% acetic acid (5000 mL). The resulting solution was stirred overnight at room temperature. The resulting mixture was concentrated under reduced pressure. The resulting solution was diluted with ethyl acetate. The resulting mixture was washed with sodium bicarbonate (aq). The mixture was dried over anhydrous sodium sulfate and concentrated under reduced pressure. This resulted in 440 g (crude) of 21-22 as yellow oil. MS m/z [M+Na]+(ESI): 333.

Preparation of Intermediate (21-23): To a solution of 21-22 (500 g, 1.61 mol, 1.00 eq.) in 1,4-dioxane (5000 mL) was added a solution of sodium periodate (345 g, 1.61 mol, 1.00 eq.) in water (5000 mL) dropwise with stirring at 0° C. The resulting solution was stirred for 2 h at room temperature. The resulting solution was diluted with ethyl acetate. The resulting mixture was washed with water. The mixture was dried over anhydrous sodium sulfate and concentrated under reduced pressure. This resulted in 400 g (crude) of 21-23 as yellow oil. MS m/z [M+H]+(ESI): 279.

Preparation of Intermediate (21-24): To a solution of 21-23 (250 g, 898.3 mmol, 1.00 eq.) in tetrahydrofuran/water (1250/1250 mL) was added formaldehyde solution (37%, 600 mL) at room temperature. To this was added 2N sodium hydroxide (1500 mL, 3.12 eq.) dropwise with stirring at 0° C. The resulting solution was stirred overnight at room temperature. The resulting solution was extracted with ethyl acetate and the organic layers combined. The resulting mixture was washed with water. The mixture was dried over anhydrous sodium sulfate and concentrated under reduced pressure. This resulted in 191 g (crude) of 21-24 as yellow oil. MS m/z [M+Na]+(ESI): 333.

Preparation of Intermediate (21-25): To a solution of 21-24 (300 g, 966.7 mmol, 1.00 eq.) in pyridine (3000 mL) with an inert atmosphere of nitrogen was added benzoyl chloride (409.4 g, 2.91 mol, 3.01 eq.) dropwise with stirring at 0° C. and then stirred for 2 h at room temperature. The resulting solution was diluted with ethyl acetate. The resulting mixture was washed with sodium bicarbonate (aq). The mixture was dried over anhydrous sodium sulfate and concentrated under reduced pressure. The residue was purified by column chromatography. This resulted in 410 g (82%) of 21-25 as yellow oil.

Preparation of Intermediate (21-26): To a solution of 21-25 (250 g, 482.11 mmol, 1.00 eq.) in methanol (2500 mL) was added 10% Palladium carbon (125 g) and aceticacid (29 g, 482.11 mmol 1.00 eq.). Then H₂ (gas) was inserted. The resulting solution was stirred for 72 h at 50° C. The solids were filtered out. The resulting mixture was concentrated under reduced pressure. The resulting solution was diluted with dichloromethane and washed with Sat. sodium bicarbonate (aq). The mixture was dried over anhydrous sodium sulfate and concentrated under reduced pressure. This resulted in 185 g (90%) of 21-26 as light yellow oil.

Preparation of Intermediate (21-27): To a solution of 21-26 (128 g, 299.06 mmol, 1.00 eq.) in dichloromethane (900 mL) with an inert atmosphere of nitrogen was added pyridine (300 mL) at room temperature. To this was added trifluoromethane sulfonic anhydride (109.4 g, 387.9 mmol, 1.30 eq.) dropwise with stirring at −20° C. The resulting solution was stirred for 2 h at −20° C. The resulting solution was diluted with ethyl acetate. The resulting mixture was washed with water and brine. The mixture was dried over anhydrous sodium sulfate and concentrated under reduced pressure. This resulted in 158 g (crude) of 21-27 as yellow oil.

Preparation of Intermediate (21-28): To a solution of 21-27 (158 g, 281.89 mmol, 1.00 eq.) in N,N-dimethylformamide (1500 mL) with an inert atmosphere of nitrogen was added Sodium azide (55 g, 846.02 mmol, 3.00 eq.) and Tetrabutylammonium iodide (10.4 g, 28.18 mmol, 0.10 eq.)

at room temperature. The resulting solution was stirred overnight at 100° C. The reaction was then quenched by the addition of water/ice. The resulting solution was extracted with ethyl acetate and the organic layers combined. The resulting mixture was washed with water and brine. The mixture was dried over anhydrous sodium sulfate and concentrated under reduced pressure. The residue was purified by column chromatography. This resulted in 58 g (45%) of 21-28 as yellow oil.

Preparation of Intermediate (21-29): To a solution of 21-28 (70 g, 154.4 mmol, 1.00 eq.) in methanol/water (850/150 mL) was added potassiumcarbonate (6.4 g, 46.0 mmol, 0.30 eq.). The resulting solution was stirred for 5 h at 0° C. The pH value of the solution was adjusted to 7 with 10% hydrochloric acid. The resulting mixture was concentrated under reduced pressure. The resulting solution was diluted with ethyl acetate and washed with water. The mixture was dried over anhydrous sodium sulfate and concentrated under reduced pressure. The residue was purified by column chromatography. This resulted in 26.7 g (71%) of 21-29 as a white solid.

Preparation of Intermediate (21-30): To a solution of 21-29 (12 g, 48.93 mmol, 1.00 eq.) in dichloromethane (360 mL) with an inert atmosphere of nitrogen was followed by the addition of Triethylamine (14.85 g, 146.75 mmol, 3.00 eq.) at room temperature. To this was added tert-butyl (chloro)diphenylsilane (13.5 g, 49.12 mmol, 1.00 eq.) dropwise with stirring at 0° C. The resulting solution was stirred overnight at room temperature. The resulting solution was diluted with dichloromethane and washed with water. The mixture was dried over anhydrous sodium sulfate and concentrated under reduced pressure. The residue was purified by column chromatography. This resulted in 12.8 g (54%) of 21-30 as a white solid. MS m/z [M+Na]+(ESI): 506.

Preparation of Intermediate (21-31): To a solution of oxalyl chloride (5.1 mL, 1.50 eq.) in dichloromethane (300 mL) with an inert atmosphere of nitrogen was added dimethyl sulphoxide (8.1 mL, 3.00 eq.) dropwise with stirring at −78° C. The resulting solution was stirred at −78° C. for 30 min. To this was added a solution of 21-30 (26 g, 43 mmol, 1.00 eq.) in dichloromethane (100 mL) dropwise with stirring at −78° C., stirred for an additional 45 min at −78° C. Then triethylamine (23.5 mL, 4.50 eq.) was added, and allowed to react, with stirring, for an additional 1 h at 25° C. The resulting solution was diluted with dichloromethane, and was washed with hydrogen chloride, saturated sodium bicarbonate, and saturated sodium chloride respectively. The mixture was dried over anhydrous sodium sulfate, filtered, and concentrated under vacuum. This resulted in 20 g (80%) of 21-31 as colorless oil.

Preparation of Intermediate (21-32): To a solution of 21-31 (20 g, 41.53 mmol, 1.00 eq.) in ether (200 mL) with an inert atmosphere of nitrogen, was added methylmagnesium bromide (3M) (28 mL, 62.30 mmol, 1.50 eq.) dropwise with stirred at −100° C. The resulting solution was stirred for 2 hours at −100° C. The reaction was then quenched by the addition of saturated ammonium chloride (50 mL) and diluted with ethyl acetate. The resulting mixture was washed with water and saturated sodium chloride respectively. The organic layer was dried over anhydrous sodium sulfate, filtered, and concentrated under reduced pressure. This resulted in 14.5 g (70%) of 21-32 as colorless oil. MS m/z [M+Na]+(ESI): 520.

Preparation of Intermediate (21-33): To a solution of PH21-32 (15 g, 30.14 mmol, 1.00 eq.) in pyridine (150 mL) with an inert atmosphere of nitrogen, was added methanesulfonyl chloride (4.5 g, 39.28 mmol, 1.30 eq.) dropwise with stirred at 0-5° C. The resulting solution was stirred for 3 hours at 0-5° C. The reaction was then quenched by the addition of methanol (20 mL) and diluted with ethyl acetate. The resulting mixture was washed with water and saturated sodium chloride. The organic layer was dried over anhydrous sodium sulfate, filtered, and concentrated under reduced pressure. This resulted in 13.8 g (70%) of 21-33 as a brown solid. MS m/z [M+Na]+(ESI): 598.

Preparation of Intermediate (21-34): To a solution of 21-33 (10 g, 17.37 mmol, 1.00 eq.) in acetic acid (150 mL) with an inert atmosphere of nitrogen, was added acetyl acetate (19.5 g, 191.01 mmol, 11.00 eq.) and sulfuric acid (170 mg, 1.73 mmol, 0.10 eq.). The resulting solution was stirred for 1 hour at room temperature. The resulting solution was diluted with ethyl acetate. The resulting mixture was washed with water and Sat. sodium chloride. The mixture was dried over anhydrous sodium sulfate and concentrated. The crude product was purified by Flash-Prep-HPLC. This resulted in 6.5 g (60%) of 21-34 as a yellow solid. MS m/z [M+Na]+(ESI): 642.

Preparation of Intermediate (21-35): To a solution of 5-methyl-1, 2, 3, 4-tetrahydropyrimidine-2, 4-dione (1.5 g, 11.90 mmol, 1.50 eq.) in Acetonitrile (125 mL) with an inert atmosphere of nitrogen, was added N, O-Bis(trimethylsilyl) acetamide (5.75 g, 28.19 mmol, 3.50 eq.) at room temperature. The resulting solution was stirred for 2 h at 80° C. To this was added 21-34 (5 g, 8.07 mmol, 1.00 eq.) at 0° C., and then trimethylsilyl trifluoromethanesulfonate (2.34 g, 10.53 mmol, 1.30 eq.) was added dropwise with stirring at 0° C. The resulting solution was allowed to react, with stirring, for an additional 6 h at 80° C. The reaction mixture was cooled to 0° C., quenched by the addition of Sat. ammonium chloride. The resulting solution was extracted with ethyl acetate and the organic layers combined and dried over anhydrous sodium sulfate and concentrated. The residue was purified by column chromatography. This resulted in 4.5 g (81%) of 21-35 as a white solid. MS m/z [M+H]+(ESI): 686.

Preparation of Intermediate (21-36): To a solution of 21-35 (9 g, 13.12 mmol, 1.00 eq.) in methanol (90 mL) with an inert atmosphere of nitrogen, was added potassium carbonate (5.4 g, 38.79 mmol, 3.00 eq.). The resulting solution was stirred for 2 hours at 65° C. and diluted with ethyl acetate. The resulting mixture was washed with water and Sat. sodium chloride. The organic layer was dried over anhydrous sodium sulfate and concentrated. The crude product was purified by Flash-Prep-HPLC. This resulted in 5 g (70%) of 21-36 as a white solid. MS m/z [M+H]+(ESI): 548.

Preparation of Intermediate (21-37): To a solution of 21-36 (6 g, 10.96 mmol, 1.00 eq.) in tetrahydrofuran (60 mL) was added 10% Palladium on activated carbon (2 g). The flask was evacuated and flushed five times with hydrogen. The resulting solution was stirred for 8 hours at room temperature. The solids were filtered out. The resulting mixture was concentrated under reduced pressure. This resulted in 5.3 g (93%) of 21-37R and 21-37S as a white solid. Then the mixture was separated by Prep-SFC. This resulted in 3.5 g as a white solid. MS m/z [M+H]+(ESI): 522.

Preparation of Intermediate (21-38): To a solution of 21-37 (3.5 g, 6.71 mmol, 1.00 eq.) in pyridine (35 mL) with an inert atmosphere of nitrogen was added 1-(chlorodiphenylmethyl)-4-methoxybenzene (2.7 g, 8.74 mmol, 1.30 eq.) at room temperature. The resulting solution was stirred for 2 hours at room temperature. The reaction was then quenched by the addition of methanol (20 mL). The resulting solution was diluted with ethyl acetate. The resulting mixture was washed with Sat. sodium bicarbonate and brine.

The organic layer was dried over anhydrous sodium sulfate and concentrated. The residue was purified by column chromatography. This resulted in 4 g (75%) of 21-38 as a white solid. MS m/z [M−H]− (ESI): 792.

Preparation of Intermediate (21-39): To a solution of 21-38 (4 g, 5.04 mmol, 1.00 eq.) in dichloromethane (40 mL) with an inert atmosphere of nitrogen, was added triethylamine (1 g, 9.9 mmol, 2.0 eq.) at room temperature. To this was added Triethylamine trihydrofluoride (0.97 g, 7.56 mmol, 1.50 eq.) at room temperature. The resulting solution was stirred for 12 hours at room temperature and diluted with dichloromethane. The resulting mixture was washed with water. The mixture was dried over anhydrous sodium sulfate and concentrated. The crude product was purified by Flash-Prep-HPLC. This resulted in 2.3 g (80%) of 21-39 as a white solid. 1H NMR (DMSO-$d_6$, 300 Hz, ppm): δ 11.33 (s, 1H), 7.45 (m, 5H), 7.20 (m, 8H), 6.80 (m, 2H), 5.35 (t, J=5.1 Hz, 1H), 5.15 (s, 1H), 4.23 (m, 1H), 4.05 (m, 1H), 3.81 (m, 1H), 3.73 (s, 3H), 2.92 (d, J=9.7 Hz, 1H), 2.25 (d, J=9.8 Hz, 1H), 2.05 (s, 1H), 1.54 (s, 3H), 1.12 (d, J=6.1 Hz, 3H).

Preparation of (21-40): To a solution of 21-39 in dichloromethane (23 mL) with an inert atmosphere of nitrogen was added Bis(diisopropylamino)(2-cyanoethoxy)phosphine (1.62 g, 5.38 mmol, 1.30 eq.) at room temperature. To this was added 4, 5-Dicyanoimidazole (490 mg, 4.15 mmol, 1.10 eq.) at room temperature. The resulting solution was stirred for 1 hour at room temperature and diluted with dichloromethane. Then the mixture was washed with water. The organic layer was dried over anhydrous sodium sulfate and concentrated. The crude product was purified by Flash-Prep-HPLC. This resulted in 2.3 g (70%) of 21-40 as a white solid. MS m/z [M−H]−(ESI): 754. 1H NMR (DMSO-$d_6$, 400 Hz, ppm) δ 11.37 (s, 1H), 7.45 (m, 4H), 7.28 (m, 9H), 6.80 (m, 2H), 5.18 (d, J=6.3 Hz, 1H), 4.35 (m, 1H), 4.21 (m, 1H), 4.01 (m, 1H), 3.7 (m, 6H), 3.6 (m, 1H), 2.90 (m, 3H), 2.33 (m, 1H), 2.13 (m, 1H), 1.59 (d, J=21.6 Hz, 3H), 1.20 (m, 15H). P NMR (DMSO-$d_6$, 400 Hz, ppm): 147.45, 147.08.

Example 18

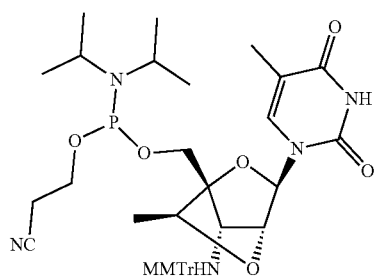

Scheme 20

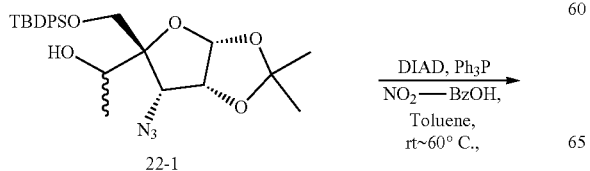

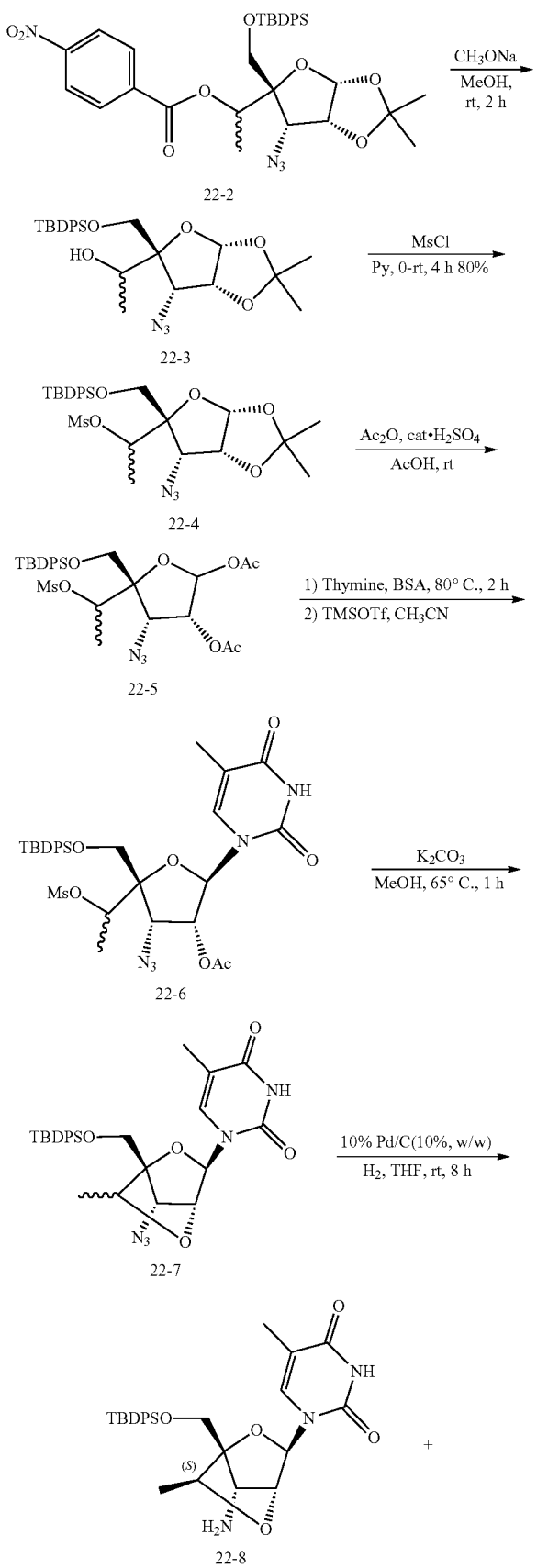

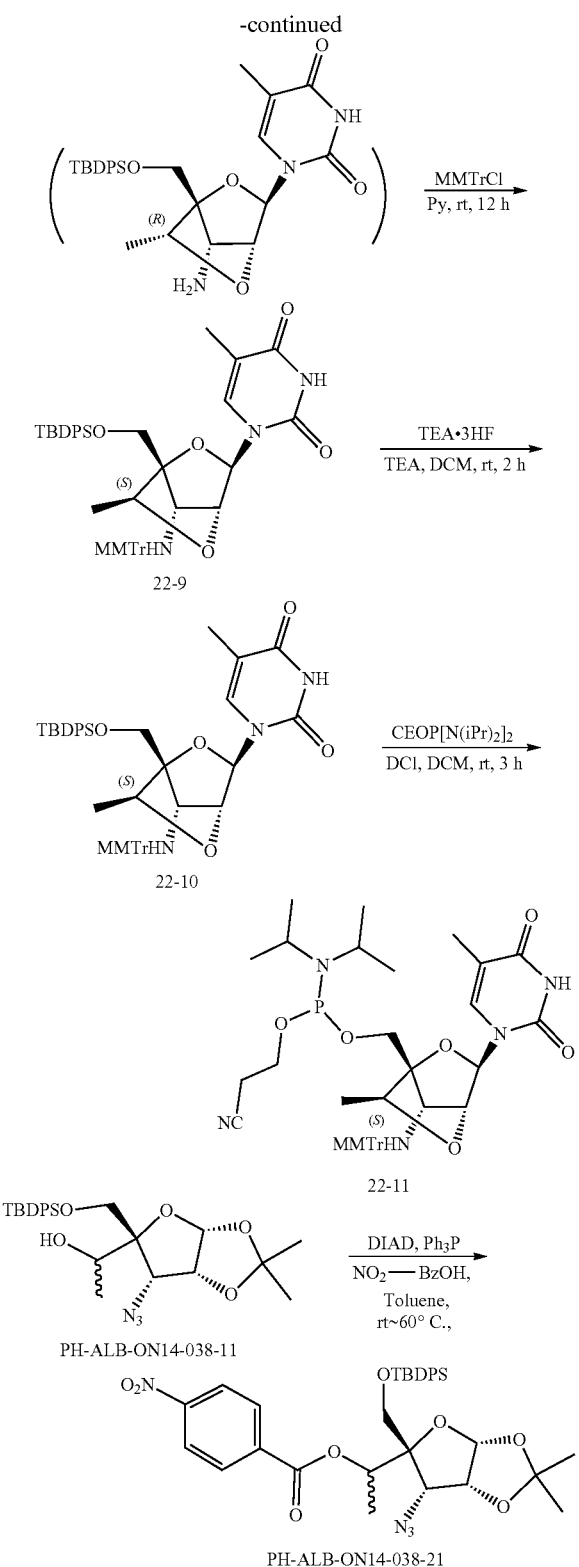

was stirred for 2 h at room temperature. To this was added 22-1 (10 g, 20.09 mmol, 1.00 eq.) at room temperature. The resulting solution was allowed to react for an additional 8 h at 60° C. The reaction mixture was diluted with ethyl acetate. The resulting mixture was washed with water and saturated sodium chloride respectively. The mixture was dried over anhydrous sodium sulfate and concentrated. The crude product was purified by Flash-Prep-HPLC. This resulted in 5 g (38%) of 22-2 as a yellow solid.

Preparation of Intermediate (22-3): To a solution of 22-2 (27.5 g, 42.52 mmol, 1.00 eq.) in methanol (300 mL), with an inert atmosphere of nitrogen, was added sodium hydroxide (4.6 g, 85 mmol, 2.0 eq.) at 0° C. The resulting solution was stirred for 2 hours at 25° C. The pH value of the solution was adjusted to 8 with acetic acid. The resulting mixture was concentrated and then diluted with ethyl acetate. The resulting mixture was washed with water and saturated sodium chloride. The organic layer was dried over anhydrous sodium sulfate and concentrated. The crude product was purified by Flash-Prep-HPLC. This resulted in 16.5 g (78%) of 22-3 as yellow oil.

Preparation of Intermediate (22-4): To a solution of 22-3 (16.5 g, 33.15 mmol, 1.00 eq.) in pyridine (160 mL) with an inert atmosphere of nitrogen, was added methanesulfonyl chloride (4.95 g, 43.23 mmol, 1.30 eq.) dropwise with stirred at 0-5° C. The resulting solution was stirred for 3 hours at 0-5° C. The reaction was then quenched by the addition of methanol (30 mL) and diluted with ethyl acetate. The resulting mixture was washed with water and Sat. sodium chloride. The mixture was dried over anhydrous calcium chloride and concentrated under reduced pressure. This resulted in 15.3 g (70%) of 22-4 as a brown solid. MS m/z [M+Na]+(ESI): 598.

Preparation of Intermediate (22-5): To a solution of 22-4 (15.3 g, 26.57 mmol, 1.00 eq.) in acetic acid (150 mL) with an inert atmosphere of nitrogen, was added acetyl acetate (30 g, 292.2 mmol, 11.00 eq.) and sulfuric acid (260 mg, 2.65 mmol, 0.10 eq.). The resulting solution was stirred for 1 hour at room temperature and diluted with ethyl acetate. The resulting mixture was washed with water and Sat. sodium chloride. The organic layer was dried over anhydrous sodium sulfate and concentrated. The crude product was purified by Flash-Prep-HPLC. This resulted in 10 g (60%) of 22-5 as a yellow solid. MS m/z [M+Na]+(ESI): 642.

Preparation of Intermediate (22-6): To a solution of 5-methyl-1, 2, 3, 4-tetrahydropyrimidine-2, 4-dione (3.0 g, 23.8 mmol, 1.50 eq.) in Acetonitrile (250 mL) with an inert atmosphere of nitrogen, was added N, O-Bis (trimethylsilyl) acetamide (11.5 g, 56.1 mmol, 3.50 eq.) at room temperature. The resulting solution was stirred for 2 h at 80° C. To this was added 22-5 (10 g, 16.14 mmol, 1.00 eq.) at 0° C., and then trimethylsilyl trifluoromethanesulfonate (4.68 g, 21.06 mmol, 1.30 eq.) was added dropwise with stirring at 0° C. The resulting solution was allowed to react, with stirring, for an additional 6 h at 80° C. The reaction mixture was cooled to 0° C., quenched by the addition of Sat. ammonium chloride. The resulting solution was extracted with ethyl acetate and the organic layers combined and dried over anhydrous sodium sulfate and concentrated. The residue was purified by column chromatography. This resulted in 9 g (81%) of 22-6 as a white solid. MS m/z [M+H]+(ESI): 686.

Preparation of Intermediate (22-7): To a solution of 22-6 (9 g, 13.12 mmol, 1.00 eq.) in methanol (90 mL) with an inert atmosphere of nitrogen, was added potassium carbonate (5.4 g, 38.79 mmol, 3.00 eq.) at room temperature. The Preparation of Intermediate (22-2): To a solution of triphenylphosphane (10.5 g, 40.03 mmol, 2.00 eq.) in Toluene (100 mL) with an inert atmosphere of nitrogen, was added diisopropyl azodicarboxylate (8.10 g, 40.03 mmol, 2.00 eq.) at room temperature. To this was added p-nitrobenzoic acid (6.70 g, 40.03 mmol, 2.00 eq.) at 0° C. The resulting solution resulting solution was stirred for 2 hours at 65° C. The resulting solution was diluted with ethyl acetate. The resulting mixture was washed with water and Sat. sodium chloride. The organic layer was dried over anhydrous sodium sulfate and concentrated. The crude product was purified by Flash-Prep-HPLC. This resulted in 5 g (70%) of 22-7 as a white solid. MS m/z [M+H]+(ESI): 548.

Preparation of Intermediate (22-8): To a solution of 22-7 (5 g, 9.13 mmol, 1.00 eq.) in tetrahydrofuran (50 mL) was added 10% Palladium on activated carbon (2 g). The flask was evacuated and flushed five times with hydrogen. The resulting solution was stirred for 8 hours at room temperature. The solids were filtered out. The resulting mixture was concentrated under reduced pressure. This resulted in 4.4 g (93%) of 22-8R and 22-8 as a white solid. Then the mixture was separated by Prep-SFC. This resulted in 1.9 g 22-8 as a white solid. MS m/z [M+H]+(ESI): 522.

Preparation of Intermediate (22-9): To a solution of 22-8 (1.9 g, 3.64 mmol, 1.00 eq.) in pyridine (20 mL) with an inert atmosphere of nitrogen, was added 1-(chlorodiphenyl-methyl)-4-methoxybenzene (1.23 g, 4.01 mmol, 1.10 eq.) at room temperature. The resulting solution was stirred for 2 hours at room temperature. The reaction was then quenched by the addition of methanol (10 mL). The resulting solution was diluted with ethyl acetate. The resulting mixture was washed with Sat. sodium bicarbonate and Sat. sodium chloride. The organic layer was dried over anhydrous sodium sulfate and concentrated. The residue was purified by column chromatography. This resulted in 2.3 g (80%) of 22-9 as a white solid. MS m/z [M−H]− (ESI): 792.

Preparation of Intermediate (22-10): To a solution of 22-9 (2.3 g, 2.90 mmol, 1.00 eq.) in dichloromethane (20 mL) with an inert atmosphere of nitrogen, was added triethyl-amine (723 mg, 7.25 mmol, 2.50 eq.) at room temperature. To this was added triethylamine trihydrofluoride (2.8 g, 17.4 mmol, 6.00 eq.) at room temperature and the resulting solution was stirred for 2 hours at 25° C. The resulting solution was diluted with dichloromethane, washed with water and saturated sodium chloride respectively. The organic layer was dried over anhydrous sodium sulfate, filtered, and concentrated. The crude product was purified by Flash-Prep-HPLC. This resulted in 1.7 g (80%) of 22-10 as a white solid. 1H NMR (DMSO-$d_6$, 400 Hz, ppm) 611.33 (s, 1H), 7.41 (m, 4H), 7.20 (m, 7H), 7.19 (m, 2H), 6.80 (m, 2H), 5.25 (t, J=5.2 Hz, 1H), 5.15 (s, 1H), 4.15 (m, 2H), 3.91 (q, J=6.7 Hz, 1H), 3.73 (s, 3H), 2.73 (d, J=9.5 Hz, 1H), 2.25 (m, 1H), 2.05 (m, 1H), 1.55 (s, 3H), 1.38 (d, J=6.8 Hz, 3H).

Preparation of (22-11): To a solution of 22-10 (1.77 g, 3.19 mmol, 1.00 eq.) in dichloromethane (20 mL) with an inert atmosphere of nitrogen, was added Bis(diisopropy-lamino)(2-cyanoethoxy)phosphine (1.35 g, 4.3 mmol, 1.4 eq.) at room temperature. To this was added 4, 5-Dicyano-imidazole (451 mg, 3.6 mmol, 1.20 eq.) at room temperature. The resulting solution was stirred for 2 hours at 25° C. and diluted with dichloromethane. The resulting mixture was washed with water and saturated sodium chloride respectively. The organic layer was dried over anhydrous sodium sulfate, filtered, and concentrated. The crude product was purified by Flash-Prep-HPLC. This resulted in 1.82 g (76%) of 22-11 as a white solid. MS m/z [M−H]−(ESI): 754. 1H NMR (DMSO-$d_6$, 400 Hz, ppm) δ 11.4 (d, J=9.8 Hz, 1H), 7.40 (m, 4H), 7.28 (m, 8H), 7.07 (m, 1H), 6.79 (m, 2H), 5.22 (d, J=4.0 Hz, 1H), 4.38 (m, 1H), 4.27 (m, 1H), 4.01 (q, J=6.7 Hz, 1H), 3.7 (m, 7H), 2.82 (m, 1H), 2.70 (m, 1H), 2.13 (m, 1H), 2.32 (d, J=60.2 Hz, 1H), 2.13 (dd, J=28.6 Hz and 6.0 Hz, 1H), 1.60 (d, J=18.0 Hz, 3H), 1.45 (t, J=6.9 Hz, 3H), 1.20 (m, 12H). P NMR (DMSO-$d_6$, 400 Hz, ppm): δ 148.03, 147.53.

Example 19

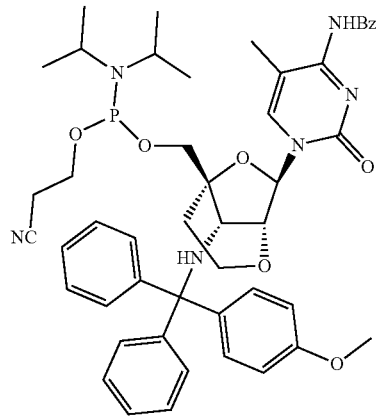

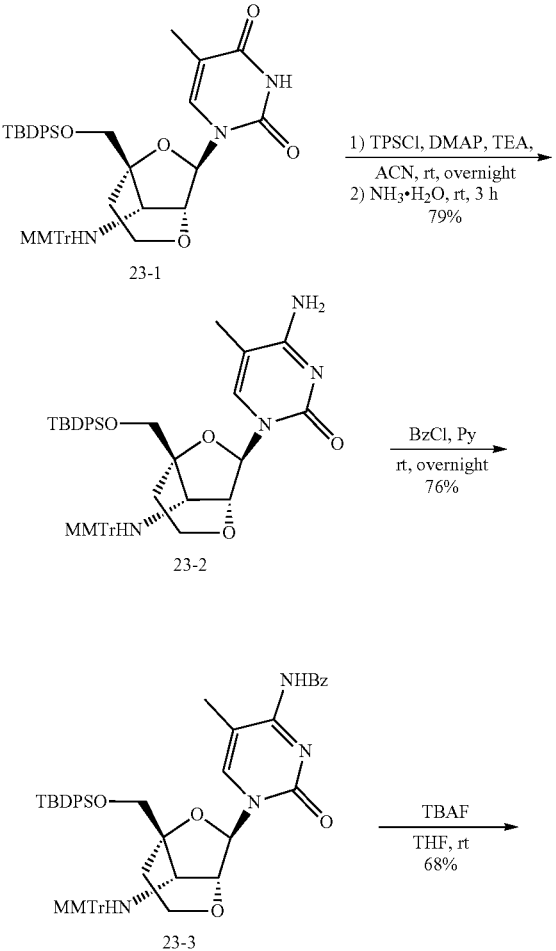

Scheme 21

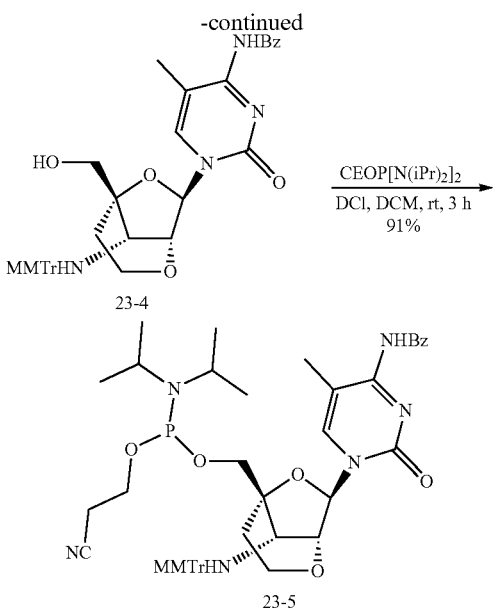

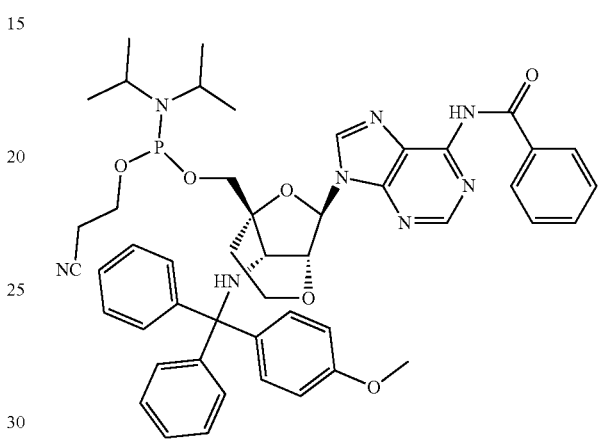

Preparation of Intermediate (23-2): To a solution of 23-1 (7.2 g, 9.07 mmol, 1.0 eq.) in Acetonitrile (70 mL) with an inert atmosphere of nitrogen, was added Triethylamine (2.75 g, 27.24 mmol, 3.0 eq.), 4-(dimethylamino)-pyridin (3.4 g, 27.24 mmol, 3.0 eq.) and 2, 4, 6-Triisopropylbenzenesulfonyl chloride (8.226 g, 27.24 mmol, 3.0 eq.). The resulting solution was stirred for 12 h at room temperature. Then ammoniumhydroxide (20 mL) was added and stirred for 1 hour at room temperature. The resulting solution was extracted with dichloromethane. The organic layers combined and washed with water, dried over anhydrous sodium sulfate, concentrated. The crude product was purified by Flash-Prep-HPLC. This resulted in 5.7 g (79%) of 23-2 as a yellow solid MS m/z [M−H]−(ESI):791.

Preparation of Intermediate (23-3): To a solution of 23-2 (5.7 g, 7.20 mmol, 1.00 eq.) in Pyridine (70 mL) with an inert atmosphere of nitrogen, was added Benzoyl chloride (1.14 g, 1.2 eq.) dropwise at 0° C. The resulting solution was stirred for 12 h at room temperature. The reaction was then quenched by the addition of methanol. The resulting mixture was concentrated. The residue was purified by column chromatography. This resulted in 5 g (76%) of 23-3 as a light yellow solid. MS m/z [M−H]− (ESI): 895.

Preparation of Intermediate (23-4): To a solution of 23-3 (5 g, 5.58 mmol, 1.00 eq.) in Tetrahydrofuran (50 mL) was added tetrabutylammonium fluoride (1M in tetrahydrofuran, 11 mL, 2.0 eq.). The resulting solution was stirred for 4 h at room temperature. The resulting mixture was concentrated. The crude product was purified by Flash-Prep-HPLC. This resulted in 2.5 g (68%) of 23-4 as a white solid. MS m/z [M−H]−(ESI): 657. 1H NMR (DMSO-$d_6$, 300 Hz, ppm): δ 13.08 (s, 1H), 8.32-8.18 (m, 2H), 7.70-7.35 (m, 8H), 7.31-7.08 (m, 8H), 6.75 (m, 2H), 5.68 (s, 1H), 5.33 (s, 1H), 4.01-3.91 (m, 1H), 3.79 (m, 3H), 3.69 (s, 3H), 2.85 (m, 1H), 2.46-2.05 (m, 2H), 1.88 (s, 3H), 1.70 (s, 1H), 1.36 (m, 1H).

Preparation of (23-5): To a solution of 23-4 (2.5 g, 3.80 mmol, 1.00 eq.) in dichloromethane (25 mL) with an inert atmosphere of nitrogen was added Bis(diisopropylamino) (2-cyanoethoxy)phosphine (1.7 g, 5.70 mmol, 1.50 eq.) at room temperature. To this was added 4, 5-Dicyanoimidazole (490 mg, 4.17 mmol, 1.10 eq.) at room temperature. The resulting solution was stirred for 3 h at room temperature and diluted with dichloromethane. The resulting mixture was washed with water. The organic layer was dried over anhydrous sodium sulfate and concentrated. The crude product was purified by Flash-Prep-HPLC. This resulted in 2.9710 g (91%) of 23-5 as a white solid. MS m/z [M+H]+ (ESI): 859. 1H NMR (DMSO-$d_6$, 300 Hz, ppm): δ 13.07 (s, 1H), 8.15 (m, 2H), 7.70-7.42 (m, 8H), 7.23 (m, 8H), 6.75 (m, 2H), 5.81-5.68 (m, 1H), 4.17-3.97 (m, 1H), 3.96-3.55 (m, 9H), 3.10-2.55 (m, 4H), 2.38-2.19 (m, 1H), 1.98 (m, 4H), 1.81-1.38 (m, 2H), 1.20 (m, 12H). P NMR (DMSO-$d_6$, 300 Hz, ppm): 148.11, 145.59.

Example 20

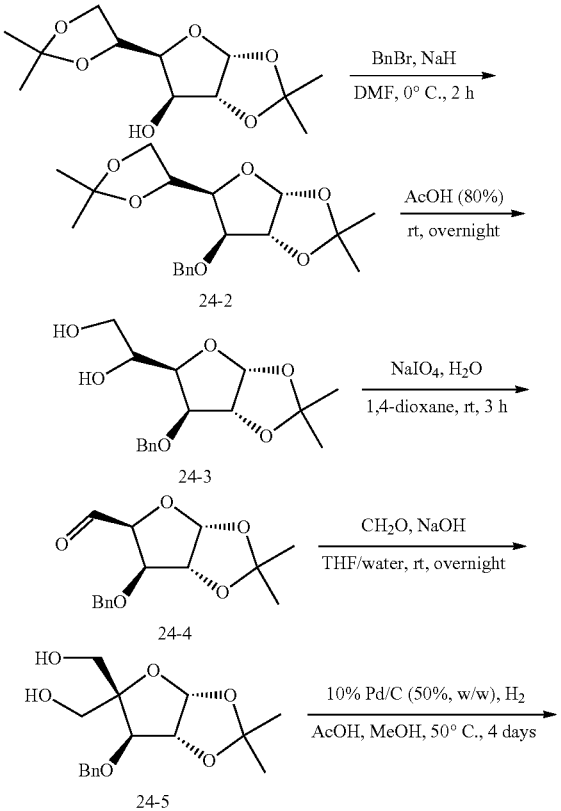

Scheme 22

-continued
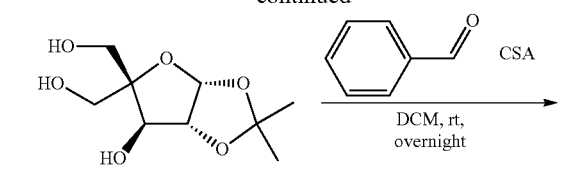
24-6
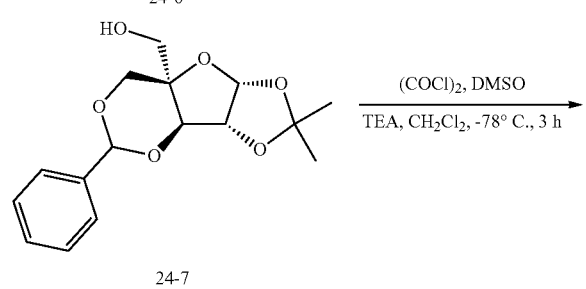
24-7
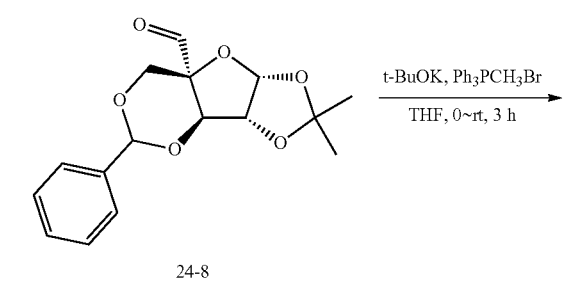
24-8
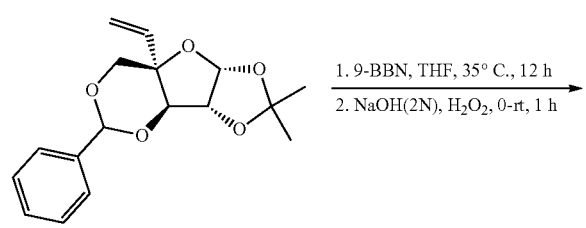
24-9
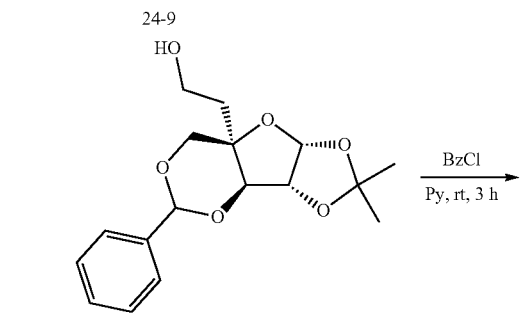
24-10
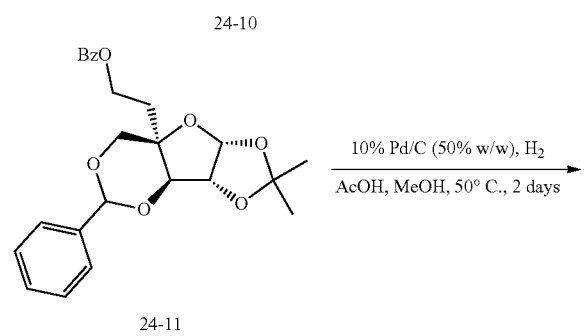
24-11
-continued
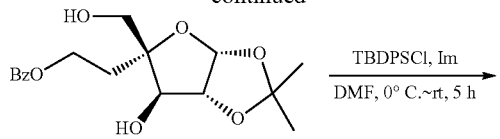
24-12
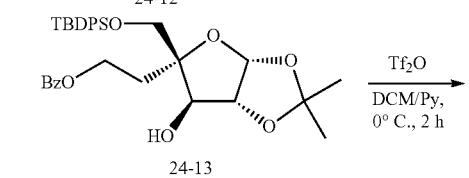
24-13
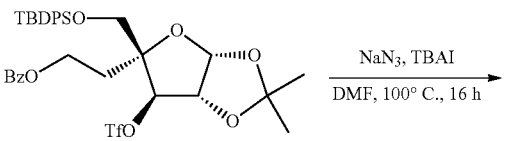
24-14
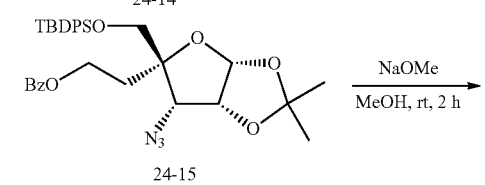
24-15
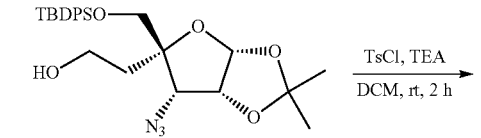
24-16
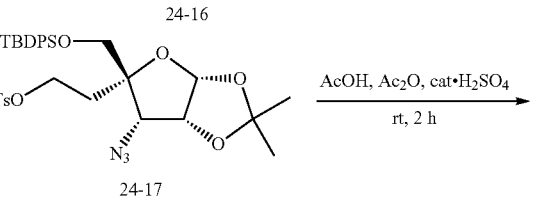
24-17
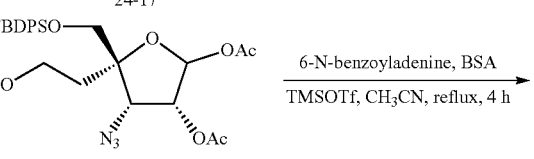
24-18
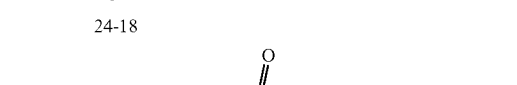
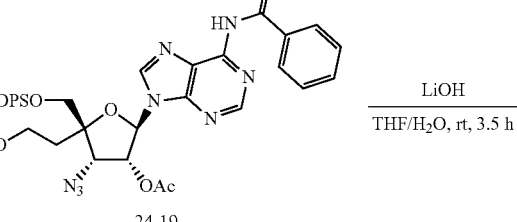
24-19
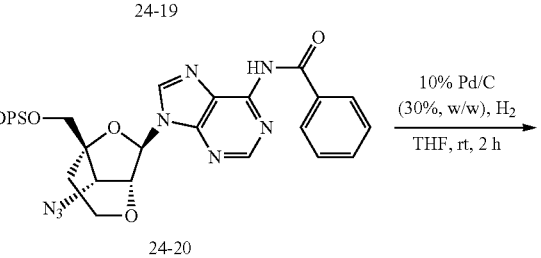
24-20

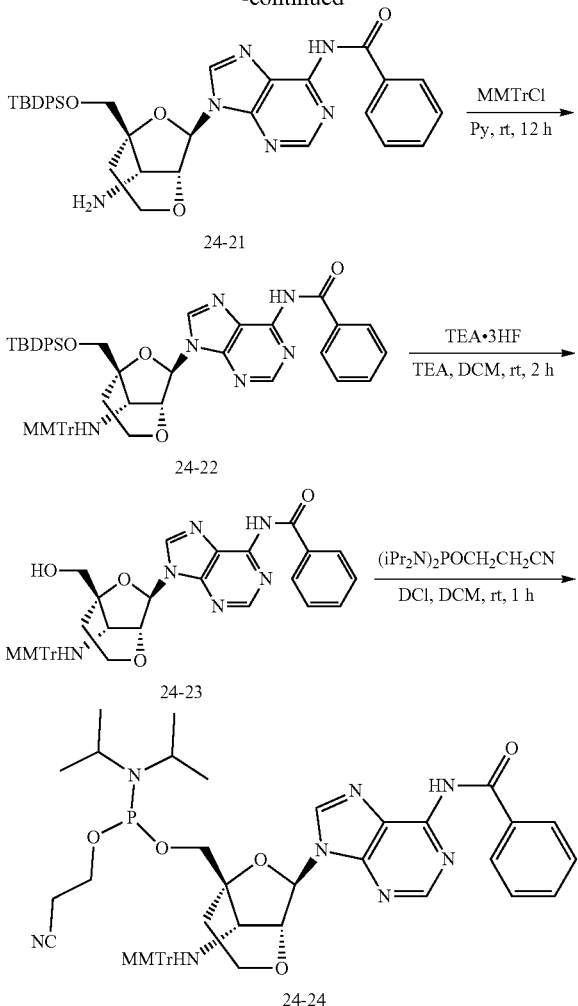

Preparation of Intermediate (24-2): To a solution of (3aR,5S,6S,6aR)-5-(2,2-dimethyl-1,3-dioxolan-4-yl)-2,2-dimethyl-tetrahydro-2H-furo[2,3-d][1,3]dioxol-6-ol (500 g, 1.92 mol, 1.00 eq.) in N,N-dimethylformamide (5000 mL) with an inert atmosphere of nitrogen, was added (bromomethyl) benzene (345 g, 2.02 mol, 1.05 eq.) at room temperature. Sodium hydride (123 g, 3.0 mol, 1.60 eq.) was added for several batches at 0° C. The resulting solution was stirred for 2 h at 25° C. The reaction was then quenched by the addition of Saturated ammoniumchloride (2000 mL). The resulting solution was extracted with ethyl acetate and the organic layers combined, dried over anhydrous sodium sulfate, filtered and concentrated. This resulted in 670 g (crude) of 24-2 as yellow oil. This crude product was used in the next step without further purification. MS m/z [M+H]+(ESI): 351.

Preparation of Intermediate (24-3): 24-2 (300 g, 856.14 mmol, 1.00 eq.) was dissolved acetic acid (80% in water, 3000 mL). The resulting solution was stirred overnight at room temperature. The resulting mixture was concentrated and diluted with ethyl acetate. The resulting mixture was washed with Saturated sodium bicarbonate respectively. The organic phase was dried over anhydrous sodium sulfate, filtered and concentrated. This resulted in 237 g (crude) of 24-3 as yellow oil. This crude product was used in the next step without further purification. MS m/z [M+Na]+(ESI): 333.

Preparation of Intermediate (24-4): To a solution of 24-3 (200 g, 644.44 mmol, 1.00 eq.) in 1,4-dioxane (2000 mL) was added a solution of sodium periodate (138 g, 644.44 mmol, 1.00 eq.) in water (2000 mL) dropwise with stirring at 0° C. The resulting solution was stirred for 2 h at room temperature. The resulting solution was diluted with ethyl acetate and washed with water. The organic phase was dried over anhydrous sodium sulfate, filtered and concentrated. This resulted in 160 g (crude) of 24-4 as yellow oil. This crude product was used in the next step without further purification. MS m/z [M+H]+(ESI): 279.

Preparation of Intermediate (24-5): To a solution of 24-4 (200 g, 718.64 mmol, 1.00 eq.) in tetrahydrofuran/water (1000 mL/1000 mL) was added Formaldehyde Solution (37%, 480 mL) at room temperature. To this was added 2N sodium hydroxide (1200 mL, 3.12 eq.) dropwise with stirring at 0° C. The resulting solution was stirred overnight at room temperature. The reaction mixture was extracted with ethyl acetate and the organic layers combined. The organic layer was washed with water. The organic phase was dried over anhydrous sodium sulfate, filtered and concentrated. This resulted in 152.8 g (crude) of 24-5 as yellow oil. This crude product was used in the next step without further purification. MS m/z [M+Na]+(ESI): 333.

Preparation of Intermediate (24-6): To a solution of 24-5 (500 g, 1.61 mmol, 1.00 eq.) in methanol/Acetic acid (5000/500 mL) in a 20-L pressure tank reactor with an inert atmosphere of nitrogen, was added 10% Palladium on activated carbon (250 g). The pressure tank was evacuated and flushed five times with hydrogen. The resulting solution was stirred for 4 days at 50° C. (8 atm). The solids were filtered out. The resulting mixture was concentrated. The residue was purified by column chromatography. This resulted in 280 g (79%) of 24-6 as a white solid.

Preparation of Intermediate (24-7): To a solution of 24-6 (200 g, 908.2 mmol, 1.00 eq.) in dichloromethane (6000 mL) with an inert atmosphere of nitrogen, was added benzaldehyde (436.0 g, 2722.9 mmol, 3.00 eq.) dropwise with stirring at 0° C. Then camphorsulfonic acid (2 g) was added at 0° C. The resulting solution was stirred overnight at room temperature. The reaction was then quenched by the addition of 2000 mL Saturated sodium bicarbonate. The resulting solution was extracted with dichloromethane and the organic layers combined. The organic phase was dried over anhydrous sodium sulfate, filtered and concentrated. The residue was purified by column chromatography. This resulted in 13.5 g (48%) of 24-7 as a white solid. MS m/z [M+Na]+(ESI): 331. 1H NMR (DMSO-d$_6$, 400 Hz, ppm): δ 7.44-7.30 (m, 6H), 5.97 (d, J=4.1 Hz, 1H), 5.46 (s, 1H), 5.06 (t, J=5.4 Hz, 1H), 4.64-4.52 (m, 2H), 4.14 (d, J=13.0 Hz, 1H), 4.08-3.93 (m, 1H), 3.74-3.65 (m, 1H), 3.38 (m, 1H), 1.46 (s, 3H), 1.23 (s, 3H).

Preparation of Intermediate (24-8): To a solution of oxalyl chloride (30.9 g, 243.31 mmol, 1.50 eq.) in dichloromethane (1000 mL) with an inert atmosphere of nitrogen, was added of dimethyl sulfoxide (37.9 g, 485.09 mmol, 3.00 eq.) dropwise with stirring at −78° C. The resulting solution was stirred for 30 min at −78° C. To this was added a solution of 24-7 (50 g, 162.17 mmol, 1.00 eq.) in dichloromethane (200 mL) dropwise with stirring at −78° C. The resulting solution was allowed to react, with stirring, for an additional 1.5 h at −78° C. Then was added triethylamine (73.9 g, 730.31 mmol, 4.50 eq.) dropwise with stirring at −78° C. The resulting solution was allowed to react, with stirring, for an additional 2 h at −78° C. The resulting solution was diluted with dichloromethane and washed with 5% hydrochloric acid, Saturated sodiumbicarbonate, and Saturated sodium chloride. The organic phase was dried over anhydrous sodium sulfate, filtered and concentrated. This resulted in 49 g (crude) of 24-8 as a white solid. This crude product was used in the next step without further purification. MS m/z [M+H]+(ESI): 307.

Preparation of Intermediate (24-9): To a solution of methyltriphenylphosphonium bromide (139.8 g, 2.00 eq.) in tetrahydrofuran (600 mL) with an inert atmosphere of nitrogen, was added Potassium tert-butoxide (43.8 g, 390.33 mmol, 2.00 eq.). The resulting solution was stirred for 30 min at room temperature. To this a solution of 24-8 (60 g, 195.87 mmol, 1.00 eq.) in tetrahydrofuran (150 mL) was added dropwise with stirring at 0° C. The resulting solution was allowed to react, with stirring, for an additional 2 h at room temperature. The reaction was then quenched by the addition of Saturated Ammonium chloride (400 mL). The resulting solution was extracted with ethyl acetate and the organic layers combined. The organic layer was washed with water, and Saturated sodium chloride. The organic phase was dried over anhydrous sodium sulfate, filtered and concentrated. The residue was purified by column chromatography. This resulted in 38.7 g (65%) of 24-9 as a white solid. MS m/z [M+H]+(ESI): 305.

Preparation of Intermediate (24-10): To a solution of 24-9 (60 g, 197.16 mmol, 1.00 eq.) in tetrahydrofuran (600 mL) with an inert atmosphere of nitrogen, was added 9-Borabicyclo[3.3.1]nonane (0.5M in tetrahydrofuran, 789 mL, 2.00 eq.). The resulting solution was stirred overnight at 35° C. Then sodium hydroxide (2N in water, 591 mL, 6.00 eq.) was added at room temperature. To this was added hydrogen peroxide (30%, 120 mL, 6.00 eq.) dropwise with stirring at room temperature. The resulting solution was allowed to react. The resulting solution was extracted with dichloromethane and the organic layers combined. The organic phase was dried over anhydrous sodium sulfate, filtered and concentrated. The residue was purified by column chromatography. This resulted in 43.5 g (68%) of 24-10 as a white solid. MS m/z [M+Na]+(ESI): 345.

Preparation of Intermediate (24-11): To a solution of 24-10 (100 g, 310.2 mmol, 1.00 eq.) in pyridine (1000 mL) with an inert atmosphere of nitrogen, was added benzoyl chloride (130 g, 924.8 mmol, 3.00 eq.) dropwise with stirring at 0° C. The resulting solution was stirred for 3 h at room temperature. The reaction was then quenched by the addition of methanol (200 mL). The resulting mixture was concentrated. The solid was diluted with ethyl acetate. The resulting mixture was washed with water and Saturated sodium chloride. The organic phase was dried over anhydrous sodium sulfate, filtered and concentrated. The residue was purified by column chromatography. This resulted in 110 g (83%) of 24-11 as a white solid. MS m/z [M+Na]+(ESI): 449.

Preparation of Intermediate (24-12): To a solution of 24-11 (200 g, 469 mmol, 1.00 eq.) in methanol/tetrahydrofuran (500/100 mL) was added 10% Palladium on activated carbon (100 g). The flask was evacuated and flushed five times with hydrogen. The resulting solution was stirred for 48 h at 40° C. The solids were filtered out. The resulting mixture was concentrated. The residue was purified by column chromatography. This resulted in 35 g (88%) of 24-12 as colorless oil. MS m/z [M+Na]+(ESI): 361.

Preparation of Intermediate (24-13): To a solution of 24-12 (50 g, 147.77 mmol, 1.00 eq.) and imidazole (19.5 g, 286.43 mmol, 2.00 eq.) in N,N-dimethylformamide (500 mL) with an inert atmosphere of nitrogen, was added tert-Butyldiphenylsilane (44.5 g, 1.10 eq.) dropwise with stirring at 0° C. The resulting solution was stirred for 2 h at room temperature. The reaction was then quenched by the addition of methanol (100 mL). The resulting mixture was concentrated. The residue was dissolved in dichloromethane. The resulting mixture was washed with water and Saturated sodium chloride. The organic phase was dried over anhydrous sodium sulfate, filtered and concentrated. The residue was purified by column chromatography. This resulted in 60 g (70%) of 24-13 as a solid. MS m/z [M+Na]+(ESI): 599. 1H NMR (DMSO-$d_6$, 300 Hz, ppm): 7.90-7.80 (m, 2H), 7.72-7.54 (m, 5H), 7.49-7.30 (m, 8H), 5.85 (d, J=4.4 Hz, 1H), 5.59 (d, J=4.9 Hz, 1H), 4.54 (m, 1H), 4.37 (t, J=7.0 Hz, 2H), 4.09 (m, 1H), 3.29 (s, 2H), 2.22 (m, 2H), 1.42 (s, 3H), 1.21 (s, 3H), 0.96 (s, 9H).

Preparation of Intermediate (24-14): To a solution of 24-13 (64 g, 110.97 mmol, 1.00 eq.) in dichloromethane/pyridine (448/134 mL) with an inert atmosphere of nitrogen, was added Trifluoromethanesulfonic anhydride (46.9 g, 166.23 mmol, 1.50 eq.) dropwise with stirring at 0° C. The resulting solution was stirred for 2 h at 0° C. The resulting solution was diluted with dichloromethane. The resulting mixture was washed with water and Saturated sodium chloride. The organic phase was dried over anhydrous sodium sulfate, filtered and concentrated. This resulted in 78 g (crude) of 24-14 as a solid. This crude product was used in the next step without further purification. MS m/z [M+Na]+(ESI): 731.

Preparation of Intermediate (24-15): To a solution of 24-14 (78 g, 110.04 mmol, 1.00 eq.) and Tetrabutylammonium iodide (4 g, 10.83 mmol, 0.10 eq.) in N,N-dimethylformamide (800 mL) with an inert atmosphere of nitrogen, was added Sodium azide (21.5 g, 330.72 mmol, 3.00 eq.). The resulting solution was stirred overnight at 100° C. The reaction was then quenched by the addition of ice water (200 mL). The resulting solution was diluted with ethyl acetate. The resulting mixture was washed with water and Saturated sodium chloride. The organic phase was dried over anhydrous sodium sulfate, filtered and concentrated. The residue was purified by column chromatography. This resulted in 45 g (68%) of 24-15 as brown oil. MS m/z [M+Na]+(ESI):624.

Preparation of Intermediate (24-16): To a solution of 24-15 (91 g, 151.22 mmol, 1.00 eq.) in methanol (900 mL) with an inert atmosphere of nitrogen, was added sodium methoxide (30% in methanol, 50 mL, 2.00 eq.). The resulting solution was stirred for 2 h at room temperature. The resulting solution was extracted with ethyl acetate and the organic layers combined. The organic layer was washed with water and Saturated sodium chloride. The organic phase was dried over anhydrous sodium sulfate, filtered and concentrated. The residue was purified by column chromatography. This resulted in 55 g (73%) of 24-16 as a white solid. MS m/z [M+Na]+(ESI):520.

Preparation of Intermediate (24-17): To a solution of 24-16 (56 g, 112.53 mmol, 1.00 eq.) and triethylamine (67.2 g, 664.10 mmol, 6.00 eq.) in dichloromethane (825 mL) with an inert atmosphere of nitrogen, was added 4-dimethylaminopyridine (1 g, 8.19 mmol, 0.31 eq.) and 4-toluene sulfonyl chloride (31.5 g, 165.22 mmol, 1.50 eq.) in order at room temperature. The resulting solution was stirred for 2 h at room temperature. The resulting solution was diluted with dichloromethane. The resulting mixture was washed with water and Saturated sodium chloride. The organic phase was dried over anhydrous sodium sulfate, filtered and concentrated. The residue was purified by column chromatography. This resulted in 55 g (75%) of 24-17 as colorless oil. MS m/z [M+Na]+(ESI):674.

Preparation of Intermediate (24-18): To a solution of 24-17 (100 g, 153.4 mmol, 1.00 eq.) in acetic acid (1000 mL) with an inert atmosphere of nitrogen, were added acetyl acetate (17.2 g, 168.48 mmol, 11.00 eq.) and sulfuric acid (300 mg, 3.08 mmol, 0.20 eq.). The resulting solution was stirred for 2 h at room temperature. The reaction was then quenched by the addition of ice water (600 mL). The resulting solution was extracted with ethyl acetate. The resulting mixture was washed water and Saturated sodium chloride. The organic phase was dried over anhydrous sodium sulfate, filtered and concentrated. The residue was purified by column chromatography. This resulted in 52 g (49%) of 24-18 as a brown solid. MS m/z [M+Na]+(ESI): 718.

Preparation of Intermediate (24-19): To a solution of 6-N-benzoyladenine (6.7 g, 1.50 eq.) in acetonitrile (100 mL) with an inert atmosphere of nitrogen, was added N,O-Bis(trimethylsilyl)acetamide (18.9 g, 92.91 mmol, 5.00 eq.). The resulting solution was stirred for 1 h at 85° C. This was followed by the addition of 24-18 (13 g, 18.68 mmol, 1.00 eq.) in acetonitrile (100 mL) at 0° C. To this trifluoromethanesulfonic acid trimethylsilyl ester (20.7 g, 92.91 mmol, 5.00 eq.) was added dropwise a at 0° C. The resulting solution was allowed to react, with stirring, for an additional 4 h at 85° C. The reaction was then quenched by the addition of Saturated sodium bicarbonate (100 mL). The resulting solution was extracted with ethyl acetate and the organic layers combined. The organic layer was washed with water and Saturated sodium chloride. The organic phase was dried over anhydrous sodium sulfate, filtered and concentrated. The crude product was purified by Flash-Prep-HPLC. This resulted in 8 g (49%) of 24-19 as a white solid. MS m/z [M+H]+(ESI):875.

Preparation of Intermediate (24-20): To a solution of 24-19 (7.4 g, 8.46 mmol, 1.00 eq.) in tetrahydrofuran (55 mL) with an inert atmosphere of nitrogen, was added a solution of lithium hydroxide (1.01 g, 42.17 mmol, 5.00 eq.) in water (25 mL) at 0° C. The resulting solution was stirred for 4 h at room temperature. The resulting solution was diluted with ethyl acetate. The resulting mixture was washed with water and Saturated sodium chloride. The organic phase was dried over anhydrous sodium sulfate, filtered and concentrated. The residue was purified by column chromatography. This resulted in 4.3 g (77%) of 24-20 as a white solid. MS m/z [M+H]+(ESI):661.

Preparation of Intermediate (24-21): To a solution of 24-20 (4 g, 6.05 mmol, 1.00 eq.) in tetrahydrofuran (40 mL), was added 10% Palladium on activated carbon (1.2 g). The flask was evacuated and flushed five times with hydrogen. The resulting solution was stirred for 3 h at 25° C. The solids were filtered out. The resulting mixture was concentrated. This resulted in 3.8 g (99%) of 24-21 as a white solid. MS m/z [M+H]+(ESI):635.

Preparation of Intermediate (24-22): To a solution of 24-21 (3.8 g, 5.99 mmol, 1.00 eq.) in pyridine (38 mL) with an inert atmosphere of nitrogen, was added 4-Methoxytriphenylmethyl chloride (2.0 g, 6.59 mmol, 1.10 eq.) at 0° C. The resulting solution was stirred for 3 h at 25° C. The reaction was then quenched by the addition of methanol (5 mL). The resulting mixture was concentrated. The residue was dissolved in dichloromethane. The resulting mixture was washed with water and Saturated sodium chloride. The organic phase was dried over anhydrous sodium sulfate, filtered and concentrated. The crude product was purified by Flash-Prep-HPLC. This resulted in 2.7 g (50%) of 24-22 as a white solid. MS m/z [M+H]+(ESI):908.

Preparation of Intermediate (24-23): To a solution of 24-22 (2.7 g, 2.98 mmol, 1.00 eq.) in dichloromethane (27 mL) with an inert atmosphere of nitrogen, was added triethylamine (750 mg, 7.41 mmol, 2.50 eq.) and triethylamine trihydrofluoride (2.87 g, 17.80 mmol, 6.00 eq.) in order. The resulting solution was stirred for 2 h at 25° C. The resulting solution was diluted with dichloromethane. The resulting mixture was washed with water and Saturated sodium chloride. The organic phase was dried over anhydrous sodium sulfate, filtered and concentrated. The crude product was purified by Flash-Prep-HPLC. This resulted in 1.8 g (90%) of 24-23 as a white solid. MS m/z [M+H]+(ESI):669. 1H NMR (DMSO-d$_6$, 300 Hz, ppm): δ 11.18 (s, 1H), 8.63 (d, J=13.7 Hz, 2H), 8.13-8.03 (m, 2H), 7.71-7.49 (m, 3H), 7.42-7.29 (m, 4H), 7.23-6.92 (m, 8H), 6.62-6.51 (m, 2H), 6.25 (s, 1H), 5.27 (t, J=4.3 Hz, 1H), 4.04 (m, J=12.0 Hz, 4.6 Hz, 1H), 3.88 (t, J=5.5 Hz, 3H), 3.57 (s, 3H), 3.04 (d, J=10.6 Hz, 1H), 2.41 (d, J=10.8 Hz, 1H), 2.20 (m, J=12.2 Hz, 7.7 Hz, 1H), 1.57 (d, J=2.5 Hz, 1H), 1.44 (d, J=11.7 Hz, 1H).

Preparation of (24-24): To a solution of 24-23 (1.8 g, 2.69 mmol, 1.00 eq.) in dichloromethane (20 mL) with an inert atmosphere of nitrogen, was added Bis(diisopropylamino)(2-cyanoethoxy)phosphine (1.26 g, 1.40 eq.) and added 4,5-Dicyanoimidazole (422 mg, 1.20 eq.) in order at 0° C. The resulting solution was stirred for 1 h at 25° C. The resulting solution was diluted with dichloromethane. The resulting mixture was washed with Saturated sodium bicarbonate and Saturated sodium chloride. The organic phase was dried over anhydrous sodium sulfate, filtered and concentrated. The crude product was purified by Flash-Prep-HPLC. This resulted in 2.1 g (77%) of 24-24 as a white solid. MS m/z [M+H]+(ESI):869. 1H NMR (DMSO-d$_6$, 300 Hz, ppm): δ 11.20 (s, 1H), 8.62 (d, J=17.2 Hz, 1H), 8.40 (m, 1H), 8.13-8.03 (m, 2H), 7.65 (m, 1H), 7.56 (m, 2H), 7.47-7.33 (m, 4H), 7.21 (t, J=8.3 Hz, 2H), 7.15-6.92 (m, 6H), 6.59 (d, J=8.5 Hz, 2H), 6.31 (d, J=3.6 Hz, 1H), 4.22-4.02 (m, 1H), 4.00-3.37 (m, 9H), 3.04 (d, J=10.6 Hz, 1H), 2.92-2.67 (m, 2H), 2.55 (d, J=11.3 Hz, 1H), 2.31 (m, 1H), 1.73-1.47 (m, 2H), 1.27-0.99 (m, 13H), 0.93-0.76 (m, 1H). P-NMR (DMSO-d6, 300 Hz, ppm): 6148.21, 147.04.

Example 21

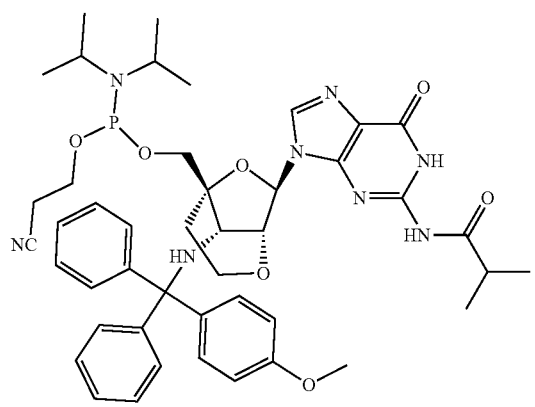 [SMILES: COc1ccc(C(N[C@H]2[C@H]3OCC[C@]2(COP(OCCC#N)N(C(C)C)C(C)C)O[C@H]3n2cnc3c(=O)[nH]c(NC(=O)C(C)C)nc32)(c2ccccc2)c2ccccc2)cc1]

Scheme 23

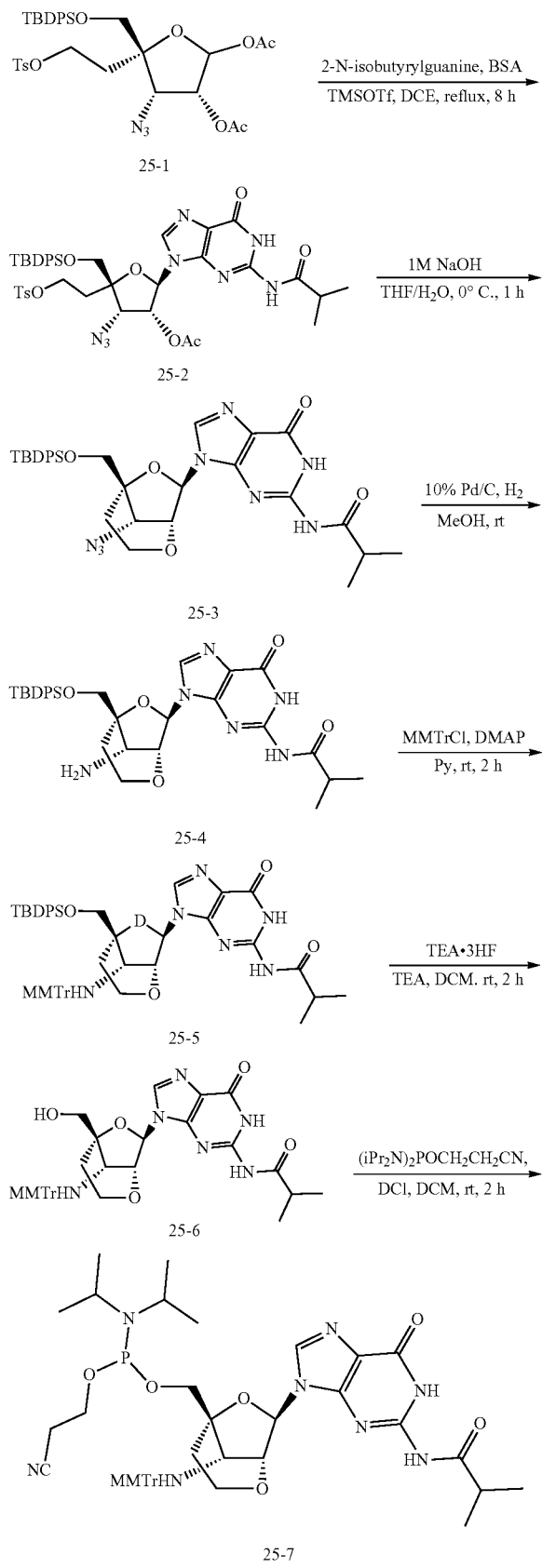

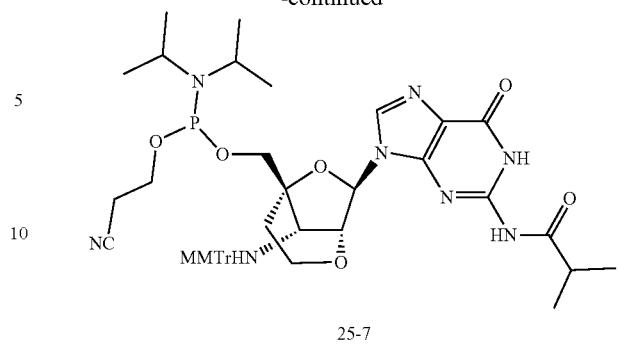

Preparation of Intermediate (25-2): To a solution of N-2-acetylguanine (12.4 g, 56.36 mmol, 3.00 eq.) in 1, 2-dichloroethane (200 mL) with an inert atmosphere of nitrogen, was added N, O-Bis (trimethylsilyl) acetamide (19 g, 93.6 mmol, 5.00 eq.) at room temperature. The resulting solution was stirred for 3 h at 85° C. To this was added 25-1 (13 g, 18.68 mmol, 1.00 eq.) at 0° C., and then trimethylsilyl trifluoromethanesulfonate (20.8 g, 93.58 mmol, 5.00 eq.) was added dropwise with stirring at 0° C. The resulting solution was allowed to react, with stirring, for an additional 2 h at 80° C. The reaction mixture was cooled to 0° C., quenched by the addition of saturated ammonium chloride (80 mL). The resulting solution was extracted with ethyl acetate and the organic layers combined and dried over anhydrous sodium sulfate, filtered, and concentrated. The residue was purified by column chromatography. This resulted in 5.6 g (35%) of 25-2 as a white solid. MS m/z [M+H]+(ESI): 857.

Preparation of Intermediate (25-3): To a solution of 25-2 (5.6 g, 6.53 mmol, 1.00 eq.) in tetrahydrofuran (56 mL) with an inert atmosphere of nitrogen, was added 1M sodium hydroxide (56 mL) at 0° C. The resulting solution was stirred for 1 h at 0° C. The pH value of the solution was adjusted to 7 with acetic acid. The resulting solution was diluted with ethyl acetate. The resulting mixture was washed with water and saturated sodium chloride respectively. The organic layer was dried over anhydrous sodium sulfate, filtered, and concentrated. The crude product was purified by Flash-Prep-HPLC. This resulted in 2.9 g (69%) of 25-3 as a white solid.

Preparation of Intermediate (25-4): To a solution of 25-3 (2.9 g, 4.51 mmol, 1.00 eq.) in tetrahydrofuran (30 mL) was added 10% Palladium on activated carbon (1.2 g). The flask was evacuated and flushed five times with hydrogen. The resulting solution was stirred for 5 hours at room temperature. The solids were filtered out. The resulting mixture was concentrated under reduced pressure. This resulted in 2.5 g (90%) of 25-4 as a white solid.

Preparation of Intermediate (25-5): To a solution of 25-4 (2.5 g, 4.05 mmol, 1.00 eq.) in pyridine (25 mL) with an inert atmosphere of nitrogen, was added 1-(chlorodiphenylmethyl)-4-methoxybenzene (1.9 g, 6.15 mmol, 1.50 eq.) and 4-dimethylaminopyridine (150 mg, 1.23 mmol, 0.30 eq.) in order at room temperature. The resulting solution was stirred for 2 h at room temperature and then quenched by the addition of methanol (10 mL). The resulting solution was diluted with ethyl acetate. The resulting mixture was washed with water and saturated sodium chloride respectively. The organic layer was dried over anhydrous sodium sulfate, filtered, and concentrated. The crude product was purified by Flash-Prep-HPLC. This resulted in 2.7 g (75%) of 25-5 as a white solid.

Preparation of Intermediate (25-6): To a solution of 25-5 (2.7 g, 3.04 mmol, 1.00 eq.) in dichloromethane (30 mL) with an inert atmosphere of nitrogen was added triethylamine (1 g, 9.88 mmol, 3.00 eq.) at room temperature. To this was added triethylamine trihydrofluoride (1.5 g, 9.32 mmol, 3.0 eq.) at room temperature. The resulting solution was stirred for 2 hours at 25° C. and diluted with dichloromethane. The resulting mixture was washed with water and saturated sodium chloride respectively. The organic layer was dried over anhydrous sodium sulfate, filtered, and concentrated. The crude product was purified by Flash-Prep-HPLC. This resulted in 1.7 g (86%) of 25-6 as a white solid. MS m/z [M+H]+(ESI): 651. 1H NMR (DMSO-d$_6$, 400 Hz, ppm) δ 12.16 (s, 1H), 11.77 (s, 1H), 8.15 (s, 1H), 7.42 (m, 4H), 7.15 (m, 8H), 6.56 (d, J=8.4 Hz, 2H), 5.97 (s, 1H), 5.22 (t, J=4.3 Hz, 1H), 4.01 (m, 1H), 3.85 (m, 2H), 3.73 (m, 1H), 3.60 (s, 3H), 3.01 (m, 1H), 2.82 (m, 1H), 2.39 (d, J=10.9 Hz, 1H), 2.17 (m, 1H), 1.58 (d, J=2.6 Hz, 1H), 1.41 (m, 1H), 1.18 (d, J=6.8 Hz, 3H), 1.12 (d, J=6.8 Hz, 3H.

Preparation of (25-7): To a solution of 25-6 (1.7 g, 2.61 mmol, 1.00 eq.) in dichloromethane (17 mL) with an inert atmosphere of nitrogen was added Bis (diisopropylamino) (2-cyanoethoxy) phosphine (950 mg, 3.16 mmol, 1.30 eq.) at room temperature. To this was added 4, 5-Dicyanoimidazole (340 mg, 2.91 mmol, 1.10 eq.) at room temperature. The resulting solution was stirred for 2 hours at 25° C. and diluted with dichloromethane. The resulting mixture was washed with water and saturated sodium chloride respectively. The organic layer was dried over anhydrous sodium sulfate, filtered, and concentrated. The crude product was purified by Flash-Prep-HPLC. This resulted in 1.8 g (81%) of 25-7 as a white solid. MS m/z [M+H]+(ESI): 851. H NMR (DMSO-d$_6$, 400 Hz, ppm) δ 12.18 (s, 1H), 11.80 (s, 1H), 7.98 (d, J=64.4 Hz, 1H), 7.47 (m, 4H), 7.15 (m, 8H), 6.56 (m, 2H), 6.01 (d, J=10.0 Hz, 1H), 3.95 (m, 3H), 3.77 (m, 2H), 3.66 (m, 1H), 3.59 (d, J=9.8 Hz, 3H), 3.38 (m, 2H), 2.91 (m, 4H), 2.30 (m, 1H), 1.55 (m, 2H), 1.15 (m, 14H), 1.04 (d, J=6.7 Hz, 4H). P NMR (DMSO-d$_6$, 400 Hz, ppm): 148.62, 147.09.

Example 22

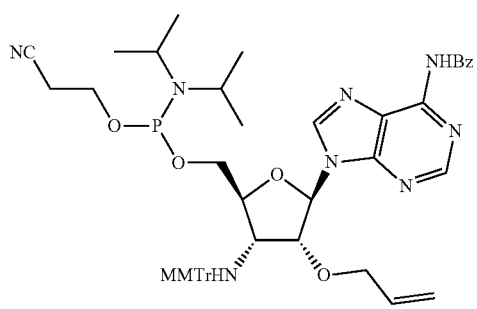

The synthesis of the 2'-O-vinyl adenosine analog 26-8 was achieved as shown in scheme 26. Intermediate 6-2 was treated with NH$_3$/MeOH to afford compound 26-1. To avoid side reactions of the vinyl moiety with the azide, the C3'-azide was reduced with a reducing agent such as H$_2$, Pd/C to afford intermediate 26-2 whose free 3'-NH$_2$ was protected with MMTr protecting group to form 26-3. After deprotection of the N6 position of the base to give 26-4, alkylation was carried out with allyl bromide to obtain 26-5. This approach used reduction of the C3'-azide prior to alkylation to avoid side reactions of the vinyl moiety with the azide. Reprotection of N6 position with benzyl chloride afforded compound 26-6 that was 5'-deprotected with Py/NaOH/MeOH/H$_2$O to give 26-7. Standard phosphitylation conditions were used to achieve target compound 26-8.

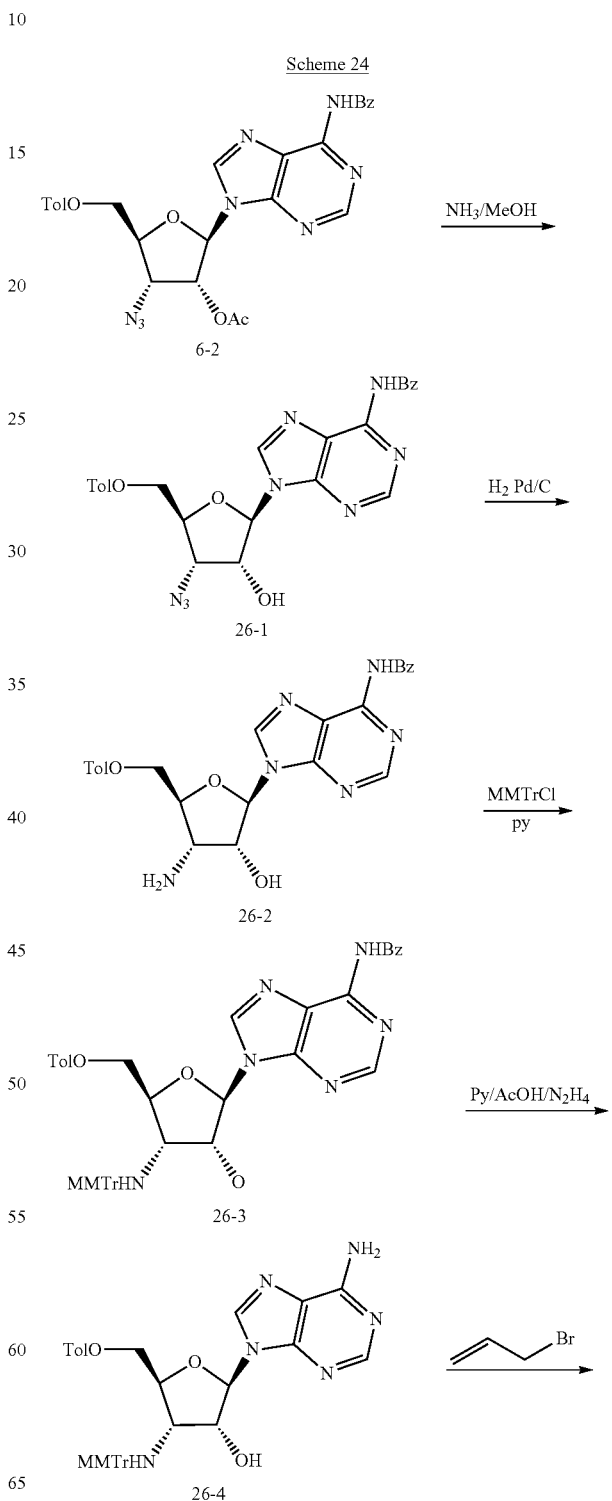

Scheme 24

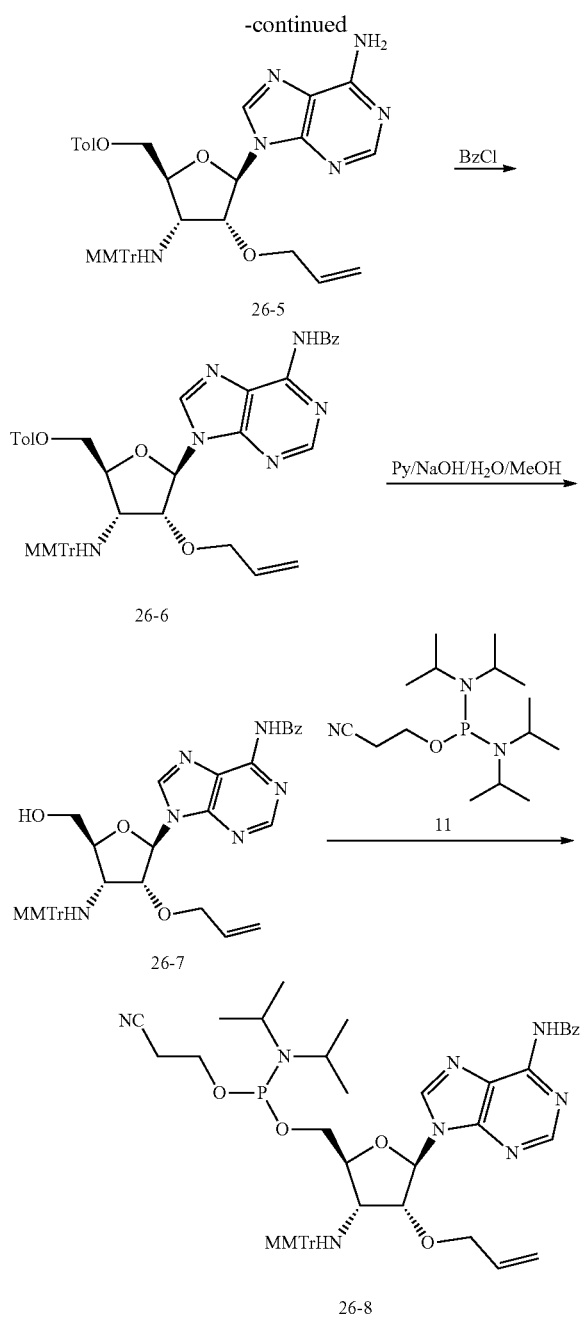

Preparation of Intermediate 26-1: To a solution of 6-2 (32.6 g, 58.6 mmol) in methanol (500 mL) was added NH$_3$—H$_2$O (50 mL) at 0° C. The reaction mixture was stirred at 0° C. for 2 h and concentrated, the residue was dissolved in EA, washed with brine, dried over anhydrous Na$_2$SO$_4$, the solvent was removed and the residue was purified on silica gel to give 26-1 (28.5 g, 55.4 mmol, 94.62% yield) as a yellow solid. ESI-LCMS: m/z 515 [M+H]$^+$.

Preparation of Intermediate 26-2: To a solution of 26-1 (28.5 g, 55.4 mmol) in THF (400.00 mL) was added Pd/C (3.0 g), the mixture was stirred at r.t. for 6 h under H$_2$. The mixture was filtered and the filtrate was concentrated to afford 26-2 (21.5 g, 44.1 mmol, 79.60% yield) as a gray solid. ESI-LCMS: m/z 489 [M+H]$^+$.

Preparation of Intermediate 26-3: MMTrCl (20.4 g, 66.1 mmol) was added to a solution of 26-2 (21.5 g, 44.1 mmol) in pyridine (300 mL). The mixture was stirred at room temperature for 1 h. The reaction was quenched with MeOH and concentrated to obtained a residue which was purified on silica gel to give 26-3 (22.0 g, 28.9 mmol, 65.53% yield) as a white solid. ESI-LCMS: m/z 761 [M+H]+.

Preparation of Intermediate 26-4: To a solution of 26-3 (22.0 g, 28.9 mmol) in a mixture of pyridine (200 mL) and AcOH (50 mL), was added hydrazine hydrate (80%) (173.5 mmol, 10 mL), and the reaction was stirred at room temperature for 15 h. The reaction was poured into ice water, extracted with EA, washed with brine and dried over anhydrous Na$_2$SO$_4$, concentrated to obtain the crude product which was purified on silica gel to give 26-4 (18.0 g, 27.4 mmol, 94.79% yield) as a white solid. ESI-LCMS: m/z 657 [M+H]+.

Preparation of Intermediate 26-5: Ag$_2$O (9.5 g, 41.1 mmol, 1.33 mL) and NaI (8.2 g, 54.8 mmol) were added to a solution of 26-4 (18 g, 27.4 mmol) and vinyl bromide (6.6 g, 54.8 mmol) in dry DMF (250 mL) were added the mixture was stirred at room temperature for 1.5 h. The reaction was poured into ice water, extracted with EA, washed with brine and dried over anhydrous Na$_2$SO$_4$, concentrated to obtain the crude product which was purified by recrystallization (PE:EA=1:1) to give 26-5 (12.1 g, 17.3 mmol, 63.36% yield) as a white solid. $^1$H-NMR (400 MHz, DMSO-d$_6$): δ=7.99 (d, J=2.0 Hz, 1H), 7.53-7.48 (m, 6H), 7.40-7.37 (m, 2H), 7.28 (br s, 2H, exchanged with D$_2$O), 7.21-7.14 (m, 6H), 7.09-7.04 (m, 2H), 6.68 (d, J=9.2 Hz, 2H), 5.93 (s, 1H), 5.87-5.77 (m, 1H), 5.22-5.16 (m, 1H), 5.10-5.07 (m, 1H), 4.81-4.78 (m, 1H), 4.68 (dd, J=3.2, 12.4 Hz, 1H), 4.05-3.99 (m, 1H), 3.94-3.89 (m, 1H), 3.53 (s, 3H), 3.22-3.18 (m, 1H), 2.92 (d, J=10.8 Hz, 1H, exchanged with D$_2$O), 2.49 (d, J=4.8 Hz, 1H), 2.37 (s, 3H). ESI-LCMS: m/z 697 [M+H]$^+$.

Preparation of Intermediate 26-6: BzCl (4.8 g, 34.4 mmol) was added dropwise to a solution of 26-5 (12 g, 17.2 mmol) in pyridine (120 mL) at 0° C. After the mixture was stirred for 1 h at r.t., 300 mL H$_2$O and 500 mL EA were added to separate the solution, the aqueous phase was extracted by EA. The combined organic layers were washed with brine, dried over Na$_2$SO$_4$, concentrated to obtain the crude product 26-6 (16.2 g) as a yellow oil. ESI-LCMS: m/z 801 [M+H]$^+$.

Preparation of Intermediate 26-7: To a solution of the crude 26-6 (16.2 g) in pyridine (200 mL) was added 2N NaOH (MeOH:H2O=4:1) (50 mL) dropwise at 0° C. The mixture was stirred at 0° C. for 0.5 h and then neutralized with saturated NH$_4$Cl (aq) to give the pH=7-8, and 500 mL H$_2$O. 800 mL of EA were added to separate the solution, the aqueous was extracted with EA, the combined organic layers were washed with brine, dried over Na$_2$SO$_4$, and concentrated to obtain the crude product which was purified by MPLC to give 26-7 (9.3 g, 13.6 mmol, 79.07% yield over two steps) as a white solid. $^1$H-NMR (400 MHz, DMSO-d$_6$): δ=11.15 (s, 1H, exchanged with D$_2$O), 8.68 (s, 1H), 8.65 (s, 1H), 8.07-8.05 (m, 2H), 7.67-7.63 (m, 1H), 7.57-7.53 (m, 2H), 7.44-7.41 (m, 4H), 7.27 (d, J=9.2 Hz, 2H), 7.20-7.16 (m, 4H), 7.13-7.09 (m, 2H), 6.72 (d, J=9.2 Hz, 2H), 6.08 (s, 1H), 5.93-5.83 (m, 1H), 5.27-5.22 (m, 1H), 5.18 (t, J=4.0 Hz, 1H, exchanged with D$_2$O), 5.13-5.10 (m, 1H), 4.11-3.99 (m, 4H), 3.64 (s, 3H), 3.46-3.42 (m, 1H), 3.38-3.32 (m, 1H), 2.71 (d, J=10.8 Hz, 1H, exchanged with D$_2$O), 1.91 (d, J=4.4 Hz, 1H). ESI-LCMS: m/z 683 [M+H]$^+$.

Preparation of 26-8: Phosphitylation reagent (3.4 g, 11.4 mmol) was added under Ar to a solution of 26-7 (6.5 g, 9.5 mmol) and DCI (1.1 g, 9.5 mmol) in dry DCM (70 mL). The mixture was stirred at r.t. for 1 h. Then the reaction was washed with 10% NaHCO₃ (aq) and brine, dried over Na₂SO₄, and concentrated to obtain the crude product which was purified by Flash-Prep-HPLC. This resulted in to give 26-8 (7.1 g, 8.0 mmol, 84.46% yield) as a white solid. ¹H-NMR (400 MHz, CDCl₃): δ=9.02 (br s, 1H), 8.74 (d, J=10.4 Hz, 1H), 8.37 (d, J=108.4 Hz, 1H), 8.04 (t, J=7.2 Hz, 2H), 7.65-7.61 (m, 1H), 7.57-7.53 (m, 2H), 7.51-7.48 (m, 4H), 7.41-7.38 (m, 2H), 7.21-7.10 (m, 6H), 6.73-6.70 (m, 2H), 6.03 (d, J=2.4 Hz, 1H), 5.91-5.79 (m, 1H), 5.31-5.21 (m, 2H), 5.17-5.13 (m, 1H), 4.40-4.25 (m, 2H), 4.16-4.08 (m, 1H), 4.05-3.94 (m, 1H), 3.89-3.80 (m, 1H), 3.72 (dd, J=0.8, 10.8 Hz, 3H), 3.70-3.47 (m, 4H), 3.42-3.35 (m, 1H), 2.86 (dd, J=10.8, 23.2 Hz, 1H), 2.68-2.51 (m, 2H), 1.62 (dd, J=4.4, 210.8 Hz, 1H), 1.26-1.18 (m, 12H). ³¹P NMR (162 MHz, CDCl₃): 148.85, 148.24. ESI-LCMS: m/z 883 [M+H]+.

Example 23

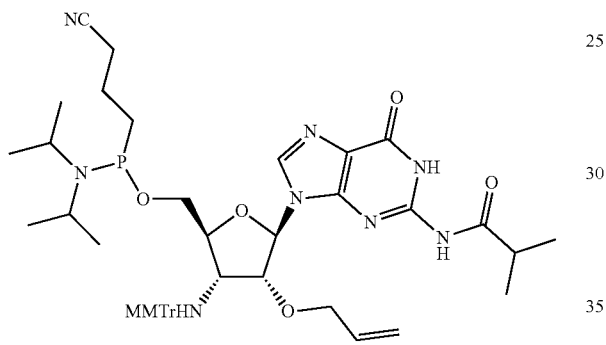

The synthesis of guanosine-based 2'-vinyl phosphoramidate 27-9 was accomplished as shown in scheme 27. The C3'-azide of compound 7-2 was reduced to the corresponding amine to obtain 27-1. 3'-amine protection with N-Boc yielded intermediate 27-2. 2'-O-allylation was carried out by using allylbromide in the presence of Ag₂O and NaI to form intermediate 27-3. Boc protection at the 3'-NH position was found to afford higher alkylation yields as compared to MMTr for this particular case. MMTr cleavage of the exocyclic amino to give 27-4 followed by deprotection with iBuCl gave compound 27-5. Then, deprotection of the 3'amine gave 27-6 which after reprotection with MMTrCl yielded 27-7. Cleavage of the 5'-tol group to form 27-8 and final phosphitylation gave target compound 27-9.

Scheme 25

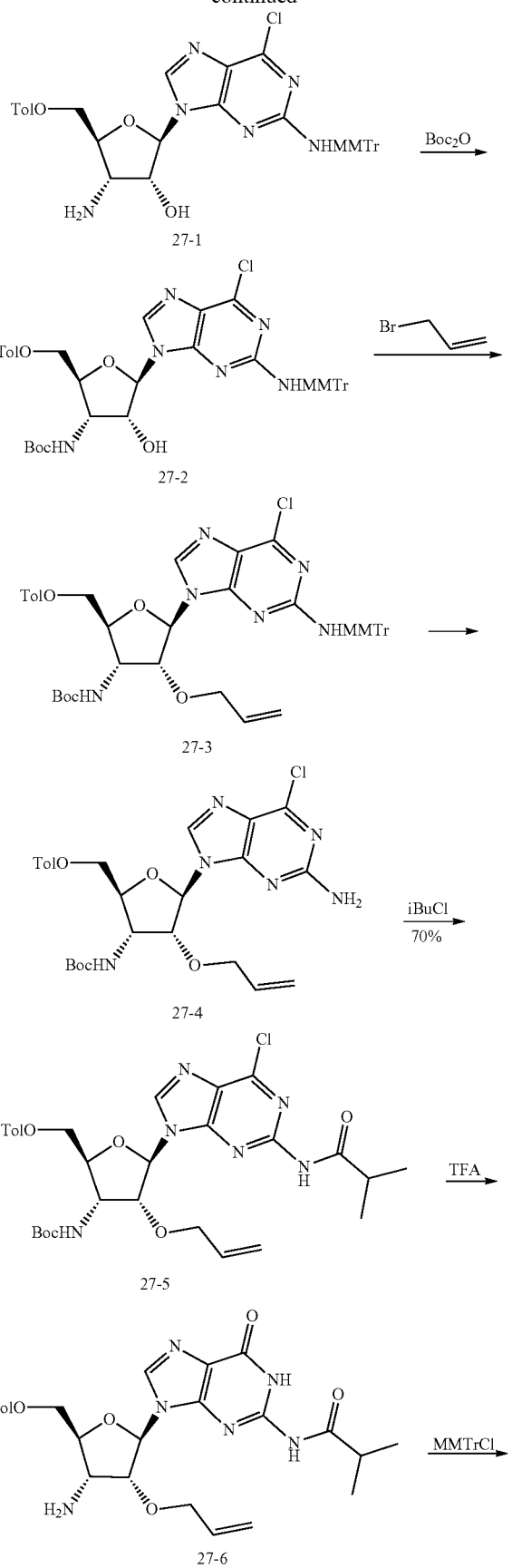

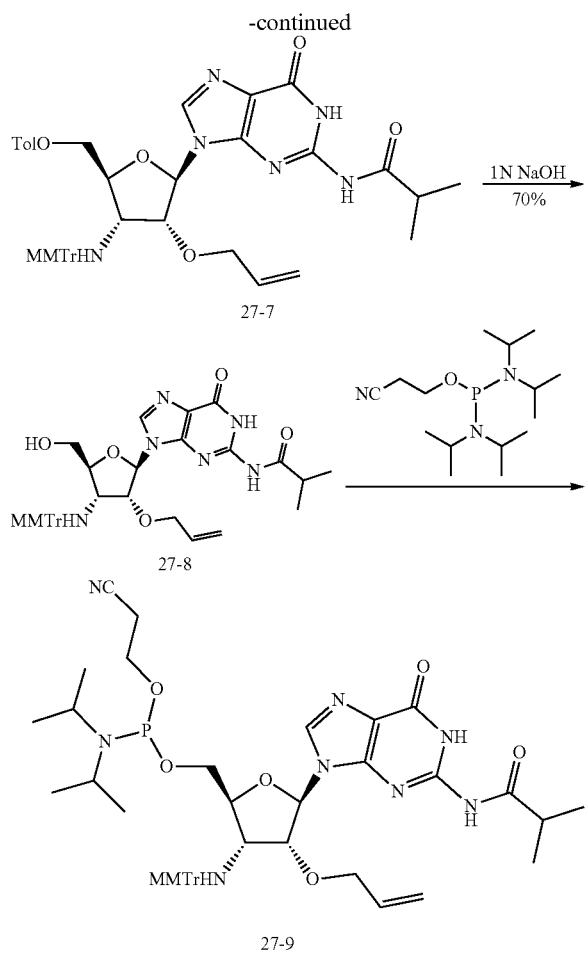

Preparation of Intermediate (27-1): To a solution of 7-2 (50.5 g, 69.7 mmol) in THF (500 mL) were added PPh₃ (27.4 g, 104.5 mmol) and H2O (1.3 g, 69.7 mmol). The mixture was stirred at 60° C. for 15 h. The reaction was concentrated and the residue was purified on silica gel to give 27-1 (41.1 g, 59.3 mmol, 85.08% yield) as a white solid. ESI-LCMS: m/z 691 [M+H]⁺.

Preparation of Intermediate (27-2): To a solution of 27-1 (41.1 g, 59.3 mmol) in a mixture of THF (300 mL) and sat. NaHCO₃ (aq) (200 mL) was added Boc₂O (15.5 g, 71.2 mmol). The mixture was stirred at room temperature for 2 h, extracted with EA, washed with brine and dried over anhydrous Na₂SO₄. Finally, it was concentrated to obtain the crude product which was purified on silica gel to give 27-2 (46.2 g, 58.2 mmol, 98.00% yield) as a white solid. ESI-LCMS: m/z 791 [M+H]⁺.

Preparation of Intermediate (27-3): Vinyl bromide (45 g, 56.8 mmol) and 27-2 (10.3 g, 85.3 mmol) in dry DMF (400 mL), were added Ag₂O (19.7 g, 85.3 mmol) and NaI (12.8 g, 85.3 mmol), the mixture was stirred at room temperature for 0.5 h, poured into ice water, extracted with EA, washed with brine and dried over anhydrous Na₂SO₄, concentrated to obtain the crude product which was purified on silica gel to give 27-3 (35.3 g, 42.4 mmol, 74.66% yield) as a white solid. ESI-LCMS: m/z 831 [M+H]⁺.

Preparation of Intermediate (27-4): TCA (100 g, 42.1 mmol) was added to solution of 27-3 (35 g, 42.1 mmol) in DCM (400 mL) and the mixture was stirred at room temperature for 4 h. After this time, the reaction mixture was neutralized with saturated NaHCO₃ (aq) to give pH=8-9. EA was added and washed with brine. The organic layers were dried over Na₂SO₄ and concentrated to obtain the crude product which was purified on silica gel to give 27-4 (18.5 g, 33.1 mmol, 78.61% yield) as a white solid. ESI-LCMS: m/z 559 [M+Na]⁺.

Preparation of Intermediate (27-5): iBuCl (5.2 g, 48.3 mmol) was added dropwise to a solution of 27-4 (18 g, 32.2 mmol) in pyridine (200 mL) at 0° C. After the mixture was stirred at 0° C. for 0.5 h, 500 mL H₂O and 800 mL EA were added to separate the solution. The aqueous phase was extracted with EA, the combined organic layer was washed with brine, dried over Na₂SO₄ and finally concentrated to obtain the crude product which was purified on silica gel to give 27-5 (18.1 g, 28.77 mmol, 89.35% yield) as a white solid. ESI-LCMS: m/z 629 [M+H]⁺.

Preparation of Intermediate (27-6): 27-5 (18 g, 28.6 mmol) was dissolved in a mixture of TFA (180 mL) and H₂O (60 mL). The reaction was stirred at room temperature for 15 h and neutralized with saturated NaHCO₃ (aq). The crude was extracted with EA, washed with brine, and dried over anhydrous Na₂SO₄. After concentration, purification on silica gel afforded 27-6 (12.5 g, 24.5 mmol, 85.57% yield) as a white solid. ESI-LCMS: m/z 511 [M+H]⁺.

Preparation of Intermediate (27-7): To a solution of 27-6 (12.5 g, 24.5 mmol) in anhydrous DCM (150 mL), were added collidine (5.9 g, 49.0 mmol), AgNO₃ (6.2 g, 36.7 mmol), and MMTr-Cl (11.3 g, 36.7 mmol) and the mixture was stirred at r.t. for 1 h under N₂. After the reaction reached completion, the crude reaction mixture was filtered, washed with H₂O, dried over Na₂SO₄, and concentrated to give a residue which was purified on silica gel to afford the crude product 27-7 (18.5 g, 23.6 mmol, 96.56% yield) as a white solid. ESI-LCMS: m/z 783 [M+H]⁺.

Preparation of Intermediate (27-8): To a solution of crude 27-7 (18.5 g, 23.6 mmol) in pyridine (200 mL) 2N NaOH was added dropwise (in MeOH:H₂O=4:1) (50 mL) dropwise at 0° C., the mixture was stirred at 0° C. for 15 min. The mixture was neutralized with saturated NH₄Cl (aq) to give pH=7-8, and 500 mL H₂O and 800 mL EA were added. The aqueous phase was extracted by EA, the combined organic layers were washed with brine, dried over Na₂SO₄, and concentrated to obtain the crude product which was purified by MPLC to give 27-8 (12.1 g, 18.2 mmol, 77.21%) as a white solid. ¹H-NMR (400 MHz, CDCl₃): δ=12.13 (s, 1H, exchanged with D₂O), 11.34 (s, 1H, exchanged with D₂O), 8.11 (s, 1H), 7.47-7.43 (m, 4H), 7.28-7.21 (m, 6H), 7.17-7.13 (m, 2H), 6.77-6.75 (m, 2H), 5.89-5.80 (m, 2H), 5.25-5.20 (m, 1H), 5.13-5.09 (m, 1H), 4.03-3.92 (m, 4H), 3.65 (s, 3H), 3.46-3.41 (m, 1H), 3.31-3.24 (m, 1H), 2.87-2.80 (m, 1H), 2.73 (d, J=10.0 Hz, 1H, exchanged with D₂O), 1.91 (d, J=4.8 Hz, 1H), 1.16 (dd, J=6.8, 11.2 Hz, 6H). ESI-LCMS: m/z 665 [M+H]⁺.

Preparation of (27-9): To a solution of 27-8 (7.5 g, 11.3 mmol) and DCI (1.5 g, 12.4 mmol) in dry DCM (80 mL) was added the phosphitylation reagent (4.4 g, 14.7 mmol) under Ar. The mixture was stirred at r.t. for 1 h, washed with 10% NaHCO₃ (aq) and brine, dried over Na₂SO₄ and concentrated to obtain the crude product which was purified by Flash-Prep-HPLC. This resulted in to give 27-9 (7.4 g, 8.5 mmol, 75.79% yield) as a white solid. ¹H-NMR (400 MHz, CDCl₃): δ=7.90 (d, J=119.2 Hz, 1H), 754-7.51 (m, 4H), 7.42-7.37 (m, 2H), 7.28-7.12 (m, 6H), 6.78-6.72 (m, 2H), 5.79-5.65 (m, 2H), 5.18-5.04 (m, 2H), 4.30-4.09 (m, 3H), 3.93-3.33 (m, 10H), 2.86 (dd, J=10.0, 28.8 Hz, 1H), 2.72-

2.52 (m, 3H), 2.10 (dd, J=4.8, 211.6 Hz, 1H), 1.28-1.11 (m, 18H). $^{31}$P NMR (162 MHz, CDCl$_3$): 149.14, 148.15. ESI-LCMS: m/z 865 [M+H]$^+$.

Example 24

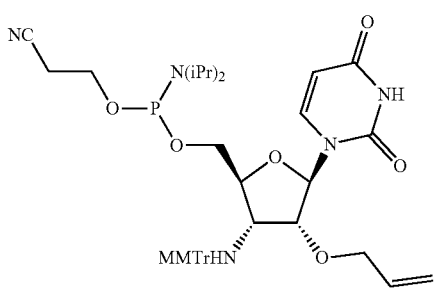

The synthesis of the 2'-O-allyl uridine phosphoramidite 28-5 was achieved as shown below in scheme 28. Briefly, MMTrCl-mediated protection of the 3'NH2 group of 8-5 afforded compound 28-4 that was alkylated with allylbromide to give 28-2. Deprotection of the propiolate group was accomplished with pyrrolidine leading to the formation of 28-3. Then, cleavage of the 5'-ester gave intermediate 28-4 that was phosphitylated to afford target phosphoramidite 28-5.

Scheme 26

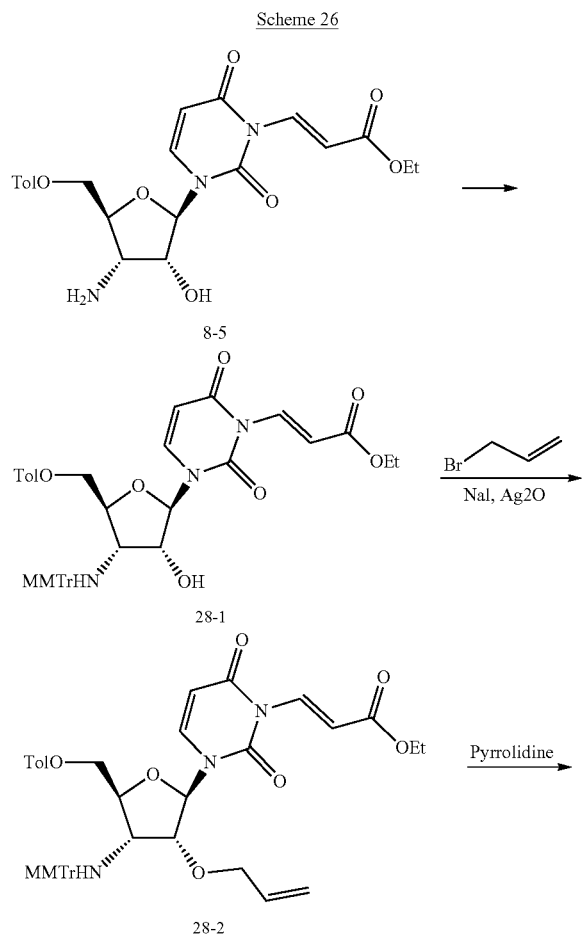

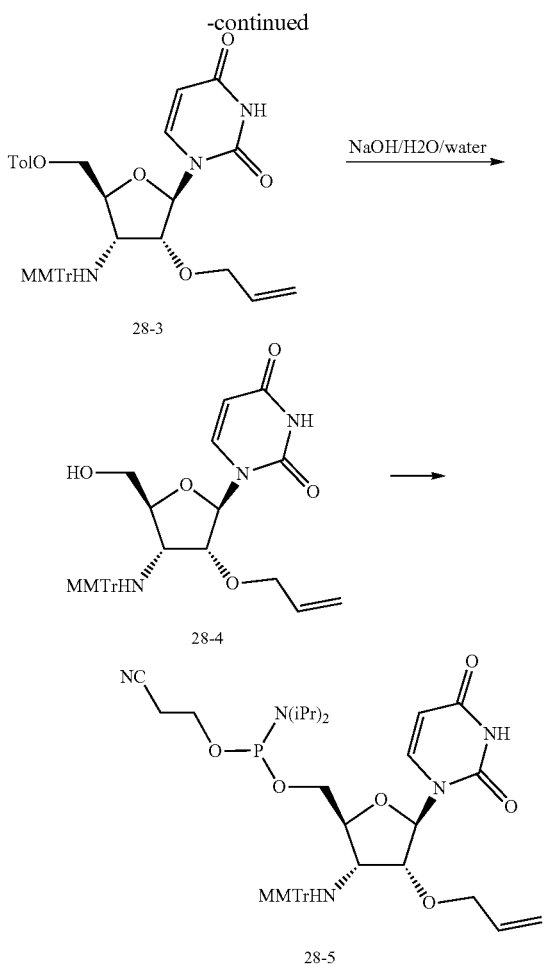

Preparation of Intermediate (28-1): MMTrCl (15.3 g, 49.6 mmol) was added under Ar to a solution of 8-5 (19.0 g, 41.3 mmol) in pyridine (300 mL), the mixture was stirred at room temperature for 1 h. Quenched with MeOH and concentrated to obtain a residue which was purified on silica gel to give 7 (24.5 g, 33.4 mmol, 80.97% yield) as a white solid. $^1$H-NMR (400 MHz, DMSO-d$_6$): δ=8.08 (d, J=14.8 Hz, 1H), 7.59-7.48 (m, 7H), 7.35-7.28 (m, 4H), 7.23-7.16 (m, 4H), 7.12-7.03 (m, 2H), 6.87 (d, J=14.8 Hz, 1H), 6.73 (d, J=4.8 Hz, 1H), 5.93 (d, J=4.4 Hz, 1H, exchanged with D$_2$O), 5.42-5.40 (m, 2H), 4.73 (d, J=12.4 Hz, 1H), 4.61 (dd, J=2.8, 12.8 Hz, 1H), 4.28-4.19 (m, 3H), 3.58 (s, 3H), 3.13-3.04 (m, 2H), 2.38 (s, 3H), 2.15 (t, J=4.0 Hz, 1H), 1.27 (t, J=7.2 Hz, 3H). ESI-LCMS: m/z 732 [M+H]$^+$.

Preparation of Intermediate (28-2): To a solution of 28-1 (22.5 g, 30.7 mmol) and allyl bromide (7.4 g, 61.5 mmol) in dry DMF (250 mL), were added NaI (9.2 g, 61.5 mmol) and Ag$_2$O (10.7 g, 46.1 mmol) under Ar, the mixture was stirred at room temperature for 0.5 h. The reaction was poured into ice water, extracted with EA, washed with brine and dried over anhydrous Na$_2$SO$_4$, concentrated to obtain the crude product which was purified on silica gel to give 28-2 (18.8 g, 24.3 mmol, 79.22% yield) as a white solid. $^1$H-NMR (400 MHz, DMSO-d$_6$): δ=8.06 (d, J=14.8 Hz, 1H), 7.59 (t, J=8.0 Hz, 3H), 7.50 (t, J=8.4 Hz, 4H), 7.33 (d, J=8.4 Hz, 2H), 7.27 (d, J=8.0 Hz, 2H), 7.22-7.15 (m, 4H), 7.10 (t, J=7.2 Hz, 1H), 7.04 (t, J=7.6 Hz, 1H), 6.87 (dd, J=2.4, 22.8 Hz, 1H), 6.72 (d, J=8.8 Hz, 2H), 5.88-5.78 (m, 1H), 5.38 (d, J=8.0 Hz, 1H), 5.22 (dd, J=1.6, 17.2 Hz, 1H), 5.11-5.08 (m, 1H), 4.87-4.75

(m, 2H), 4.34 (d, J=10.4 Hz, 1H), 4.20 (dd, J=7.2, 14.4 Hz, 2H), 4.06-3.99 (m, 1H), 3.55 (s, 3H), 3.32-3.30 (m, 2H), 2.79 (d, J=10.4 Hz, 1H, exchanged with D$_2$O), 2.37 (s, 3H), 1.84 (d, J=4.4 Hz, 1H), 1.26 (t, J=7.2 Hz, 3H). ESI-LCMS: m/z 772 [M+H]$^+$.

Preparation of Intermediate (28-3): Pyrrolidine (1.8 g, 25.9 mmol) was added to a solution of 28-2 (20.0 g, 25.9 mmol) in acetonitrile (200 mL). The mixture was stirred at room temperature for 15 h. The solvent was evaporated and the residue was purified on silica gel to give 28-3 (15.5 g, 23.0 mmol, 88.81% yield) as a slightly yellow solid. ESI-LCMS: m/z 696 [M+Na]$^+$.

Preparation of Intermediate (28-4): A mixture of 28-3 (6.0 g, 8.9 mmol) and 2 N NaOH (in MeOH: H$_2$O=4:1) (60 mL) was stirred at r.t. for 0.5 h. After TLC showed that 28-3 was consumed completely, 28-4 was extracted with DCM and washed with brine, dried over Na$_2$SO$_4$, and concentrated to obtain the crude product which was purified by MPLC to give 28-4 (4.3 g, 7.7 mmol, 87.05%) as a white solid. $^1$H-NMR (400 MHz, DMSO-d$_6$): δ=11.27 (s, 1H, exchanged with D$_2$O), 7.97 (d, J=8.0 Hz, 1H), 7.47-7.44 (m, 4H), 7.34 (d, J=8.8 Hz, 2H), 7.27 (t, J=7.2 Hz, 4H), 7.21-7.17 (m, 2H), 6.84 (d, J=8.8 Hz, 2H), 5.86-5.76 (m, 1H), 5.25-5.49 (m, 2H), 5.20-5.15 (m, 1H), 5.08-5.05 (m, 1H), 4.06-4.01 (m, 2H), 3.96-3.90 (m, 2H), 3.72 (s, 3H), 3.30-3.25 (m, 1H), 3.16-3.09 (m, 1H), 2.69 (d, J=10.4 Hz, 1H, exchanged with D$_2$O), 1.57 (d, J=4.4 Hz, 1H). ESI-LCMS: m/z 556 [M+H]$^+$.

Preparation of (28-5): To a solution of 28-4 (4.3 g, 7.7 mmol) and DCI (999 mg, 8.5 mmol) in dry DCM (40 mL) was added 28-4 (3.0 g, 10.0 mmol) under Ar. The mixture was stirred at r.t. for 1 h. The reaction was washed with 10% NaHCO$_3$ (aq.) and brine, dried over Na$_2$SO$_4$ and concentrated to obtain the crude product which was purified Flash-Prep-HPLC. 28-5 (4.4 g, 5.8 mmol, 75.68% yield) was obtained as a white solid. $^1$H-NMR (400 MHz, CDCl$_3$): δ=7.80 (dd, J=8.0, 182.4 Hz, 1H), 7.55-7-43 (m, 6H), 7.30-7.18 (m, 6H), 6.82-6.78 (m, 2H), 5.84-5.74 (m, 1H), 5.66 (d, J=4.8 Hz, 1H), 5.60 (d, J=8.0 Hz, 1H), 5.22-5.17 (m, 1H), 5.11-5.08 (m, 1H), 4.32-4.29 (m, 1H), 4.19-4.01 (m, 3H), 3.89-3.81 (m, 1H), 3.78 (s, 3H), 3.66-3.46 (m, 3H), 3.39-3.35 (m, 1H), 3.22-3.01 (m, 1H), 2.94-2.88 (m, 1H), 2.64-2.44 (m, 1H), 1.52 (dd, J=4.8, 140.0 Hz, 1H), 1.25-1.15 (m, 12H). $^{31}$P-NMR (162 MHz, CDCl$_3$): 149.16, 148.20. ESI-LCMS: m/z 756 [M+H]$^+$.

Example 25

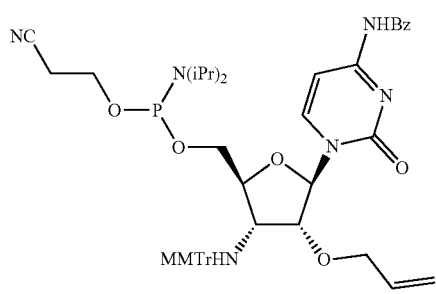

Scheme 27

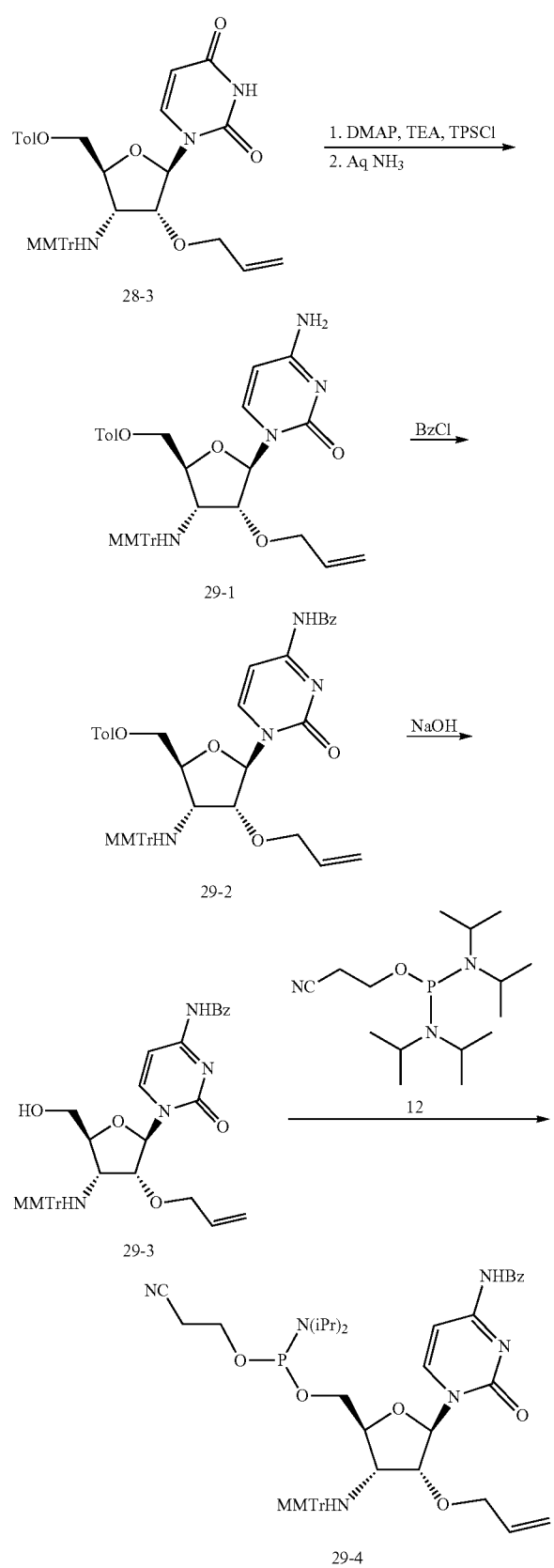

Preparation of Intermediate (29-1): DMAP (3.6 g, 29.7 mmol), TEA (3.0 g, 29.6 mmol, 4 mL) and TPSCl (6.7 g, 22.2 were added under Ar to solution of 28-3 (10.0 g, 14.8 mmol) in dry acetonitrile (100 mL) were added mmol). After the mixture was stirred at r.t. for 1 h, conc. NH$_3$—H$_2$O (25 mL) was added, and the reaction was stirred at r.t. for another 15 h. Upon of completion, the solvent was removed, and the residue was dissolved in EA, washed with sat. NH$_4$Cl (aq) and brine, dried over anhydrous Na$_2$SO$_4$, and concentrated to obtain the crude product which was purified on silica gel to give 29-1 (8.9 g, 13.2 mmol, 89.14% yield) as a pale yellow solid. $^1$H-NMR (400 MHz, DMSO-d$_6$): δ=7.59 (d, J=7.6 Hz, 2H, exchanged with D$_2$O), 7.50-7.43 (m, 5H), 7.35-7.29 (m, 4H), 7.22-7.17 (m, 6H), 7.14-7.06 (m, 2H), 6.71 (d, J=9.2 Hz, 2H), 5.88-5.79 (m, 1H), 5.55 (s, 1H), 5.39 (d, J=7.2 Hz, 1H), 5.22 (dd, J=1.6, 17.2 Hz, 1H), 5.08 (dd, J=1.2, 10.4 Hz, 1H), 4.88-4.76 (m, 2H), 4.31-4.28 (m, 1H), 4.09-4.04 (m, 1H), 3.58 (s, 3H), 3.29-3.25 (m, 1H), 3.20-3.14 (m, 1H), 2.79 (d, J=9.2 Hz, 1H, changed with D$_2$O), 2.41 (s, 3H), 1.61 (d, J=4.4 Hz, 1H). ESI-LCMS: m/z 673 [M+H]$^+$.

Preparation of Intermediate (29-2): To a solution of 29-1 (8.5 g, 12.6 mmol) in pyridine (80 mL), BzCl was added dropwise at 0° C. (2.1 g, 15.1 mmol). After the mixture was stirred for 1 h at r.t., 300 mL H$_2$O and 500 mL EA were added. The aqueous layer was extracted by EA, the combined organic layer was washed with brine, dried over Na$_2$SO$_4$, and concentrated to obtain the crude product 29-2 (11.30 g) as a yellow oil. ESI-LCMS: m/z 777 [M+H]$^+$.

Preparation of Intermediate (29-3): 2N NaOH (60 mL, MeOH:H$_2$O=4:1) was added dropwise at 0° C. to a solution of the crude product 29-2 (12.0 g, 15.4 mmol) in pyridine (120 mL). The mixture was stirred at 0° C. for 15 min and then neutralized with saturated NH$_4$Cl (aq.). 500 mL H$_2$O and 800 mL EA were added. The aqueous phase was extracted by EA, the combined organic layers were washed with brine, dried over Na$_2$SO$_4$, and concentrated to obtain the crude product which was purified on silica gel to give 29-3 (6.5 g, 9.8 mmol, 66.2% yield over two steps) as a white solid. $^1$H-NMR (400 MHz, CDCl$_3$): δ=8.47 (d, J=7.6 Hz, 1H), 7.92 (d, J=7.6 Hz, 1H), 7.65-7.60 (m, 1H), 7.54-7.50 (m, 6H), 7.47-7.44 (m, 2H), 7.29-7.22 (m, 6H), 6.85-6.78 (m, 2H), 5.90-5.80 (m, 1H), 5.74 (s, 1H), 5.28-5.23 (m, 1H), 5.14-5.11 (m, 1H), 4.30-4.25 (m, 3H), 4.18-4.15 (m, 1H), 3.79 (s, 3H), 3.54-3.48 (m, 1H), 3.13-3.07 (m, 1H), 2.84 (d, J=10.8 Hz, 1H), 1.92 (d, J=4.4 Hz, 1H). ESI-LCMS: m/z 659 [M+H]+.

Preparation of (29-4): CEP[N(iPr)$_2$]$_2$ (2.4 g, 8.1 mmol) was added under Ar to a solution of 29-3 (3.8 g, 5.8 mmol) and DCI (816 mg, 6.9 mmol) in dry DCM (40 mL). The mixture was stirred at r.t. for 1 h. The reaction mixture was washed with 10% NaHCO$_3$ (aq.) and brine, dried over Na$_2$SO$_4$ and concentrated to obtain the crude product which was purified Flash-Prep-HPLC. 29-4 (3.9 g, 4.5 mmol, 78.69% yield) was obtained as a white solid. $^1$H-NMR (400 MHz, CDCl$_3$): δ=8.67 (d, J=7.6 Hz, 1H), 7.94-7.91 (m, 2H), 7.64 (t, J=7.2 Hz, 1H), 7.56-7.42 (m, 8H), 7.28-7.20 (m, 6H), 6.81-6.77 (m, 2H), 5.87-5.78 (m, 1H), 5.74 (d, J=4.0 Hz, 1H), 5.25-5.20 (m, 1H), 5.11-5.08 (m, 1H), 4.43-4.34 (m, 1H), 4.27-4.21 (m, 2H), 4.15-4.09 (m, 1H), 3.94-3.84 (m, 1H), 3.79 (d, J=1.6 Hz, 3H), 3.73-3.56 (m, 3H), 3.46-3.42 (m, 1H), 3.22-3.03 (m, 1H), 2.87 (t, J=10.0 Hz, 1H), 2.69 (t, J=6.4 Hz, 1H), 2.63-2.54 (m, 1H), 1.72 (dd, J=4.4, 105.6 Hz, 1H), 1.30-1.22 (m, 12H). $^{31}$P-NMR (162 MHz, CDCl$_3$): 149.00, 148.08. ESI-LCMS: m/z 859 [M+H]$^+$.

Example 26—Synthesis of oligonucleotides

The modified oligonucleotides are synthesized on an ABI-394 synthesizer using the 93-step cycle written with modifications to deblock, coupling and wait steps. The solid support is 3'-NHTr-5'-LCAA-CPG. Each oligonucleotide is individually synthesized using methods described herein.

The modified oligonucleotides can be purified by anion-exchange HPLC. The buffers are, e.g., 20 mM sodium phosphate in 10% CH$_3$CN, pH 8.5 (buffer A) and 20 mM sodium phosphate in 10% CH$_3$CN, 1.8 M NaBr, pH 8.5 (buffer B). Fractions containing full-length oligonucleotides are pooled, desalted, and lyophilized.

The purified dry oligomer are then desalted using Sephadex G-25 M (Amersham Biosciences). The cartridge is conditioned with 10 mL of deionized water thrice. Finally the purified oligomer is dissolved thoroughly in RNAse free water is applied to the cartridge with very slow drop wise elution. The salt free oligomer is eluted with deionized water directly into a screw cap vial.

Approximately 0.10 OD of oligomer is dissolved in water and then pipetted in special vials for IEX-HPLC and LC/MS analysis. Analytical HPLC and ES LC-MS establishes the integrity of the oligonucleotides. The purity and molecular weight are determined by HPLC analysis (60° C., IEX-Thermo DNAPac PA-100, A—25 mM sodium phosphate 10% acetonitrile pH 11, B—1.8 M NaBr 25 mM sodium phosphate 10% acetonitrile pH 11; RPIP— Waters XBridge OST C18, A—100 mM HFIP 7 mM TEA B— 7:3 methanol/acetonitrile) and ESI-MS analysis using Promass Deconvolution for Xcalibur (Novatia, Newtown, PA).

What is claimed is:

1. A compound represented by Formula (II):

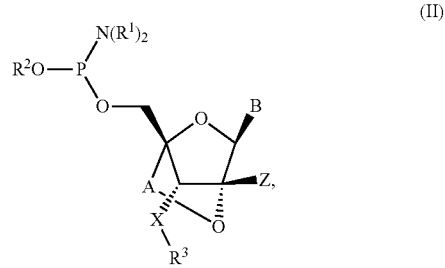

(II)

wherein

X is O;

Z is H;

B is a nucleobase selected from the group consisting of adenine (A), guanine (G), cytosine (C), uracil (U), 6-N-benzoyladenine (A$^{Bz}$), 4-N-benzoylcytosine (C$^{Bz}$), and 2-N-isobutyrylguanine (G$^{iBu}$);

each R$^1$ is independently C$_{1-6}$ alkyl or C$_{3-6}$ cycloalkyl;

R$^2$ is —CH$_2$CH$_2$CN or C$_{1-6}$ alkyl;

or one R$^1$ and R$^2$ together form an optionally substituted heterocycloalkyl ring comprising one to six carbon atoms;

R$^3$ is H or an alcohol protecting group selected from the group consisting of tert-butyldimethylsilyl (TBMDS), tert-butyldiphenylsilyl (TBDPS), tnisopropylsilyl (TIPS), trityl, monomethoxytrityl (MMTr), and tritolyl;

A is —(CR'R')$_{1-2}$—; and each R' is independently H or Me.

2. The compound of claim 1, wherein R$^1$ is C$_{2-3}$ alkyl.

3. The compound of claim 1, wherein R$^1$ is isopropyl.

4. The compound of claim 1, wherein R$^3$ is trityl.

5. The compound of claim 1, wherein R$^3$ is tritolyl.

6. The compound of claim 1, wherein B is adenine (A) or guanine (G).

7. The compound of claim 1, wherein B is 6-N-benzoyladenine ($A^{Bz}$), 4-N-benzoylcytosine ($C^{Bz}$), or 2-N-isobutyrylguanine ($G^{iBu}$).

8. The compound of claim 1, wherein $R^2$ is —$CH_2CH_2CN$.

9. The compound of claim 1, wherein $R^2$ is —$CH_2CH_2CN$ and each $R^1$ is isopropyl.

10. The compound of claim 1, wherein A is —(CR'R')—.

11. The compound of claim 1, wherein A is —(CR'R')$_2$—.

12. The compound of claim 1, wherein each R' is H.

13. The compound of claim 1, wherein one R' is Me and every other R' is H.

14. A composition comprising the compound of claim 1 and one or more reactants or solvents or impurities.

15. The composition of claim 14, wherein the composition has a purity of 95% or more.

16. The composition of claim 15, wherein the composition has a purity of 99% or more.

17. A method of making an oligonucleotide, the method comprising the steps of (i) deblocking the compound of claim 1 to form a deblocked intermediate, and (ii) coupling the deblocked intermediate with a nucleoside monomer to form the oligonucleotide, wherein $R^3$ is an alcohol protecting group selected from the group consisting of tert-butyldimethylsilyl (TBMDS), tert-butyldiphenylsilyl (TBDPS), triisopropylsilyl (TIPS), trityl, monomethoxytrityl (MMTr), and tritolyl, and wherein the deblocking comprises removal of the $R^3$ group.

18. A compound selected from:

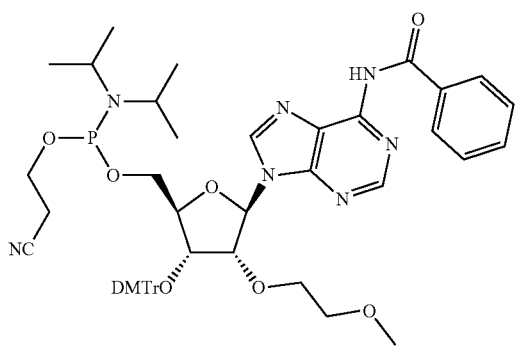

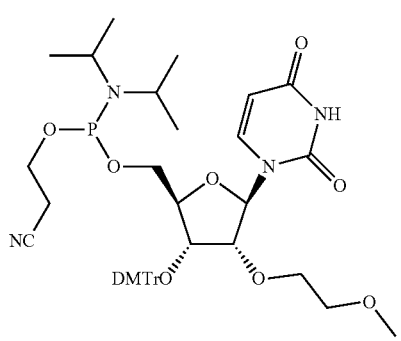

-continued

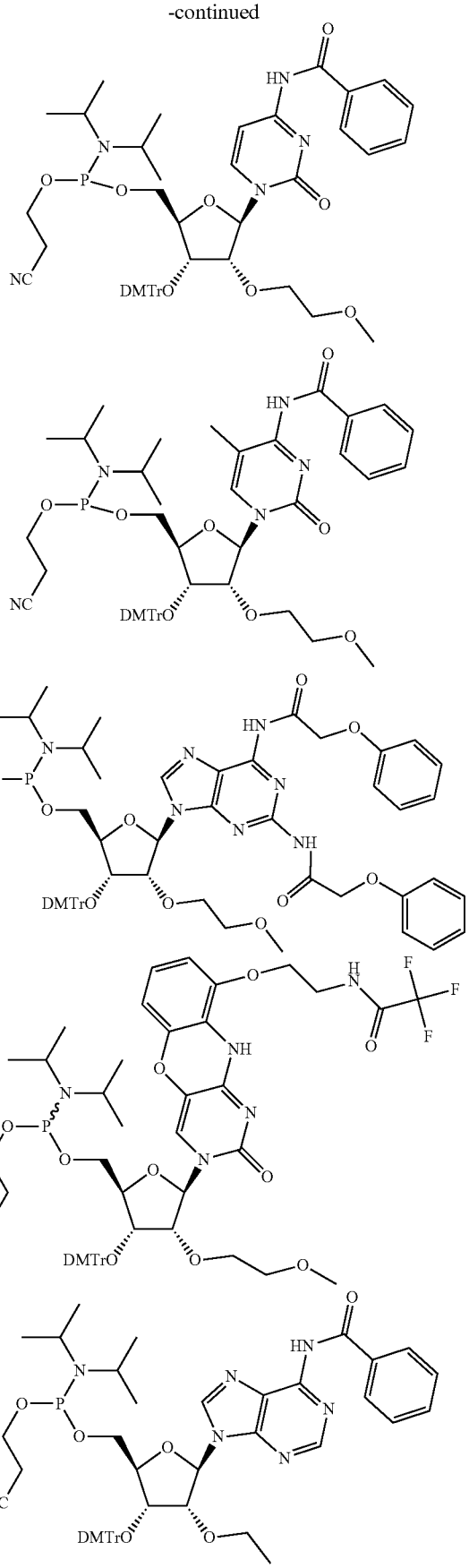

141
-continued
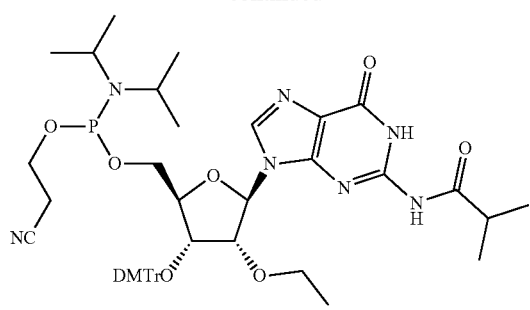
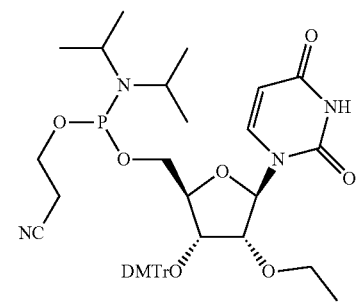
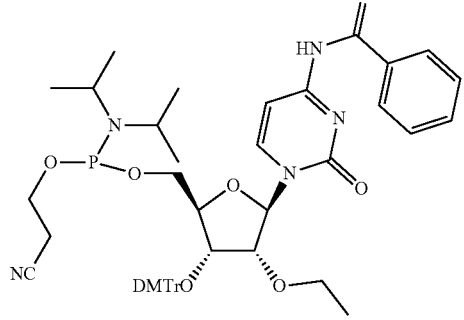
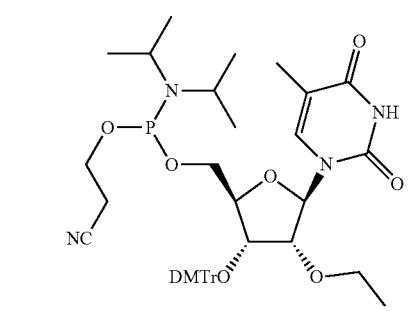
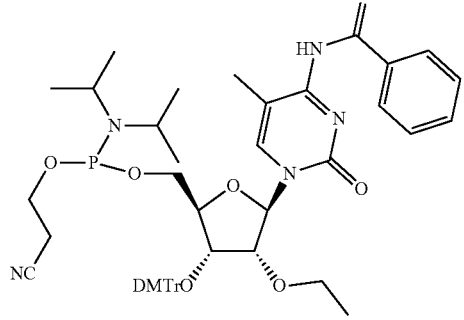
142
-continued
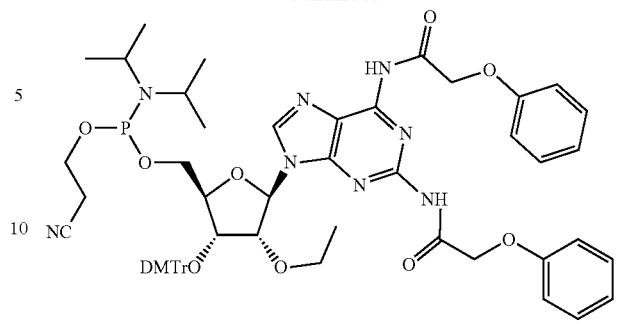
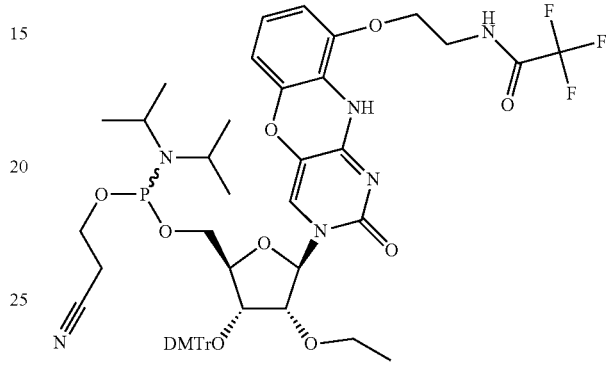
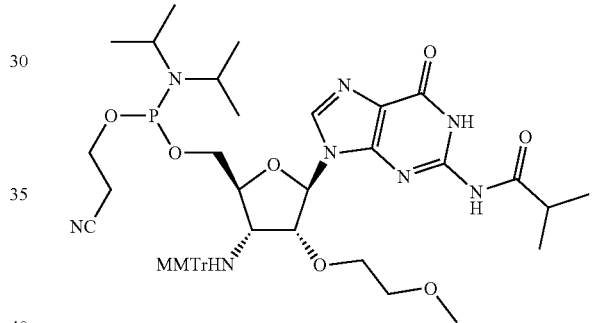
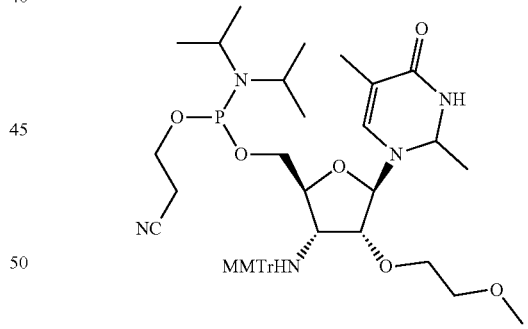
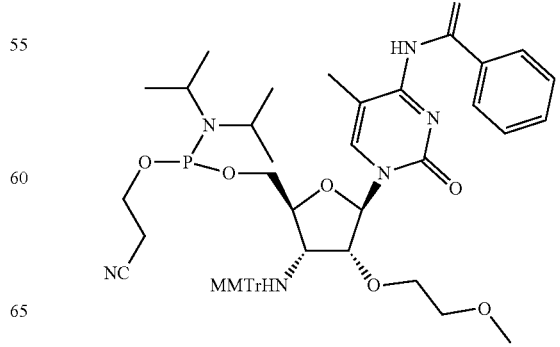

143
-continued
144
-continued
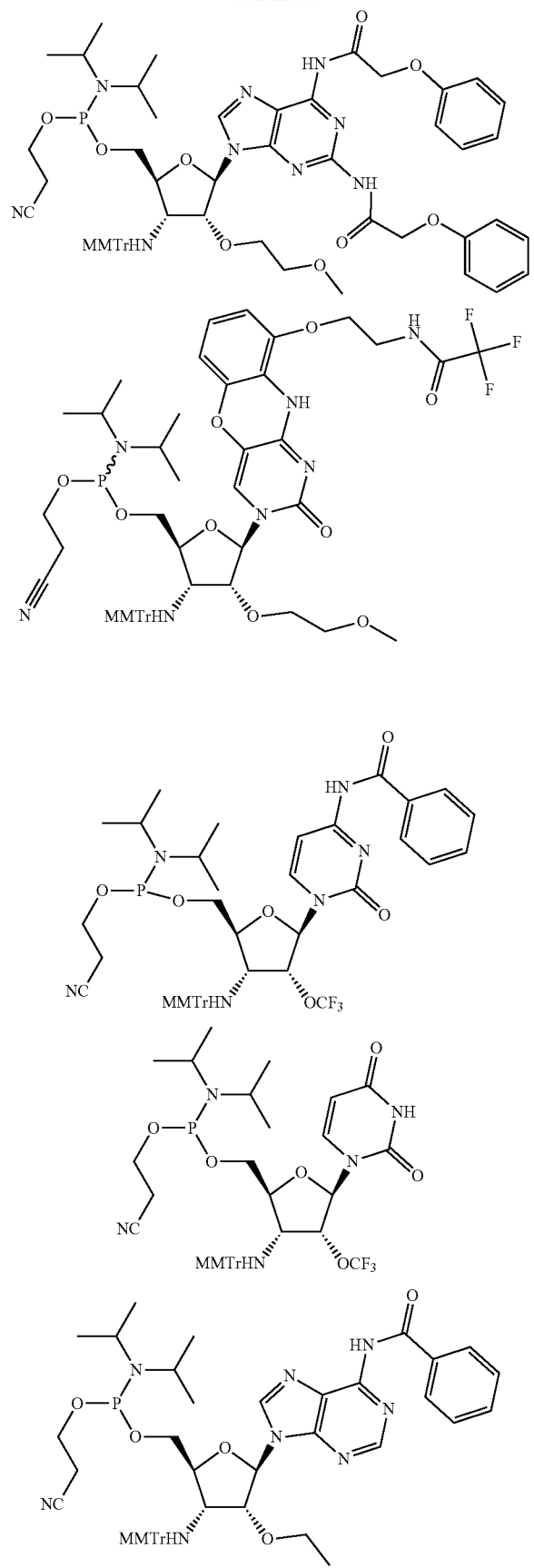
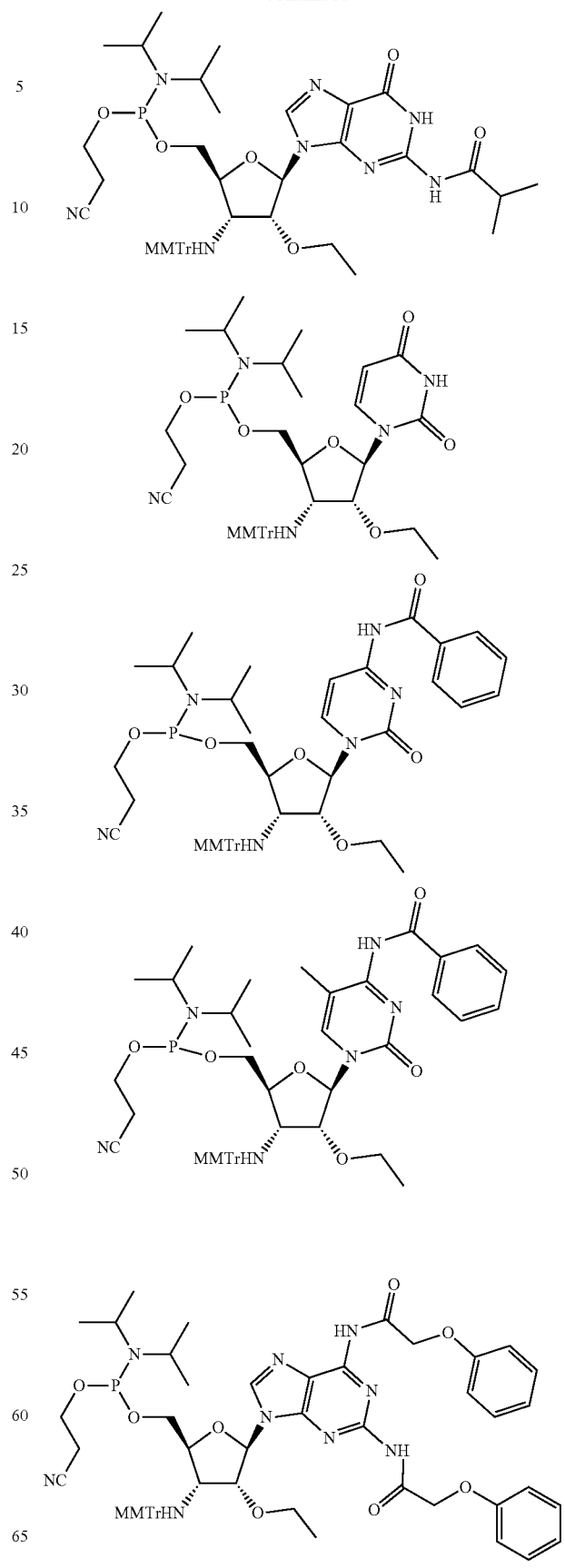

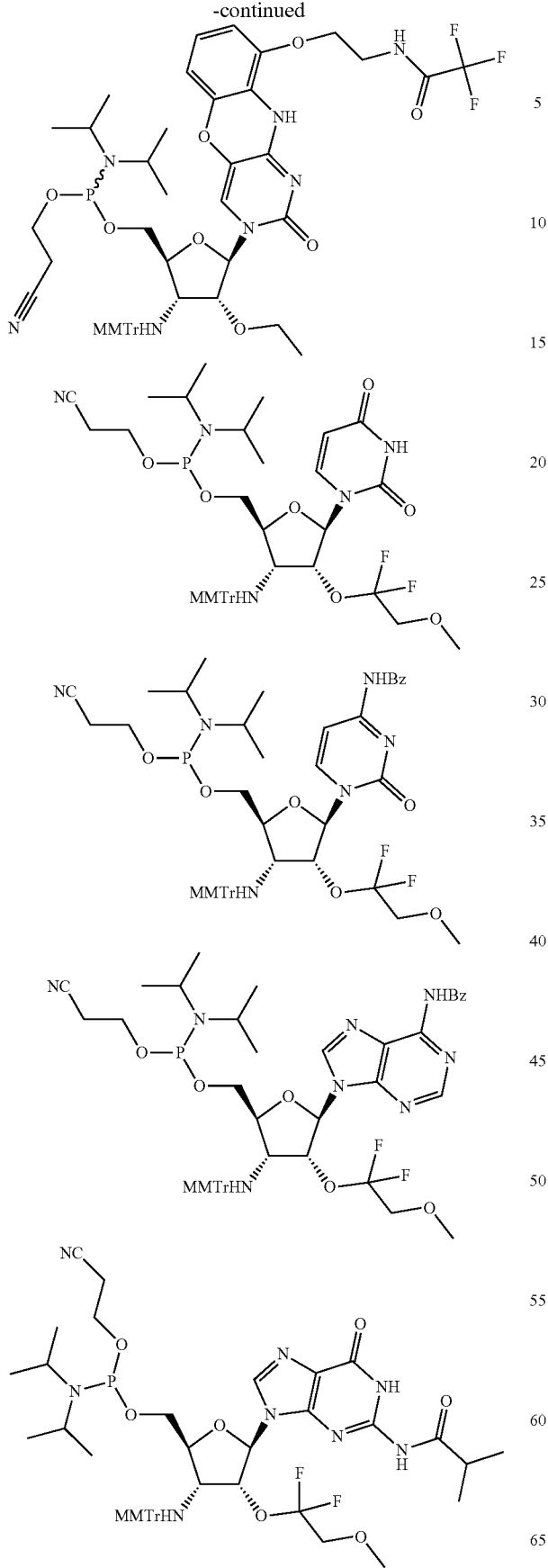
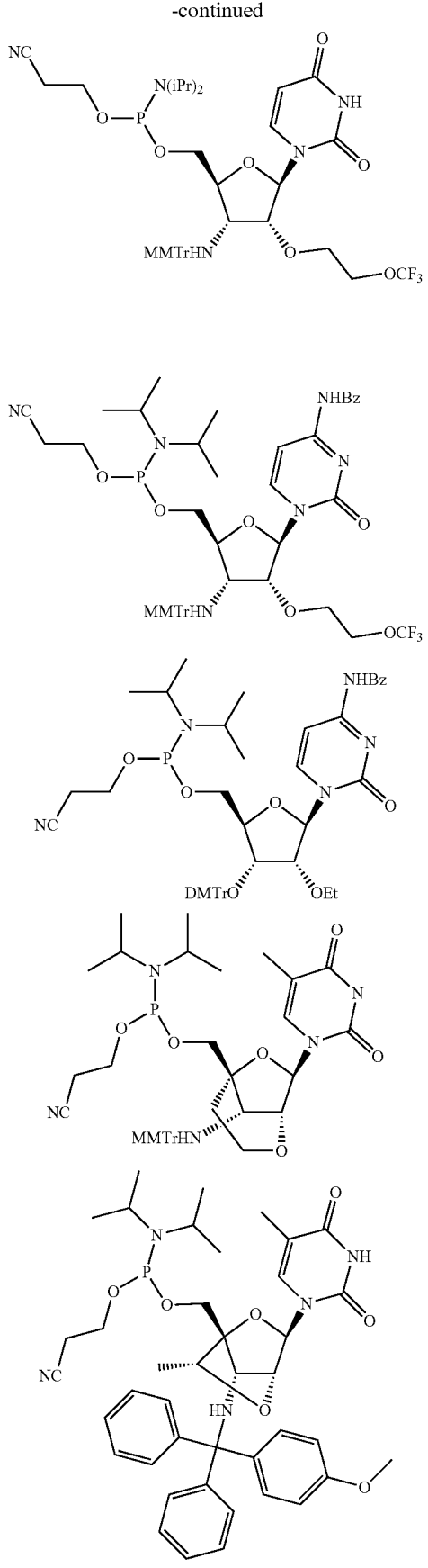

147
-continued
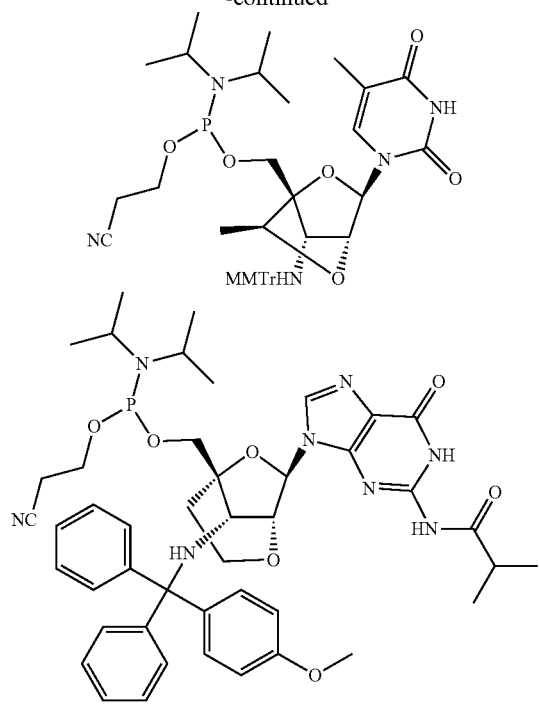
148
-continued
and
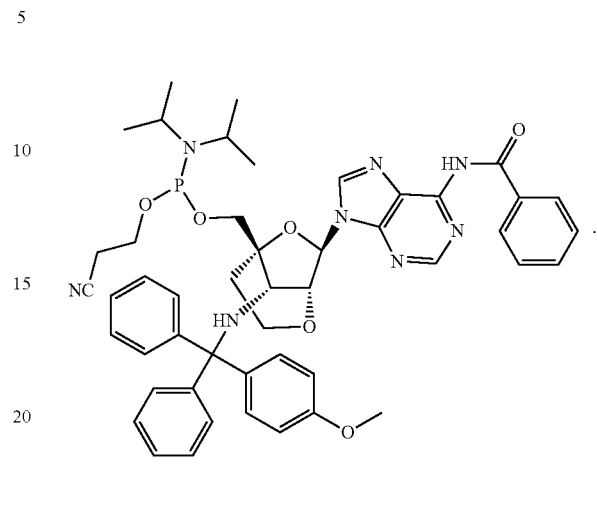
* * * * *

UNITED STATES PATENT AND TRADEMARK OFFICE
CERTIFICATE OF CORRECTION

PATENT NO. : 12,428,441 B2  
APPLICATION NO. : 18/672651  
DATED : September 30, 2025  
INVENTOR(S) : Sergei Gryaznov et al.

Page 1 of 1

It is certified that error appears in the above-identified patent and that said Letters Patent is hereby corrected as shown below:

In the Claims

In Claim 18, at Column 142, Lines 40-53, Delete the structure shown and insert:

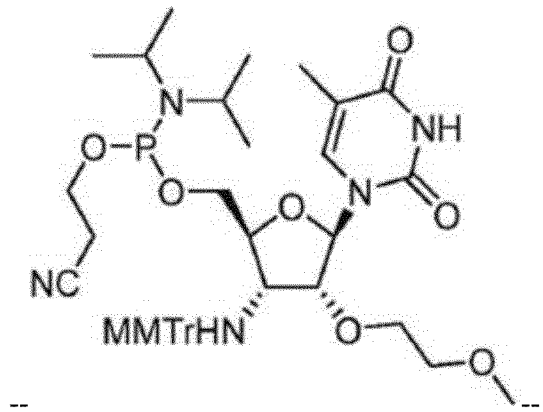

In Claim 18, at Column 146, Lines 39-50, Delete the structure shown and insert:

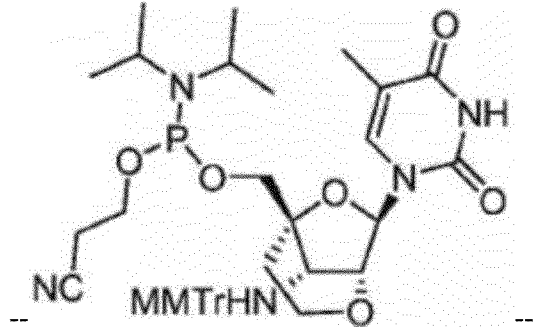

Signed and Sealed this  
Twenty-eighth Day of October, 2025

John A. Squires  
*Director of the United States Patent and Trademark Office*